(12) United States Patent
Kashiwagi et al.

(10) Patent No.: US 7,553,650 B2
(45) Date of Patent: Jun. 30, 2009

(54) POLYNUCLEOTIDE ENCODING A MUTANT TRANSGLUTAMINASE

(75) Inventors: Tatsuki Kashiwagi, Kawasaki (JP); Nobuhisa Shimba, Kawasaki (JP); Kohki Ishikawa, Kawasaki (JP); Ei-ichiro Suzuki, Kawasaki (JP); Keiichi Yokoyama, Kawasaki (JP); Kazuo Hirayama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 39 days.

(21) Appl. No.: 11/505,438

(22) Filed: Aug. 17, 2006

(65) Prior Publication Data

US 2006/0275872 A1 Dec. 7, 2006

Related U.S. Application Data

(60) Division of application No. 10/365,434, filed on Feb. 13, 2003, now abandoned, which is a continuation of application No. PCT/JP01/07038, filed on Aug. 15, 2001.

(30) Foreign Application Priority Data

| Aug. 17, 2000 | (JP) | ............................ 2000-247664 |
| Dec. 27, 2000 | (JP) | ............................ 2000-396695 |

(51) Int. Cl.
  *C12N 9/10* (2006.01)
  *C12N 9/00* (2006.01)
  *C12N 1/20* (2006.01)
  *C12N 15/00* (2006.01)
  *C07H 21/04* (2006.01)

(52) U.S. Cl. .................... 435/193; 435/183; 435/252.3; 435/320.1; 536/23.2

(58) Field of Classification Search ........................ None
See application file for complete search history.

(56) References Cited

U.S. PATENT DOCUMENTS

| 5,156,956 A | 10/1992 | Motoki et al. |
| 5,252,469 A | 10/1993 | Andou et al. |
| 5,420,025 A | 5/1995 | Takagi et al. |
| 5,965,402 A | 10/1999 | Black et al. |
| 5,965,442 A | 10/1999 | Kaneko et al. |

FOREIGN PATENT DOCUMENTS

| DE | 198 14 860 | 10/1999 |
| EP | 0 889 133 | 1/1999 |
| EP | 1 219 713 | 7/2002 |
| EP | 1 225 217 | 7/2002 |
| RU | 2 105 812 | 2/1998 |
| WO | WO 96/06931 | 3/1996 |
| WO | WO 00/70026 | 11/2000 |

OTHER PUBLICATIONS

Houchins et al. Immunogenetics. 1993;37(2):102-7.*
Chica et al. Curr Opin Biotechnol. Aug. 2005;16(4):378-84.*
Date et al. J Biotechnol. Jun. 10, 2004;110(3):219-26.*
P. Mariani, et al., "Ligand-Induced Conformational Changes in Tissue Transglutaminase: Monte Carlo Analysis of Small-Angle Scattering Data", Biophysical Journal, vol. 78, No. 6, Jun. 2000, pp. 3240-3251.
R. Casadio, et al., "The Structural Basis for the Regulation of Tissue Transglutaminase by Calcium Ions", Eur. J. Biochem, vol. 262, No. 3, 1999, pp. 672-679.
V.C. Yee, et al., "Three-Dimensional Structure of a Transglutaminase: Human Blood Coagulation Factor XIII", Proc. Nat'l. Acad. Sci. USA, vol. 91, No. 15, Jul. 1994, pp. 7296-7300.
K. Washizu, et al., "Molecular Cloning of the Gene for Microbial Transglutaminase from *Streptoverticillium* and its Expression in *Streptomyces lividans*", Biosci. Biotech. Bioche., vol. 58, No. 1, 1994, pp. 82-87.
T. Kanaji, et al., "Primary Structure of Microbial Transglutaminase from *Streptoverticillium* SP. Strain S-8112", J. Biological Chemistry, vol. 269, No. 16, 1993, pp. 11565-11572.

\* cited by examiner

*Primary Examiner*—Christian L Fronda
(74) *Attorney, Agent, or Firm*—Oblon, Spivak, McClelland, Maier & Neustadt, P.C.

(57) ABSTRACT

The present invention relates to a method for designing and preparing mutant transglutaminases on the basis of the three-dimensional structure of MTG derived from *Streptoverticillium mobaraense* (MTG), and the mutant MTG thus prepared. The present invention provides a method for modifying MTG on the basis of the three-dimensional structure, and transglutaminase having reactivity on the substrate improved by the method. In the present invention, the binding site of MTG for the substrate is extrapolated based on the three-dimensional structure obtained by X-ray crystal structure analysis of MTG crystals, and the mutant transglutaminases are designed and produced by replacing, inserting or deleting amino acid residues positioned at the substrate-binding site of the transglutaminase.

4 Claims, 59 Drawing Sheets

FIG.3

Streptoverticillium mobaraence
Streptoverticillium cinnamoneum

```
          +         +         +         +         +         +
---DSDDRVTPPAEPLDRMPDPYRPSYGRAETVVNNYIRKWQQVYSHRDGRKQQMTEEQR
SRAPSDDRETPPAEPLDRMPEAYRAYGGRATTVVNNYIRKWQQVYSHRDGKKQQMTEEQR
   **** ********** **   *** ******************** *********

+         +         +         +         +         +
EWLSYGCVGVTWVNSGQYPTNRLAFASFDEDRFKNELKNGRPRSGETRAEFEGRVAKESF
EKLSYGCVGVTWVNSGPYPTNRLAFGPFDENKYKNDLKNTSPRPDETRAEFEGR-IKGSF
* ************** ******** *** ** *** ** ********* * **

+         +         +         +         +         +
DEEKGFQRAREVASVMNRALENAHDESAYLDNLKKELANGNDALRNEDARSPFYSALRNT
DEGKGFKRARDVASVMNKARENAHDEGTYINNLKTELTN-NNALRREDSRSNFYSALRNT
** *** *** ****** * ****** *  *** ** * * *** ** ** ********

+         +         +         +         +         +
PSFKERNGGNHDPSRMKAVIYSKHFWSGQDRSSSADKRKYGDPDAFRPAPGTGLVDMSRD
PSFKERDGGNYDPSKMKAVIYSKHFWSGQDQRGSSDKRKYGDPEAFRPVPGTGLVDMSKD
****** *** *** **** ********** * ******** **** ********* *

+         +         +         +         +         +
RNIPRSPTSPGEGFVNFDYGWFGAQTEADADKTVWTHGNHYHAPNGSLGAMHVYESKFRN
RSIPRSPAKPGEGTVNFDYGWFGAQTEADRDKTTWTHGDHYHAPNSDLGPMHVHESKFRK
* *****   **** *************** *** ***** ****** ** *** *****

+         +         +
WSEGYSDFDRGAYVITFIPKSWNTAPDKVKQGWP
WSAGYADF--GAYVITFIPKSWNTAPAKVEQGWP
** ** ** **************** ** ***
```

FIG.4

Streptoverticillium mobaraence
Streptomyces lydicus

```
         +         +         +         +         +         +
DSDDRVTPPAEPLDRMPDPYRPSYGRAETVVNNYIRKWQQVYSHRDGRKQQMTEEQREWL
AADERVTPPAEPLNRMPDAYRAYGGRATTVVNNYIRKWQQVYAHRDGIQQQMTEEQREKL
  * ********* **** **   *** **************  ****  ********* *

+         +         +         +         +         +
SYGCVGVTWVNSGQYPTNRLAFASFDEDRFKNELKNGRPRSGETRAEFEGRVAKESFDEE
SYGCVGITWVNSGPYPTNKLAFAFFDENKYKSDLENSRPRPNETQAEFEGRIVKDSFDEG
****** ****** **** **** *** * *  *  ***  *  ****** * *  ****

+         +         +         +         +         +
KGFQRAREVASVMNRALENAHDESAYLDNLKKELANGNDALRNEDARSPFYSALRNTPSF
KGFKRARDVASVMNKALDSAHDEGTYIDNLKTELANKNDALRYEDGRSNFYSALRNTPSF
*** *** ****** **  **** * ***** **** ****  **  * ***********

+         +         +         +         +         +
KERNGGNHDPSRMKAVIYSKHFWSGQDRSSSADKRKYGDPDAFRPAPGTGLVDMSRDRNI
KERDGGNYDPSKMKAVVYSKHFWSGQDQRGSSDKRKYGDPDAFRPDQGTGLVDMSKDRNI
*** *** *** **** ********** * ** ************** ******* ****

+         +         +         +         +         +
PRSPTSPGEGFVNFDYGWFGAQTEADADKTVWTHGNHYHAPNGSLGAMHVYESKFRNWSE
PRSPAQPGESWVNFDYGWFGAQTESDADKTIWTHANHYHAPNGGLGPMNVYESKFRNWSA
****  ***   ************* ***** *** ********  **  *  **********

+         +         +
GYSDFDRGAYVITFIPKSWNTAPDKVKQGWP
GYADFDRGTYVITFIPKSWNTAPAEVKQGWS
** ***** ***************** ****
```

FIG.5

```
S2Y(s)   5'-GGA-GAT-ATA-CAT-ATG-GAT-TAC-GAC-GAT-CGT-GTT-ACT-CC-3'
S2Y(as)  3'-CCT-CTA-TAT-GTA-TAC-CTA-ATG-CTG-CTA-GCA-CAA-TGA-GG-5'
              M   D   Y   D   D   R   V   T

S2R(s)   5'-GGA-GAT-ATA-CAT-ATG-GAT-CGT-GAC-GAT-CGT-GTT-ACT-CC-3'
S2R(as)  3'-CCT-CTA-TAT-GTA-TAC-CTA-GCA-CTG-CTA-GCA-CAA-TGA-GG-5'
              M   D   R   D   D   R   V   T

S2D(s)   5'-GGA-GAT-ATA-CAT-ATG-GAT-GAC-GAC-GAT-CGT-GTT-ACT-CC-3'
S2D(as)  3'-CCT-CTA-TAT-GTA-TAC-CTA-CTG-CTG-CTA-GCA-CAA-TGA-GG-5'
              M   D   D   D   D   R   V   T
```

FIG.6

```
del 1-2(s)   5'-GGA-GAT-ATA-CAT-ATG-GAC-GAT-CGT-GTT-ACT-CCA-CCA-GC-3'
del 1-2(as)  3'-CCT-CTA-TAT-GTA-TAC-CTG-CTA-GCA-CAA-TGA-GGT-GGT-CG-5'
                  M   D   D   R   V   T   P   P del 1-3(s)   5'-GAA-GGA-GAT-ATA-CAT-ATG-GAT-CGT-GTT-ACT-CCA-CCA-GCT-G-3'
del 1-3(as)  3'-CTT-CCT-CTA-TAT-GTA-TAC-CTA-GCA-CAA-TGA-GGT-GGT-CGA-C-5'
                      M   D   R   V   T   P   P   A
```

FIG. 11-1

| ATOM | 1 | N | ASP A | 1 | 0.925 | 25.381 | 22.291 | 1.00 | 48.91 |
| --- | --- | --- | --- | --- | --- | --- | --- | --- | --- |
| ATOM | 2 | CA | ASP A | 1 | 0.839 | 25.292 | 20.834 | 1.00 | 45.75 |
| ATOM | 3 | C | ASP A | 1 | 0.290 | 24.001 | 20.273 | 1.00 | 44.80 |
| ATOM | 4 | O | ASP A | 1 | 0.914 | 23.123 | 19.714 | 1.00 | 45.35 |
| ATOM | 5 | CB | ASP A | 1 | 2.107 | 25.880 | 20.322 | 1.00 | 48.72 |
| ATOM | 6 | CG | ASP A | 1 | 1.941 | 27.315 | 20.793 | 1.00 | 52.66 |
| ATOM | 7 | OD1 | ASP A | 1 | 2.803 | 27.804 | 21.515 | 1.00 | 56.58 |
| ATOM | 8 | OD2 | ASP A | 1 | 0.873 | 27.891 | 20.564 | 1.00 | 52.45 |
| ATOM | 9 | N | SER A | 2 | -1.040 | 23.906 | 20.513 | 1.00 | 42.16 |
| ATOM | 10 | CA | SER A | 2 | -1.798 | 22.777 | 19.964 | 1.00 | 37.13 |
| ATOM | 11 | C | SER A | 2 | -1.778 | 22.692 | 18.455 | 1.00 | 36.45 |
| ATOM | 12 | O | SER A | 2 | -1.734 | 21.620 | 17.860 | 1.00 | 34.97 |
| ATOM | 13 | CB | SER A | 2 | -3.261 | 22.900 | 20.325 | 1.00 | 32.91 |
| ATOM | 14 | OG | SER A | 2 | -3.404 | 22.719 | 21.723 | 1.00 | 38.53 |
| ATOM | 15 | N | ASP A | 3 | -1.797 | 23.931 | 17.902 | 1.00 | 36.11 |
| ATOM | 16 | CA | ASP A | 3 | -1.732 | 24.122 | 16.447 | 1.00 | 35.01 |
| ATOM | 17 | C | ASP A | 3 | -0.336 | 24.144 | 15.826 | 1.00 | 32.91 |
| ATOM | 18 | O | ASP A | 3 | -0.088 | 24.429 | 14.652 | 1.00 | 32.22 |
| ATOM | 19 | CB | ASP A | 3 | -2.608 | 25.307 | 16.038 | 1.00 | 37.26 |
| ATOM | 20 | CG | ASP A | 3 | -3.947 | 24.806 | 15.507 | 1.00 | 41.66 |
| ATOM | 21 | OD1 | ASP A | 3 | -4.707 | 25.629 | 15.017 | 1.00 | 46.20 |
| ATOM | 22 | OD2 | ASP A | 3 | -4.246 | 23.609 | 15.576 | 1.00 | 42.11 |
| ATOM | 23 | N | ASP A | 4 | 0.580 | 23.737 | 16.694 | 1.00 | 29.74 |
| ATOM | 24 | CA | ASP A | 4 | 1.810 | 23.228 | 16.162 | 1.00 | 28.30 |
| ATOM | 25 | C | ASP A | 4 | 1.713 | 22.048 | 15.203 | 1.00 | 30.04 |
| ATOM | 26 | O | ASP A | 4 | 1.083 | 21.006 | 15.414 | 1.00 | 27.62 |
| ATOM | 27 | CB | ASP A | 4 | 2.768 | 22.967 | 17.297 | 1.00 | 28.96 |
| ATOM | 28 | CG | ASP A | 4 | 3.356 | 24.281 | 17.801 | 1.00 | 28.74 |
| ATOM | 29 | OD1 | ASP A | 4 | 4.230 | 24.239 | 18.661 | 1.00 | 31.05 |
| ATOM | 30 | OD2 | ASP A | 4 | 2.959 | 25.343 | 17.342 | 1.00 | 28.11 |
| ATOM | 31 | N | ARG A | 5 | 2.392 | 22.346 | 14.049 | 1.00 | 30.67 |
| ATOM | 32 | CA | ARG A | 5 | 2.674 | 21.343 | 13.026 | 1.00 | 27.80 |
| ATOM | 33 | C | ARG A | 5 | 3.560 | 20.221 | 13.575 | 1.00 | 29.88 |
| ATOM | 34 | O | ARG A | 5 | 4.617 | 20.417 | 14.204 | 1.00 | 27.26 |
| ATOM | 35 | CB | ARG A | 5 | 3.332 | 21.968 | 11.789 | 1.00 | 27.81 |
| ATOM | 36 | CG | ARG A | 5 | 3.862 | 20.939 | 10.740 | 1.00 | 25.08 |
| ATOM | 37 | CD | ARG A | 5 | 5.078 | 21.450 | 9.923 | 1.00 | 27.09 |
| ATOM | 38 | NE | ARG A | 5 | 6.367 | 21.414 | 10.638 | 1.00 | 19.74 |
| ATOM | 39 | CZ | ARG A | 5 | 7.104 | 20.316 | 10.627 | 1.00 | 15.41 |
| ATOM | 40 | NH1 | ARG A | 5 | 8.213 | 20.241 | 11.328 | 1.00 | 18.71 |
| ATOM | 41 | NH2 | ARG A | 5 | 6.718 | 19.289 | 9.926 | 1.00 | 15.93 |
| ATOM | 42 | N | VAL A | 6 | 3.065 | 19.006 | 13.261 | 1.00 | 26.97 |
| ATOM | 43 | CA | VAL A | 6 | 3.896 | 17.845 | 13.572 | 1.00 | 25.62 |
| ATOM | 44 | C | VAL A | 6 | 4.276 | 17.052 | 12.336 | 1.00 | 26.00 |
| ATOM | 45 | O | VAL A | 6 | 3.567 | 16.929 | 11.338 | 1.00 | 25.07 |
| ATOM | 46 | CB | VAL A | 6 | 3.302 | 16.963 | 14.727 | 1.00 | 27.92 |
| ATOM | 47 | CG1 | VAL A | 6 | 2.727 | 15.568 | 14.393 | 1.00 | 23.18 |
| ATOM | 48 | CG2 | VAL A | 6 | 2.305 | 17.806 | 15.545 | 1.00 | 28.06 |
| ATOM | 49 | N | THR A | 7 | 5.469 | 16.484 | 12.414 | 1.00 | 27.24 |
| ATOM | 50 | CA | THR A | 7 | 5.655 | 15.530 | 11.297 | 1.00 | 23.24 |
| ATOM | 51 | C | THR A | 7 | 5.075 | 14.114 | 11.549 | 1.00 | 23.77 |
| ATOM | 52 | O | THR A | 7 | 5.246 | 13.554 | 12.643 | 1.00 | 25.87 |
| ATOM | 53 | CB | THR A | 7 | 7.125 | 15.554 | 10.781 | 1.00 | 18.38 |
| ATOM | 54 | OG1 | THR A | 7 | 7.802 | 14.298 | 10.729 | 1.00 | 23.41 |

FIG. 11-2

| ATOM | 55 | CG2 | THR | A | 7 | 7.979 | 16.587 | 11.496 | 1.00 | 16.47 |
| --- | --- | --- | --- | --- | --- | --- | --- | --- | --- | --- |
| ATOM | 56 | N | PRO | A | 8 | 4.345 | 13.540 | 10.532 | 1.00 | 19.82 |
| ATOM | 57 | CA | PRO | A | 8 | 3.924 | 12.147 | 10.651 | 1.00 | 19.29 |
| ATOM | 58 | C | PRO | A | 8 | 5.106 | 11.219 | 10.929 | 1.00 | 26.68 |
| ATOM | 59 | O | PRO | A | 8 | 6.194 | 11.363 | 10.359 | 1.00 | 30.06 |
| ATOM | 60 | CB | PRO | A | 8 | 3.193 | 11.841 | 9.336 | 1.00 | 10.54 |
| ATOM | 61 | CG | PRO | A | 8 | 2.910 | 13.155 | 8.645 | 1.00 | 9.36 |
| ATOM | 62 | CD | PRO | A | 8 | 3.875 | 14.145 | 9.291 | 1.00 | 21.64 |
| ATOM | 63 | N | PRO | A | 9 | 4.832 | 10.275 | 11.886 | 1.00 | 30.34 |
| ATOM | 64 | CA | PRO | A | 9 | 5.724 | 9.125 | 12.160 | 1.00 | 25.28 |
| ATOM | 65 | C | PRO | A | 9 | 5.838 | 8.131 | 11.014 | 1.00 | 23.56 |
| ATOM | 66 | O | PRO | A | 9 | 5.004 | 7.994 | 10.137 | 1.00 | 24.12 |
| ATOM | 67 | CB | PRO | A | 9 | 5.031 | 8.447 | 13.369 | 1.00 | 25.38 |
| ATOM | 68 | CG | PRO | A | 9 | 3.547 | 8.815 | 13.234 | 1.00 | 25.69 |
| ATOM | 69 | CD | PRO | A | 9 | 3.631 | 10.257 | 12.741 | 1.00 | 28.21 |
| ATOM | 70 | N | ALA | A | 10 | 6.933 | 7.403 | 11.057 | 1.00 | 22.19 |
| ATOM | 71 | CA | ALA | A | 10 | 7.191 | 6.530 | 9.925 | 1.00 | 22.71 |
| ATOM | 72 | C | ALA | A | 10 | 6.327 | 5.340 | 9.709 | 1.00 | 23.23 |
| ATOM | 73 | O | ALA | A | 10 | 6.364 | 4.379 | 10.444 | 1.00 | 30.09 |
| ATOM | 74 | CB | ALA | ? | | 8.610 | 5.987 | 10.057 | 1.00 | 26.40 |
| ATOM | 75 | N | GLU | A | 11 | 5.638 | 5.319 | 8.606 | 1.00 | 30.46 |
| ATOM | 76 | CA | GLU | A | 11 | 5.071 | 3.991 | 8.292 | 1.00 | 30.22 |
| ATOM | 77 | C | GLU | A | 11 | 6.081 | 2.965 | 7.783 | 1.00 | 36.90 |
| ATOM | 78 | O | GLU | A | 11 | 6.890 | 3.220 | 6.885 | 1.00 | 41.15 |
| ATOM | 79 | CB | GLU | A | 11 | 3.900 | 4.107 | 7.316 | 1.00 | 23.88 |
| ATOM | 80 | CG | GLU | A | 11 | 2.951 | 5.286 | 7.700 | 1.00 | 26.60 |
| ATOM | 81 | CD | GLU | A | 11 | 2.013 | 5.039 | 8.874 | 1.00 | 25.94 |
| ATOM | 82 | OE1 | GLU | A | 11 | 1.618 | 5.987 | 9.516 | 1.00 | 31.83 |
| ATOM | 83 | OE2 | GLU | A | 11 | 1.615 | 3.910 | 9.161 | 1.00 | 31.55 |
| ATOM | 84 | N | PRO | A | 12 | 5.987 | 1.743 | 8.362 | 1.00 | 37.32 |
| ATOM | 85 | CA | PRO | A | 12 | 6.513 | 0.535 | 7.674 | 1.00 | 38.26 |
| ATOM | 86 | C | PRO | A | 12 | 6.258 | 0.410 | 6.149 | 1.00 | 38.17 |
| ATOM | 87 | O | PRO | A | 12 | 5.148 | 0.605 | 5.663 | 1.00 | 39.62 |
| ATOM | 88 | CB | PRO | A | 12 | 5.843 | -0.596 | 8.478 | 1.00 | 36.14 |
| ATOM | 89 | CG | PRO | A | 12 | 5.616 | -0.024 | 9.878 | 1.00 | 36.95 |
| ATOM | 90 | CD | PRO | A | 12 | 5.327 | 1.452 | 9.632 | 1.00 | 37.07 |
| ATOM | 91 | N | LEU | A | 13 | 7.297 | 0.099 | 5.368 | 1.00 | 37.85 |
| ATOM | 92 | CA | LEU | A | 13 | 6.866 | -0.016 | 3.955 | 1.00 | 42.59 |
| ATOM | 93 | C | LEU | A | 13 | 6.108 | -1.256 | 3.488 | 1.00 | 43.23 |
| ATOM | 94 | O | LEU | A | 13 | 5.578 | -1.336 | 2.376 | 1.00 | 43.35 |
| ATOM | 95 | CB | LEU | A | 13 | 7.959 | 0.362 | 2.927 | 1.00 | 46.72 |
| ATOM | 96 | CG | LEU | A | 13 | 8.970 | -0.711 | 2.473 | 1.00 | 43.32 |
| ATOM | 97 | CD1 | LEU | A | 13 | 10.395 | -0.140 | 2.466 | 1.00 | 45.26 |
| ATOM | 98 | CD2 | LEU | A | 13 | 8.594 | -1.401 | 1.156 | 1.00 | 42.64 |
| ATOM | 99 | N | ASP | A | 14 | 6.089 | -2.224 | 4.402 | 1.00 | 46.28 |
| ATOM | 100 | CA | ASP | A | 14 | 5.187 | -3.386 | 4.286 | 1.00 | 47.70 |
| ATOM | 101 | C | ASP | A | 14 | 3.657 | -3.166 | 4.425 | 1.00 | 44.10 |
| ATOM | 102 | O | ASP | A | 14 | 2.850 | -3.746 | 3.696 | 1.00 | 46.23 |
| ATOM | 103 | CB | ASP | A | 14 | 5.704 | -4.516 | 5.208 | 1.00 | 54.01 |
| ATOM | 104 | CG | ASP | A | 14 | 5.862 | -4.101 | 6.671 | 1.00 | 61.54 |
| ATOM | 105 | OD1 | ASP | A | 14 | 6.648 | -3.187 | 6.949 | 1.00 | 66.60 |
| ATOM | 106 | OD2 | ASP | A | 14 | 5.197 | -4.691 | 7.524 | 1.00 | 63.50 |
| ATOM | 107 | N | ARG | A | 15 | 3.269 | -2.270 | 5.345 | 1.00 | 38.95 |
| ATOM | 108 | CA | ARG | A | 15 | 1.809 | -2.145 | 5.510 | 1.00 | 37.97 |

FIG. 11-3

| ATOM | 109 | C   | ARG A | 15 | 0.995   | -1.334 | 4.520  | 1.00 | 36.60 |
|------|-----|-----|-------|----|---------|--------|--------|------|-------|
| ATOM | 110 | O   | ARG A | 15 | 1.225   | -0.162 | 4.249  | 1.00 | 35.92 |
| ATOM | 111 | CB  | ARG A | 15 | 1.459   | -1.669 | 6.897  | 1.00 | 37.88 |
| ATOM | 112 | CG  | ARG A | 15 | 2.011   | -0.277 | 7.122  | 1.00 | 35.04 |
| ATOM | 113 | CD  | ARG A | 15 | 2.063   | -0.007 | 8.600  | 1.00 | 38.32 |
| ATOM | 114 | NE  | ARG A | 15 | 0.752   | 0.099  | 9.216  | 1.00 | 37.09 |
| ATOM | 115 | CZ  | ARG A | 15 | 0.673   | 0.871  | 10.291 | 1.00 | 41.24 |
| ATOM | 116 | NH1 | ARG A | 15 | -0.531  | 1.108  | 10.796 | 1.00 | 42.76 |
| ATOM | 117 | NH2 | ARG A | 15 | 1.781   | 1.390  | 10.810 | 1.00 | 33.20 |
| ATOM | 118 | N   | MET A | 16 | -0.027  | -2.032 | 4.028  | 1.00 | 36.39 |
| ATOM | 119 | CA  | MET A | 16 | -1.027  | -1.333 | 3.214  | 1.00 | 35.74 |
| ATOM | 120 | C   | MET A | 16 | -1.753  | -0.156 | 3.893  | 1.00 | 33.12 |
| ATOM | 121 | O   | MET A | 16 | -1.834  | -0.048 | 5.118  | 1.00 | 36.90 |
| ATOM | 122 | CB  | MET A | 16 | -2.055  | -2.330 | 2.624  | 1.00 | 40.20 |
| ATOM | 123 | CG  | MET A | 16 | -1.437  | -3.618 | 2.083  | 1.00 | 46.70 |
| ATOM | 124 | SD  | MET A | 16 | -0.109  | -3.428 | 0.883  | 1.00 | 52.34 |
| ATOM | 125 | CE  | MET A | 16 | 0.505   | -5.104 | 1.089  | 1.00 | 49.81 |
| ATOM | 126 | N   | PRO A | 17 | -2.306  | 0.734  | 3.046  | 1.00 | 29.24 |
| ATOM | 127 | CA  | PRO A | 17 | -3.401  | 1.633  | 3.505  | 1.00 | 27.57 |
| ATOM | 128 | C   | PRO A | 17 | -4.849  | 1.069  | 3.634  | 1.00 | 27.61 |
| ATOM | 129 | O   | PRO A | 17 | -5.185  | 0.001  | 3.136  | 1.00 | 26.19 |
| ATOM | 130 | CB  | PRO A | 17 | -3.308  | 2.766  | 2.473  | 1.00 | 27.39 |
| ATOM | 131 | CG  | PRO A | 17 | -2.698  | 2.153  | 1.205  | 1.00 | 25.73 |
| ATOM | 132 | CD  | PRO A | 17 | -1.899  | 0.939  | 1.663  | 1.00 | 25.16 |
| ATOM | 133 | N   | ASP A | 18 | -5.708  | 1.853  | 4.305  | 1.00 | 27.37 |
| ATOM | 134 | CA  | ASP A | 18 | -7.087  | 1.388  | 4.473  | 1.00 | 26.75 |
| ATOM | 135 | C   | ASP A | 18 | -7.958  | 1.807  | 3.276  | 1.00 | 30.94 |
| ATOM | 136 | O   | ASP A | 18 | -7.714  | 2.775  | 2.562  | 1.00 | 31.32 |
| ATOM | 137 | CB  | ASP A | 18 | -7.741  | 1.961  | 5.757  | 1.00 | 21.69 |
| ATOM | 138 | CG  | ASP A | 18 | -7.046  | 1.749  | 7.117  | 1.00 | 23.26 |
| ATOM | 139 | OD1 | ASP A | 18 | -7.205  | 2.630  | 7.961  | 1.00 | 19.90 |
| ATOM | 140 | OD2 | ASP A | 18 | -6.382  | 0.739  | 7.398  | 1.00 | 26.12 |
| ATOM | 141 | N   | PRO A | 19 | -9.067  | 1.067  | 3.072  | 1.00 | 35.35 |
| ATOM | 142 | CA  | PRO A | 19 | -10.056 | 1.453  | 2.056  | 1.00 | 35.02 |
| ATOM | 143 | C   | PRO A | 19 | -10.623 | 2.868  | 2.106  | 1.00 | 33.75 |
| ATOM | 144 | O   | PRO A | 19 | -11.382 | 3.227  | 3.009  | 1.00 | 37.16 |
| ATOM | 145 | CB  | PRO A | 19 | -11.196 | 0.444  | 2.297  | 1.00 | 36.87 |
| ATOM | 146 | CG  | PRO A | 19 | -10.557 | -0.789 | 2.911  | 1.00 | 38.30 |
| ATOM | 147 | CD  | PRO A | 19 | -9.424  | -0.183 | 3.739  | 1.00 | 37.01 |
| ATOM | 148 | N   | TYR A | 20 | -10.372 | 3.587  | 1.001  | 1.00 | 30.34 |
| ATOM | 149 | CA  | TYR A | 20 | -11.201 | 4.729  | 0.563  | 1.00 | 24.21 |
| ATOM | 150 | C   | TYR A | 20 | -11.584 | 4.799  | -0.896 | 1.00 | 25.44 |
| ATOM | 151 | O   | TYR A | 20 | -11.034 | 4.151  | -1.775 | 1.00 | 22.19 |
| ATOM | 152 | CB  | TYR A | 20 | -10.694 | 6.105  | 0.984  | 1.00 | 21.49 |
| ATOM | 153 | CG  | TYR A | 20 | -9.342  | 6.551  | 0.483  | 1.00 | 24.00 |
| ATOM | 154 | CD1 | TYR A | 20 | -9.312  | 7.622  | -0.428 | 1.00 | 27.84 |
| ATOM | 155 | CD2 | TYR A | 20 | -8.146  | 5.945  | 0.953  | 1.00 | 25.70 |
| ATOM | 156 | CE1 | TYR A | 20 | -8.060  | 8.104  | -0.877 | 1.00 | 29.20 |
| ATOM | 157 | CE2 | TYR A | 20 | -6.898  | 6.395  | 0.462  | 1.00 | 27.32 |
| ATOM | 158 | CZ  | TYR A | 20 | -6.872  | 7.495  | -0.424 | 1.00 | 26.21 |
| ATOM | 159 | OH  | TYR A | 20 | -5.671  | 8.021  | -0.832 | 1.00 | 24.69 |
| ATOM | 160 | N   | ARG A | 21 | -12.626 | 5.605  | -1.099 | 1.00 | 25.50 |
| ATOM | 161 | CA  | ARG A | 21 | -13.271 | 5.577  | -2.417 | 1.00 | 26.08 |
| ATOM | 162 | C   | ARG A | 21 | -13.763 | 6.983  | -2.645 | 1.00 | 22.75 |

FIG. 11-4

| ATOM | 163 | O   | ARG A | 21 | -14.154 | 7.589  | -1.656 | 1.00 | 18.88 |
| ATOM | 164 | CB  | ARG A | 21 | -14.304 | 4.396  | -2.586 | 1.00 | 29.98 |
| ATOM | 165 | CG  | ARG A | 21 | -15.734 | 4.501  | -1.966 | 1.00 | 43.32 |
| ATOM | 166 | CD  | ARG A | 21 | -16.083 | 3.879  | -0.566 | 1.00 | 45.00 |
| ATOM | 167 | NE  | ARG A | 21 | -15.390 | 4.397  | 0.651  | 1.00 | 36.20 |
| ATOM | 168 | CZ  | ARG A | 21 | -14.578 | 3.627  | 1.374  | 1.00 | 28.05 |
| ATOM | 169 | NH1 | ARG A | 21 | -14.062 | 4.103  | 2.485  | 1.00 | 22.97 |
| ATOM | 170 | NH2 | ARG A | 21 | -14.272 | 2.412  | 0.962  | 1.00 | 21.36 |
| ATOM | 171 | N   | PRO A | 22 | -13.671 | 7.526  | -3.901 | 1.00 | 23.15 |
| ATOM | 172 | CA  | PRO A | 22 | -14.180 | 8.884  | -4.149 | 1.00 | 21.58 |
| ATOM | 173 | C   | PRO A | 22 | -15.688 | 9.078  | -3.991 | 1.00 | 23.40 |
| ATOM | 174 | O   | PRO A | 22 | -16.561 | 8.345  | -4.476 | 1.00 | 17.35 |
| ATOM | 175 | CB  | PRO A | 22 | -13.750 | 9.220  | -5.603 | 1.00 | 16.17 |
| ATOM | 176 | CG  | PRO A | 22 | -13.660 | 7.865  | -6.303 | 1.00 | 19.68 |
| ATOM | 177 | CD  | PRO A | 22 | -13.187 | 6.931  | -5.159 | 1.00 | 26.58 |
| ATOM | 178 | N   | SER A | 23 | -15.927 | 10.239 | -3.358 | 1.00 | 26.09 |
| ATOM | 179 | CA  | SER A | 23 | -17.279 | 10.795 | -3.432 | 1.00 | 24.61 |
| ATOM | 180 | C   | SER A | 23 | -17.416 | 12.061 | -4.222 | 1.00 | 22.52 |
| ATOM | 181 | O   | SER A | 23 | -16.728 | 13.018 | -3.952 | 1.00 | 24.86 |
| ATOM | 182 | CB  | SER A | 23 | -17.781 | 11.065 | -2.029 | 1.00 | 22.76 |
| ATOM | 183 | OG  | SER A | 23 | -19.153 | 11.420 | -2.139 | 1.00 | 26.45 |
| ATOM | 184 | N   | TYR A | 24 | -18.281 | 12.045 | -5.229 | 1.00 | 24.49 |
| ATOM | 185 | CA  | TYR A | 24 | -18.411 | 13.166 | -6.210 | 1.00 | 33.23 |
| ATOM | 186 | C   | TYR A | 24 | -17.190 | 13.868 | -6.803 | 1.00 | 34.36 |
| ATOM | 187 | O   | TYR A | 24 | -17.019 | 15.092 | -6.780 | 1.00 | 28.45 |
| ATOM | 188 | CB  | TYR A | 24 | -19.388 | 14.245 | -5.782 | 1.00 | 37.29 |
| ATOM | 189 | CG  | TYR A | 24 | -20.738 | 13.595 | -5.671 | 1.00 | 44.60 |
| ATOM | 190 | CD1 | TYR A | 24 | -21.376 | 13.055 | -6.826 | 1.00 | 46.69 |
| ATOM | 191 | CD2 | TYR A | 24 | -21.295 | 13.512 | -4.377 | 1.00 | 41.57 |
| ATOM | 192 | CE1 | TYR A | 24 | -22.610 | 12.386 | -6.650 | 1.00 | 48.48 |
| ATOM | 193 | CE2 | TYR A | 24 | -22.523 | 12.861 | -4.221 | 1.00 | 42.08 |
| ATOM | 194 | CZ  | TYR A | 24 | -23.184 | 12.330 | -5.349 | 1.00 | 47.26 |
| ATOM | 195 | OH  | TYR A | 24 | -24.437 | 11.771 | -5.147 | 1.00 | 51.50 |
| ATOM | 196 | N   | GLY A | 25 | -16.308 | 12.950 | -7.251 | 1.00 | 34.31 |
| ATOM | 197 | CA  | GLY A | 25 | -15.019 | 13.453 | -7.684 | 1.00 | 34.16 |
| ATOM | 198 | C   | GLY A | 25 | -13.863 | 13.589 | -6.704 | 1.00 | 31.34 |
| ATOM | 199 | O   | GLY A | 25 | -12.732 | 13.565 | -7.141 | 1.00 | 32.93 |
| ATOM | 200 | N   | ARG A | 26 | -14.113 | 13.724 | -5.408 | 1.00 | 28.99 |
| ATOM | 201 | CA  | ARG A | 26 | -12.966 | 13.704 | -4.476 | 1.00 | 26.60 |
| ATOM | 202 | C   | ARG A | 26 | -12.779 | 12.430 | -3.675 | 1.00 | 19.78 |
| ATOM | 203 | O   | ARG A | 26 | -13.722 | 11.791 | -3.260 | 1.00 | 21.06 |
| ATOM | 204 | CB  | ARG A | 26 | -13.092 | 14.717 | -3.364 | 1.00 | 34.28 |
| ATOM | 205 | CG  | ARG A | 26 | -12.879 | 16.209 | -3.554 | 1.00 | 42.98 |
| ATOM | 206 | CD  | ARG A | 26 | -13.448 | 16.861 | -2.282 | 1.00 | 46.02 |
| ATOM | 207 | NE  | ARG A | 26 | -13.214 | 18.300 | -2.196 | 1.00 | 52.70 |
| ATOM | 208 | CZ  | ARG A | 26 | -13.634 | 18.968 | -1.154 | 1.00 | 56.54 |
| ATOM | 209 | NH1 | ARG A | 26 | -14.517 | 18.445 | -0.364 | 1.00 | 61.18 |
| ATOM | 210 | NH2 | ARG A | 26 | -13.159 | 20.152 | -0.915 | 1.00 | 56.93 |
| ATOM | 211 | N   | ALA A | 27 | -11.552 | 12.135 | -3.387 | 1.00 | 13.05 |
| ATOM | 212 | CA  | ALA A | 27 | -11.320 | 11.153 | -2.341 | 1.00 | 12.57 |
| ATOM | 213 | C   | ALA A | 27 | -10.335 | 11.719 | -1.369 | 1.00 | 15.59 |
| ATOM | 214 | O   | ALA A | 27 | -9.730  | 12.739 | -1.652 | 1.00 | 18.99 |
| ATOM | 215 | CB  | ALA A | 27 | -10.777 | 9.805  | -2.845 | 1.00 | 13.33 |
| ATOM | 216 | N   | GLU A | 28 | -10.242 | 11.075 | -0.214 | 1.00 | 18.99 |

FIG. 11-5

| | | | | | | | | |
|---|---|---|---|---|---|---|---|---|
| ATOM | 217 | CA  | GLU A | 28 | -9.386  | 11.615 | 0.858  | 1.00 20.52 |
| ATOM | 218 | C   | GLU A | 28 | -9.141  | 10.604 | 1.936  | 1.00 16.92 |
| ATOM | 219 | O   | GLU A | 28 | -9.907  | 9.669  | 2.056  | 1.00 16.80 |
| ATOM | 220 | CB  | GLU A | 28 | -9.962  | 12.915 | 1.437  | 1.00 23.53 |
| ATOM | 221 | CG  | GLU A | 28 | -11.195 | 12.783 | 2.328  | 1.00 21.21 |
| ATOM | 222 | CD  | GLU A | 28 | -10.823 | 12.433 | 3.751  | 1.00 20.37 |
| ATOM | 223 | OE1 | GLU A | 28 | -11.692 | 12.036 | 4.495  | 1.00 17.91 |
| ATOM | 224 | OE2 | GLU A | 28 | -9.672  | 12.551 | 4.125  | 1.00 23.84 |
| ATOM | 225 | N   | THR A | 29 | -8.017  | 10.782 | 2.619  | 1.00 19.21 |
| ATOM | 226 | CA  | THR A | 29 | -7.597  | 9.966  | 3.785  | 1.00 19.93 |
| ATOM | 227 | C   | THR A | 29 | -6.584  | 10.677 | 4.653  | 1.00 17.11 |
| ATOM | 228 | O   | THR A | 29 | -5.906  | 11.589 | 4.203  | 1.00 19.32 |
| ATOM | 229 | CB  | THR A | 29 | -7.044  | 8.590  | 3.407  | 1.00 23.37 |
| ATOM | 230 | OG1 | THR A | 29 | -6.819  | 7.791  | 4.599  | 1.00 26.73 |
| ATOM | 231 | CG2 | THR A | 29 | -5.754  | 8.726  | 2.537  | 1.00 21.33 |
| ATOM | 232 | N   | VAL A | 30 | -6.477  | 10.291 | 5.940  | 1.00 19.71 |
| ATOM | 233 | CA  | VAL A | 30 | -5.574  | 11.082 | 6.841  | 1.00 18.08 |
| ATOM | 234 | C   | VAL A | 30 | -4.121  | 11.061 | 6.318  | 1.00 18.25 |
| ATOM | 235 | O   | VAL A | 30 | -3.812  | 10.081 | 5.659  | 1.00 19.98 |
| ATOM | 236 | CB  | VAL A | 30 | -5.445  | 10.510 | 8.271  | 1.00 13.11 |
| ATOM | 237 | CG1 | VAL A | 30 | -5.976  | 9.084  | 8.368  | 1.00 6.27 |
| ATOM | 238 | CG2 | VAL A | 30 | -5.635  | 11.562 | 9.350  | 1.00 8.00 |
| ATOM | 239 | N   | VAL A | 31 | -3.222  | 12.007 | 6.674  | 1.00 18.42 |
| ATOM | 240 | CA  | VAL A | 31 | -1.838  | 11.809 | 6.143  | 1.00 18.87 |
| ATOM | 241 | C   | VAL A | 31 | -1.167  | 10.469 | 6.359  | 1.00 23.59 |
| ATOM | 242 | O   | VAL A | 31 | -0.341  | 10.016 | 5.580  | 1.00 25.59 |
| ATOM | 243 | CB  | VAL A | 31 | -0.757  | 12.610 | 6.717  | 1.00 10.83 |
| ATOM | 244 | CG1 | VAL A | 31 | -1.243  | 13.392 | 7.871  | 1.00 2.70 |
| ATOM | 245 | CG2 | VAL A | 31 | 0.051   | 13.213 | 5.577  | 1.00 12.78 |
| ATOM | 246 | N   | ASN A | 32 | -1.565  | 9.833  | 7.486  | 1.00 24.13 |
| ATOM | 247 | CA  | ASN A | 32 | -0.835  | 8.593  | 7.842  | 1.00 19.99 |
| ATOM | 248 | C   | ASN A | 32 | -1.034  | 7.510  | 6.819  | 1.00 20.73 |
| ATOM | 249 | O   | ASN A | 32 | -0.151  | 6.933  | 6.189  | 1.00 24.64 |
| ATOM | 250 | CB  | ASN A | 32 | -1.247  | 8.055  | 9.206  | 1.00 15.20 |
| ATOM | 251 | CG  | ASN A | 32 | -1.364  | 9.138  | 10.208 | 1.00 9.53 |
| ATOM | 252 | OD1 | ASN A | 32 | -0.458  | 9.584  | 10.877 | 1.00 17.95 |
| ATOM | 253 | ND2 | ASN A | 32 | -2.586  | 9.632  | 10.264 | 1.00 17.70 |
| ATOM | 254 | N   | ASN A | 33 | -2.360  | 7.359  | 6.614  | 1.00 17.16 |
| ATOM | 255 | CA  | ASN A | 33 | -2.854  | 6.481  | 5.571  | 1.00 17.87 |
| ATOM | 256 | C   | ASN A | 33 | -2.355  | 6.746  | 4.146  | 1.00 21.49 |
| ATOM | 257 | O   | ASN A | 33 | -2.092  | 5.824  | 3.383  | 1.00 21.26 |
| ATOM | 258 | CB  | ASN A | 33 | -4.377  | 6.391  | 5.618  | 1.00 15.57 |
| ATOM | 259 | CG  | ASN A | 33 | -4.772  | 5.118  | 4.929  | 1.00 16.12 |
| ATOM | 260 | OD1 | ASN A | 33 | -5.482  | 5.010  | 3.958  | 1.00 18.81 |
| ATOM | 261 | ND2 | ASN A | 33 | -4.190  | 4.075  | 5.477  | 1.00 19.15 |
| ATOM | 262 | N   | TYR A | 34 | -2.202  | 8.051  | 3.871  | 1.00 22.27 |
| ATOM | 263 | CA  | TYR A | 34 | -1.711  | 8.476  | 2.548  | 1.00 23.74 |
| ATOM | 264 | C   | TYR A | 34 | -0.269  | 8.047  | 2.353  | 1.00 25.87 |
| ATOM | 265 | O   | TYR A | 34 | 0.072   | 7.452  | 1.329  | 1.00 22.19 |
| ATOM | 266 | CB  | TYR A | 34 | -1.886  | 10.016 | 2.291  | 1.00 22.69 |
| ATOM | 267 | CG  | TYR A | 34 | -1.483  | 10.363 | 0.875  | 1.00 17.94 |
| ATOM | 268 | CD1 | TYR A | 34 | -2.356  | 9.889  | -0.132 | 1.00 17.78 |
| ATOM | 269 | CD2 | TYR A | 34 | -0.280  | 11.087 | 0.593  | 1.00 12.30 |
| ATOM | 270 | CE1 | TYR A | 34 | -1.979  | 10.066 | -1.462 | 1.00 14.95 |

FIG. 11-6

| | | | | | | | | | |
|---|---|---|---|---|---|---|---|---|---|
| ATOM | 271 | CE2 | TYR A | 34 | 0.084 | 11.283 | -0.761 | 1.00 | 4.20 |
| ATOM | 272 | CZ | TYR A | 34 | -0.782 | 10.756 | -1.757 | 1.00 | 13.34 |
| ATOM | 273 | OH | TYR A | 34 | -0.506 | 10.891 | -3.099 | 1.00 | 15.74 |
| ATOM | 274 | N | ILE A | 35 | 0.537 | 8.304 | 3.428 | 1.00 | 22.29 |
| ATOM | 275 | CA | ILE A | 35 | 1.895 | 7.731 | 3.431 | 1.00 | 23.39 |
| ATOM | 276 | C | ILE A | 35 | 2.014 | 6.246 | 3.122 | 1.00 | 22.60 |
| ATOM | 277 | O | ILE A | 35 | 2.777 | 5.820 | 2.265 | 1.00 | 22.84 |
| ATOM | 278 | CB | ILE A | 35 | 2.637 | 8.001 | 4.716 | 1.00 | 21.82 |
| ATOM | 279 | CG1 | ILE A | 35 | 2.698 | 9.522 | 4.977 | 1.00 | 23.99 |
| ATOM | 280 | CG2 | ILE A | 35 | 4.016 | 7.340 | 4.575 | 1.00 | 16.02 |
| ATOM | 281 | CD1 | ILE A | 35 | 3.355 | 9.953 | 6.304 | 1.00 | 19.57 |
| ATOM | 282 | N | ARG A | 36 | 1.167 | 5.475 | 3.806 | 1.00 | 22.24 |
| ATOM | 283 | CA | ARG A | 36 | 1.100 | 4.069 | 3.376 | 1.00 | 17.50 |
| ATOM | 284 | C | ARG A | 36 | 0.958 | 3.828 | 1.865 | 1.00 | 17.49 |
| ATOM | 285 | O | ARG A | 36 | 1.687 | 3.094 | 1.221 | 1.00 | 18.50 |
| ATOM | 286 | CB | ARG A | 36 | 0.006 | 3.335 | 4.176 | 1.00 | 16.39 |
| ATOM | 287 | CG | ARG A | 36 | 0.099 | 3.593 | 5.689 | 1.00 | 13.51 |
| ATOM | 288 | CD | ARG A | 36 | -1.042 | 2.976 | 6.507 | 1.00 | 9.36 |
| ATOM | 289 | NE | ARG A | 36 | -0.751 | 3.304 | 7.885 | 1.00 | 10.44 |
| ATOM | 290 | CZ | ARG A | 36 | -1.537 | 4.101 | 8.591 | 1.00 | 9.66 |
| ATOM | 291 | NH1 | ARG A | 36 | -1.008 | 4.876 | 9.469 | 1.00 | 7.55 |
| ATOM | 292 | NH2 | ARG A | 36 | -2.823 | 4.121 | 8.440 | 1.00 | 11.01 |
| ATOM | 293 | N | LYS A | 37 | -0.048 | 4.521 | 1.300 | 1.00 | 24.48 |
| ATOM | 294 | CA | LYS A | 37 | -0.398 | 4.437 | -0.132 | 1.00 | 24.84 |
| ATOM | 295 | C | LYS A | 37 | 0.735 | 4.901 | -1.046 | 1.00 | 28.80 |
| ATOM | 296 | O | LYS A | 37 | 1.247 | 4.202 | -1.919 | 1.00 | 33.10 |
| ATOM | 297 | CB | LYS A | 37 | -1.674 | 5.264 | -0.403 | 1.00 | 23.50 |
| ATOM | 298 | CG | LYS A | 37 | -2.144 | 5.230 | -1.874 | 1.00 | 22.13 |
| ATOM | 299 | CD | LYS A | 37 | -3.247 | 6.228 | -2.341 | 1.00 | 21.18 |
| ATOM | 300 | CE | LYS A | 37 | -3.550 | 6.084 | -3.852 | 1.00 | 18.65 |
| ATOM | 301 | NZ | LYS A | 37 | -4.768 | 6.775 | -4.290 | 1.00 | 19.96 |
| ATOM | 302 | N | TRP A | 38 | 1.178 | 6.133 | -0.755 | 1.00 | 26.91 |
| ATOM | 303 | CA | TRP A | 38 | 2.430 | 6.613 | -1.329 | 1.00 | 23.24 |
| ATOM | 304 | C | TRP A | 38 | 3.612 | 5.593 | -1.425 | 1.00 | 24.11 |
| ATOM | 305 | O | TRP A | 38 | 4.092 | 5.283 | -2.511 | 1.00 | 24.56 |
| ATOM | 306 | CB | TRP A | 38 | 2.678 | 7.912 | -0.649 | 1.00 | 16.28 |
| ATOM | 307 | CG | TRP A | 38 | 3.659 | 8.659 | -1.459 | 1.00 | 24.59 |
| ATOM | 308 | CD1 | TRP A | 38 | 3.419 | 9.714 | -2.356 | 1.00 | 25.99 |
| ATOM | 309 | CD2 | TRP A | 38 | 5.096 | 8.482 | -1.376 | 1.00 | 29.93 |
| ATOM | 310 | NE1 | TRP A | 38 | 4.620 | 10.214 | -2.801 | 1.00 | 24.95 |
| ATOM | 311 | CE2 | TRP A | 38 | 5.675 | 9.505 | -2.213 | 1.00 | 26.89 |
| ATOM | 312 | CE3 | TRP A | 38 | 5.930 | 7.554 | -0.660 | 1.00 | 26.74 |
| ATOM | 313 | CZ2 | TRP A | 38 | 7.093 | 9.613 | -2.282 | 1.00 | 30.67 |
| ATOM | 314 | CZ3 | TRP A | 38 | 7.335 | 7.669 | -0.755 | 1.00 | 26.83 |
| ATOM | 315 | CH2 | TRP A | 38 | 7.909 | 8.700 | -1.553 | 1.00 | 27.78 |
| ATOM | 316 | N | GLN A | 39 | 3.961 | 4.990 | -0.272 | 1.00 | 23.15 |
| ATOM | 317 | CA | GLN A | 39 | 4.950 | 3.897 | -0.283 | 1.00 | 20.68 |
| ATOM | 318 | C | GLN A | 39 | 4.614 | 2.673 | -1.135 | 1.00 | 24.16 |
| ATOM | 319 | O | GLN A | 39 | 5.448 | 1.949 | -1.653 | 1.00 | 28.02 |
| ATOM | 320 | CB | GLN A | 39 | 5.365 | 3.440 | 1.127 | 1.00 | 13.97 |
| ATOM | 321 | CG | GLN A | 39 | 5.795 | 4.591 | 2.031 | 1.00 | 8.61 |
| ATOM | 322 | CD | GLN A | 39 | 6.083 | 4.167 | 3.457 | 1.00 | 13.91 |
| ATOM | 323 | OE1 | GLN A | 39 | 6.756 | 4.867 | 4.215 | 1.00 | 11.75 |
| ATOM | 324 | NE2 | GLN A | 39 | 5.518 | 3.032 | 3.868 | 1.00 | 11.92 |

FIG. 11-7

| | | | | | | | | | |
|---|---|---|---|---|---|---|---|---|---|
| ATOM | 325 | N | GLN A | 40 | 3.327 | 2.447 | -1.309 | 1.00 | 25.14 |
| ATOM | 326 | CA | GLN A | 40 | 3.058 | 1.325 | -2.187 | 1.00 | 22.22 |
| ATOM | 327 | C | GLN A | 40 | 3.094 | 1.583 | -3.676 | 1.00 | 23.33 |
| ATOM | 328 | O | GLN A | 40 | 3.321 | 0.677 | -4.461 | 1.00 | 23.63 |
| ATOM | 329 | CB | GLN A | 40 | 1.713 | 0.693 | -1.855 | 1.00 | 24.06 |
| ATOM | 330 | CG | GLN A | 40 | 1.434 | 0.260 | -0.399 | 1.00 | 21.84 |
| ATOM | 331 | CD | GLN A | 40 | 2.570 | -0.543 | 0.234 | 1.00 | 18.45 |
| ATOM | 332 | OE1 | GLN A | 40 | 3.055 | -1.554 | -0.235 | 1.00 | 17.86 |
| ATOM | 333 | NE2 | GLN A | 40 | 3.073 | -0.028 | 1.344 | 1.00 | 25.91 |
| ATOM | 334 | N | VAL A | 41 | 2.784 | 2.843 | -4.034 | 1.00 | 23.99 |
| ATOM | 335 | CA | VAL A | 41 | 2.527 | 3.081 | -5.472 | 1.00 | 22.90 |
| ATOM | 336 | C | VAL A | 41 | 3.357 | 4.185 | -6.163 | 1.00 | 23.57 |
| ATOM | 337 | O | VAL A | 41 | 3.656 | 4.165 | -7.344 | 1.00 | 26.09 |
| ATOM | 338 | CB | VAL A | 41 | 1.033 | 3.348 | -5.764 | 1.00 | 22.02 |
| ATOM | 339 | CG1 | VAL A | 41 | 0.418 | 4.281 | -4.767 | 1.00 | 19.46 |
| ATOM | 340 | CG2 | VAL A | 41 | 0.156 | 2.110 | -5.881 | 1.00 | 26.58 |
| ATOM | 341 | N | TYR A | 42 | 3.711 | 5.196 | -5.369 | 1.00 | 24.01 |
| ATOM | 342 | CA | TYR A | 42 | 4.446 | 6.312 | -5.923 | 1.00 | 22.22 |
| ATOM | 343 | C | TYR A | 42 | 5.930 | 6.297 | -5.528 | 1.00 | 28.99 |
| ATOM | 344 | O | TYR A | 42 | 6.703 | 7.158 | -5.933 | 1.00 | 36.69 |
| ATOM | 345 | CB | TYR A | 42 | 3.761 | 7.624 | -5.524 | 1.00 | 19.83 |
| ATOM | 346 | CG | TYR A | 42 | 2.252 | 7.652 | -5.788 | 1.00 | 16.55 |
| ATOM | 347 | CD1 | TYR A | 42 | 1.339 | 8.103 | -4.795 | 1.00 | 12.49 |
| ATOM | 348 | CD2 | TYR A | 42 | 1.778 | 7.236 | -7.044 | 1.00 | 18.48 |
| ATOM | 349 | CE1 | TYR A | 42 | -0.060 | 8.026 | -5.039 | 1.00 | 9.62 |
| ATOM | 350 | CE2 | TYR A | 42 | 0.389 | 7.181 | -7.303 | 1.00 | 23.50 |
| ATOM | 351 | CZ | TYR A | 42 | -0.538 | 7.516 | -6.273 | 1.00 | 21.81 |
| ATOM | 352 | OH | TYR A | 42 | -1.906 | 7.275 | -6.485 | 1.00 | 19.39 |
| ATOM | 353 | N | SER A | 43 | 6.366 | 5.286 | -4.718 | 1.00 | 25.51 |
| ATOM | 354 | CA | SER A | 43 | 7.682 | 5.473 | -4.051 | 1.00 | 21.55 |
| ATOM | 355 | C | SER A | 43 | 8.980 | 4.998 | -4.690 | 1.00 | 20.99 |
| ATOM | 356 | O | SER A | 43 | 10.097 | 5.099 | -4.189 | 1.00 | 15.58 |
| ATOM | 357 | CB | SER A | 43 | 7.690 | 4.806 | -2.712 | 1.00 | 19.32 |
| ATOM | 358 | OG | SER A | 43 | 7.733 | 3.377 | -2.840 | 1.00 | 15.79 |
| ATOM | 359 | N | HIS A | 44 | 8.757 | 4.391 | -5.830 | 1.00 | 22.74 |
| ATOM | 360 | CA | HIS A | 44 | 9.868 | 3.707 | -6.452 | 1.00 | 27.73 |
| ATOM | 361 | C | HIS A | 44 | 11.035 | 4.630 | -6.921 | 1.00 | 34.49 |
| ATOM | 362 | O | HIS A | 44 | 10.849 | 5.683 | -7.532 | 1.00 | 35.88 |
| ATOM | 363 | CB | HIS A | 44 | 9.297 | 2.867 | -7.577 | 1.00 | 27.02 |
| ATOM | 364 | CG | HIS A | 44 | 8.039 | 2.103 | -7.200 | 1.00 | 30.47 |
| ATOM | 365 | ND1 | HIS A | 44 | 7.930 | 0.756 | -7.181 | 1.00 | 31.99 |
| ATOM | 366 | CD2 | HIS A | 44 | 6.766 | 2.600 | -6.960 | 1.00 | 32.07 |
| ATOM | 367 | CE1 | HIS A | 44 | 6.625 | 0.397 | -6.955 | 1.00 | 33.45 |
| ATOM | 368 | NE2 | HIS A | 44 | 5.919 | 1.550 | -6.819 | 1.00 | 36.80 |
| ATOM | 369 | N | ARG A | 45 | 12.251 | 4.186 | -6.585 | 1.00 | 38.12 |
| ATOM | 370 | CA | ARG A | 45 | 13.416 | 4.618 | -7.382 | 1.00 | 40.54 |
| ATOM | 371 | C | ARG A | 45 | 13.988 | 3.389 | -8.104 | 1.00 | 42.24 |
| ATOM | 372 | O | ARG A | 45 | 14.328 | 2.365 | -7.521 | 1.00 | 41.17 |
| ATOM | 373 | CB | ARG A | 45 | 14.420 | 5.398 | -6.503 | 1.00 | 42.17 |
| ATOM | 374 | CG | ARG A | 45 | 13.870 | 6.797 | -6.096 | 1.00 | 45.79 |
| ATOM | 375 | CD | ARG A | 45 | 13.799 | 7.178 | -4.586 | 1.00 | 51.98 |
| ATOM | 376 | NE | ARG A | 45 | 12.796 | 8.238 | -4.347 | 1.00 | 53.06 |
| ATOM | 377 | CZ | ARG A | 45 | 11.596 | 7.996 | -3.778 | 1.00 | 48.25 |
| ATOM | 378 | NH1 | ARG A | 45 | 11.398 | 7.057 | -2.876 | 1.00 | 36.56 |

FIG. 11-8

| | | | | | | | | | |
|---|---|---|---|---|---|---|---|---|---|
| ATOM | 379 | NH2 | ARG A | 45 | 10.593 | 8.758 | -4.164 | 1.00 | 49.98 |
| ATOM | 380 | N | ASP A | 46 | 13.887 | 3.460 | -9.428 | 1.00 | 43.73 |
| ATOM | 381 | CA | ASP A | 46 | 14.247 | 2.270 | -10.238 | 1.00 | 47.06 |
| ATOM | 382 | C | ASP A | 46 | 13.441 | 0.998 | -10.061 | 1.00 | 46.66 |
| ATOM | 383 | O | ASP A | 46 | 13.873 | -0.135 | -9.825 | 1.00 | 48.31 |
| ATOM | 384 | CB | ASP A | 46 | 15.743 | 1.881 | -10.248 | 1.00 | 46.80 |
| ATOM | 385 | CG | ASP A | 46 | 16.546 | 3.007 | -10.851 | 1.00 | 43.37 |
| ATOM | 386 | OD1 | ASP A | 46 | 16.284 | 3.375 | -12.019 | 1.00 | 36.32 |
| ATOM | 387 | OD2 | ASP A | 46 | 17.413 | 3.513 | -10.119 | 1.00 | 45.83 |
| ATOM | 388 | N | GLY A | 47 | 12.143 | 1.253 | -10.192 | 1.00 | 44.67 |
| ATOM | 389 | CA | GLY A | 47 | 11.251 | 0.103 | -10.044 | 1.00 | 44.18 |
| ATOM | 390 | C | GLY A | 47 | 11.181 | -0.587 | -8.679 | 1.00 | 42.76 |
| ATOM | 391 | O | GLY A | 47 | 10.419 | -1.537 | -8.545 | 1.00 | 42.54 |
| ATOM | 392 | N | ARG A | 48 | 11.998 | -0.083 | -7.705 | 1.00 | 42.60 |
| ATOM | 393 | CA | ARG A | 48 | 12.137 | -0.692 | -6.369 | 1.00 | 44.15 |
| ATOM | 394 | C | ARG A | 48 | 11.630 | 0.175 | -5.191 | 1.00 | 42.54 |
| ATOM | 395 | O | ARG A | 48 | 12.129 | 1.269 | -4.920 | 1.00 | 41.57 |
| ATOM | 396 | CB | ARG A | 48 | 13.581 | -1.238 | -6.117 | 1.00 | 49.19 |
| ATOM | 397 | CG | ARG A | 48 | 14.221 | -2.152 | -7.221 | 1.00 | 55.99 |
| ATOM | 398 | CD | ARG A | 48 | 13.517 | -3.495 | -7.555 | 1.00 | 56.05 |
| ATOM | 399 | NE | ARG A | 48 | 13.338 | -3.730 | -8.998 | 1.00 | 51.07 |
| ATOM | 400 | CZ | ARG A | 48 | 12.274 | -4.375 | -9.500 | 1.00 | 54.19 |
| ATOM | 401 | NH1 | ARG A | 48 | 11.330 | -4.894 | -8.752 | 1.00 | 51.05 |
| ATOM | 402 | NH2 | ARG A | 48 | 12.137 | -4.490 | -10.793 | 1.00 | 59.29 |
| ATOM | 403 | N | LYS A | 49 | 10.532 | -0.337 | -4.566 | 1.00 | 39.53 |
| ATOM | 404 | CA | LYS A | 49 | 9.750 | 0.538 | -3.663 | 1.00 | 39.29 |
| ATOM | 405 | C | LYS A | 49 | 10.439 | 0.950 | -2.375 | 1.00 | 36.85 |
| ATOM | 406 | O | LYS A | 49 | 11.315 | 0.233 | -1.913 | 1.00 | 44.17 |
| ATOM | 407 | CB | LYS A | 49 | 8.263 | 0.053 | -3.441 | 1.00 | 40.93 |
| ATOM | 408 | CG | LYS A | 49 | 7.870 | -1.225 | -2.687 | 1.00 | 40.04 |
| ATOM | 409 | CD | LYS A | 49 | 6.444 | -1.584 | -3.114 | 1.00 | 45.31 |
| ATOM | 410 | CE | LYS A | 49 | 5.781 | -2.809 | -2.444 | 1.00 | 51.60 |
| ATOM | 411 | NZ | LYS A | 49 | 5.276 | -2.506 | -1.081 | 1.00 | 49.18 |
| ATOM | 412 | N | GLN A | 50 | 10.049 | 2.102 | -1.817 | 1.00 | 27.32 |
| ATOM | 413 | CA | GLN A | 50 | 10.735 | 2.455 | -0.574 | 1.00 | 29.17 |
| ATOM | 414 | C | GLN A | 50 | 9.975 | 3.391 | 0.319 | 1.00 | 30.65 |
| ATOM | 415 | O | GLN A | 50 | 9.006 | 4.003 | -0.082 | 1.00 | 31.74 |
| ATOM | 416 | CB | GLN A | 50 | 12.127 | 3.058 | -0.833 | 1.00 | 35.21 |
| ATOM | 417 | CG | GLN A | 50 | 12.155 | 3.910 | -2.117 | 1.00 | 41.46 |
| ATOM | 418 | CD | GLN A | 50 | 13.547 | 3.928 | -2.707 | 1.00 | 43.02 |
| ATOM | 419 | OE1 | GLN A | 50 | 14.239 | 4.934 | -2.568 | 1.00 | 41.03 |
| ATOM | 420 | NE2 | GLN A | 50 | 13.925 | 2.811 | -3.366 | 1.00 | 35.06 |
| ATOM | 421 | N | GLN A | 51 | 10.479 | 3.494 | 1.556 | 1.00 | 33.29 |
| ATOM | 422 | CA | GLN A | 51 | 9.902 | 4.367 | 2.579 | 1.00 | 30.63 |
| ATOM | 423 | C | GLN A | 51 | 10.047 | 5.852 | 2.328 | 1.00 | 36.17 |
| ATOM | 424 | O | GLN A | 51 | 11.031 | 6.347 | 1.772 | 1.00 | 38.28 |
| ATOM | 425 | CB | GLN A | 51 | 10.529 | 4.204 | 3.952 | 1.00 | 27.05 |
| ATOM | 426 | CG | GLN A | 51 | 10.222 | 2.990 | 4.762 | 1.00 | 29.14 |
| ATOM | 427 | CD | GLN A | 51 | 10.724 | 3.289 | 6.147 | 1.00 | 30.26 |
| ATOM | 428 | OE1 | GLN A | 51 | 11.908 | 3.358 | 6.420 | 1.00 | 31.57 |
| ATOM | 429 | NE2 | GLN A | 51 | 9.765 | 3.491 | 7.039 | 1.00 | 31.23 |
| ATOM | 430 | N | MET A | 52 | 8.998 | 6.546 | 2.853 | 1.00 | 37.44 |
| ATOM | 431 | CA | MET A | 52 | 9.107 | 7.987 | 3.005 | 1.00 | 31.49 |
| ATOM | 432 | C | MET A | 52 | 10.073 | 8.358 | 4.089 | 1.00 | 30.51 |

FIG. 11-9

| ATOM | 433 | O   | MET A | 52 | 9.932  | 8.071  | 5.274  | 1.00 | 33.96 |
|------|-----|-----|-------|----|--------|--------|--------|------|-------|
| ATOM | 434 | CB  | MET A | 52 | 7.733  | 8.626  | 3.158  | 1.00 | 28.44 |
| ATOM | 435 | CG  | MET A | 52 | 7.751  | 10.085 | 2.760  | 1.00 | 25.24 |
| ATOM | 436 | SD  | MET A | 52 | 6.162  | 10.921 | 2.692  | 1.00 | 22.95 |
| ATOM | 437 | CE  | MET A | 52 | 5.177  | 9.684  | 1.883  | 1.00 | 20.97 |
| ATOM | 438 | N   | THR A | 53 | 11.112 | 9.020  | 3.602  | 1.00 | 29.45 |
| ATOM | 439 | CA  | THR A | 53 | 12.058 | 9.635  | 4.536  | 1.00 | 31.64 |
| ATOM | 440 | C   | THR A | 53 | 11.412 | 10.466 | 5.636  | 1.00 | 30.70 |
| ATOM | 441 | O   | THR A | 53 | 10.376 | 11.068 | 5.454  | 1.00 | 27.13 |
| ATOM | 442 | CB  | THR A | 53 | 13.050 | 10.536 | 3.762  | 1.00 | 33.39 |
| ATOM | 443 | OG1 | THR A | 53 | 13.667 | 9.803  | 2.695  | 1.00 | 37.56 |
| ATOM | 444 | CG2 | THR A | 53 | 14.170 | 11.145 | 4.627  | 1.00 | 33.84 |
| ATOM | 445 | N   | GLU A | 54 | 12.089 | 10.531 | 6.769  | 1.00 | 33.11 |
| ATOM | 446 | CA  | GLU A | 54 | 11.845 | 11.636 | 7.696  | 1.00 | 31.84 |
| ATOM | 447 | C   | GLU A | 54 | 11.657 | 12.969 | 6.994  | 1.00 | 30.52 |
| ATOM | 448 | O   | GLU A | 54 | 10.544 | 13.432 | 6.880  | 1.00 | 28.53 |
| ATOM | 449 | CB  | GLU A | 54 | 12.970 | 11.638 | 8.726  | 1.00 | 33.76 |
| ATOM | 450 | CG  | GLU A | 54 | 12.534 | 12.208 | 10.068 | 1.00 | 46.08 |
| ATOM | 451 | CD  | GLU A | 54 | 11.564 | 11.285 | 10.838 | 1.00 | 57.29 |
| ATOM | 452 | OE1 | GLU A | 54 | 11.004 | 11.765 | 11.832 | 1.00 | 62.50 |
| ATOM | 453 | OE2 | GLU A | 54 | 11.379 | 10.094 | 10.501 | 1.00 | 57.76 |
| ATOM | 454 | N   | GLU A | 55 | 12.743 | 13.445 | 6.349  | 1.00 | 30.03 |
| ATOM | 455 | CA  | GLU A | 55 | 12.653 | 14.697 | 5.555  | 1.00 | 26.78 |
| ATOM | 456 | C   | GLU A | 55 | 11.501 | 14.795 | 4.580  | 1.00 | 23.88 |
| ATOM | 457 | O   | GLU A | 55 | 10.628 | 15.645 | 4.592  | 1.00 | 22.44 |
| ATOM | 458 | CB  | GLU A | 55 | 13.953 | 14.981 | 4.815  | 1.00 | 29.90 |
| ATOM | 459 | CG  | GLU A | 55 | 14.084 | 16.444 | 4.364  | 1.00 | 41.71 |
| ATOM | 460 | CD  | GLU A | 55 | 15.493 | 16.868 | 3.896  | 1.00 | 41.01 |
| ATOM | 461 | OE1 | GLU A | 55 | 15.962 | 16.364 | 2.877  | 1.00 | 37.24 |
| ATOM | 462 | OE2 | GLU A | 55 | 16.090 | 17.743 | 4.549  | 1.00 | 38.48 |
| ATOM | 463 | N   | GLN A | 56 | 11.431 | 13.789 | 3.750  | 1.00 | 21.70 |
| ATOM | 464 | CA  | GLN A | 56 | 10.172 | 13.737 | 2.997  | 1.00 | 19.29 |
| ATOM | 465 | C   | GLN A | 56 | 8.785  | 13.820 | 3.771  | 1.00 | 22.59 |
| ATOM | 466 | O   | GLN A | 56 | 7.838  | 14.523 | 3.456  | 1.00 | 24.75 |
| ATOM | 467 | CB  | GLN A | 56 | 10.381 | 12.482 | 2.178  | 1.00 | 17.64 |
| ATOM | 468 | CG  | GLN A | 56 | 10.349 | 12.607 | 0.680  | 1.00 | 14.89 |
| ATOM | 469 | CD  | GLN A | 56 | 10.650 | 11.224 | 0.176  | 1.00 | 12.59 |
| ATOM | 470 | OE1 | GLN A | 56 | 11.183 | 10.342 | 0.786  | 1.00 | 21.90 |
| ATOM | 471 | NE2 | GLN A | 56 | 10.274 | 10.982 | -1.014 | 1.00 | 24.33 |
| ATOM | 472 | N   | ARG A | 57 | 8.677  | 13.071 | 4.850  | 1.00 | 25.95 |
| ATOM | 473 | CA  | ARG A | 57 | 7.507  | 13.195 | 5.711  | 1.00 | 28.86 |
| ATOM | 474 | C   | ARG A | 57 | 7.243  | 14.589 | 6.304  | 1.00 | 29.90 |
| ATOM | 475 | O   | ARG A | 57 | 6.108  | 15.051 | 6.355  | 1.00 | 32.86 |
| ATOM | 476 | CB  | ARG A | 57 | 7.571  | 12.149 | 6.848  | 1.00 | 31.92 |
| ATOM | 477 | CG  | ARG A | 57 | 6.823  | 10.850 | 6.549  | 1.00 | 34.92 |
| ATOM | 478 | CD  | ARG A | 57 | 6.765  | 9.811  | 7.688  | 1.00 | 34.44 |
| ATOM | 479 | NE  | ARG A | 57 | 7.967  | 8.992  | 7.820  | 1.00 | 31.24 |
| ATOM | 480 | CZ  | ARG A | 57 | 8.922  | 9.272  | 8.691  | 1.00 | 30.81 |
| ATOM | 481 | NH1 | ARG A | 57 | 8.776  | 10.196 | 9.595  | 1.00 | 30.79 |
| ATOM | 482 | NH2 | ARG A | 57 | 10.046 | 8.614  | 8.642  | 1.00 | 34.72 |
| ATOM | 483 | N   | GLU A | 58 | 8.337  | 15.259 | 6.742  | 1.00 | 29.08 |
| ATOM | 484 | CA  | GLU A | 58 | 8.332  | 16.654 | 7.275  | 1.00 | 26.33 |
| ATOM | 485 | C   | GLU A | 58 | 7.813  | 17.680 | 6.237  | 1.00 | 25.65 |
| ATOM | 486 | O   | GLU A | 58 | 7.005  | 18.563 | 6.467  | 1.00 | 22.45 |

FIG. 11-10

| | | | | | | | | | |
|---|---|---|---|---|---|---|---|---|---|
| ATOM | 487 | CB | GLU | A | 58 | 9.744 | 17.038 | 7.775 | 1.00 27.62 |
| ATOM | 488 | CG | GLU | A | 58 | 10.510 | 15.914 | 8.567 | 1.00 36.56 |
| ATOM | 489 | CD | GLU | A | 58 | 11.988 | 16.231 | 8.948 | 1.00 41.95 |
| ATOM | 490 | OE1 | GLU | A | 58 | 12.339 | 17.420 | 8.960 | 1.00 39.06 |
| ATOM | 491 | OE2 | GLU | A | 58 | 12.783 | 15.302 | 9.233 | 1.00 41.06 |
| ATOM | 492 | N | TRP | A | 59 | 8.250 | 17.470 | 5.000 | 1.00 22.95 |
| ATOM | 493 | CA | TRP | A | 59 | 7.751 | 18.328 | 3.924 | 1.00 21.72 |
| ATOM | 494 | C | TRP | A | 59 | 6.270 | 18.150 | 3.679 | 1.00 21.49 |
| ATOM | 495 | O | TRP | A | 59 | 5.461 | 19.085 | 3.600 | 1.00 25.63 |
| ATOM | 496 | CB | TRP | A | 59 | 8.467 | 18.041 | 2.592 | 1.00 20.73 |
| ATOM | 497 | CG | TRP | A | 59 | 9.955 | 18.368 | 2.547 | 1.00 20.92 |
| ATOM | 498 | CD1 | TRP | A | 59 | 10.712 | 19.100 | 3.479 | 1.00 15.81 |
| ATOM | 499 | CD2 | TRP | A | 59 | 10.898 | 17.938 | 1.520 | 1.00 22.58 |
| ATOM | 500 | NE1 | TRP | A | 59 | 12.018 | 19.137 | 3.109 | 1.00 23.40 |
| ATOM | 501 | CE2 | TRP | A | 59 | 12.185 | 18.431 | 1.912 | 1.00 24.20 |
| ATOM | 502 | CE3 | TRP | A | 59 | 10.762 | 17.170 | 0.336 | 1.00 19.00 |
| ATOM | 503 | CZ2 | TRP | A | 59 | 13.310 | 18.146 | 1.119 | 1.00 22.19 |
| ATOM | 504 | CZ3 | TRP | A | 59 | 11.890 | 16.888 | -0.432 | 1.00 15.93 |
| ATOM | 505 | CH2 | TRP | A | 59 | 13.149 | 17.375 | -0.043 | 1.00 21.15 |
| ATOM | 506 | N | LEU | A | 60 | 5.937 | 16.845 | 3.614 | 1.00 17.12 |
| ATOM | 507 | CA | LEU | A | 60 | 4.543 | 16.467 | 3.351 | 1.00 14.22 |
| ATOM | 508 | C | LEU | A | 60 | 3.547 | 17.247 | 4.221 | 1.00 16.71 |
| ATOM | 509 | O | LEU | A | 60 | 2.565 | 17.840 | 3.806 | 1.00 15.93 |
| ATOM | 510 | CB | LEU | A | 60 | 4.441 | 14.958 | 3.533 | 1.00 6.31 |
| ATOM | 511 | CG | LEU | A | 60 | 3.068 | 14.335 | 3.205 | 1.00 7.85 |
| ATOM | 512 | CD1 | LEU | A | 60 | 3.149 | 12.833 | 3.225 | 1.00 4.47 |
| ATOM | 513 | CD2 | LEU | A | 60 | 2.389 | 14.807 | 1.908 | 1.00 16.63 |
| ATOM | 514 | N | SER | A | 61 | 3.970 | 17.275 | 5.494 | 1.00 20.78 |
| ATOM | 515 | CA | SER | A | 61 | 3.227 | 17.935 | 6.571 | 1.00 23.09 |
| ATOM | 516 | C | SER | A | 61 | 2.917 | 19.421 | 6.528 | 1.00 21.99 |
| ATOM | 517 | O | SER | A | 61 | 2.249 | 19.945 | 7.407 | 1.00 23.39 |
| ATOM | 518 | CB | SER | A | 61 | 3.875 | 17.628 | 7.926 | 1.00 24.28 |
| ATOM | 519 | OG | SER | A | 61 | 5.073 | 18.389 | 8.158 | 1.00 22.43 |
| ATOM | 520 | N | TYR | A | 62 | 3.431 | 20.113 | 5.508 | 1.00 22.68 |
| ATOM | 521 | CA | TYR | A | 62 | 3.090 | 21.535 | 5.414 | 1.00 18.11 |
| ATOM | 522 | C | TYR | A | 62 | 1.759 | 21.780 | 4.734 | 1.00 20.24 |
| ATOM | 523 | O | TYR | A | 62 | 1.305 | 22.901 | 4.599 | 1.00 21.74 |
| ATOM | 524 | CB | TYR | A | 62 | 4.123 | 22.331 | 4.626 | 1.00 17.85 |
| ATOM | 525 | CG | TYR | A | 62 | 5.383 | 22.579 | 5.407 | 1.00 14.95 |
| ATOM | 526 | CD1 | TYR | A | 62 | 5.671 | 23.880 | 5.901 | 1.00 19.36 |
| ATOM | 527 | CD2 | TYR | A | 62 | 6.244 | 21.516 | 5.645 | 1.00 9.61 |
| ATOM | 528 | CE1 | TYR | A | 62 | 6.779 | 24.075 | 6.766 | 1.00 18.38 |
| ATOM | 529 | CE2 | TYR | A | 62 | 7.316 | 21.712 | 6.545 | 1.00 8.24 |
| ATOM | 530 | CZ | TYR | A | 62 | 7.543 | 22.955 | 7.163 | 1.00 13.90 |
| ATOM | 531 | OH | TYR | A | 62 | 8.502 | 23.051 | 8.185 | 1.00 14.54 |
| ATOM | 532 | N | GLY | A | 63 | 1.105 | 20.700 | 4.290 | 1.00 22.44 |
| ATOM | 533 | CA | GLY | A | 63 | -0.248 | 20.962 | 3.793 | 1.00 20.61 |
| ATOM | 534 | C | GLY | A | 63 | -0.500 | 20.928 | 2.303 | 1.00 22.92 |
| ATOM | 535 | O | GLY | A | 63 | 0.024 | 20.040 | 1.651 | 1.00 28.43 |
| ATOM | 536 | N | CYS | A | 64 | -1.291 | 21.929 | 1.787 | 1.00 23.61 |
| ATOM | 537 | CA | CYS | A | 64 | -1.627 | 22.138 | 0.339 | 1.00 23.18 |
| ATOM | 538 | C | CYS | A | 64 | -0.370 | 21.714 | -0.512 | 1.00 27.31 |
| ATOM | 539 | O | CYS | A | 64 | -0.336 | 20.824 | -1.356 | 1.00 27.51 |
| ATOM | 540 | CB | CYS | A | 64 | -2.047 | 23.654 | 0.150 | 1.00 13.91 |

FIG. 11-11

| ATOM | 541 | SG  | CYS A | 64 | -2.263 | 24.712 | 1.747  | 1.00 | 24.61 |
|------|-----|-----|-------|----|--------|--------|--------|------|-------|
| ATOM | 542 | N   | VAL A | 65 | 0.771  | 22.348 | -0.079 | 1.00 | 26.31 |
| ATOM | 543 | CA  | VAL A | 65 | 2.077  | 22.186 | -0.753 | 1.00 | 25.84 |
| ATOM | 544 | C   | VAL A | 65 | 2.812  | 20.859 | -0.676 | 1.00 | 25.81 |
| ATOM | 545 | O   | VAL A | 65 | 3.544  | 20.446 | -1.565 | 1.00 | 29.83 |
| ATOM | 546 | CB  | VAL A | 65 | 3.063  | 23.344 | -0.392 | 1.00 | 25.76 |
| ATOM | 547 | CG1 | VAL A | 65 | 4.274  | 23.446 | -1.358 | 1.00 | 22.10 |
| ATOM | 548 | CG2 | VAL A | 65 | 3.523  | 23.275 | 1.074  | 1.00 | 23.11 |
| ATOM | 549 | N   | GLY A | 66 | 2.655  | 20.210 | 0.456  | 1.00 | 25.94 |
| ATOM | 550 | CA  | GLY A | 66 | 3.619  | 19.154 | 0.782  | 1.00 | 21.35 |
| ATOM | 551 | C   | GLY A | 66 | 3.810  | 17.974 | -0.154 | 1.00 | 13.97 |
| ATOM | 552 | O   | GLY A | 66 | 4.847  | 17.347 | -0.104 | 1.00 | 12.69 |
| ATOM | 553 | N   | VAL A | 67 | 2.797  | 17.697 | -0.982 | 1.00 | 14.48 |
| ATOM | 554 | CA  | VAL A | 67 | 2.884  | 16.590 | -1.968 | 1.00 | 18.13 |
| ATOM | 555 | C   | VAL A | 67 | 3.520  | 16.951 | -3.343 | 1.00 | 18.29 |
| ATOM | 556 | O   | VAL A | 67 | 4.346  | 16.283 | -3.923 | 1.00 | 10.43 |
| ATOM | 557 | CB  | VAL A | 67 | 1.596  | 15.663 | -2.018 | 1.00 | 17.82 |
| ATOM | 558 | CG1 | VAL A | 67 | 1.104  | 15.120 | -3.382 | 1.00 | 11.58 |
| ATOM | 559 | CG2 | VAL A | 67 | 0.467  | 16.168 | -1.127 | 1.00 | 21.55 |
| ATOM | 560 | N   | THR A | 68 | 3.222  | 18.146 | -3.793 | 1.00 | 19.76 |
| ATOM | 561 | CA  | THR A | 68 | 4.212  | 18.723 | -4.711 | 1.00 | 19.97 |
| ATOM | 562 | C   | THR A | 68 | 5.693  | 18.801 | -4.254 | 1.00 | 17.63 |
| ATOM | 563 | O   | THR A | 68 | 6.547  | 18.130 | -4.785 | 1.00 | 20.80 |
| ATOM | 564 | CB  | THR A | 68 | 3.659  | 20.074 | -5.180 | 1.00 | 19.74 |
| ATOM | 565 | OG1 | THR A | 68 | 2.374  | 19.891 | -5.795 | 1.00 | 19.05 |
| ATOM | 566 | CG2 | THR A | 68 | 4.587  | 20.767 | -6.158 | 1.00 | 23.67 |
| ATOM | 567 | N   | TRP A | 69 | 6.044  | 19.540 | -3.229 | 1.00 | 15.19 |
| ATOM | 568 | CA  | TRP A | 69 | 7.403  | 19.304 | -2.652 | 1.00 | 13.68 |
| ATOM | 569 | C   | TRP A | 69 | 7.939  | 17.866 | -2.583 | 1.00 | 15.63 |
| ATOM | 570 | O   | TRP A | 69 | 8.860  | 17.565 | -3.301 | 1.00 | 20.24 |
| ATOM | 571 | CB  | TRP A | 69 | 7.392  | 19.867 | -1.270 | 1.00 | 14.71 |
| ATOM | 572 | CG  | TRP A | 69 | 8.707  | 20.340 | -0.698 | 1.00 | 18.11 |
| ATOM | 573 | CD1 | TRP A | 69 | 10.007 | 20.237 | -1.192 | 1.00 | 17.86 |
| ATOM | 574 | CD2 | TRP A | 69 | 8.819  | 21.002 | 0.585  | 1.00 | 15.59 |
| ATOM | 575 | NE1 | TRP A | 69 | 10.879 | 20.764 | -0.299 | 1.00 | 18.72 |
| ATOM | 576 | CE2 | TRP A | 69 | 10.195 | 21.232 | 0.815  | 1.00 | 10.21 |
| ATOM | 577 | CE3 | TRP A | 69 | 7.847  | 21.475 | 1.511  | 1.00 | 16.23 |
| ATOM | 578 | CZ2 | TRP A | 69 | 10.608 | 21.890 | 2.000  | 1.00 | 19.05 |
| ATOM | 579 | CZ3 | TRP A | 69 | 8.268  | 22.170 | 2.681  | 1.00 | 23.34 |
| ATOM | 580 | CH2 | TRP A | 69 | 9.656  | 22.361 | 2.941  | 1.00 | 21.38 |
| ATOM | 581 | N   | VAL A | 70 | 7.363  | 16.941 | -1.791 | 1.00 | 18.45 |
| ATOM | 582 | CA  | VAL A | 70 | 7.866  | 15.543 | -1.926 | 1.00 | 19.88 |
| ATOM | 583 | C   | VAL A | 70 | 8.000  | 14.929 | -3.336 | 1.00 | 22.35 |
| ATOM | 584 | O   | VAL A | 70 | 8.958  | 14.247 | -3.689 | 1.00 | 24.86 |
| ATOM | 585 | CB  | VAL A | 70 | 7.249  | 14.428 | -0.957 | 1.00 | 17.46 |
| ATOM | 586 | CG1 | VAL A | 70 | 6.040  | 13.668 | -1.427 | 1.00 | 18.87 |
| ATOM | 587 | CG2 | VAL A | 70 | 6.912  | 14.926 | 0.406  | 1.00 | 12.24 |
| ATOM | 588 | N   | ASN A | 71 | 6.950  | 15.162 | -4.122 | 1.00 | 24.19 |
| ATOM | 589 | CA  | ASN A | 71 | 6.872  | 14.454 | -5.407 | 1.00 | 21.71 |
| ATOM | 590 | C   | ASN A | 71 | 7.829  | 14.990 | -6.519 | 1.00 | 21.79 |
| ATOM | 591 | O   | ASN A | 71 | 8.383  | 14.271 | -7.355 | 1.00 | 22.42 |
| ATOM | 592 | CB  | ASN A | 71 | 5.403  | 14.455 | -5.825 | 1.00 | 19.44 |
| ATOM | 593 | CG  | ASN A | 71 | 4.678  | 13.225 | -5.329 | 1.00 | 20.20 |
| ATOM | 594 | OD1 | ASN A | 71 | 5.142  | 12.402 | -4.547 | 1.00 | 19.21 |

FIG. 11-12

| | | | | | | | | |
|---|---|---|---|---|---|---|---|---|
| ATOM | 595 | ND2 | ASN A | 71 | 3.511 | 13.055 | -5.942 | 1.00 13.50 |
| ATOM | 596 | N | SER A | 72 | 8.002 | 16.333 | -6.433 | 1.00 16.66 |
| ATOM | 597 | CA | SER A | 72 | 9.020 | 17.073 | -7.216 | 1.00 15.75 |
| ATOM | 598 | C | SER A | 72 | 10.420 | 17.199 | -6.675 | 1.00 18.33 |
| ATOM | 599 | O | SER A | 72 | 11.346 | 17.520 | -7.394 | 1.00 20.81 |
| ATOM | 600 | CB | SER A | 72 | 8.615 | 18.483 | -7.618 | 1.00 8.17 |
| ATOM | 601 | OG | SER A | 72 | 8.895 | 19.471 | -6.625 | 1.00 17.17 |
| ATOM | 602 | N | GLY A | 73 | 10.525 | 16.978 | -5.353 | 1.00 18.48 |
| ATOM | 603 | CA | GLY A | 73 | 11.812 | 17.007 | -4.675 | 1.00 17.45 |
| ATOM | 604 | C | GLY A | 73 | 12.256 | 18.379 | -4.265 | 1.00 20.76 |
| ATOM | 605 | O | GLY A | 73 | 13.255 | 18.583 | -3.583 | 1.00 25.72 |
| ATOM | 606 | N | GLN A | 74 | 11.472 | 19.365 | -4.696 | 1.00 20.79 |
| ATOM | 607 | CA | GLN A | 74 | 11.848 | 20.723 | -4.296 | 1.00 26.18 |
| ATOM | 608 | C | GLN A | 74 | 10.671 | 21.582 | -3.918 | 1.00 28.13 |
| ATOM | 609 | O | GLN A | 74 | 9.553 | 21.357 | -4.369 | 1.00 27.33 |
| ATOM | 610 | CB | GLN A | 74 | 12.500 | 21.545 | -5.399 | 1.00 31.16 |
| ATOM | 611 | CG | GLN A | 74 | 13.635 | 20.927 | -6.235 | 1.00 36.26 |
| ATOM | 612 | CD | GLN A | 74 | 14.927 | 20.766 | -5.453 | 1.00 33.25 |
| ATOM | 613 | OE1 | GLN A | 74 | 15.541 | 21.717 | -5.003 | 1.00 33.27 |
| ATOM | 614 | NE2 | GLN A | 74 | 15.366 | 19.521 | -5.358 | 1.00 25.87 |
| ATOM | 615 | N | TYR A | 75 | 10.960 | 22.598 | -3.082 | 1.00 27.62 |
| ATOM | 616 | CA | TYR A | 75 | 9.875 | 23.554 | -2.887 | 1.00 25.71 |
| ATOM | 617 | C | TYR A | 75 | 9.573 | 24.255 | -4.204 | 1.00 26.20 |
| ATOM | 618 | O | TYR A | 75 | 10.495 | 24.682 | -4.891 | 1.00 26.09 |
| ATOM | 619 | CB | TYR A | 75 | 10.226 | 24.528 | -1.743 | 1.00 22.10 |
| ATOM | 620 | CG | TYR A | 75 | 8.996 | 25.233 | -1.181 | 1.00 26.52 |
| ATOM | 621 | CD1 | TYR A | 75 | 8.467 | 26.355 | -1.850 | 1.00 24.99 |
| ATOM | 622 | CD2 | TYR A | 75 | 8.421 | 24.784 | 0.042 | 1.00 31.57 |
| ATOM | 623 | CE1 | TYR A | 75 | 7.380 | 27.047 | -1.279 | 1.00 30.51 |
| ATOM | 624 | CE2 | TYR A | 75 | 7.304 | 25.456 | 0.598 | 1.00 26.49 |
| ATOM | 625 | CZ | TYR A | 75 | 6.774 | 26.564 | -0.085 | 1.00 28.74 |
| ATOM | 626 | OH | TYR A | 75 | 5.631 | 27.182 | 0.394 | 1.00 25.24 |
| ATOM | 627 | N | PRO A | 76 | 8.272 | 24.306 | -4.566 | 1.00 27.22 |
| ATOM | 628 | CA | PRO A | 76 | 7.810 | 24.980 | -5.795 | 1.00 26.99 |
| ATOM | 629 | C | PRO A | 76 | 6.264 | 26.422 | -6.040 | 1.00 27.01 |
| ATOM | 630 | O | PRO A | 76 | 7.828 | 27.376 | -5.380 | 1.00 27.79 |
| ATOM | 631 | CB | PRO A | 76 | 6.306 | 25.000 | -5.633 | 1.00 29.01 |
| ATOM | 632 | CG | PRO A | 76 | 5.954 | 23.837 | -4.723 | 1.00 28.90 |
| ATOM | 633 | CD | PRO A | 76 | 7.174 | 23.716 | -3.816 | 1.00 28.17 |
| ATOM | 634 | N | THR A | 77 | 9.124 | 26.539 | -7.078 | 1.00 25.64 |
| ATOM | 635 | CA | THR A | 77 | 9.465 | 27.871 | -7.644 | 1.00 24.10 |
| ATOM | 636 | C | THR A | 77 | 8.394 | 28.505 | -8.545 | 1.00 20.29 |
| ATOM | 637 | O | THR A | 77 | 8.271 | 29.713 | -8.640 | 1.00 19.97 |
| ATOM | 638 | CB | THR A | 77 | 10.738 | 27.837 | -8.502 | 1.00 23.22 |
| ATOM | 639 | OG1 | THR A | 77 | 10.444 | 27.258 | -9.794 | 1.00 25.06 |
| ATOM | 640 | CG2 | THR A | 77 | 11.911 | 27.134 | -7.824 | 1.00 19.74 |
| ATOM | 641 | N | ASN A | 78 | 7.635 | 27.631 | -9.240 | 1.00 18.11 |
| ATOM | 642 | CA | ASN A | 78 | 6.637 | 28.220 | -10.141 | 1.00 17.42 |
| ATOM | 643 | C | ASN A | 78 | 7.115 | 29.159 | -11.321 | 1.00 13.97 |
| ATOM | 644 | O | ASN A | 78 | 6.373 | 29.938 | -11.898 | 1.00 9.48 |
| ATOM | 645 | CB | ASN A | 78 | 5.548 | 28.934 | -9.298 | 1.00 19.04 |
| ATOM | 646 | CG | ASN A | 78 | 4.938 | 28.018 | -8.250 | 1.00 23.02 |
| ATOM | 647 | OD1 | ASN A | 78 | 4.354 | 26.981 | -8.494 | 1.00 28.90 |
| ATOM | 648 | ND2 | ASN A | 78 | 5.041 | 28.453 | -7.015 | 1.00 21.45 |

FIG. 11-13

| | | | | | | | | | |
|---|---|---|---|---|---|---|---|---|---|
| ATOM | 649 | N | ARG | A | 79 | 8.395 | 29.042 | -11.665 | 1.00 17.50 |
| ATOM | 650 | CA | ARG | A | 79 | 8.988 | 29.939 | -12.666 | 1.00 19.55 |
| ATOM | 651 | C | ARG | A | 79 | 8.420 | 29.818 | -14.068 | 1.00 18.79 |
| ATOM | 652 | O | ARG | A | 79 | 8.200 | 30.768 | -14.810 | 1.00 22.91 |
| ATOM | 653 | CB | ARG | A | 79 | 10.523 | 29.760 | -12.702 | 1.00 20.44 |
| ATOM | 654 | CG | ARG | A | 79 | 11.163 | 31.160 | -12.666 | 1.00 30.21 |
| ATOM | 655 | CD | ARG | A | 79 | 12.702 | 31.417 | -12.580 | 1.00 33.39 |
| ATOM | 656 | NE | ARG | A | 79 | 13.546 | 30.977 | -13.723 | 1.00 34.36 |
| ATOM | 657 | CZ | ARG | A | 79 | 14.335 | 31.836 | -14.402 | 1.00 34.42 |
| ATOM | 658 | NH1 | ARG | A | 79 | 14.223 | 33.120 | -14.178 | 1.00 31.41 |
| ATOM | 659 | NH2 | ARG | A | 79 | 15.210 | 31.419 | -15.306 | 1.00 33.46 |
| ATOM | 660 | N | LEU | A | 80 | 8.170 | 28.563 | -14.417 | 1.00 16.57 |
| ATOM | 661 | CA | LEU | A | 80 | 7.548 | 28.311 | -15.723 | 1.00 13.83 |
| ATOM | 662 | C | LEU | A | 80 | 6.118 | 27.906 | -15.580 | 1.00 11.98 |
| ATOM | 663 | O | LEU | A | 80 | 5.815 | 26.752 | -15.301 | 1.00 15.38 |
| ATOM | 664 | CB | LEU | A | 80 | 8.336 | 27.202 | -16.485 | 1.00 10.08 |
| ATOM | 665 | CG | LEU | A | 80 | 7.738 | 26.545 | -17.737 | 1.00 4.93 |
| ATOM | 666 | CD1 | LEU | A | 80 | 8.669 | 25.469 | -18.299 | 1.00 4.46 |
| ATOM | 667 | CD2 | LEU | A | 80 | 7.342 | 27.544 | -18.805 | 1.00 10.65 |
| ATOM | 668 | N | ALA | A | 81 | 5.255 | 28.906 | -15.751 | 1.00 12.64 |
| ATOM | 669 | CA | ALA | A | 81 | 3.843 | 28.687 | -15.422 | 1.00 10.04 |
| ATOM | 670 | C | ALA | A | 81 | 2.986 | 29.205 | -16.504 | 1.00 12.89 |
| ATOM | 671 | O | ALA | A | 81 | 3.300 | 30.278 | -16.995 | 1.00 12.80 |
| ATOM | 672 | CB | ALA | A | 81 | 3.527 | 29.537 | -14.225 | 1.00 13.89 |
| ATOM | 673 | N | PHE | A | 82 | 1.943 | 28.447 | -16.894 | 1.00 13.74 |
| ATOM | 674 | CA | PHE | A | 82 | 0.978 | 28.964 | -17.907 | 1.00 15.69 |
| ATOM | 675 | C | PHE | A | 82 | -0.436 | 29.215 | -17.349 | 1.00 18.85 |
| ATOM | 676 | O | PHE | A | 82 | -0.866 | 28.696 | -16.306 | 1.00 18.91 |
| ATOM | 677 | CB | PHE | A | 82 | 0.760 | 28.024 | -19.121 | 1.00 13.18 |
| ATOM | 678 | CG | PHE | A | 82 | 2.010 | 27.638 | -19.852 | 1.00 16.15 |
| ATOM | 679 | CD1 | PHE | A | 82 | 2.861 | 26.628 | -19.297 | 1.00 16.90 |
| ATOM | 680 | CD2 | PHE | A | 82 | 2.345 | 28.307 | -21.074 | 1.00 14.89 |
| ATOM | 681 | CE1 | PHE | A | 82 | 4.136 | 26.393 | -19.887 | 1.00 12.87 |
| ATOM | 682 | CE2 | PHE | A | 82 | 3.608 | 28.050 | -21.682 | 1.00 7.35 |
| ATOM | 683 | CZ | PHE | A | 82 | 4.508 | 27.149 | -21.044 | 1.00 14.60 |
| ATOM | 684 | N | ALA | A | 83 | -1.160 | 30.002 | -18.155 | 1.00 17.67 |
| ATOM | 685 | CA | ALA | A | 83 | -2.619 | 30.139 | -17.961 | 1.00 16.58 |
| ATOM | 686 | C | ALA | A | 83 | -3.243 | 30.653 | -19.258 | 1.00 14.53 |
| ATOM | 687 | O | ALA | A | 83 | -2.573 | 31.067 | -20.181 | 1.00 19.50 |
| ATOM | 688 | CB | ALA | A | 83 | -2.911 | 31.112 | -16.812 | 1.00 13.06 |
| ATOM | 689 | N | SER | A | 84 | -4.538 | 30.584 | -19.320 | 1.00 13.33 |
| ATOM | 690 | CA | SER | A | 84 | -5.400 | 31.050 | -20.415 | 1.00 12.66 |
| ATOM | 691 | C | SER | A | 84 | -6.286 | 32.209 | -19.941 | 1.00 18.72 |
| ATOM | 692 | O | SER | A | 84 | -6.990 | 32.118 | -18.932 | 1.00 26.46 |
| ATOM | 693 | CB | SER | A | 84 | -6.334 | 29.923 | -20.869 | 1.00 5.36 |
| ATOM | 694 | OG | SER | A | 84 | -7.198 | 30.390 | -21.894 | 1.00 6.80 |
| ATOM | 695 | N | PHE | A | 85 | -6.244 | 33.320 | -20.677 | 1.00 13.26 |
| ATOM | 696 | CA | PHE | A | 85 | -7.174 | 34.364 | -20.317 | 1.00 9.46 |
| ATOM | 697 | C | PHE | A | 85 | -7.790 | 34.927 | -21.601 | 1.00 16.58 |
| ATOM | 698 | O | PHE | A | 85 | -7.099 | 35.110 | -22.580 | 1.00 15.11 |
| ATOM | 699 | CB | PHE | A | 85 | -6.372 | 35.325 | -19.486 | 1.00 12.20 |
| ATOM | 700 | CG | PHE | A | 85 | -7.081 | 36.657 | -19.163 | 1.00 16.58 |
| ATOM | 701 | CD1 | PHE | A | 85 | -7.302 | 37.626 | -20.164 | 1.00 15.68 |
| ATOM | 702 | CD2 | PHE | A | 85 | -7.525 | 36.898 | -17.850 | 1.00 17.32 |

FIG. 11-14

| ATOM | 703 | CE1 | PHE A | 85 | -8.037 | 38.776 | -19.881 | 1.00 | 15.08 |
|---|---|---|---|---|---|---|---|---|---|
| ATOM | 704 | CE2 | PHE A | 85 | -8.248 | 38.062 | -17.546 | 1.00 | 12.93 |
| ATOM | 705 | CZ | PHE A | 85 | -8.524 | 38.963 | -18.586 | 1.00 | 17.52 |
| ATOM | 706 | N | ASP A | 86 | -9.116 | 35.179 | -21.581 | 1.00 | 23.45 |
| ATOM | 707 | CA | ASP A | 86 | -9.798 | 35.756 | -22.753 | 1.00 | 24.75 |
| ATOM | 708 | C | ASP A | 86 | -9.793 | 37.247 | -22.685 | 1.00 | 25.50 |
| ATOM | 709 | O | ASP A | 86 | -10.597 | 37.857 | -21.996 | 1.00 | 25.92 |
| ATOM | 710 | CB | ASP A | 86 | -11.242 | 35.259 | -22.914 | 1.00 | 28.91 |
| ATOM | 711 | CG | ASP A | 86 | -11.901 | 35.707 | -24.237 | 1.00 | 31.20 |
| ATOM | 712 | OD1 | ASP A | 86 | -11.441 | 36.655 | -24.892 | 1.00 | 28.19 |
| ATOM | 713 | OD2 | ASP A | 86 | -12.904 | 35.108 | -24.635 | 1.00 | 34.30 |
| ATOM | 714 | N | GLU A | 87 | -8.821 | 37.788 | -23.425 | 1.00 | 27.17 |
| ATOM | 715 | CA | GLU A | 87 | -8.601 | 39.237 | -23.460 | 1.00 | 25.77 |
| ATOM | 716 | C | GLU A | 87 | -9.724 | 40.016 | -24.091 | 1.00 | 28.28 |
| ATOM | 717 | O | GLU A | 87 | -10.043 | 41.173 | -23.793 | 1.00 | 31.47 |
| ATOM | 718 | CB | GLU A | 87 | -7.332 | 39.551 | -24.209 | 1.00 | 22.39 |
| ATOM | 719 | CG | GLU A | 87 | -6.120 | 39.582 | -23.277 | 1.00 | 26.50 |
| ATOM | 720 | CD | GLU A | 87 | -6.090 | 40.814 | -22.374 | 1.00 | 27.20 |
| ATOM | 721 | OE1 | GLU A | 87 | -5.256 | 40.832 | -21.469 | 1.00 | 27.58 |
| ATOM | 722 | OE2 | GLU A | 87 | -6.872 | 41.759 | -22.568 | 1.00 | 29.29 |
| ATOM | 723 | N | ASP A | 88 | -10.375 | 39.255 | -24.977 | 1.00 | 25.63 |
| ATOM | 724 | CA | ASP A | 88 | -11.578 | 39.856 | -25.545 | 1.00 | 28.97 |
| ATOM | 725 | C | ASP A | 88 | -12.908 | 39.962 | -24.700 | 1.00 | 30.55 |
| ATOM | 726 | O | ASP A | 88 | -13.552 | 41.003 | -24.538 | 1.00 | 29.81 |
| ATOM | 727 | CB | ASP A | 88 | -11.756 | 39.284 | -26.945 | 1.00 | 28.55 |
| ATOM | 728 | CG | ASP A | 88 | -12.135 | 40.450 | -27.798 | 1.00 | 32.08 |
| ATOM | 729 | OD1 | ASP A | 88 | -11.384 | 41.425 | -27.830 | 1.00 | 33.90 |
| ATOM | 730 | OD2 | ASP A | 88 | -13.205 | 40.406 | -28.383 | 1.00 | 39.05 |
| ATOM | 731 | N | ARG A | 89 | -13.247 | 38.830 | -24.049 | 1.00 | 29.43 |
| ATOM | 732 | CA | ARG A | 89 | -14.183 | 38.851 | -22.923 | 1.00 | 24.85 |
| ATOM | 733 | C | ARG A | 89 | -13.883 | 39.985 | -21.966 | 1.00 | 27.50 |
| ATOM | 734 | O | ARG A | 89 | -14.711 | 40.823 | -21.663 | 1.00 | 28.97 |
| ATOM | 735 | CB | ARG A | 89 | -14.083 | 37.603 | -22.052 | 1.00 | 21.09 |
| ATOM | 736 | CG | ARG A | 89 | -15.243 | 36.655 | -22.048 | 1.00 | 21.98 |
| ATOM | 737 | CD | ARG A | 89 | -15.101 | 35.565 | -20.957 | 1.00 | 23.86 |
| ATOM | 738 | NE | ARG A | 89 | -15.595 | 36.012 | -19.649 | 1.00 | 27.41 |
| ATOM | 739 | CZ | ARG A | 89 | -16.493 | 35.286 | -19.012 | 1.00 | 30.64 |
| ATOM | 740 | NH1 | ARG A | 89 | -16.944 | 34.186 | -19.582 | 1.00 | 34.67 |
| ATOM | 741 | NH2 | ARG A | 89 | -16.939 | 35.663 | -17.829 | 1.00 | 32.33 |
| ATOM | 742 | N | PHE A | 90 | -12.639 | 40.020 | -21.500 | 1.00 | 27.94 |
| ATOM | 743 | CA | PHE A | 90 | -12.319 | 41.085 | -20.547 | 1.00 | 26.67 |
| ATOM | 744 | C | PHE A | 90 | -12.582 | 42.500 | -21.036 | 1.00 | 30.60 |
| ATOM | 745 | O | PHE A | 90 | -13.166 | 43.329 | -20.345 | 1.00 | 29.68 |
| ATOM | 746 | CB | PHE A | 90 | -10.864 | 40.937 | -20.106 | 1.00 | 25.90 |
| ATOM | 747 | CG | PHE A | 90 | -10.473 | 41.903 | -19.003 | 1.00 | 24.88 |
| ATOM | 748 | CD1 | PHE A | 90 | -9.603 | 42.977 | -19.333 | 1.00 | 23.73 |
| ATOM | 749 | CD2 | PHE A | 90 | -10.966 | 41.702 | -17.681 | 1.00 | 21.67 |
| ATOM | 750 | CE1 | PHE A | 90 | -9.193 | 43.836 | -18.296 | 1.00 | 26.18 |
| ATOM | 751 | CE2 | PHE A | 90 | -10.556 | 42.571 | -16.644 | 1.00 | 22.18 |
| ATOM | 752 | CZ | PHE A | 90 | -9.663 | 43.620 | -16.963 | 1.00 | 24.34 |
| ATOM | 753 | N | LYS A | 91 | -12.149 | 42.767 | -22.282 | 1.00 | 34.09 |
| ATOM | 754 | CA | LYS A | 91 | -12.334 | 44.191 | -22.591 | 1.00 | 38.08 |
| ATOM | 755 | C | LYS A | 91 | -13.767 | 44.616 | -22.970 | 1.00 | 38.58 |
| ATOM | 756 | O | LYS A | 91 | -14.200 | 45.751 | -22.788 | 1.00 | 37.74 |

FIG. 11-15

| | | | | | | | | | |
|---|---|---|---|---|---|---|---|---|---|
| ATOM | 757 | CB | LYS | A | 91 | -11.270 | 44.733 | -23.571 | 1.00 39.18 |
| ATOM | 758 | CG | LYS | A | 91 | -11.273 | 44.214 | -25.007 | 1.00 35.89 |
| ATOM | 759 | CD | LYS | A | 91 | -11.093 | 45.409 | -25.944 | 1.00 38.56 |
| ATOM | 760 | CE | LYS | A | 91 | -10.905 | 45.015 | -27.414 | 1.00 47.58 |
| ATOM | 761 | NZ | LYS | A | 91 | -11.895 | 44.020 | -27.922 | 1.00 51.93 |
| ATOM | 762 | N | ASN | A | 92 | -14.498 | 43.616 | -23.517 | 1.00 37.73 |
| ATOM | 763 | CA | ASN | A | 92 | -15.951 | 43.782 | -23.738 | 1.00 38.58 |
| ATOM | 764 | C | ASN | A | 92 | -16.930 | 43.659 | -22.507 | 1.00 36.42 |
| ATOM | 765 | O | ASN | A | 92 | -17.739 | 44.544 | -22.351 | 1.00 37.85 |
| ATOM | 766 | CB | ASN | A | 92 | -16.400 | 43.006 | -25.024 | 1.00 41.50 |
| ATOM | 767 | CG | ASN | A | 92 | -16.059 | 43.750 | -26.336 | 1.00 41.35 |
| ATOM | 768 | OD1 | ASN | A | 92 | -16.629 | 43.579 | -27.402 | 1.00 42.47 |
| ATOM | 769 | ND2 | ASN | A | 92 | -15.135 | 44.687 | -26.251 | 1.00 40.56 |
| ATOM | 770 | N | GLU | A | 93 | -16.794 | 42.699 | -21.581 | 1.00 35.99 |
| ATOM | 771 | CA | GLU | A | 93 | -17.285 | 43.032 | -20.220 | 1.00 35.86 |
| ATOM | 772 | C | GLU | A | 93 | -16.859 | 44.364 | -19.689 | 1.00 38.06 |
| ATOM | 773 | O | GLU | A | 93 | -17.657 | 45.277 | -19.491 | 1.00 42.41 |
| ATOM | 774 | CB | GLU | A | 93 | -16.942 | 42.067 | -19.075 | 1.00 35.20 |
| ATOM | 775 | CG | GLU | A | 93 | -18.017 | 40.996 | -18.763 | 1.00 34.00 |
| ATOM | 776 | CD | GLU | A | 93 | -19.454 | 41.552 | -18.856 | 1.00 38.53 |
| ATOM | 777 | OE1 | GLU | A | 93 | -19.921 | 42.296 | -17.974 | 1.00 35.85 |
| ATOM | 778 | OE2 | GLU | A | 93 | -20.123 | 41.213 | -19.842 | 1.00 43.94 |
| ATOM | 779 | N | LEU | A | 94 | -15.536 | 44.517 | -19.547 | 1.00 37.19 |
| ATOM | 780 | CA | LEU | A | 94 | -15.048 | 45.819 | -19.026 | 1.00 37.15 |
| ATOM | 781 | C | LEU | A | 94 | -15.673 | 47.144 | -19.467 | 1.00 41.82 |
| ATOM | 782 | O | LEU | A | 94 | -15.906 | 48.094 | -18.704 | 1.00 45.86 |
| ATOM | 783 | CB | LEU | A | 94 | -13.598 | 45.975 | -19.304 | 1.00 34.26 |
| ATOM | 784 | CG | LEU | A | 94 | -12.899 | 46.393 | -18.060 | 1.00 28.86 |
| ATOM | 785 | CD1 | LEU | A | 94 | -11.433 | 46.724 | -18.328 | 1.00 28.63 |
| ATOM | 786 | CD2 | LEU | A | 94 | -13.114 | 45.348 | -16.999 | 1.00 32.77 |
| ATOM | 787 | N | LYS | A | 95 | -15.939 | 47.178 | -20.767 | 1.00 45.23 |
| ATOM | 788 | CA | LYS | A | 95 | -16.577 | 48.388 | -21.248 | 1.00 51.14 |
| ATOM | 789 | C | LYS | A | 95 | -17.861 | 48.286 | -22.130 | 1.00 53.34 |
| ATOM | 790 | O | LYS | A | 95 | -18.254 | 49.278 | -22.724 | 1.00 59.55 |
| ATOM | 791 | CB | LYS | A | 95 | -15.474 | 49.328 | -21.815 | 1.00 58.38 |
| ATOM | 792 | CG | LYS | A | 95 | -14.970 | 50.573 | -21.006 | 1.00 64.40 |
| ATOM | 793 | CD | LYS | A | 95 | -14.145 | 50.305 | -19.729 | 1.00 67.77 |
| ATOM | 794 | CE | LYS | A | 95 | -13.832 | 51.541 | -18.870 | 1.00 70.28 |
| ATOM | 795 | NZ | LYS | A | 95 | -15.058 | 52.327 | -18.626 | 1.00 69.29 |
| ATOM | 796 | N | ASN | A | 96 | -18.531 | 47.111 | -22.167 | 1.00 49.39 |
| ATOM | 797 | CA | ASN | A | 96 | -19.931 | 47.006 | -22.687 | 1.00 46.76 |
| ATOM | 798 | C | ASN | A | 96 | -20.883 | 46.287 | -21.716 | 1.00 48.11 |
| ATOM | 799 | O | ASN | A | 96 | -22.094 | 46.227 | -21.878 | 1.00 50.87 |
| ATOM | 800 | CB | ASN | A | 96 | -20.086 | 46.219 | -24.015 | 1.00 47.21 |
| ATOM | 801 | CG | ASN | A | 96 | -19.294 | 46.728 | -25.232 | 1.00 49.06 |
| ATOM | 802 | OD1 | ASN | A | 96 | -19.829 | 47.158 | -26.233 | 1.00 55.04 |
| ATOM | 803 | ND2 | ASN | A | 96 | -17.972 | 46.620 | -25.180 | 1.00 44.47 |
| ATOM | 804 | N | GLY | A | 97 | -20.270 | 45.691 | -20.690 | 1.00 48.39 |
| ATOM | 805 | CA | GLY | A | 97 | -21.074 | 45.056 | -19.638 | 1.00 46.32 |
| ATOM | 806 | C | GLY | A | 97 | -21.208 | 45.859 | -18.348 | 1.00 42.63 |
| ATOM | 807 | O | GLY | A | 97 | -20.801 | 47.016 | -18.243 | 1.00 44.55 |
| ATOM | 808 | N | ARG | A | 98 | -21.869 | 45.228 | -17.370 | 1.00 38.43 |
| ATOM | 809 | CA | ARG | A | 98 | -22.463 | 46.098 | -16.358 | 1.00 33.82 |
| ATOM | 810 | C | ARG | A | 98 | -22.560 | 45.547 | -14.938 | 1.00 28.28 |

FIG. 11-16

| | | | | | | | | |
|---|---|---|---|---|---|---|---|---|
| ATOM | 811 | O | ARG | A | 98 | -23.098 | 44.466 | -14.703 | 1.00 | 32.04 |
| ATOM | 812 | CB | ARG | A | 98 | -23.763 | 46.576 | -17.013 | 1.00 | 40.79 |
| ATOM | 813 | CG | ARG | A | 98 | -24.887 | 47.244 | -16.217 | 1.00 | 50.04 |
| ATOM | 814 | CD | ARG | A | 98 | -25.803 | 46.183 | -15.586 | 1.00 | 62.76 |
| ATOM | 815 | NE | ARG | A | 98 | -26.336 | 45.188 | -16.555 | 1.00 | 66.92 |
| ATOM | 816 | CZ | ARG | A | 98 | -26.399 | 43.858 | -16.323 | 1.00 | 62.44 |
| ATOM | 817 | NH1 | ARG | A | 98 | -25.826 | 43.315 | -15.257 | 1.00 | 58.60 |
| ATOM | 818 | NH2 | ARG | A | 98 | -27.049 | 43.114 | -17.193 | 1.00 | 55.06 |
| ATOM | 819 | N | PRO | A | 99 | -22.054 | 46.339 | -13.965 | 1.00 | 23.05 |
| ATOM | 820 | CA | PRO | A | 99 | -21.921 | 45.870 | -12.553 | 1.00 | 24.28 |
| ATOM | 821 | C | PRO | A | 99 | -23.190 | 45.313 | -11.823 | 1.00 | 28.37 |
| ATOM | 822 | O | PRO | A | 99 | -24.325 | 45.504 | -12.240 | 1.00 | 31.64 |
| ATOM | 823 | CB | PRO | A | 99 | -21.356 | 47.115 | -11.857 | 1.00 | 21.49 |
| ATOM | 824 | CG | PRO | A | 99 | -20.840 | 48.099 | -12.940 | 1.00 | 13.61 |
| ATOM | 825 | CD | PRO | A | 99 | -21.649 | 47.720 | -14.161 | 1.00 | 18.00 |
| ATOM | 826 | N | ARG | A | 100 | -23.043 | 44.628 | -10.702 | 1.00 | 29.17 |
| ATOM | 827 | CA | ARG | A | 100 | -24.302 | 44.066 | -10.166 | 1.00 | 32.04 |
| ATOM | 828 | C | ARG | A | 100 | -24.782 | 44.266 | -8.698 | 1.00 | 34.89 |
| ATOM | 829 | O | ARG | A | 100 | -24.102 | 44.117 | -7.694 | 1.00 | 35.10 |
| ATOM | 830 | CB | ARG | A | 100 | -24.475 | 42.634 | -10.686 | 1.00 | 29.57 |
| ATOM | 831 | CG | ARG | A | 100 | -23.578 | 41.591 | -10.060 | 1.00 | 22.29 |
| ATOM | 832 | CD | ARG | A | 100 | -23.256 | 40.500 | -11.065 | 1.00 | 21.50 |
| ATOM | 833 | NE | ARG | A | 100 | -22.731 | 39.248 | -10.511 | 1.00 | 29.71 |
| ATOM | 834 | CZ | ARG | A | 100 | -21.929 | 39.088 | -9.435 | 1.00 | 31.94 |
| ATOM | 835 | NH1 | ARG | A | 100 | -21.511 | 40.093 | -8.690 | 1.00 | 40.59 |
| ATOM | 836 | NH2 | ARG | A | 100 | -21.488 | 37.876 | -9.138 | 1.00 | 18.05 |
| ATOM | 837 | N | SER | A | 101 | -26.048 | 44.724 | -8.658 | 1.00 | 38.56 |
| ATOM | 838 | CA | SER | A | 101 | -26.605 | 45.574 | -7.574 | 1.00 | 36.97 |
| ATOM | 839 | C | SER | A | 101 | -25.606 | 45.878 | -6.449 | 1.00 | 32.12 |
| ATOM | 840 | O | SER | A | 101 | -25.321 | 45.074 | -5.587 | 1.00 | 32.97 |
| ATOM | 841 | CB | SER | A | 101 | -28.030 | 45.019 | -7.131 | 1.00 | 41.83 |
| ATOM | 842 | OG | SER | A | 101 | -29.085 | 45.966 | -6.722 | 1.00 | 44.88 |
| ATOM | 843 | N | GLY | A | 102 | -24.985 | 47.053 | -6.507 | 1.00 | 32.11 |
| ATOM | 844 | CA | GLY | A | 102 | -24.199 | 47.369 | -5.286 | 1.00 | 28.76 |
| ATOM | 845 | C | GLY | A | 102 | -22.703 | 47.098 | -5.256 | 1.00 | 27.37 |
| ATOM | 846 | O | GLY | A | 102 | -21.948 | 47.558 | -4.398 | 1.00 | 29.00 |
| ATOM | 847 | N | GLU | A | 103 | -22.312 | 46.375 | -6.307 | 1.00 | 29.65 |
| ATOM | 848 | CA | GLU | A | 103 | -20.912 | 46.144 | -6.749 | 1.00 | 28.04 |
| ATOM | 849 | C | GLU | A | 103 | -20.163 | 47.371 | -7.274 | 1.00 | 26.76 |
| ATOM | 850 | O | GLU | A | 103 | -20.588 | 48.102 | -8.180 | 1.00 | 25.16 |
| ATOM | 851 | CB | GLU | A | 103 | -20.965 | 45.030 | -7.811 | 1.00 | 27.74 |
| ATOM | 852 | CG | GLU | A | 103 | -19.687 | 44.248 | -8.047 | 1.00 | 25.66 |
| ATOM | 853 | CD | GLU | A | 103 | -19.930 | 43.330 | -9.191 | 1.00 | 19.29 |
| ATOM | 854 | OE1 | GLU | A | 103 | -20.432 | 43.771 | -10.209 | 1.00 | 18.76 |
| ATOM | 855 | OE2 | GLU | A | 103 | -19.636 | 42.159 | -9.074 | 1.00 | 23.11 |
| ATOM | 856 | N | THR | A | 104 | -19.015 | 47.618 | -6.630 | 1.00 | 28.58 |
| ATOM | 857 | CA | THR | A | 104 | -18.263 | 48.770 | -7.156 | 1.00 | 27.76 |
| ATOM | 858 | C | THR | A | 104 | -17.468 | 48.534 | -8.459 | 1.00 | 31.81 |
| ATOM | 859 | O | THR | A | 104 | -17.295 | 47.409 | -8.939 | 1.00 | 23.22 |
| ATOM | 860 | CB | THR | A | 104 | -17.319 | 49.337 | -6.132 | 1.00 | 30.09 |
| ATOM | 861 | OG1 | THR | A | 104 | -15.988 | 48.863 | -6.377 | 1.00 | 37.49 |
| ATOM | 862 | CG2 | THR | A | 104 | -17.828 | 49.176 | -4.693 | 1.00 | 31.81 |
| ATOM | 863 | N | ARG | A | 105 | -16.899 | 49.650 | -8.979 | 1.00 | 34.22 |
| ATOM | 864 | CA | ARG | A | 105 | -15.908 | 49.379 | -10.050 | 1.00 | 38.98 |

FIG. 11-17

| | | | | | | | | |
|---|---|---|---|---|---|---|---|---|
| ATOM | 865 | C | ARG | A | 105 | -14.738 | 48.400 | -9.755 | 1.00 | 35.18 |
| ATOM | 866 | O | ARG | A | 105 | -14.697 | 47.340 | -10.354 | 1.00 | 37.44 |
| ATOM | 867 | CB | ARG | A | 105 | -15.489 | 50.632 | -10.854 | 1.00 | 40.63 |
| ATOM | 868 | CG | ARG | A | 105 | -16.251 | 50.831 | -12.190 | 1.00 | 42.77 |
| ATOM | 869 | CD | ARG | A | 105 | -15.890 | 49.879 | -13.348 | 1.00 | 45.93 |
| ATOM | 870 | NE | ARG | A | 105 | -16.692 | 50.089 | -14.575 | 1.00 | 46.87 |
| ATOM | 871 | CZ | ARG | A | 105 | -16.318 | 49.573 | -15.769 | 1.00 | 42.32 |
| ATOM | 872 | NH1 | ARG | A | 105 | -15.084 | 49.195 | -15.977 | 1.00 | 35.76 |
| ATOM | 873 | NH2 | ARG | A | 105 | -17.206 | 49.407 | -16.745 | 1.00 | 41.00 |
| ATOM | 874 | N | ALA | A | 106 | -13.886 | 48.673 | -8.763 | 1.00 | 30.18 |
| ATOM | 875 | CA | ALA | A | 106 | -12.829 | 47.638 | -8.481 | 1.00 | 33.55 |
| ATOM | 876 | C | ALA | A | 106 | -13.224 | 46.187 | -8.396 | 1.00 | 30.55 |
| ATOM | 877 | O | ALA | A | 106 | -12.672 | 45.320 | -9.038 | 1.00 | 29.51 |
| ATOM | 878 | CB | ALA | A | 106 | -12.129 | 47.777 | -7.125 | 1.00 | 36.72 |
| ATOM | 879 | N | GLU | A | 107 | -14.278 | 46.025 | -7.569 | 1.00 | 31.01 |
| ATOM | 880 | CA | GLU | A | 107 | -15.107 | 44.825 | -7.433 | 1.00 | 26.13 |
| ATOM | 881 | C | GLU | A | 107 | -15.504 | 44.145 | -8.749 | 1.00 | 22.19 |
| ATOM | 882 | O | GLU | A | 107 | -15.091 | 43.040 | -9.112 | 1.00 | 20.78 |
| ATOM | 883 | CB | GLU | A | 107 | -16.306 | 45.260 | -6.597 | 1.00 | 25.26 |
| ATOM | 884 | CG | GLU | A | 107 | -16.878 | 44.151 | -5.739 | 1.00 | 32.57 |
| ATOM | 885 | CD | GLU | A | 107 | -17.616 | 44.690 | -4.506 | 1.00 | 39.57 |
| ATOM | 886 | OE1 | GLU | A | 107 | -17.952 | 45.884 | -4.421 | 1.00 | 40.42 |
| ATOM | 887 | OE2 | GLU | A | 107 | -17.879 | 43.881 | -3.614 | 1.00 | 43.24 |
| ATOM | 888 | N | PHE | A | 108 | -16.285 | 44.923 | -9.481 | 1.00 | 21.56 |
| ATOM | 889 | CA | PHE | A | 108 | -16.683 | 44.545 | -10.843 | 1.00 | 23.09 |
| ATOM | 890 | C | PHE | A | 108 | -15.572 | 44.047 | -11.789 | 1.00 | 27.33 |
| ATOM | 891 | O | PHE | A | 108 | -15.689 | 42.992 | -12.407 | 1.00 | 31.46 |
| ATOM | 892 | CB | PHE | A | 108 | -17.340 | 45.746 | -11.500 | 1.00 | 20.64 |
| ATOM | 893 | CG | PHE | A | 108 | -17.761 | 45.354 | -12.890 | 1.00 | 17.60 |
| ATOM | 894 | CD1 | PHE | A | 108 | -17.234 | 46.097 | -13.984 | 1.00 | 16.52 |
| ATOM | 895 | CD2 | PHE | A | 108 | -18.616 | 44.234 | -13.064 | 1.00 | 10.38 |
| ATOM | 896 | CE1 | PHE | A | 108 | -17.538 | 45.672 | -15.288 | 1.00 | 15.65 |
| ATOM | 897 | CE2 | PHE | A | 108 | -18.960 | 43.825 | -14.370 | 1.00 | 6.08 |
| ATOM | 898 | CZ | PHE | A | 108 | -18.395 | 44.539 | -15.457 | 1.00 | 13.54 |
| ATOM | 899 | N | GLU | A | 109 | -14.495 | 44.885 | -11.858 | 1.00 | 26.85 |
| ATOM | 900 | CA | GLU | A | 109 | -13.231 | 44.698 | -12.594 | 1.00 | 24.27 |
| ATOM | 901 | C | GLU | A | 109 | -12.370 | 43.516 | -12.168 | 1.00 | 24.82 |
| ATOM | 902 | O | GLU | A | 109 | -12.126 | 42.602 | -12.957 | 1.00 | 29.91 |
| ATOM | 903 | CB | GLU | A | 109 | -12.406 | 46.038 | -12.650 | 1.00 | 29.61 |
| ATOM | 904 | CG | GLU | A | 109 | -12.966 | 47.139 | -13.629 | 1.00 | 24.51 |
| ATOM | 905 | CD | GLU | A | 109 | -12.335 | 48.547 | -13.670 | 1.00 | 27.54 |
| ATOM | 906 | OE1 | GLU | A | 109 | -12.775 | 49.307 | -14.536 | 1.00 | 28.31 |
| ATOM | 907 | OE2 | GLU | A | 109 | -11.470 | 48.914 | -12.866 | 1.00 | 28.19 |
| ATOM | 908 | N | GLY | A | 110 | -11.963 | 43.490 | -10.891 | 1.00 | 19.63 |
| ATOM | 909 | CA | GLY | A | 110 | -11.386 | 42.250 | -10.328 | 1.00 | 17.95 |
| ATOM | 910 | C | GLY | A | 110 | -12.088 | 40.907 | -10.665 | 1.00 | 20.44 |
| ATOM | 911 | O | GLY | A | 110 | -11.476 | 39.993 | -11.249 | 1.00 | 20.62 |
| ATOM | 912 | N | ARG | A | 111 | -13.433 | 40.903 | -10.358 | 1.00 | 17.13 |
| ATOM | 913 | CA | ARG | A | 111 | -14.373 | 39.823 | -10.730 | 1.00 | 16.90 |
| ATOM | 914 | C | ARG | A | 111 | -14.419 | 39.442 | -12.194 | 1.00 | 13.96 |
| ATOM | 915 | O | ARG | A | 111 | -14.158 | 38.313 | -12.541 | 1.00 | 17.42 |
| ATOM | 916 | CB | ARG | A | 111 | -15.825 | 40.077 | -10.227 | 1.00 | 18.14 |
| ATOM | 917 | CG | ARG | A | 111 | -16.786 | 38.973 | -10.679 | 1.00 | 17.87 |
| ATOM | 918 | CD | ARG | A | 111 | -18.268 | 39.255 | -10.398 | 1.00 | 13.57 |

FIG. 11-18

```
ATOM    919  NE   ARG A 111     -18.903  40.298 -11.213  1.00 20.55
ATOM    920  CZ   ARG A 111     -19.487  40.111 -12.437  1.00 21.51
ATOM    921  NH1  ARG A 111     -19.381  38.987 -13.092  1.00 14.06
ATOM    922  NH2  ARG A 111     -20.145  41.085 -13.040  1.00 21.70
ATOM    923  N    VAL A 112     -14.708  40.394 -13.075  1.00 17.11
ATOM    924  CA   VAL A 112     -14.517  40.036 -14.509  1.00 19.07
ATOM    925  C    VAL A 112     -13.155  39.533 -15.005  1.00 19.13
ATOM    926  O    VAL A 112     -13.072  38.686 -15.902  1.00 24.85
ATOM    927  CB   VAL A 112     -14.978  41.123 -15.467  1.00 15.20
ATOM    928  CG1  VAL A 112     -14.268  42.449 -15.220  1.00 22.09
ATOM    929  CG2  VAL A 112     -16.455  41.272 -15.314  1.00 12.04
ATOM    930  N    ALA A 113     -12.079  40.028 -14.374  1.00 16.62
ATOM    931  CA   ALA A 113     -10.800  39.375 -14.720  1.00 16.77
ATOM    932  C    ALA A 113     -10.642  37.919 -14.272  1.00 16.16
ATOM    933  O    ALA A 113     -10.137  37.041 -14.954  1.00 15.68
ATOM    934  CB   ALA A 113      -9.590  40.179 -14.224  1.00 13.82
ATOM    935  N    LYS A 114     -11.156  37.666 -13.057  1.00 22.71
ATOM    936  CA   LYS A 114     -11.205  36.301 -12.462  1.00 18.32
ATOM    937  C    LYS A 114     -11.900  35.247 -13.318  1.00 14.25
ATOM    938  O    LYS A 114     -11.462  34.115 -13.395  1.00 16.47
ATOM    939  CB   LYS A 114     -11.804  36.392 -11.027  1.00 19.92
ATOM    940  CG   LYS A 114     -12.062  35.043 -10.326  1.00 21.14
ATOM    941  CD   LYS A 114     -13.021  35.079  -9.115  1.00 19.41
ATOM    942  CE   LYS A 114     -13.476  33.671  -8.599  1.00 20.10
ATOM    943  NZ   LYS A 114     -12.407  32.802  -8.029  1.00 23.63
ATOM    944  N    GLU A 115     -12.985  35.681 -13.953  1.00 14.12
ATOM    945  CA   GLU A 115     -13.823  34.820 -14.828  1.00 16.96
ATOM    946  C    GLU A 115     -13.509  34.792 -16.298  1.00 14.96
ATOM    947  O    GLU A 115     -14.048  33.986 -17.076  1.00 15.49
ATOM    948  CB   GLU A 115     -15.271  35.303 -14.942  1.00 21.87
ATOM    949  CG   GLU A 115     -15.835  36.206 -13.835  1.00 23.85
ATOM    950  CD   GLU A 115     -17.126  36.812 -14.359  1.00 29.52
ATOM    951  OE1  GLU A 115     -18.102  36.694 -13.616  1.00 23.66
ATOM    952  OE2  GLU A 115     -17.146  37.376 -15.492  1.00 27.06
ATOM    953  N    SER A 116     -12.658  35.785 -16.659  1.00 11.88
ATOM    954  CA   SER A 116     -12.020  35.741 -17.996  1.00 12.67
ATOM    955  C    SER A 116     -10.891  34.751 -18.110  1.00 15.03
ATOM    956  O    SER A 116     -10.562  34.296 -19.196  1.00 14.36
ATOM    957  CB   SER A 116     -11.583  37.091 -18.530  1.00  6.62
ATOM    958  OG   SER A 116     -12.746  37.967 -18.580  1.00 13.55
ATOM    959  N    PHE A 117     -10.389  34.335 -16.918  1.00 15.03
ATOM    960  CA   PHE A 117      -9.543  33.135 -16.890  1.00 15.63
ATOM    961  C    PHE A 117     -10.205  31.821 -17.338  1.00 20.59
ATOM    962  O    PHE A 117     -11.374  31.605 -17.060  1.00 23.09
ATOM    963  CB   PHE A 117      -8.909  32.943 -15.522  1.00  9.46
ATOM    964  CG   PHE A 117      -7.679  33.797 -15.336  1.00  8.12
ATOM    965  CD1  PHE A 117      -7.812  35.067 -14.754  1.00  8.36
ATOM    966  CD2  PHE A 117      -6.412  33.295 -15.736  1.00 11.00
ATOM    967  CE1  PHE A 117      -6.659  35.853 -14.559  1.00 13.99
ATOM    968  CE2  PHE A 117      -5.263  34.087 -15.568  1.00  8.23
ATOM    969  CZ   PHE A 117      -5.401  35.365 -15.001  1.00 16.91
ATOM    970  N    ASP A 118      -9.466  30.959 -18.085  1.00 21.38
ATOM    971  CA   ASP A 118     -10.004  29.601 -18.290  1.00 18.82
ATOM    972  C    ASP A 118      -9.091  28.471 -17.873  1.00 19.39
```

FIG. 11-19

| | | | | | | | | |
|---|---|---|---|---|---|---|---|---|
| ATOM | 973 | O | ASP | A | 118 | -7.956 | 28.290 -18.336 | 1.00 26.23 |
| ATOM | 974 | CB | ASP | A | 118 | -10.459 | 29.468 -19.719 | 1.00 21.20 |
| ATOM | 975 | CG | ASP | A | 118 | -11.020 | 28.120 -20.091 | 1.00 22.97 |
| ATOM | 976 | OD1 | ASP | A | 118 | -11.009 | 27.161 -19.312 | 1.00 27.23 |
| ATOM | 977 | OD2 | ASP | A | 118 | -11.444 | 28.037 -21.222 | 1.00 22.40 |
| ATOM | 978 | N | GLU | A | 119 | -9.596 | 27.692 -16.927 | 1.00 17.81 |
| ATOM | 979 | CA | GLU | A | 119 | -8.601 | 26.760 -16.405 | 1.00 20.94 |
| ATOM | 980 | C | GLU | A | 119 | -8.340 | 25.483 -17.161 | 1.00 22.31 |
| ATOM | 981 | O | GLU | A | 119 | -7.239 | 24.912 -17.191 | 1.00 21.07 |
| ATOM | 982 | CB | GLU | A | 119 | -8.812 | 26.466 -14.935 | 1.00 25.42 |
| ATOM | 983 | CG | GLU | A | 119 | -8.965 | 27.712 -14.084 | 1.00 28.52 |
| ATOM | 984 | CD | GLU | A | 119 | -8.291 | 27.543 -12.736 | 1.00 31.25 |
| ATOM | 985 | OE1 | GLU | A | 119 | -7.939 | 28.577 -12.173 | 1.00 36.83 |
| ATOM | 986 | OE2 | GLU | A | 119 | -8.100 | 26.416 -12.270 | 1.00 29.27 |
| ATOM | 987 | N | GLU | A | 120 | -9.440 | 25.079 -17.818 | 1.00 22.07 |
| ATOM | 988 | CA | GLU | A | 120 | -9.322 | 23.862 -18.597 | 1.00 21.92 |
| ATOM | 989 | C | GLU | A | 120 | -8.303 | 24.024 -19.723 | 1.00 18.57 |
| ATOM | 990 | O | GLU | A | 120 | -7.279 | 23.358 -19.776 | 1.00 17.98 |
| ATOM | 991 | CB | GLU | A | 120 | -10.731 | 23.431 -19.005 | 1.00 27.25 |
| ATOM | 992 | CG | GLU | A | 120 | -11.015 | 21.909 -18.899 | 1.00 28.77 |
| ATOM | 993 | CD | GLU | A | 120 | -11.537 | 21.360 -20.207 | 1.00 28.28 |
| ATOM | 994 | OE1 | GLU | A | 120 | -11.962 | 22.153 -21.060 | 1.00 35.26 |
| ATOM | 995 | OE2 | GLU | A | 120 | -11.436 | 20.152 -20.396 | 1.00 25.76 |
| ATOM | 996 | N | LYS | A | 121 | -8.531 | 25.128 -20.469 | 1.00 21.73 |
| ATOM | 997 | CA | LYS | A | 121 | -7.545 | 25.722 -21.409 | 1.00 17.65 |
| ATOM | 998 | C | LYS | A | 121 | -6.103 | 26.072 -20.970 | 1.00 16.02 |
| ATOM | 999 | O | LYS | A | 121 | -5.144 | 25.688 -21.606 | 1.00 14.81 |
| ATOM | 1000 | CB | LYS | A | 121 | -8.073 | 26.973 -22.079 | 1.00 14.48 |
| ATOM | 1001 | CG | LYS | A | 121 | -9.191 | 26.842 -23.096 | 1.00 12.70 |
| ATOM | 1002 | CD | LYS | A | 121 | -9.205 | 28.160 -23.894 | 1.00 19.10 |
| ATOM | 1003 | CE | LYS | A | 121 | -10.488 | 28.396 -24.713 | 1.00 21.24 |
| ATOM | 1004 | NZ | LYS | A | 121 | -11.400 | 29.173 -23.862 | 1.00 39.38 |
| ATOM | 1005 | N | GLY | A | 122 | -5.941 | 26.777 -19.849 | 1.00 20.09 |
| ATOM | 1006 | CA | GLY | A | 122 | -4.618 | 26.769 -19.192 | 1.00 11.05 |
| ATOM | 1007 | C | GLY | A | 122 | -3.990 | 25.429 -18.816 | 1.00 15.61 |
| ATOM | 1008 | O | GLY | A | 122 | -2.775 | 25.277 -18.756 | 1.00 22.58 |
| ATOM | 1009 | N | PHE | A | 123 | -4.820 | 24.408 -18.573 | 1.00 16.90 |
| ATOM | 1010 | CA | PHE | A | 123 | -4.218 | 23.106 -18.206 | 1.00 14.70 |
| ATOM | 1011 | C | PHE | A | 123 | -3.743 | 22.339 -19.423 | 1.00 12.50 |
| ATOM | 1012 | O | PHE | A | 123 | -2.637 | 21.841 -19.498 | 1.00 14.15 |
| ATOM | 1013 | CB | PHE | A | 123 | -5.208 | 22.277 -17.330 | 1.00 6.43 |
| ATOM | 1014 | CG | PHE | A | 123 | -4.835 | 20.798 -17.261 | 1.00 6.51 |
| ATOM | 1015 | CD1 | PHE | A | 123 | -3.500 | 20.373 -17.058 | 1.00 9.52 |
| ATOM | 1016 | CD2 | PHE | A | 123 | -5.850 | 19.826 -17.371 | 1.00 6.25 |
| ATOM | 1017 | CE1 | PHE | A | 123 | -3.187 | 19.002 -16.899 | 1.00 8.18 |
| ATOM | 1018 | CE2 | PHE | A | 123 | -5.541 | 18.451 -17.198 | 1.00 3.83 |
| ATOM | 1019 | CZ | PHE | A | 123 | -4.221 | 18.044 -16.961 | 1.00 5.79 |
| ATOM | 1020 | N | GLN | A | 124 | -4.635 | 22.274 -20.411 | 1.00 14.29 |
| ATOM | 1021 | CA | GLN | A | 124 | -4.136 | 21.729 -21.681 | 1.00 21.67 |
| ATOM | 1022 | C | GLN | A | 124 | -2.956 | 22.471 -22.323 | 1.00 15.80 |
| ATOM | 1023 | O | GLN | A | 124 | -1.991 | 21.895 -22.739 | 1.00 16.83 |
| ATOM | 1024 | CB | GLN | A | 124 | -5.278 | 21.406 -22.677 | 1.00 29.24 |
| ATOM | 1025 | CG | GLN | A | 124 | -5.396 | 22.440 -23.808 | 1.00 43.21 |
| ATOM | 1026 | CD | GLN | A | 124 | -6.649 | 22.252 -24.666 | 1.00 54.84 |

FIG. 11-20

| | | | | | | | | |
|---|---|---|---|---|---|---|---|---|
| ATOM | 1027 | OE1 | GLN | A | 124 | -7.735 | 22.771 | -24.400 | 1.00 | 58.86 |
| ATOM | 1028 | NE2 | GLN | A | 124 | -6.429 | 21.567 | -25.789 | 1.00 | 54.86 |
| ATOM | 1029 | N | ARG | A | 125 | -2.981 | 23.789 | -22.263 | 1.00 | 17.29 |
| ATOM | 1030 | CA | ARG | A | 125 | -1.737 | 24.492 | -22.537 | 1.00 | 13.51 |
| ATOM | 1031 | C | ARG | A | 125 | -0.467 | 24.029 | -21.830 | 1.00 | 17.93 |
| ATOM | 1032 | O | ARG | A | 125 | 0.491 | 23.625 | -22.476 | 1.00 | 26.29 |
| ATOM | 1033 | CB | ARG | A | 125 | -1.931 | 25.960 | -22.374 | 1.00 | 2.00 |
| ATOM | 1034 | CG | ARG | A | 125 | -0.716 | 26.776 | -22.799 | 1.00 | 11.83 |
| ATOM | 1035 | CD | ARG | A | 125 | -0.234 | 26.555 | -24.244 | 1.00 | 14.92 |
| ATOM | 1036 | NE | ARG | A | 125 | 0.906 | 27.395 | -24.578 | 1.00 | 19.60 |
| ATOM | 1037 | CZ | ARG | A | 125 | 1.614 | 27.214 | -25.707 | 1.00 | 17.17 |
| ATOM | 1038 | NH1 | ARG | A | 125 | 1.363 | 26.182 | -26.518 | 1.00 | 5.57 |
| ATOM | 1039 | NH2 | ARG | A | 125 | 2.546 | 28.139 | -25.979 | 1.00 | 7.65 |
| ATOM | 1040 | N | ALA | A | 126 | -0.444 | 24.025 | -20.505 | 1.00 | 18.87 |
| ATOM | 1041 | CA | ALA | A | 126 | 0.769 | 23.405 | -19.956 | 1.00 | 15.97 |
| ATOM | 1042 | C | ALA | A | 126 | 1.060 | 21.897 | -20.252 | 1.00 | 19.86 |
| ATOM | 1043 | O | ALA | A | 126 | 2.168 | 21.356 | -20.246 | 1.00 | 21.06 |
| ATOM | 1044 | CB | ALA | A | 126 | 0.851 | 23.710 | -18.495 | 1.00 | 9.43 |
| ATOM | 1045 | N | ARG | A | 127 | -0.024 | 21.236 | -20.602 | 1.00 | 19.10 |
| ATOM | 1046 | CA | ARG | A | 127 | 0.090 | 19.834 | -20.956 | 1.00 | 19.24 |
| ATOM | 1047 | C | ARG | A | 127 | 0.576 | 19.483 | -22.385 | 1.00 | 20.13 |
| ATOM | 1048 | O | ARG | A | 127 | 1.403 | 18.607 | -22.590 | 1.00 | 24.62 |
| ATOM | 1049 | CB | ARG | A | 127 | -1.294 | 19.286 | -20.617 | 1.00 | 19.85 |
| ATOM | 1050 | CG | ARG | A | 127 | -1.426 | 17.838 | -20.245 | 1.00 | 9.30 |
| ATOM | 1051 | CD | ARG | A | 127 | -2.857 | 17.398 | -20.549 | 1.00 | 16.41 |
| ATOM | 1052 | NE | ARG | A | 127 | -2.942 | 15.976 | -20.206 | 1.00 | 26.67 |
| ATOM | 1053 | CZ | ARG | A | 127 | -3.974 | 15.128 | -20.110 | 1.00 | 24.30 |
| ATOM | 1054 | NH1 | ARG | A | 127 | -5.199 | 15.386 | -20.518 | 1.00 | 22.82 |
| ATOM | 1055 | NH2 | ARG | A | 127 | -3.721 | 13.966 | -19.561 | 1.00 | 20.92 |
| ATOM | 1056 | N | GLU | A | 128 | 0.095 | 20.222 | -23.374 | 1.00 | 20.08 |
| ATOM | 1057 | CA | GLU | A | 128 | 0.677 | 20.319 | -24.742 | 1.00 | 22.77 |
| ATOM | 1058 | C | GLU | A | 128 | 2.131 | 20.842 | -24.863 | 1.00 | 21.60 |
| ATOM | 1059 | O | GLU | A | 128 | 3.025 | 20.314 | -25.531 | 1.00 | 19.22 |
| ATOM | 1060 | CB | GLU | A | 128 | -0.203 | 21.234 | -25.578 | 1.00 | 22.16 |
| ATOM | 1061 | CG | GLU | A | 128 | -1.573 | 20.540 | -25.674 | 1.00 | 28.09 |
| ATOM | 1062 | CD | GLU | A | 128 | -2.679 | 21.344 | -26.393 | 1.00 | 33.99 |
| ATOM | 1063 | OE1 | GLU | A | 128 | -3.719 | 20.721 | -26.668 | 1.00 | 31.71 |
| ATOM | 1064 | OE2 | GLU | A | 128 | -2.523 | 22.556 | -26.657 | 1.00 | 32.77 |
| ATOM | 1065 | N | VAL | A | 129 | 2.359 | 21.889 | -24.069 | 1.00 | 21.02 |
| ATOM | 1066 | CA | VAL | A | 129 | 3.764 | 22.234 | -23.840 | 1.00 | 17.12 |
| ATOM | 1067 | C | VAL | A | 129 | 4.629 | 21.171 | -23.190 | 1.00 | 20.61 |
| ATOM | 1068 | O | VAL | A | 129 | 5.725 | 20.883 | -23.650 | 1.00 | 26.74 |
| ATOM | 1069 | CB | VAL | A | 129 | 3.905 | 23.568 | -23.141 | 1.00 | 9.17 |
| ATOM | 1070 | CG1 | VAL | A | 129 | 3.206 | 24.703 | -23.830 | 1.00 | 6.18 |
| ATOM | 1071 | CG2 | VAL | A | 129 | 5.346 | 23.964 | -23.151 | 1.00 | 17.33 |
| ATOM | 1072 | N | ALA | A | 130 | 4.097 | 20.524 | -22.145 | 1.00 | 21.40 |
| ATOM | 1073 | CA | ALA | A | 130 | 4.879 | 19.426 | -21.572 | 1.00 | 20.28 |
| ATOM | 1074 | C | ALA | A | 130 | 5.189 | 18.249 | -22.519 | 1.00 | 19.81 |
| ATOM | 1075 | O | ALA | A | 130 | 6.313 | 17.790 | -22.693 | 1.00 | 17.16 |
| ATOM | 1076 | CB | ALA | A | 130 | 4.265 | 18.983 | -20.245 | 1.00 | 11.81 |
| ATOM | 1077 | N | SER | A | 131 | 4.138 | 17.854 | -23.233 | 1.00 | 16.85 |
| ATOM | 1078 | CA | SER | A | 131 | 4.365 | 16.957 | -24.353 | 1.00 | 22.01 |
| ATOM | 1079 | C | SER | A | 131 | 5.472 | 17.315 | -25.336 | 1.00 | 23.46 |
| ATOM | 1080 | O | SER | A | 131 | 6.307 | 16.471 | -25.605 | 1.00 | 29.86 |

FIG. 11-21

| ATOM | 1081 | CB | SER A 131 | 3.078 | 16.657 | -25.157 | 1.00 | 32.42 |
| ATOM | 1082 | OG | SER A 131 | 3.036 | 17.309 | -26.487 | 1.00 | 45.09 |
| ATOM | 1083 | N | VAL A 132 | 5.481 | 18.565 | -25.862 | 1.00 | 19.47 |
| ATOM | 1084 | CA | VAL A 132 | 6.621 | 19.050 | -26.674 | 1.00 | 14.97 |
| ATOM | 1085 | C | VAL A 132 | 8.004 | 18.994 | -26.006 | 1.00 | 21.73 |
| ATOM | 1086 | O | VAL A 132 | 9.030 | 18.512 | -26.499 | 1.00 | 26.32 |
| ATOM | 1087 | CB | VAL A 132 | 6.421 | 20.509 | -27.078 | 1.00 | 10.50 |
| ATOM | 1088 | CG1 | VAL A 132 | 5.092 | 20.712 | -27.793 | 1.00 | 2.00 |
| ATOM | 1089 | CG2 | VAL A 132 | 7.617 | 21.008 | -27.943 | 1.00 | 13.68 |
| ATOM | 1090 | N | MET A 133 | 7.990 | 19.517 | -24.765 | 1.00 | 21.73 |
| ATOM | 1091 | CA | MET A 133 | 9.244 | 19.429 | -24.033 | 1.00 | 18.13 |
| ATOM | 1092 | C | MET A 133 | 9.782 | 18.004 | -23.822 | 1.00 | 20.90 |
| ATOM | 1093 | O | MET A 133 | 10.966 | 17.712 | -23.799 | 1.00 | 23.94 |
| ATOM | 1094 | CB | MET A 133 | 9.034 | 20.162 | -22.752 | 1.00 | 15.41 |
| ATOM | 1095 | CG | MET A 133 | 8.631 | 21.653 | -22.828 | 1.00 | 16.45 |
| ATOM | 1096 | SD | MET A 133 | 8.671 | 22.417 | -21.164 | 1.00 | 17.36 |
| ATOM | 1097 | CE | MET A 133 | 10.252 | 23.273 | -21.063 | 1.00 | 19.95 |
| ATOM | 1098 | N | ASN A 134 | 8.812 | 17.109 | -23.731 | 1.00 | 20.45 |
| ATOM | 1099 | CA | ASN A 134 | 9.099 | 15.722 | -23.543 | 1.00 | 21.89 |
| ATOM | 1100 | C | ASN A 134 | 9.530 | 14.988 | -24.772 | 1.00 | 24.92 |
| ATOM | 1101 | O | ASN A 134 | 10.562 | 14.351 | -24.781 | 1.00 | 27.06 |
| ATOM | 1102 | CB | ASN A 134 | 7.898 | 15.082 | -22.888 | 1.00 | 28.60 |
| ATOM | 1103 | CG | ASN A 134 | 8.406 | 14.618 | -21.557 | 1.00 | 34.90 |
| ATOM | 1104 | OD1 | ASN A 134 | 8.343 | 15.294 | -20.561 | 1.00 | 32.71 |
| ATOM | 1105 | ND2 | ASN A 134 | 9.053 | 13.465 | -21.558 | 1.00 | 45.71 |
| ATOM | 1106 | N | ARG A 135 | 8.778 | 15.171 | -25.860 | 1.00 | 25.28 |
| ATOM | 1107 | CA | ARG A 135 | 9.364 | 14.667 | -27.119 | 1.00 | 27.44 |
| ATOM | 1108 | C | ARG A 135 | 10.760 | 15.241 | -27.464 | 1.00 | 26.60 |
| ATOM | 1109 | O | ARG A 135 | 11.613 | 14.555 | -28.001 | 1.00 | 30.11 |
| ATOM | 1110 | CB | ARG A 135 | 8.308 | 14.684 | -28.281 | 1.00 | 27.03 |
| ATOM | 1111 | CG | ARG A 135 | 7.179 | 13.642 | -27.996 | 1.00 | 34.55 |
| ATOM | 1112 | CD | ARG A 135 | 5.818 | 13.581 | -28.785 | 1.00 | 35.93 |
| ATOM | 1113 | NE | ARG A 135 | 4.831 | 14.663 | -28.514 | 1.00 | 33.67 |
| ATOM | 1114 | CZ | ARG A 135 | 4.961 | 15.825 | -29.155 | 1.00 | 33.25 |
| ATOM | 1115 | NH1 | ARG A 135 | 5.904 | 15.928 | -30.039 | 1.00 | 35.00 |
| ATOM | 1116 | NH2 | ARG A 135 | 4.218 | 16.877 | -28.926 | 1.00 | 21.96 |
| ATOM | 1117 | N | ALA A 136 | 11.013 | 16.515 | -27.038 | 1.00 | 27.07 |
| ATOM | 1118 | CA | ALA A 136 | 12.364 | 17.111 | -27.152 | 1.00 | 24.50 |
| ATOM | 1119 | C | ALA A 136 | 13.462 | 16.590 | -26.261 | 1.00 | 26.01 |
| ATOM | 1120 | O | ALA A 136 | 14.627 | 16.961 | -26.348 | 1.00 | 28.12 |
| ATOM | 1121 | CB | ALA A 136 | 12.423 | 18.601 | -26.894 | 1.00 | 18.63 |
| ATOM | 1122 | N | LEU A 137 | 13.067 | 15.682 | -25.386 | 1.00 | 24.74 |
| ATOM | 1123 | CA | LEU A 137 | 14.180 | 15.176 | -24.619 | 1.00 | 22.40 |
| ATOM | 1124 | C | LEU A 137 | 14.447 | 13.690 | -24.739 | 1.00 | 23.23 |
| ATOM | 1125 | O | LEU A 137 | 15.418 | 13.131 | -24.244 | 1.00 | 17.56 |
| ATOM | 1126 | CB | LEU A 137 | 14.112 | 15.859 | -23.258 | 1.00 | 21.30 |
| ATOM | 1127 | CG | LEU A 137 | 13.494 | 15.262 | -21.978 | 1.00 | 21.33 |
| ATOM | 1128 | CD1 | LEU A 137 | 12.344 | 14.274 | -22.182 | 1.00 | 13.98 |
| ATOM | 1129 | CD2 | LEU A 137 | 13.287 | 16.393 | -20.942 | 1.00 | 18.23 |
| ATOM | 1130 | N | GLU A 138 | 13.546 | 13.084 | -25.541 | 1.00 | 30.05 |
| ATOM | 1131 | CA | GLU A 138 | 13.381 | 11.611 | -25.595 | 1.00 | 41.12 |
| ATOM | 1132 | C | GLU A 138 | 14.636 | 10.795 | -25.947 | 1.00 | 49.33 |
| ATOM | 1133 | O | GLU A 138 | 14.949 | 9.699 | -25.464 | 1.00 | 51.88 |
| ATOM | 1134 | CB | GLU A 138 | 12.191 | 11.197 | -26.523 | 1.00 | 40.25 |

FIG. 11-22

```
ATOM   1135  CG  GLU A 138      11.191  10.239 -25.854  1.00 41.18
ATOM   1136  CD  GLU A 138      10.548  10.899 -24.617  1.00 45.73
ATOM   1137  OE1 GLU A 138      11.150  10.869 -23.510  1.00 45.83
ATOM   1138  OE2 GLU A 138       9.435  11.430 -24.767  1.00 42.99
ATOM   1139  N   ASN A 139      15.349  11.485 -26.853  1.00 53.32
ATOM   1140  CA  ASN A 139      16.562  10.995 -27.513  1.00 53.92
ATOM   1141  C   ASN A 139      17.792  11.866 -27.299  1.00 50.93
ATOM   1142  O   ASN A 139      18.813  11.711 -27.966  1.00 54.85
ATOM   1143  CB  ASN A 139      16.255  10.936 -29.019  1.00 57.01
ATOM   1144  CG  ASN A 139      15.918  12.326 -29.543  1.00 56.92
ATOM   1145  OD1 ASN A 139      15.004  12.986 -29.090  1.00 56.34
ATOM   1146  ND2 ASN A 139      16.716  12.772 -30.495  1.00 60.09
ATOM   1147  N   ALA A 140      17.587  12.877 -26.438  1.00 43.70
ATOM   1148  CA  ALA A 140      18.573  13.954 -26.402  1.00 36.27
ATOM   1149  C   ALA A 140      19.538  13.850 -25.254  1.00 33.44
ATOM   1150  O   ALA A 140      19.213  14.288 -24.176  1.00 34.29
ATOM   1151  CB  ALA A 140      17.889  15.291 -26.306  1.00 27.20
ATOM   1152  N   HIS A 141      20.716  13.263 -25.531  1.00 29.70
ATOM   1153  CA  HIS A 141      21.670  13.017 -24.432  1.00 23.14
ATOM   1154  C   HIS A 141      22.548  14.116 -23.873  1.00 20.71
ATOM   1155  O   HIS A 141      23.340  13.924 -22.970  1.00 20.00
ATOM   1156  CB  HIS A 141      22.581  11.848 -24.731  1.00 21.44
ATOM   1157  CG  HIS A 141      21.803  10.594 -25.029  1.00 22.00
ATOM   1158  ND1 HIS A 141      21.467   9.728 -24.069  1.00 23.28
ATOM   1159  CD2 HIS A 141      21.336  10.108 -26.253  1.00 21.33
ATOM   1160  CE1 HIS A 141      20.779   8.683 -24.650  1.00 22.65
ATOM   1161  NE2 HIS A 141      20.709   8.926 -25.998  1.00 26.82
ATOM   1162  N   ASP A 142      22.377  15.298 -24.415  1.00 24.13
ATOM   1163  CA  ASP A 142      22.913  16.507 -23.751  1.00 25.36
ATOM   1164  C   ASP A 142      21.900  17.685 -23.882  1.00 23.65
ATOM   1165  O   ASP A 142      20.919  17.616 -24.653  1.00 20.09
ATOM   1166  CB  ASP A 142      24.311  16.829 -24.325  1.00 29.37
ATOM   1167  CG  ASP A 142      24.212  17.007 -25.834  1.00 40.64
ATOM   1168  OD1 ASP A 142      24.524  16.062 -26.547  1.00 46.31
ATOM   1169  OD2 ASP A 142      23.772  18.068 -26.293  1.00 44.80
ATOM   1170  N   GLU A 143      22.127  18.780 -23.114  1.00 24.28
ATOM   1171  CA  GLU A 143      21.077  19.829 -23.312  1.00 26.39
ATOM   1172  C   GLU A 143      20.828  20.552 -24.670  1.00 28.86
ATOM   1173  O   GLU A 143      19.693  20.703 -25.127  1.00 25.07
ATOM   1174  CB  GLU A 143      20.926  20.790 -22.149  1.00 21.14
ATOM   1175  CG  GLU A 143      21.727  22.064 -22.244  1.00 27.19
ATOM   1176  CD  GLU A 143      20.960  23.195 -21.567  1.00 31.34
ATOM   1177  OE1 GLU A 143      21.555  24.087 -20.960  1.00 40.28
ATOM   1178  OE2 GLU A 143      19.735  23.226 -21.663  1.00 40.56
ATOM   1179  N   SER A 144      21.955  20.894 -25.342  1.00 27.47
ATOM   1180  CA  SER A 144      21.968  21.144 -26.797  1.00 23.70
ATOM   1181  C   SER A 144      21.062  20.309 -27.641  1.00 24.18
ATOM   1182  O   SER A 144      20.144  20.832 -28.238  1.00 32.43
ATOM   1183  CB  SER A 144      23.328  20.903 -27.475  1.00 25.14
ATOM   1184  OG  SER A 144      24.235  21.902 -27.072  1.00 24.97
ATOM   1185  N   ALA A 145      21.278  18.988 -27.696  1.00 22.50
ATOM   1186  CA  ALA A 145      20.373  18.188 -28.543  1.00 18.67
ATOM   1187  C   ALA A 145      18.886  18.443 -28.244  1.00 23.07
ATOM   1188  O   ALA A 145      17.979  18.564 -29.075  1.00 21.69
```

FIG.11-23

| ATOM | 1189 | CB  | ALA A 145 | 20.688 | 16.683 | -28.320 | 1.00 | 15.56 |
|------|------|-----|-----------|--------|--------|---------|------|-------|
| ATOM | 1190 | N   | TYR A 146 | 18.688 | 18.586 | -26.894 | 1.00 | 28.25 |
| ATOM | 1191 | CA  | TYR A 146 | 17.351 | 18.967 | -26.374 | 1.00 | 26.04 |
| ATOM | 1192 | C   | TYR A 146 | 16.849 | 20.304 | -26.963 | 1.00 | 24.30 |
| ATOM | 1193 | O   | TYR A 146 | 15.912 | 20.374 | -27.753 | 1.00 | 20.88 |
| ATOM | 1194 | CB  | TYR A 146 | 17.337 | 18.829 | -24.811 | 1.00 | 24.05 |
| ATOM | 1195 | CG  | TYR A 146 | 16.221 | 19.569 | -24.073 | 1.00 | 25.13 |
| ATOM | 1196 | CD1 | TYR A 146 | 14.872 | 19.118 | -24.094 | 1.00 | 20.60 |
| ATOM | 1197 | CD2 | TYR A 146 | 16.572 | 20.759 | -23.401 | 1.00 | 28.34 |
| ATOM | 1198 | CE1 | TYR A 146 | 13.878 | 19.867 | -23.433 | 1.00 | 21.13 |
| ATOM | 1199 | CE2 | TYR A 146 | 15.566 | 21.508 | -22.753 | 1.00 | 29.25 |
| ATOM | 1200 | CZ  | TYR A 146 | 14.233 | 21.032 | -22.711 | 1.00 | 26.86 |
| ATOM | 1201 | OH  | TYR A 146 | 13.297 | 21.685 | -21.897 | 1.00 | 21.00 |
| ATOM | 1202 | N   | LEU A 147 | 17.550 | 21.375 | -26.581 | 1.00 | 22.67 |
| ATOM | 1203 | CA  | LEU A 147 | 17.124 | 22.671 | -27.059 | 1.00 | 21.92 |
| ATOM | 1204 | C   | LEU A 147 | 16.928 | 22.834 | -28.546 | 1.00 | 23.94 |
| ATOM | 1205 | O   | LEU A 147 | 16.088 | 23.600 | -29.016 | 1.00 | 24.44 |
| ATOM | 1206 | CB  | LEU A 147 | 18.129 | 23.709 | -26.669 | 1.00 | 20.94 |
| ATOM | 1207 | CG  | LEU A 147 | 18.474 | 23.807 | -25.219 | 1.00 | 16.58 |
| ATOM | 1208 | CD1 | LEU A 147 | 17.362 | 24.405 | -24.355 | 1.00 | 16.40 |
| ATOM | 1209 | CD2 | LEU A 147 | 19.676 | 24.727 | -25.192 | 1.00 | 13.02 |
| ATOM | 1210 | N   | ASP A 148 | 17.787 | 22.112 | -29.263 | 1.00 | 24.07 |
| ATOM | 1211 | CA  | ASP A 148 | 17.684 | 22.123 | -30.734 | 1.00 | 24.95 |
| ATOM | 1212 | C   | ASP A 148 | 16.406 | 21.589 | -31.268 | 1.00 | 21.78 |
| ATOM | 1213 | O   | ASP A 148 | 15.726 | 22.321 | -31.993 | 1.00 | 22.91 |
| ATOM | 1214 | CB  | ASP A 148 | 18.815 | 21.354 | -31.451 | 1.00 | 29.39 |
| ATOM | 1215 | CG  | ASP A 148 | 20.143 | 22.050 | -31.345 | 1.00 | 29.90 |
| ATOM | 1216 | OD1 | ASP A 148 | 21.068 | 21.445 | -31.837 | 1.00 | 33.24 |
| ATOM | 1217 | OD2 | ASP A 148 | 20.282 | 23.169 | -30.797 | 1.00 | 36.69 |
| ATOM | 1218 | N   | ASN A 149 | 16.125 | 20.345 | -30.760 | 1.00 | 22.40 |
| ATOM | 1219 | CA  | ASN A 149 | 14.863 | 19.562 | -30.836 | 1.00 | 23.62 |
| ATOM | 1220 | C   | ASN A 149 | 13.569 | 20.296 | -30.451 | 1.00 | 20.30 |
| ATOM | 1221 | O   | ASN A 149 | 12.631 | 20.494 | -31.218 | 1.00 | 23.88 |
| ATOM | 1222 | CB  | ASN A 149 | 14.911 | 18.317 | -29.935 | 1.00 | 28.49 |
| ATOM | 1223 | CG  | ASN A 149 | 15.796 | 17.150 | -30.392 | 1.00 | 27.83 |
| ATOM | 1224 | OD1 | ASN A 149 | 16.126 | 16.974 | -31.550 | 1.00 | 26.61 |
| ATOM | 1225 | ND2 | ASN A 149 | 16.132 | 16.305 | -29.403 | 1.00 | 21.69 |
| ATOM | 1226 | N   | LEU A 150 | 13.609 | 20.800 | -29.231 | 1.00 | 18.53 |
| ATOM | 1227 | CA  | LEU A 150 | 12.692 | 21.872 | -28.816 | 1.00 | 19.50 |
| ATOM | 1228 | C   | LEU A 150 | 12.380 | 22.987 | -29.819 | 1.00 | 21.48 |
| ATOM | 1229 | O   | LEU A 150 | 11.298 | 23.130 | -30.406 | 1.00 | 24.33 |
| ATOM | 1230 | CB  | LEU A 150 | 13.209 | 22.465 | -27.489 | 1.00 | 19.61 |
| ATOM | 1231 | CG  | LEU A 150 | 12.198 | 23.245 | -26.650 | 1.00 | 16.89 |
| ATOM | 1232 | CD1 | LEU A 150 | 12.771 | 23.366 | -25.244 | 1.00 | 22.25 |
| ATOM | 1233 | CD2 | LEU A 150 | 10.753 | 22.667 | -26.639 | 1.00 | 19.57 |
| ATOM | 1234 | N   | LYS A 151 | 13.437 | 23.783 | -30.036 | 1.00 | 20.26 |
| ATOM | 1235 | CA  | LYS A 151 | 13.263 | 24.786 | -31.062 | 1.00 | 18.29 |
| ATOM | 1236 | C   | LYS A 151 | 12.564 | 24.290 | -32.376 | 1.00 | 17.36 |
| ATOM | 1237 | O   | LYS A 151 | 11.738 | 24.986 | -32.950 | 1.00 | 19.65 |
| ATOM | 1238 | CB  | LYS A 151 | 14.607 | 25.471 | -31.273 | 1.00 | 16.45 |
| ATOM | 1239 | CG  | LYS A 151 | 15.376 | 26.160 | -30.163 | 1.00 | 18.22 |
| ATOM | 1240 | CD  | LYS A 151 | 16.875 | 26.151 | -30.596 | 1.00 | 32.78 |
| ATOM | 1241 | CE  | LYS A 151 | 18.100 | 26.312 | -29.606 | 1.00 | 36.46 |
| ATOM | 1242 | NZ  | LYS A 151 | 19.394 | 25.692 | -30.089 | 1.00 | 30.10 |

FIG. 11-24

```
ATOM   1243  N    LYS A 152      12.873  23.053 -32.838  1.00 14.10
ATOM   1244  CA   LYS A 152      12.311  22.607 -34.134  1.00 14.19
ATOM   1245  C    LYS A 152      10.788  22.380 -34.238  1.00 20.55
ATOM   1246  O    LYS A 152      10.069  22.816 -35.171  1.00 17.83
ATOM   1247  CB   LYS A 152      12.999  21.312 -34.615  1.00 17.74
ATOM   1248  CG   LYS A 152      12.544  20.856 -36.027  1.00 21.38
ATOM   1249  CD   LYS A 152      12.511  19.359 -36.394  1.00 24.41
ATOM   1250  CE   LYS A 152      13.849  18.639 -36.281  1.00 31.69
ATOM   1251  NZ   LYS A 152      14.940  19.460 -36.842  1.00 42.38
ATOM   1252  N    GLU A 153      10.364  21.643 -33.157  1.00 22.65
ATOM   1253  CA   GLU A 153       8.908  21.399 -32.895  1.00 19.18
ATOM   1254  C    GLU A 153       8.088  22.708 -32.701  1.00 13.41
ATOM   1255  O    GLU A 153       7.099  23.032 -33.319  1.00 15.31
ATOM   1256  CB   GLU A 153       8.745  20.326 -31.759  1.00 16.42
ATOM   1257  CG   GLU A 153       7.231  19.969 -31.730  1.00 21.23
ATOM   1258  CD   GLU A 153       6.763  18.668 -31.095  1.00 15.07
ATOM   1259  OE1  GLU A 153       7.536  17.925 -30.511  1.00 24.12
ATOM   1260  OE2  GLU A 153       5.580  18.361 -31.201  1.00 18.77
ATOM   1261  N    LEU A 154       8.671  23.583 -31.899  1.00 12.59
ATOM   1262  CA   LEU A 154       8.083  24.894 -31.645  1.00 13.52
ATOM   1263  C    LEU A 154       7.821  25.709 -32.867  1.00 16.17
ATOM   1264  O    LEU A 154       6.685  25.999 -33.191  1.00 20.45
ATOM   1265  CB   LEU A 154       9.054  25.581 -30.693  1.00 19.40
ATOM   1266  CG   LEU A 154       8.671  25.767 -29.225  1.00 22.90
ATOM   1267  CD1  LEU A 154       9.922  25.982 -28.373  1.00 26.77
ATOM   1268  CD2  LEU A 154       7.810  24.660 -28.652  1.00 24.81
ATOM   1269  N    ALA A 155       8.933  26.005 -33.582  1.00 16.40
ATOM   1270  CA   ALA A 155       8.915  26.502 -34.979  1.00 16.98
ATOM   1271  C    ALA A 155       7.999  25.803 -35.996  1.00 18.10
ATOM   1272  O    ALA A 155       7.301  26.326 -36.849  1.00 18.63
ATOM   1273  CB   ALA A 155      10.304  26.309 -35.550  1.00 18.78
ATOM   1274  N    ASN A 156       8.019  24.482 -35.859  1.00 23.57
ATOM   1275  CA   ASN A 156       7.093  23.702 -36.695  1.00 22.37
ATOM   1276  C    ASN A 156       5.578  23.852 -36.456  1.00 18.99
ATOM   1277  O    ASN A 156       4.830  23.940 -37.407  1.00 12.95
ATOM   1278  CB   ASN A 156       7.514  22.251 -36.594  1.00 32.07
ATOM   1279  CG   ASN A 156       7.758  21.743 -37.967  1.00 39.49
ATOM   1280  OD1  ASN A 156       8.823  21.238 -38.285  1.00 51.60
ATOM   1281  ND2  ASN A 156       6.739  21.880 -38.809  1.00 38.48
ATOM   1282  N    GLY A 157       5.187  23.914 -35.173  1.00 16.62
ATOM   1283  CA   GLY A 157       3.845  24.369 -34.767  1.00 17.93
ATOM   1284  C    GLY A 157       3.525  25.865 -34.728  1.00 20.65
ATOM   1285  O    GLY A 157       2.448  26.345 -34.382  1.00 23.97
ATOM   1286  N    ASN A 158       4.552  26.621 -35.148  1.00 20.43
ATOM   1287  CA   ASN A 158       4.426  28.079 -35.197  1.00 17.37
ATOM   1288  C    ASN A 158       4.022  28.669 -33.846  1.00 15.42
ATOM   1289  O    ASN A 158       3.248  29.598 -33.687  1.00 18.44
ATOM   1290  CB   ASN A 158       3.569  28.486 -36.409  1.00 17.52
ATOM   1291  CG   ASN A 158       4.373  28.296 -37.689  1.00 15.75
ATOM   1292  OD1  ASN A 158       5.290  29.014 -37.970  1.00 21.82
ATOM   1293  ND2  ASN A 158       4.005  27.366 -38.528  1.00 11.00
ATOM   1294  N    ASP A 159       4.677  28.070 -32.859  1.00 14.16
ATOM   1295  CA   ASP A 159       4.348  28.371 -31.474  1.00 16.19
ATOM   1296  C    ASP A 159       5.064  29.564 -30.918  1.00 16.31
```

FIG. 11-25

| ATOM | 1297 | O   | ASP A 159 | 6.280  | 29.700 | -31.093 | 1.00 | 19.15 |
|------|------|-----|-----------|--------|--------|---------|------|-------|
| ATOM | 1298 | CB  | ASP A 159 | 4.653  | 27.179 | -30.543 | 1.00 | 20.38 |
| ATOM | 1299 | CG  | ASP A 159 | 3.875  | 27.324 | -29.226 | 1.00 | 19.14 |
| ATOM | 1300 | OD1 | ASP A 159 | 4.321  | 28.021 | -28.324 | 1.00 | 16.17 |
| ATOM | 1301 | OD2 | ASP A 159 | 2.803  | 26.758 | -29.103 | 1.00 | 21.51 |
| ATOM | 1302 | N   | ALA A 160 | 4.297  | 30.429 | -30.208 | 1.00 | 10.75 |
| ATOM | 1303 | CA  | ALA A 160 | 4.891  | 31.661 | -29.707 | 1.00 | 5.46  |
| ATOM | 1304 | C   | ALA A 160 | 6.072  | 31.425 | -28.796 | 1.00 | 7.55  |
| ATOM | 1305 | O   | ALA A 160 | 7.002  | 32.195 | -28.632 | 1.00 | 11.64 |
| ATOM | 1306 | CB  | ALA A 160 | 3.870  | 32.495 | -28.964 | 1.00 | 2.58  |
| ATOM | 1307 | N   | LEU A 161 | 6.040  | 30.277 | -28.177 | 1.00 | 10.41 |
| ATOM | 1308 | CA  | LEU A 161 | 7.164  | 29.929 | -27.292 | 1.00 | 13.10 |
| ATOM | 1309 | C   | LEU A 161 | 8.562  | 29.893 | -27.997 | 1.00 | 19.26 |
| ATOM | 1310 | O   | LEU A 161 | 9.618  | 30.183 | -27.453 | 1.00 | 24.14 |
| ATOM | 1311 | CB  | LEU A 161 | 6.748  | 28.606 | -26.702 | 1.00 | 7.62  |
| ATOM | 1312 | CG  | LEU A 161 | 6.573  | 28.362 | -25.217 | 1.00 | 12.44 |
| ATOM | 1313 | CD1 | LEU A 161 | 5.497  | 27.285 | -25.096 | 1.00 | 7.34  |
| ATOM | 1314 | CD2 | LEU A 161 | 6.470  | 29.573 | -24.299 | 1.00 | 8.33  |
| ATOM | 1315 | N   | ARG A 162 | 8.520  | 29.590 | -29.300 | 1.00 | 17.91 |
| ATOM | 1316 | CA  | ARG A 162 | 9.741  | 29.614 | -30.054 | 1.00 | 22.53 |
| ATOM | 1317 | C   | ARG A 162 | 10.657 | 30.816 | -29.838 | 1.00 | 23.84 |
| ATOM | 1318 | O   | ARG A 162 | 11.877 | 30.712 | -29.840 | 1.00 | 22.72 |
| ATOM | 1319 | CB  | ARG A 162 | 9.383  | 29.470 | -31.529 | 1.00 | 24.77 |
| ATOM | 1320 | CG  | ARG A 162 | 10.634 | 29.346 | -32.431 | 1.00 | 26.52 |
| ATOM | 1321 | CD  | ARG A 162 | 11.546 | 28.196 | -31.967 | 1.00 | 29.71 |
| ATOM | 1322 | NE  | ARG A 162 | 12.638 | 28.024 | -32.891 | 1.00 | 32.46 |
| ATOM | 1323 | CZ  | ARG A 162 | 13.689 | 28.824 | -32.761 | 1.00 | 35.13 |
| ATOM | 1324 | NH1 | ARG A 162 | 14.693 | 28.655 | -33.572 | 1.00 | 33.09 |
| ATOM | 1325 | NH2 | ARG A 162 | 13.739 | 29.769 | -31.846 | 1.00 | 31.93 |
| ATOM | 1326 | N   | ASN A 163 | 9.978  | 31.946 | -29.692 | 1.00 | 26.28 |
| ATOM | 1327 | CA  | ASN A 163 | 10.741 | 33.191 | -29.668 | 1.00 | 30.73 |
| ATOM | 1328 | C   | ASN A 163 | 11.200 | 33.640 | -28.319 | 1.00 | 28.91 |
| ATOM | 1329 | O   | ASN A 163 | 11.753 | 34.729 | -28.200 | 1.00 | 32.90 |
| ATOM | 1330 | CB  | ASN A 163 | 9.975  | 34.353 | -30.287 | 1.00 | 37.23 |
| ATOM | 1331 | CG  | ASN A 163 | 9.577  | 34.008 | -31.700 | 1.00 | 44.29 |
| ATOM | 1332 | OD1 | ASN A 163 | 10.405 | 33.698 | -32.555 | 1.00 | 52.13 |
| ATOM | 1333 | ND2 | ASN A 163 | 8.254  | 34.031 | -31.919 | 1.00 | 42.06 |
| ATOM | 1334 | N   | GLU A 164 | 10.934 | 32.769 | -27.339 | 1.00 | 22.38 |
| ATOM | 1335 | CA  | GLU A 164 | 11.356 | 33.091 | -25.990 | 1.00 | 19.95 |
| ATOM | 1336 | C   | GLU A 164 | 12.878 | 33.197 | -25.854 | 1.00 | 23.12 |
| ATOM | 1337 | O   | GLU A 164 | 13.615 | 32.303 | -26.246 | 1.00 | 23.70 |
| ATOM | 1338 | CB  | GLU A 164 | 10.841 | 32.001 | -25.044 | 1.00 | 19.62 |
| ATOM | 1339 | CG  | GLU A 164 | 9.354  | 32.053 | -24.646 | 1.00 | 6.89  |
| ATOM | 1340 | CD  | GLU A 164 | 9.124  | 33.290 | -23.840 | 1.00 | 4.89  |
| ATOM | 1341 | OE1 | GLU A 164 | 9.767  | 33.492 | -22.818 | 1.00 | 2.84  |
| ATOM | 1342 | OE2 | GLU A 164 | 8.323  | 34.090 | -24.292 | 1.00 | 9.70  |
| ATOM | 1343 | N   | ASP A 165 | 13.318 | 34.314 | -25.281 | 1.00 | 19.81 |
| ATOM | 1344 | CA  | ASP A 165 | 14.645 | 34.398 | -24.698 | 1.00 | 20.09 |
| ATOM | 1345 | C   | ASP A 165 | 15.392 | 33.129 | -24.183 | 1.00 | 21.62 |
| ATOM | 1346 | O   | ASP A 165 | 14.805 | 32.106 | -23.919 | 1.00 | 25.28 |
| ATOM | 1347 | CB  | ASP A 165 | 14.416 | 35.444 | -23.650 | 1.00 | 30.45 |
| ATOM | 1348 | CG  | ASP A 165 | 15.390 | 36.550 | -23.854 | 1.00 | 36.14 |
| ATOM | 1349 | OD1 | ASP A 165 | 16.572 | 36.280 | -23.567 | 1.00 | 41.59 |
| ATOM | 1350 | OD2 | ASP A 165 | 14.962 | 37.636 | -24.282 | 1.00 | 35.91 |

FIG. 11-26

| | | | | | | | | | |
|---|---|---|---|---|---|---|---|---|---|
| ATOM | 1351 | N | ALA | A | 166 | 16.733 | 33.113 | -24.033 | 1.00 22.50 |
| ATOM | 1352 | CA | ALA | A | 166 | 17.353 | 31.775 | -23.863 | 1.00 18.58 |
| ATOM | 1353 | C | ALA | A | 166 | 17.915 | 31.385 | -22.509 | 1.00 22.02 |
| ATOM | 1354 | O | ALA | A | 166 | 18.270 | 30.233 | -22.177 | 1.00 21.81 |
| ATOM | 1355 | CB | ALA | A | 166 | 18.468 | 31.606 | -24.853 | 1.00 24.93 |
| ATOM | 1356 | N | ARG | A | 167 | 17.918 | 32.490 | -21.743 | 1.00 24.93 |
| ATOM | 1357 | CA | ARG | A | 167 | 17.704 | 32.643 | -20.291 | 1.00 29.26 |
| ATOM | 1358 | C | ARG | A | 167 | 16.239 | 32.910 | -19.775 | 1.00 28.31 |
| ATOM | 1359 | O | ARG | A | 167 | 15.940 | 33.139 | -18.605 | 1.00 34.21 |
| ATOM | 1360 | CB | ARG | A | 167 | 18.697 | 33.701 | -19.796 | 1.00 29.00 |
| ATOM | 1361 | CG | ARG | A | 167 | 20.082 | 33.030 | -19.648 | 1.00 41.29 |
| ATOM | 1362 | CD | ARG | A | 167 | 20.136 | 31.838 | -18.655 | 1.00 42.25 |
| ATOM | 1363 | NE | ARG | A | 167 | 21.437 | 31.165 | -18.684 | 1.00 47.05 |
| ATOM | 1364 | CZ | ARG | A | 167 | 22.386 | 31.284 | -17.756 | 1.00 49.75 |
| ATOM | 1365 | NH1 | ARG | A | 167 | 23.539 | 30.679 | -17.932 | 1.00 52.71 |
| ATOM | 1366 | NH2 | ARG | A | 167 | 22.214 | 32.004 | -16.684 | 1.00 50.51 |
| ATOM | 1367 | N | SER | A | 168 | 15.299 | 32.776 | -20.696 | 1.00 24.53 |
| ATOM | 1368 | CA | SER | A | 168 | 13.904 | 32.741 | -20.259 | 1.00 24.27 |
| ATOM | 1369 | C | SER | A | 168 | 13.632 | 31.562 | -19.342 | 1.00 25.32 |
| ATOM | 1370 | O | SER | A | 168 | 14.253 | 30.499 | -19.557 | 1.00 21.71 |
| ATOM | 1371 | CB | SER | A | 168 | 12.938 | 32.514 | -21.425 | 1.00 19.08 |
| ATOM | 1372 | OG | SER | A | 168 | 13.031 | 31.122 | -21.776 | 1.00 22.22 |
| ATOM | 1373 | N | PRO | A | 169 | 12.617 | 31.775 | -18.413 | 1.00 23.69 |
| ATOM | 1374 | CA | PRO | A | 169 | 12.031 | 30.684 | -17.623 | 1.00 19.02 |
| ATOM | 1375 | C | PRO | A | 169 | 11.730 | 29.415 | -18.376 | 1.00 21.60 |
| ATOM | 1376 | O | PRO | A | 169 | 12.018 | 28.354 | -17.861 | 1.00 27.67 |
| ATOM | 1377 | CB | PRO | A | 169 | 10.802 | 31.323 | -16.979 | 1.00 19.26 |
| ATOM | 1378 | CG | PRO | A | 169 | 11.168 | 32.799 | -16.797 | 1.00 14.12 |
| ATOM | 1379 | CD | PRO | A | 169 | 11.911 | 33.041 | -18.122 | 1.00 24.15 |
| ATOM | 1380 | N | PHE | A | 170 | 11.215 | 29.541 | -19.616 | 1.00 22.17 |
| ATOM | 1381 | CA | PHE | A | 170 | 10.924 | 28.374 | -20.489 | 1.00 19.90 |
| ATOM | 1382 | C | PHE | A | 170 | 12.094 | 27.542 | -21.004 | 1.00 21.58 |
| ATOM | 1383 | O | PHE | A | 170 | 12.090 | 26.322 | -21.073 | 1.00 20.63 |
| ATOM | 1384 | CB | PHE | A | 170 | 10.089 | 28.836 | -21.711 | 1.00 22.74 |
| ATOM | 1385 | CG | PHE | A | 170 | 9.854 | 27.731 | -22.751 | 1.00 25.80 |
| ATOM | 1386 | CD1 | PHE | A | 170 | 10.352 | 27.890 | -24.056 | 1.00 25.41 |
| ATOM | 1387 | CD2 | PHE | A | 170 | 9.155 | 26.557 | -22.417 | 1.00 26.87 |
| ATOM | 1388 | CE1 | PHE | A | 170 | 10.217 | 26.850 | -25.008 | 1.00 29.45 |
| ATOM | 1389 | CE2 | PHE | A | 170 | 9.000 | 25.521 | -23.373 | 1.00 32.72 |
| ATOM | 1390 | CZ | PHE | A | 170 | 9.566 | 25.649 | -24.661 | 1.00 31.44 |
| ATOM | 1391 | N | TYR | A | 171 | 13.112 | 28.294 | -21.399 | 1.00 22.22 |
| ATOM | 1392 | CA | TYR | A | 171 | 14.277 | 27.585 | -21.910 | 1.00 20.77 |
| ATOM | 1393 | C | TYR | A | 171 | 15.223 | 27.096 | -20.805 | 1.00 18.93 |
| ATOM | 1394 | O | TYR | A | 171 | 15.758 | 25.993 | -20.759 | 1.00 20.44 |
| ATOM | 1395 | CB | TYR | A | 171 | 14.923 | 28.514 | -22.961 | 1.00 17.22 |
| ATOM | 1396 | CG | TYR | A | 171 | 14.256 | 28.395 | -24.328 | 1.00 12.48 |
| ATOM | 1397 | CD1 | TYR | A | 171 | 13.933 | 29.567 | -25.031 | 1.00 10.69 |
| ATOM | 1398 | CD2 | TYR | A | 171 | 14.027 | 27.117 | -24.914 | 1.00 18.67 |
| ATOM | 1399 | CE1 | TYR | A | 171 | 13.375 | 29.456 | -26.311 | 1.00 12.02 |
| ATOM | 1400 | CE2 | TYR | A | 171 | 13.478 | 27.017 | -26.210 | 1.00 12.53 |
| ATOM | 1401 | CZ | TYR | A | 171 | 13.125 | 28.197 | -26.882 | 1.00 10.69 |
| ATOM | 1402 | OH | TYR | A | 171 | 12.501 | 28.142 | -28.130 | 1.00 15.50 |
| ATOM | 1403 | N | SER | A | 172 | 15.366 | 27.984 | -19.815 | 1.00 17.32 |
| ATOM | 1404 | CA | SER | A | 172 | 16.117 | 27.520 | -18.628 | 1.00 22.81 |

FIG.11-27

```
ATOM   1405  C    SER A 172     15.610  26.319 -17.814  1.00 24.53
ATOM   1406  O    SER A 172     16.246  25.835 -16.885  1.00 28.27
ATOM   1407  CB   SER A 172     16.259  28.529 -17.492  1.00 25.45
ATOM   1408  OG   SER A 172     16.212  29.892 -17.909  1.00 34.26
ATOM   1409  N    ALA A 173     14.393  25.913 -18.114  1.00 21.74
ATOM   1410  CA   ALA A 173     13.682  25.148 -17.114  1.00 20.35
ATOM   1411  C    ALA A 173     14.383  23.821 -16.739  1.00 21.96
ATOM   1412  O    ALA A 173     14.592  23.443 -15.579  1.00 24.34
ATOM   1413  CB   ALA A 173     12.261  24.961 -17.655  1.00 11.33
ATOM   1414  N    LEU A 174     14.821  23.143 -17.802  1.00 20.38
ATOM   1415  CA   LEU A 174     15.558  21.893 -17.541  1.00 25.17
ATOM   1416  C    LEU A 174     16.965  22.002 -16.884  1.00 29.42
ATOM   1417  O    LEU A 174     17.199  21.356 -15.889  1.00 32.72
ATOM   1418  CB   LEU A 174     15.576  21.072 -18.820  1.00 26.20
ATOM   1419  CG   LEU A 174     16.355  19.782 -18.667  1.00 27.83
ATOM   1420  CD1  LEU A 174     16.965  19.373 -20.005  1.00 26.81
ATOM   1421  CD2  LEU A 174     15.543  18.676 -18.021  1.00 22.28
ATOM   1422  N    ARG A 175     17.881  22.868 -17.389  1.00 32.63
ATOM   1423  CA   ARG A 175     19.184  23.190 -16.699  1.00 30.41
ATOM   1424  C    ARG A 175     18.993  23.833 -15.315  1.00 31.35
ATOM   1425  O    ARG A 175     19.854  23.953 -14.433  1.00 33.33
ATOM   1426  CB   ARG A 175     20.077  24.158 -17.537  1.00 23.18
ATOM   1427  CG   ARG A 175     19.508  25.592 -17.523  1.00 19.24
ATOM   1428  CD   ARG A 175     20.285  26.715 -18.198  1.00 24.94
ATOM   1429  NE   ARG A 175     20.012  26.643 -19.629  1.00 28.54
ATOM   1430  CZ   ARG A 175     19.542  27.672 -20.325  1.00 24.11
ATOM   1431  NH1  ARG A 175     19.485  28.874 -19.814  1.00 18.91
ATOM   1432  NH2  ARG A 175     19.148  27.500 -21.561  1.00 28.67
ATOM   1433  N    ASN A 176     17.744  24.254 -15.141  1.00 27.91
ATOM   1434  CA   ASN A 176     17.478  24.739 -13.806  1.00 27.34
ATOM   1435  C    ASN A 176     16.790  23.819 -12.789  1.00 26.31
ATOM   1436  O    ASN A 176     16.864  24.039 -11.587  1.00 32.41
ATOM   1437  CB   ASN A 176     16.844  26.086 -13.927  1.00 31.23
ATOM   1438  CG   ASN A 176     17.928  27.045 -14.241  1.00 29.36
ATOM   1439  OD1  ASN A 176     19.085  26.713 -14.429  1.00 33.90
ATOM   1440  ND2  ASN A 176     17.533  28.296 -14.198  1.00 30.40
ATOM   1441  N    THR A 177     16.224  22.739 -13.270  1.00 20.46
ATOM   1442  CA   THR A 177     15.864  21.790 -12.233  1.00 23.50
ATOM   1443  C    THR A 177     16.993  21.057 -11.526  1.00 26.28
ATOM   1444  O    THR A 177     17.730  20.301 -12.131  1.00 30.21
ATOM   1445  CB   THR A 177     14.801  20.816 -12.736  1.00 22.89
ATOM   1446  OG1  THR A 177     14.921  19.484 -12.235  1.00 31.31
ATOM   1447  CG2  THR A 177     14.734  20.731 -14.226  1.00 24.04
ATOM   1448  N    PRO A 178     17.138  21.235 -10.179  1.00 27.32
ATOM   1449  CA   PRO A 178     18.245  20.553  -9.473  1.00 22.63
ATOM   1450  C    PRO A 178     18.508  19.058  -9.724  1.00 22.23
ATOM   1451  O    PRO A 178     19.599  18.613  -9.993  1.00 24.81
ATOM   1452  CB   PRO A 178     17.960  20.988  -8.025  1.00 25.04
ATOM   1453  CG   PRO A 178     17.315  22.383  -8.131  1.00 21.18
ATOM   1454  CD   PRO A 178     16.373  22.136  -9.297  1.00 24.25
ATOM   1455  N    SER A 179     17.474  18.272  -9.738  1.00 20.93
ATOM   1456  CA   SER A 179     17.777  16.928 -10.236  1.00 24.32
ATOM   1457  C    SER A 179     18.481  16.694 -11.650  1.00 28.90
ATOM   1458  O    SER A 179     19.237  15.745 -11.882  1.00 22.64
```

FIG. 11-28

| ATOM | 1459 | CB  | SER A 179 | 16.549 | 15.982 | -10.033 | 1.00 | 24.35 |
|------|------|-----|-----------|--------|--------|---------|------|-------|
| ATOM | 1460 | OG  | SER A 179 | 15.386 | 16.308 | -10.828 | 1.00 | 24.61 |
| ATOM | 1461 | N   | PHE A 180 | 18.263 | 17.639 | -12.626 | 1.00 | 28.13 |
| ATOM | 1462 | CA  | PHE A 180 | 19.030 | 17.533 | -13.915 | 1.00 | 27.92 |
| ATOM | 1463 | C   | PHE A 180 | 20.544 | 17.224 | -13.826 | 1.00 | 22.81 |
| ATOM | 1464 | O   | PHE A 180 | 21.085 | 16.286 | -14.380 | 1.00 | 20.73 |
| ATOM | 1465 | CB  | PHE A 180 | 18.935 | 18.834 | -14.731 | 1.00 | 25.60 |
| ATOM | 1466 | CG  | PHE A 180 | 19.473 | 18.630 | -16.122 | 1.00 | 20.36 |
| ATOM | 1467 | CD1 | PHE A 180 | 18.968 | 17.576 | -16.891 | 1.00 | 16.56 |
| ATOM | 1468 | CD2 | PHE A 180 | 20.468 | 19.509 | -16.608 | 1.00 | 23.32 |
| ATOM | 1469 | CE1 | PHE A 180 | 19.411 | 17.465 | -18.214 | 1.00 | 29.72 |
| ATOM | 1470 | CE2 | PHE A 180 | 20.948 | 19.365 | -17.922 | 1.00 | 21.81 |
| ATOM | 1471 | CZ  | PHE A 180 | 20.370 | 18.379 | -18.739 | 1.00 | 24.95 |
| ATOM | 1472 | N   | LYS A 181 | 21.150 | 18.123 | -13.048 | 1.00 | 19.23 |
| ATOM | 1473 | CA  | LYS A 181 | 22.537 | 18.189 | -12.647 | 1.00 | 23.25 |
| ATOM | 1474 | C   | LYS A 181 | 23.174 | 17.061 | -11.828 | 1.00 | 28.77 |
| ATOM | 1475 | O   | LYS A 181 | 24.365 | 17.052 | -11.529 | 1.00 | 32.90 |
| ATOM | 1476 | CB  | LYS A 181 | 22.627 | 19.544 | -12.006 | 1.00 | 21.21 |
| ATOM | 1477 | CG  | LYS A 181 | 22.262 | 20.481 | -13.157 | 1.00 | 20.21 |
| ATOM | 1478 | CD  | LYS A 181 | 21.278 | 21.573 | -12.761 | 1.00 | 28.49 |
| ATOM | 1479 | CE  | LYS A 181 | 21.777 | 22.675 | -11.829 | 1.00 | 28.68 |
| ATOM | 1480 | NZ  | LYS A 181 | 20.781 | 23.751 | -11.923 | 1.00 | 26.37 |
| ATOM | 1481 | N   | GLU A 182 | 22.328 | 16.066 | -11.531 | 1.00 | 32.31 |
| ATOM | 1482 | CA  | GLU A 182 | 22.694 | 15.024 | -10.577 | 1.00 | 33.17 |
| ATOM | 1483 | C   | GLU A 182 | 23.354 | 13.747 | -11.030 | 1.00 | 37.04 |
| ATOM | 1484 | O   | GLU A 182 | 22.931 | 13.154 | -12.008 | 1.00 | 36.94 |
| ATOM | 1485 | CB  | GLU A 182 | 21.478 | 14.628 |  -9.790 | 1.00 | 33.77 |
| ATOM | 1486 | CG  | GLU A 182 | 21.224 | 15.737 |  -8.763 | 1.00 | 44.95 |
| ATOM | 1487 | CD  | GLU A 182 | 22.414 | 15.992 |  -7.819 | 1.00 | 49.36 |
| ATOM | 1488 | OE1 | GLU A 182 | 22.362 | 17.022 |  -7.160 | 1.00 | 50.91 |
| ATOM | 1489 | OE2 | GLU A 182 | 23.376 | 15.191 |  -7.722 | 1.00 | 53.17 |
| ATOM | 1490 | N   | ARG A 183 | 24.401 | 13.257 | -10.299 | 1.00 | 41.56 |
| ATOM | 1491 | CA  | ARG A 183 | 24.878 | 11.913 | -10.730 | 1.00 | 42.81 |
| ATOM | 1492 | C   | ARG A 183 | 23.725 | 10.913 | -10.656 | 1.00 | 43.03 |
| ATOM | 1493 | O   | ARG A 183 | 23.188 | 10.388 | -11.631 | 1.00 | 41.45 |
| ATOM | 1494 | CB  | ARG A 183 | 26.108 | 11.371 |  -9.945 | 1.00 | 43.97 |
| ATOM | 1495 | CG  | ARG A 183 | 27.088 | 12.479 |  -9.536 | 1.00 | 48.33 |
| ATOM | 1496 | CD  | ARG A 183 | 28.172 | 12.087 |  -8.535 | 1.00 | 53.50 |
| ATOM | 1497 | NE  | ARG A 183 | 29.345 | 11.380 |  -9.078 | 1.00 | 63.03 |
| ATOM | 1498 | CZ  | ARG A 183 | 30.090 | 10.611 |  -8.257 | 1.00 | 67.04 |
| ATOM | 1499 | NH1 | ARG A 183 | 29.569 | 10.147 |  -7.150 | 1.00 | 74.64 |
| ATOM | 1500 | NH2 | ARG A 183 | 31.346 | 10.314 |  -8.521 | 1.00 | 63.98 |
| ATOM | 1501 | N   | ASN A 184 | 23.274 | 10.834 |  -9.390 | 1.00 | 44.17 |
| ATOM | 1502 | CA  | ASN A 184 | 22.031 | 10.144 |  -9.020 | 1.00 | 44.38 |
| ATOM | 1503 | C   | ASN A 184 | 20.795 | 10.132 |  -9.995 | 1.00 | 42.70 |
| ATOM | 1504 | O   | ASN A 184 | 20.267 |  9.071 | -10.309 | 1.00 | 45.10 |
| ATOM | 1505 | CB  | ASN A 184 | 21.731 | 10.473 |  -7.515 | 1.00 | 51.31 |
| ATOM | 1506 | CG  | ASN A 184 | 21.481 | 11.964 |  -7.125 | 1.00 | 55.73 |
| ATOM | 1507 | OD1 | ASN A 184 | 20.349 | 12.423 |  -7.000 | 1.00 | 56.91 |
| ATOM | 1508 | ND2 | ASN A 184 | 22.575 | 12.691 |  -6.889 | 1.00 | 56.69 |
| ATOM | 1509 | N   | GLY A 185 | 20.349 | 11.295 | -10.506 | 1.00 | 37.58 |
| ATOM | 1510 | CA  | GLY A 185 | 19.182 | 11.185 | -11.399 | 1.00 | 36.63 |
| ATOM | 1511 | C   | GLY A 185 | 19.083 | 12.263 | -12.475 | 1.00 | 36.03 |
| ATOM | 1512 | O   | GLY A 185 | 19.172 | 13.418 | -12.134 | 1.00 | 36.27 |

FIG. 11-29

| ATOM | 1513 | N | GLY | A | 186 | 18.999 | 11.881 | -13.770 | 1.00 | 34.60 |
| ATOM | 1514 | CA | GLY | A | 186 | 19.340 | 12.911 | -14.802 | 1.00 | 34.54 |
| ATOM | 1515 | C | GLY | A | 186 | 20.775 | 12.966 | -15.421 | 1.00 | 34.05 |
| ATOM | 1516 | O | GLY | A | 186 | 21.074 | 12.470 | -16.502 | 1.00 | 33.54 |
| ATOM | 1517 | N | ASN | A | 187 | 21.705 | 13.535 | -14.642 | 1.00 | 31.76 |
| ATOM | 1518 | CA | ASN | A | 187 | 23.148 | 13.476 | -14.974 | 1.00 | 31.53 |
| ATOM | 1519 | C | ASN | A | 187 | 23.607 | 14.273 | -16.189 | 1.00 | 31.08 |
| ATOM | 1520 | O | ASN | A | 187 | 24.558 | 13.982 | -16.902 | 1.00 | 33.80 |
| ATOM | 1521 | CB | ASN | A | 187 | 23.633 | 12.019 | -14.923 | 1.00 | 32.69 |
| ATOM | 1522 | CG | ASN | A | 187 | 25.141 | 11.763 | -14.933 | 1.00 | 31.62 |
| ATOM | 1523 | OD1 | ASN | A | 187 | 25.524 | 10.633 | -15.152 | 1.00 | 28.60 |
| ATOM | 1524 | ND2 | ASN | A | 187 | 25.985 | 12.759 | -14.665 | 1.00 | 30.60 |
| ATOM | 1525 | N | HIS | A | 188 | 22.853 | 15.357 | -16.329 | 1.00 | 28.32 |
| ATOM | 1526 | CA | HIS | A | 188 | 23.000 | 16.307 | -17.432 | 1.00 | 27.38 |
| ATOM | 1527 | C | HIS | A | 188 | 22.540 | 15.763 | -18.789 | 1.00 | 27.52 |
| ATOM | 1528 | O | HIS | A | 188 | 22.717 | 16.374 | -19.842 | 1.00 | 33.01 |
| ATOM | 1529 | CB | HIS | A | 188 | 24.395 | 16.995 | -17.495 | 1.00 | 26.21 |
| ATOM | 1530 | CG | HIS | A | 188 | 24.779 | 17.817 | -16.257 | 1.00 | 15.13 |
| ATOM | 1531 | ND1 | HIS | A | 188 | 25.502 | 17.362 | -15.205 | 1.00 | 5.09 |
| ATOM | 1532 | CD2 | HIS | A | 188 | 24.581 | 19.186 | -16.093 | 1.00 | 11.65 |
| ATOM | 1533 | CE1 | HIS | A | 188 | 25.788 | 18.444 | -14.404 | 1.00 | 9.35 |
| ATOM | 1534 | NE2 | HIS | A | 188 | 25.210 | 19.568 | -14.946 | 1.00 | 10.80 |
| ATOM | 1535 | N | ASP | A | 189 | 21.833 | 14.638 | -18.656 | 1.00 | 23.22 |
| ATOM | 1536 | CA | ASP | A | 189 | 21.195 | 14.024 | -19.807 | 1.00 | 22.65 |
| ATOM | 1537 | C | ASP | A | 189 | 19.655 | 14.255 | -19.776 | 1.00 | 26.02 |
| ATOM | 1538 | O | ASP | A | 189 | 18.876 | 13.697 | -19.003 | 1.00 | 26.20 |
| ATOM | 1539 | CB | ASP | A | 189 | 21.688 | 12.549 | -19.813 | 1.00 | 12.72 |
| ATOM | 1540 | CG | ASP | A | 189 | 21.065 | 11.642 | -20.863 | 1.00 | 23.84 |
| ATOM | 1541 | OD1 | ASP | A | 189 | 21.391 | 10.474 | -20.821 | 1.00 | 29.35 |
| ATOM | 1542 | OD2 | ASP | A | 189 | 20.220 | 12.017 | -21.693 | 1.00 | 24.58 |
| ATOM | 1543 | N | PRO | A | 190 | 19.189 | 15.161 | -20.679 | 1.00 | 30.08 |
| ATOM | 1544 | CA | PRO | A | 190 | 17.744 | 15.281 | -20.946 | 1.00 | 29.62 |
| ATOM | 1545 | C | PRO | A | 190 | 16.960 | 13.959 | -21.006 | 1.00 | 29.68 |
| ATOM | 1546 | O | PRO | A | 190 | 15.936 | 13.742 | -20.368 | 1.00 | 30.31 |
| ATOM | 1547 | CB | PRO | A | 190 | 17.701 | 16.011 | -22.318 | 1.00 | 25.85 |
| ATOM | 1548 | CG | PRO | A | 190 | 18.975 | 16.811 | -22.398 | 1.00 | 22.72 |
| ATOM | 1549 | CD | PRO | A | 190 | 19.978 | 15.999 | -21.575 | 1.00 | 28.38 |
| ATOM | 1550 | N | SER | A | 191 | 17.476 | 13.041 | -21.819 | 1.00 | 30.53 |
| ATOM | 1551 | CA | SER | A | 191 | 16.730 | 11.796 | -21.923 | 1.00 | 26.19 |
| ATOM | 1552 | C | SER | A | 191 | 16.425 | 11.065 | -20.630 | 1.00 | 23.12 |
| ATOM | 1553 | O | SER | A | 191 | 15.419 | 10.343 | -20.582 | 1.00 | 22.70 |
| ATOM | 1554 | CB | SER | A | 191 | 17.325 | 10.878 | -23.014 | 1.00 | 30.05 |
| ATOM | 1555 | OG | SER | A | 191 | 18.408 | 10.026 | -22.571 | 1.00 | 27.98 |
| ATOM | 1556 | N | ARG | A | 192 | 17.266 | 11.353 | -19.583 | 1.00 | 20.87 |
| ATOM | 1557 | CA | ARG | A | 192 | 16.972 | 10.807 | -18.241 | 1.00 | 26.06 |
| ATOM | 1558 | C | ARG | A | 192 | 15.860 | 11.446 | -17.397 | 1.00 | 29.09 |
| ATOM | 1559 | O | ARG | A | 192 | 15.658 | 11.109 | -16.234 | 1.00 | 30.24 |
| ATOM | 1560 | CB | ARG | A | 192 | 18.214 | 10.691 | -17.364 | 1.00 | 25.34 |
| ATOM | 1561 | CG | ARG | A | 192 | 19.177 | 9.638 | -17.879 | 1.00 | 27.62 |
| ATOM | 1562 | CD | ARG | A | 192 | 19.774 | 8.798 | -16.756 | 1.00 | 29.94 |
| ATOM | 1563 | NE | ARG | A | 192 | 20.590 | 9.569 | -15.809 | 1.00 | 33.35 |
| ATOM | 1564 | CZ | ARG | A | 192 | 20.717 | 9.153 | -14.521 | 1.00 | 34.49 |
| ATOM | 1565 | NH1 | ARG | A | 192 | 19.953 | 8.202 | -14.044 | 1.00 | 36.40 |
| ATOM | 1566 | NH2 | ARG | A | 192 | 21.595 | 9.671 | -13.693 | 1.00 | 29.72 |

FIG. 11-30

| ATOM | 1567 | N | MET A 193 | 15.172 | 12.400 | -18.045 | 1.00 | 27.27 |
|---|---|---|---|---|---|---|---|---|
| ATOM | 1568 | CA | MET A 193 | 14.105 | 13.170 | -17.425 | 1.00 | 26.72 |
| ATOM | 1569 | C | MET A 193 | 12.679 | 13.018 | -18.002 | 1.00 | 29.42 |
| ATOM | 1570 | O | MET A 193 | 12.386 | 12.376 | -19.017 | 1.00 | 32.95 |
| ATOM | 1571 | CB | MET A 193 | 14.527 | 14.618 | -17.298 | 1.00 | 20.81 |
| ATOM | 1572 | CG | MET A 193 | 15.855 | 14.715 | -16.556 | 1.00 | 21.25 |
| ATOM | 1573 | SD | MET A 193 | 15.941 | 14.972 | -14.742 | 1.00 | 20.46 |
| ATOM | 1574 | CE | MET A 193 | 15.517 | 16.695 | -14.574 | 1.00 | 24.66 |
| ATOM | 1575 | N | LYS A 194 | 11.766 | 13.615 | -17.227 | 1.00 | 29.33 |
| ATOM | 1576 | CA | LYS A 194 | 10.316 | 13.636 | -17.487 | 1.00 | 25.03 |
| ATOM | 1577 | C | LYS A 194 | 9.836 | 15.045 | -17.111 | 1.00 | 25.47 |
| ATOM | 1578 | O | LYS A 194 | 10.149 | 15.583 | -16.051 | 1.00 | 29.48 |
| ATOM | 1579 | CB | LYS A 194 | 9.644 | 12.657 | -16.548 | 1.00 | 18.07 |
| ATOM | 1580 | CG | LYS A 194 | 8.746 | 11.505 | -17.018 | 1.00 | 26.00 |
| ATOM | 1581 | CD | LYS A 194 | 7.982 | 10.953 | -15.767 | 1.00 | 30.99 |
| ATOM | 1582 | CE | LYS A 194 | 7.239 | 9.595 | -15.905 | 1.00 | 35.90 |
| ATOM | 1583 | NZ | LYS A 194 | 5.788 | 9.665 | -16.224 | 1.00 | 36.29 |
| ATOM | 1584 | N | ALA A 195 | 9.076 | 15.632 | -18.005 | 1.00 | 26.61 |
| ATOM | 1585 | CA | ALA A 195 | 8.191 | 16.713 | -17.571 | 1.00 | 28.31 |
| ATOM | 1586 | C | ALA A 195 | 6.952 | 16.377 | -16.688 | 1.00 | 27.62 |
| ATOM | 1587 | O | ALA A 195 | 6.171 | 15.448 | -16.888 | 1.00 | 28.58 |
| ATOM | 1588 | CB | ALA A 195 | 7.788 | 17.576 | -18.766 | 1.00 | 27.29 |
| ATOM | 1589 | N | VAL A 196 | 6.879 | 17.210 | -15.630 | 1.00 | 25.65 |
| ATOM | 1590 | CA | VAL A 196 | 5.773 | 17.196 | -14.693 | 1.00 | 24.13 |
| ATOM | 1591 | C | VAL A 196 | 5.111 | 18.522 | -14.473 | 1.00 | 26.74 |
| ATOM | 1592 | O | VAL A 196 | 5.734 | 19.595 | -14.451 | 1.00 | 25.52 |
| ATOM | 1593 | CB | VAL A 196 | 6.115 | 16.582 | -13.343 | 1.00 | 20.95 |
| ATOM | 1594 | CG1 | VAL A 196 | 7.250 | 17.264 | -12.622 | 1.00 | 22.30 |
| ATOM | 1595 | CG2 | VAL A 196 | 6.452 | 15.126 | -13.530 | 1.00 | 23.75 |
| ATOM | 1596 | N | ILE A 197 | 3.783 | 18.341 | -14.293 | 1.00 | 23.14 |
| ATOM | 1597 | CA | ILE A 197 | 2.957 | 19.484 | -13.931 | 1.00 | 20.52 |
| ATOM | 1598 | C | ILE A 197 | 2.384 | 19.366 | -12.548 | 1.00 | 16.24 |
| ATOM | 1599 | O | ILE A 197 | 1.874 | 18.346 | -12.123 | 1.00 | 13.41 |
| ATOM | 1600 | CB | ILE A 197 | 1.846 | 19.719 | -14.967 | 1.00 | 23.42 |
| ATOM | 1601 | CG1 | ILE A 197 | 2.460 | 19.893 | -16.344 | 1.00 | 18.69 |
| ATOM | 1602 | CG2 | ILE A 197 | 0.936 | 20.931 | -14.653 | 1.00 | 25.06 |
| ATOM | 1603 | CD1 | ILE A 197 | 1.558 | 19.380 | -17.473 | 1.00 | 19.89 |
| ATOM | 1604 | N | TYR A 198 | 2.478 | 20.482 | -11.862 | 1.00 | 16.07 |
| ATOM | 1605 | CA | TYR A 198 | 1.471 | 20.756 | -10.827 | 1.00 | 15.74 |
| ATOM | 1606 | C | TYR A 198 | 0.821 | 22.099 | -11.079 | 1.00 | 19.05 |
| ATOM | 1607 | O | TYR A 198 | 1.197 | 22.781 | -12.037 | 1.00 | 17.43 |
| ATOM | 1608 | CB | TYR A 198 | 2.066 | 20.784 | -9.450 | 1.00 | 7.02 |
| ATOM | 1609 | CG | TYR A 198 | 3.174 | 21.813 | -9.348 | 1.00 | 12.29 |
| ATOM | 1610 | CD1 | TYR A 198 | 4.475 | 21.514 | -9.836 | 1.00 | 12.59 |
| ATOM | 1611 | CD2 | TYR A 198 | 2.880 | 23.071 | -8.771 | 1.00 | 15.22 |
| ATOM | 1612 | CE1 | TYR A 198 | 5.468 | 22.487 | -9.713 | 1.00 | 11.82 |
| ATOM | 1613 | CE2 | TYR A 198 | 3.875 | 24.076 | -8.705 | 1.00 | 11.81 |
| ATOM | 1614 | CZ | TYR A 198 | 5.161 | 23.741 | -9.134 | 1.00 | 11.59 |
| ATOM | 1615 | OH | TYR A 198 | 6.175 | 24.660 | -8.979 | 1.00 | 26.25 |
| ATOM | 1616 | N | SER A 199 | -0.159 | 22.439 | -10.193 | 1.00 | 21.16 |
| ATOM | 1617 | CA | SER A 199 | -0.927 | 23.736 | -10.283 | 1.00 | 17.75 |
| ATOM | 1618 | C | SER A 199 | -0.904 | 24.491 | -8.961 | 1.00 | 13.64 |
| ATOM | 1619 | O | SER A 199 | -0.876 | 23.835 | -7.933 | 1.00 | 20.29 |
| ATOM | 1620 | CB | SER A 199 | -2.390 | 23.493 | -10.721 | 1.00 | 15.06 |

FIG. 11-31

| | | | | | | | | | |
|---|---|---|---|---|---|---|---|---|---|
| ATOM | 1621 | OG | SER | A | 199 | -3.148 | 24.663 | -11.113 | 1.00 18.69 |
| ATOM | 1622 | N | LYS | A | 200 | -0.901 | 25.827 | -8.990 | 1.00 10.12 |
| ATOM | 1623 | CA | LYS | A | 200 | -1.129 | 26.673 | -7.787 | 1.00 5.88 |
| ATOM | 1624 | C | LYS | A | 200 | -2.337 | 27.545 | -7.962 | 1.00 7.68 |
| ATOM | 1625 | O | LYS | A | 200 | -2.467 | 28.169 | -9.002 | 1.00 6.74 |
| ATOM | 1626 | CB | LYS | A | 200 | -0.119 | 27.785 | -7.557 | 1.00 2.93 |
| ATOM | 1627 | CG | LYS | A | 200 | 0.055 | 28.111 | -6.092 | 1.00 3.74 |
| ATOM | 1628 | CD | LYS | A | 200 | 0.999 | 29.284 | -5.979 | 1.00 3.68 |
| ATOM | 1629 | CE | LYS | A | 200 | 1.450 | 29.485 | -4.532 | 1.00 6.98 |
| ATOM | 1630 | NZ | LYS | A | 200 | 2.184 | 30.734 | -4.279 | 1.00 14.74 |
| ATOM | 1631 | N | HIS | A | 201 | -3.165 | 27.621 | -6.904 | 1.00 12.56 |
| ATOM | 1632 | CA | HIS | A | 201 | -4.237 | 28.635 | -6.829 | 1.00 12.60 |
| ATOM | 1633 | C | HIS | A | 201 | -3.936 | 29.777 | -5.866 | 1.00 8.20 |
| ATOM | 1634 | O | HIS | A | 201 | -3.317 | 29.604 | -4.826 | 1.00 7.29 |
| ATOM | 1635 | CB | HIS | A | 201 | -5.524 | 27.978 | -6.377 | 1.00 14.05 |
| ATOM | 1636 | CG | HIS | A | 201 | -6.191 | 27.099 | -7.392 | 1.00 17.05 |
| ATOM | 1637 | ND1 | HIS | A | 201 | -7.112 | 26.176 | -7.026 | 1.00 24.32 |
| ATOM | 1638 | CD2 | HIS | A | 201 | -6.074 | 27.129 | -8.790 | 1.00 21.75 |
| ATOM | 1639 | CE1 | HIS | A | 201 | -7.582 | 25.636 | -8.202 | 1.00 28.14 |
| ATOM | 1640 | NE2 | HIS | A | 201 | -6.938 | 26.218 | -9.279 | 1.00 27.17 |
| ATOM | 1641 | N | PHE | A | 202 | -4.343 | 30.965 | -6.258 | 1.00 6.73 |
| ATOM | 1642 | CA | PHE | A | 202 | -3.689 | 32.019 | -5.481 | 1.00 3.44 |
| ATOM | 1643 | C | PHE | A | 202 | -4.360 | 33.380 | -5.610 | 1.00 3.33 |
| ATOM | 1644 | O | PHE | A | 202 | -5.289 | 33.582 | -6.378 | 1.00 8.21 |
| ATOM | 1645 | CB | PHE | A | 202 | -2.146 | 31.960 | -5.693 | 1.00 8.95 |
| ATOM | 1646 | CG | PHE | A | 202 | -1.648 | 32.415 | -7.068 | 1.00 7.73 |
| ATOM | 1647 | CD1 | PHE | A | 202 | -1.713 | 31.517 | -8.134 | 1.00 10.00 |
| ATOM | 1648 | CD2 | PHE | A | 202 | -1.170 | 33.736 | -7.243 | 1.00 4.15 |
| ATOM | 1649 | CE1 | PHE | A | 202 | -1.471 | 31.982 | -9.434 | 1.00 10.30 |
| ATOM | 1650 | CE2 | PHE | A | 202 | -0.959 | 34.194 | -8.537 | 1.00 9.10 |
| ATOM | 1651 | CZ | PHE | A | 202 | -1.208 | 33.337 | -9.634 | 1.00 5.36 |
| ATOM | 1652 | N | TRP | A | 203 | -3.911 | 34.308 | -4.820 | 1.00 9.58 |
| ATOM | 1653 | CA | TRP | A | 203 | -4.550 | 35.637 | -4.961 | 1.00 15.60 |
| ATOM | 1654 | C | TRP | A | 203 | -3.777 | 36.772 | -5.727 | 1.00 17.33 |
| ATOM | 1655 | O | TRP | A | 203 | -2.602 | 37.044 | -5.502 | 1.00 16.17 |
| ATOM | 1656 | CB | TRP | A | 203 | -4.997 | 36.069 | -3.513 | 1.00 9.00 |
| ATOM | 1657 | CG | TRP | A | 203 | -5.756 | 37.374 | -3.534 | 1.00 2.00 |
| ATOM | 1658 | CD1 | TRP | A | 203 | -5.209 | 38.609 | -3.135 | 1.00 4.61 |
| ATOM | 1659 | CD2 | TRP | A | 203 | -7.117 | 37.658 | -3.932 | 1.00 2.00 |
| ATOM | 1660 | NE1 | TRP | A | 203 | -6.130 | 39.603 | -3.240 | 1.00 8.61 |
| ATOM | 1661 | CE2 | TRP | A | 203 | -7.325 | 39.062 | -3.710 | 1.00 5.24 |
| ATOM | 1662 | CE3 | TRP | A | 203 | -8.189 | 36.867 | -4.436 | 1.00 6.01 |
| ATOM | 1663 | CZ2 | TRP | A | 203 | -8.588 | 39.638 | -3.944 | 1.00 2.00 |
| ATOM | 1664 | CZ3 | TRP | A | 203 | -9.447 | 37.468 | -4.670 | 1.00 2.67 |
| ATOM | 1665 | CH2 | TRP | A | 203 | -9.654 | 38.839 | -4.424 | 1.00 2.00 |
| ATOM | 1666 | N | SER | A | 204 | -4.507 | 37.486 | -6.603 | 1.00 21.51 |
| ATOM | 1667 | CA | SER | A | 204 | -3.980 | 38.575 | -7.439 | 1.00 21.92 |
| ATOM | 1668 | C | SER | A | 204 | -3.543 | 39.952 | -6.864 | 1.00 25.51 |
| ATOM | 1669 | O | SER | A | 204 | -2.527 | 40.574 | -7.197 | 1.00 24.66 |
| ATOM | 1670 | CB | SER | A | 204 | -5.003 | 38.786 | -8.506 | 1.00 23.00 |
| ATOM | 1671 | OG | SER | A | 204 | -5.915 | 39.818 | -8.118 | 1.00 22.25 |
| ATOM | 1672 | N | GLY | A | 205 | -4.363 | 40.445 | -5.911 | 1.00 28.86 |
| ATOM | 1673 | CA | GLY | A | 205 | -3.901 | 41.651 | -5.178 | 1.00 23.69 |
| ATOM | 1674 | C | GLY | A | 205 | -2.909 | 41.366 | -4.053 | 1.00 24.30 |

FIG. 11-32

| | | | | | | | | |
|---|---|---|---|---|---|---|---|---|
| ATOM | 1675 | O | GLY | A | 205 | -3.270 | 41.147 | -2.910 | 1.00 | 29.10 |
| ATOM | 1676 | N | GLN | A | 206 | -1.632 | 41.376 | -4.345 | 1.00 | 23.02 |
| ATOM | 1677 | CA | GLN | A | 206 | -0.820 | 41.113 | -3.143 | 1.00 | 25.67 |
| ATOM | 1678 | C | GLN | A | 206 | 0.013 | 42.222 | -2.475 | 1.00 | 35.46 |
| ATOM | 1679 | O | GLN | A | 206 | 0.847 | 42.015 | -1.576 | 1.00 | 36.42 |
| ATOM | 1680 | CB | GLN | A | 206 | 0.102 | 39.945 | -3.367 | 1.00 | 19.06 |
| ATOM | 1681 | CG | GLN | A | 206 | -0.628 | 38.820 | -4.066 | 1.00 | 15.87 |
| ATOM | 1682 | CD | GLN | A | 206 | 0.245 | 37.620 | -3.908 | 1.00 | 14.06 |
| ATOM | 1683 | OE1 | GLN | A | 206 | 1.250 | 37.725 | -3.224 | 1.00 | 12.69 |
| ATOM | 1684 | NE2 | GLN | A | 206 | -0.130 | 36.513 | -4.557 | 1.00 | 7.08 |
| ATOM | 1685 | N | ASP | A | 207 | -0.231 | 43.430 | -3.011 | 1.00 | 41.38 |
| ATOM | 1686 | CA | ASP | A | 207 | 0.708 | 44.553 | -2.777 | 1.00 | 47.22 |
| ATOM | 1687 | C | ASP | A | 207 | 0.571 | 45.321 | -1.434 | 1.00 | 51.86 |
| ATOM | 1688 | O | ASP | A | 207 | -0.517 | 45.720 | -1.041 | 1.00 | 56.05 |
| ATOM | 1689 | CB | ASP | A | 207 | 0.593 | 45.434 | -4.043 | 1.00 | 46.97 |
| ATOM | 1690 | CG | ASP | A | 207 | 1.579 | 46.579 | -4.094 | 1.00 | 47.04 |
| ATOM | 1691 | OD1 | ASP | A | 207 | 2.333 | 46.737 | -3.131 | 1.00 | 48.55 |
| ATOM | 1692 | OD2 | ASP | A | 207 | 1.584 | 47.295 | -5.099 | 1.00 | 41.74 |
| ATOM | 1693 | N | ARG | A | 208 | 1.695 | 45.501 | -0.693 | 1.00 | 55.70 |
| ATOM | 1694 | CA | ARG | A | 208 | 1.595 | 46.359 | 0.534 | 1.00 | 59.28 |
| ATOM | 1695 | C | ARG | A | 208 | 1.091 | 47.777 | 0.287 | 1.00 | 58.52 |
| ATOM | 1696 | O | ARG | A | 208 | 0.362 | 48.374 | 1.060 | 1.00 | 59.86 |
| ATOM | 1697 | CB | ARG | A | 208 | 2.929 | 46.626 | 1.275 | 1.00 | 64.79 |
| ATOM | 1698 | CG | ARG | A | 208 | 3.512 | 45.575 | 2.233 | 1.00 | 70.58 |
| ATOM | 1699 | CD | ARG | A | 208 | 4.051 | 44.319 | 1.535 | 1.00 | 73.25 |
| ATOM | 1700 | NE | ARG | A | 208 | 3.860 | 43.152 | 2.394 | 1.00 | 74.08 |
| ATOM | 1701 | CZ | ARG | A | 208 | 2.667 | 42.559 | 2.440 | 1.00 | 74.98 |
| ATOM | 1702 | NH1 | ARG | A | 208 | 1.716 | 42.883 | 1.583 | 1.00 | 74.22 |
| ATOM | 1703 | NH2 | ARG | A | 208 | 2.472 | 41.643 | 3.365 | 1.00 | 75.99 |
| ATOM | 1704 | N | SER | A | 209 | 1.571 | 48.285 | -0.853 | 1.00 | 57.11 |
| ATOM | 1705 | CA | SER | A | 209 | 1.131 | 49.563 | -1.427 | 1.00 | 56.03 |
| ATOM | 1706 | C | SER | A | 209 | -0.133 | 49.505 | -2.257 | 1.00 | 54.93 |
| ATOM | 1707 | O | SER | A | 209 | -0.567 | 50.453 | -2.900 | 1.00 | 55.23 |
| ATOM | 1708 | CB | SER | A | 209 | 2.236 | 50.141 | -2.311 | 1.00 | 57.19 |
| ATOM | 1709 | OG | SER | A | 209 | 3.413 | 50.401 | -1.512 | 1.00 | 58.43 |
| ATOM | 1710 | N | SER | A | 210 | -0.749 | 48.329 | -2.214 | 1.00 | 54.38 |
| ATOM | 1711 | CA | SER | A | 210 | -2.004 | 48.215 | -2.954 | 1.00 | 52.05 |
| ATOM | 1712 | C | SER | A | 210 | -3.113 | 49.096 | -2.414 | 1.00 | 50.90 |
| ATOM | 1713 | O | SER | A | 210 | -3.365 | 49.201 | -1.216 | 1.00 | 52.97 |
| ATOM | 1714 | CB | SER | A | 210 | -2.525 | 46.774 | -2.979 | 1.00 | 47.55 |
| ATOM | 1715 | OG | SER | A | 210 | -3.563 | 46.650 | -3.958 | 1.00 | 46.22 |
| ATOM | 1716 | N | SER | A | 211 | -3.840 | 49.710 | -3.365 | 1.00 | 47.29 |
| ATOM | 1717 | CA | SER | A | 211 | -5.116 | 50.271 | -2.903 | 1.00 | 42.52 |
| ATOM | 1718 | C | SER | A | 211 | -5.947 | 49.226 | -2.195 | 1.00 | 44.97 |
| ATOM | 1719 | O | SER | A | 211 | -5.972 | 48.072 | -2.614 | 1.00 | 47.20 |
| ATOM | 1720 | CB | SER | A | 211 | -5.945 | 50.867 | -4.035 | 1.00 | 37.16 |
| ATOM | 1721 | OG | SER | A | 211 | -6.732 | 49.895 | -4.735 | 1.00 | 38.32 |
| ATOM | 1722 | N | ALA | A | 212 | -6.627 | 49.617 | -1.124 | 1.00 | 46.59 |
| ATOM | 1723 | CA | ALA | A | 212 | -7.301 | 48.523 | -0.387 | 1.00 | 45.55 |
| ATOM | 1724 | C | ALA | A | 212 | -8.102 | 47.513 | -1.245 | 1.00 | 42.27 |
| ATOM | 1725 | O | ALA | A | 212 | -8.056 | 46.290 | -1.089 | 1.00 | 43.95 |
| ATOM | 1726 | CB | ALA | A | 212 | -8.223 | 49.114 | 0.707 | 1.00 | 46.45 |
| ATOM | 1727 | N | ASP | A | 213 | -8.770 | 48.141 | -2.224 | 1.00 | 36.90 |
| ATOM | 1728 | CA | ASP | A | 213 | -9.683 | 47.438 | -3.128 | 1.00 | 34.48 |

FIG. 11-33

```
ATOM   1729  C   ASP A 213    -9.168  46.238  -3.878  1.00 30.86
ATOM   1730  O   ASP A 213    -9.819  45.227  -4.041  1.00 26.31
ATOM   1731  CB  ASP A 213   -10.270  48.473  -4.069  1.00 37.25
ATOM   1732  CG  ASP A 213   -11.480  49.079  -3.382  1.00 41.89
ATOM   1733  OD1 ASP A 213   -11.624  48.884  -2.162  1.00 42.52
ATOM   1734  OD2 ASP A 213   -12.274  49.722  -4.081  1.00 43.51
ATOM   1735  N   LYS A 214    -7.893  46.375  -4.260  1.00 31.30
ATOM   1736  CA  LYS A 214    -7.195  45.306  -4.981  1.00 30.24
ATOM   1737  C   LYS A 214    -6.916  44.061  -4.164  1.00 30.15
ATOM   1738  O   LYS A 214    -7.112  42.920  -4.591  1.00 29.63
ATOM   1739  CB  LYS A 214    -5.872  45.779  -5.569  1.00 27.74
ATOM   1740  CG  LYS A 214    -5.835  46.995  -6.516  1.00 31.14
ATOM   1741  CD  LYS A 214    -6.765  46.999  -7.735  1.00 30.80
ATOM   1742  CE  LYS A 214    -6.359  47.918  -8.914  1.00 32.80
ATOM   1743  NZ  LYS A 214    -5.310  47.299  -9.746  1.00 37.37
ATOM   1744  N   ARG A 215    -6.473  44.400  -2.931  1.00 30.28
ATOM   1745  CA  ARG A 215    -6.206  43.439  -1.856  1.00 26.98
ATOM   1746  C   ARG A 215    -7.388  42.603  -1.440  1.00 26.09
ATOM   1747  O   ARG A 215    -7.209  41.460  -1.019  1.00 29.21
ATOM   1748  CB  ARG A 215    -5.742  44.172  -0.628  1.00 32.00
ATOM   1749  CG  ARG A 215    -4.253  44.553  -0.456  1.00 45.38
ATOM   1750  CD  ARG A 215    -3.276  43.379  -0.171  1.00 58.30
ATOM   1751  NE  ARG A 215    -3.656  42.507   0.964  1.00 63.24
ATOM   1752  CZ  ARG A 215    -3.802  41.181   0.824  1.00 58.67
ATOM   1753  NH1 ARG A 215    -3.695  40.536  -0.291  1.00 54.28
ATOM   1754  NH2 ARG A 215    -4.062  40.470   1.854  1.00 59.40
ATOM   1755  N   LYS A 216    -8.589  43.238  -1.588  1.00 25.37
ATOM   1756  CA  LYS A 216    -9.891  42.606  -1.276  1.00 23.87
ATOM   1757  C   LYS A 216   -10.846  42.176  -2.380  1.00 21.23
ATOM   1758  O   LYS A 216   -11.523  41.160  -2.280  1.00 23.38
ATOM   1759  CB  LYS A 216   -10.673  43.419  -0.265  1.00 27.43
ATOM   1760  CG  LYS A 216   -11.167  44.749  -0.784  1.00 32.86
ATOM   1761  CD  LYS A 216   -11.720  45.466   0.423  1.00 38.42
ATOM   1762  CE  LYS A 216   -10.635  45.560   1.508  1.00 43.11
ATOM   1763  NZ  LYS A 216   -11.133  44.949   2.754  1.00 47.92
ATOM   1764  N   TYR A 217   -10.820  42.943  -3.450  1.00 20.64
ATOM   1765  CA  TYR A 217   -11.560  42.605  -4.678  1.00 24.34
ATOM   1766  C   TYR A 217   -10.801  41.941  -5.903  1.00 22.25
ATOM   1767  O   TYR A 217   -11.380  41.399  -6.853  1.00 16.78
ATOM   1768  CB  TYR A 217   -12.382  43.851  -5.042  1.00 26.61
ATOM   1769  CG  TYR A 217   -13.250  44.397  -3.920  1.00 38.71
ATOM   1770  CD1 TYR A 217   -13.373  45.797  -3.797  1.00 47.35
ATOM   1771  CD2 TYR A 217   -13.995  43.546  -3.071  1.00 43.13
ATOM   1772  CE1 TYR A 217   -14.317  46.354  -2.897  1.00 51.01
ATOM   1773  CE2 TYR A 217   -14.916  44.097  -2.153  1.00 45.24
ATOM   1774  CZ  TYR A 217   -15.084  45.499  -2.076  1.00 49.73
ATOM   1775  OH  TYR A 217   -15.989  46.023  -1.159  1.00 50.79
ATOM   1776  N   GLY A 218    -9.453  42.020  -5.793  1.00 21.20
ATOM   1777  CA  GLY A 218    -8.622  41.604  -6.934  1.00 21.57
ATOM   1778  C   GLY A 218    -7.924  42.701  -7.763  1.00 18.68
ATOM   1779  O   GLY A 218    -8.420  43.796  -8.074  1.00 11.65
ATOM   1780  N   ASP A 219    -6.686  42.332  -8.143  1.00 19.59
ATOM   1781  CA  ASP A 219    -5.942  43.047  -9.215  1.00 17.46
ATOM   1782  C   ASP A 219    -6.162  42.526 -10.634  1.00 12.99
```

FIG. 11-34

```
ATOM   1783  O    ASP A 219     -5.619  41.495 -11.038  1.00 14.27
ATOM   1784  CB   ASP A 219     -4.428  43.127  -8.884  1.00 18.87
ATOM   1785  CG   ASP A 219     -3.767  44.373  -9.452  1.00 19.68
ATOM   1786  OD1  ASP A 219     -2.690  44.745  -8.992  1.00 14.80
ATOM   1787  OD2  ASP A 219     -4.323  44.995 -10.357  1.00 20.64
ATOM   1788  N    PRO A 220     -7.041  43.233 -11.404  1.00 11.17
ATOM   1789  CA   PRO A 220     -7.322  42.827 -12.792  1.00 17.58
ATOM   1790  C    PRO A 220     -6.112  42.801 -13.800  1.00 19.01
ATOM   1791  O    PRO A 220     -6.091  42.117 -14.822  1.00 23.64
ATOM   1792  CB   PRO A 220     -8.528  43.743 -13.161  1.00 13.67
ATOM   1793  CG   PRO A 220     -8.451  44.958 -12.292  1.00  4.39
ATOM   1794  CD   PRO A 220     -7.792  44.415 -11.039  1.00  6.10
ATOM   1795  N    ASP A 221     -5.069  43.513 -13.447  1.00 19.81
ATOM   1796  CA   ASP A 221     -3.856  43.481 -14.266  1.00 20.01
ATOM   1797  C    ASP A 221     -2.742  42.630 -13.721  1.00 20.87
ATOM   1798  O    ASP A 221     -1.722  42.453 -14.359  1.00 24.70
ATOM   1799  CB   ASP A 221     -3.211  44.833 -14.314  1.00 24.87
ATOM   1800  CG   ASP A 221     -4.214  45.889 -14.651  1.00 29.53
ATOM   1801  OD1  ASP A 221     -4.945  45.747 -15.656  1.00 32.52
ATOM   1802  OD2  ASP A 221     -4.267  46.834 -13.863  1.00 31.74
ATOM   1803  N    ALA A 222     -2.907  42.087 -12.506  1.00 18.36
ATOM   1804  CA   ALA A 222     -1.842  41.234 -11.977  1.00 13.75
ATOM   1805  C    ALA A 222     -1.960  39.808 -12.412  1.00 16.09
ATOM   1806  O    ALA A 222     -3.075  39.303 -12.538  1.00 15.87
ATOM   1807  CB   ALA A 222     -1.837  41.221 -10.470  1.00 15.06
ATOM   1808  N    PHE A 223     -0.766  39.178 -12.707  1.00 18.89
ATOM   1809  CA   PHE A 223     -0.797  37.782 -13.210  1.00 12.41
ATOM   1810  C    PHE A 223     -1.703  37.507 -14.418  1.00 10.53
ATOM   1811  O    PHE A 223     -2.249  36.452 -14.624  1.00 14.82
ATOM   1812  CB   PHE A 223     -1.199  36.802 -12.084  1.00 11.76
ATOM   1813  CG   PHE A 223     -0.357  36.979 -10.841  1.00 13.12
ATOM   1814  CD1  PHE A 223     -0.888  37.670  -9.740  1.00 14.49
ATOM   1815  CD2  PHE A 223      0.962  36.478 -10.813  1.00 11.61
ATOM   1816  CE1  PHE A 223     -0.055  37.963  -8.639  1.00 11.23
ATOM   1817  CE2  PHE A 223      1.782  36.725  -9.711  1.00  7.38
ATOM   1818  CZ   PHE A 223      1.268  37.495  -8.645  1.00 14.26
ATOM   1819  N    ARG A 224     -1.881  38.496 -15.257  1.00 10.59
ATOM   1820  CA   ARG A 224     -2.338  38.140 -16.605  1.00 13.17
ATOM   1821  C    ARG A 224     -1.285  37.329 -17.406  1.00 12.97
ATOM   1822  O    ARG A 224     -0.114  37.707 -17.393  1.00 23.59
ATOM   1823  CB   ARG A 224     -2.761  39.436 -17.288  1.00  6.78
ATOM   1824  CG   ARG A 224     -4.250  39.469 -17.034  1.00  8.06
ATOM   1825  CD   ARG A 224     -5.082  40.108 -18.146  1.00 12.38
ATOM   1826  NE   ARG A 224     -5.748  41.218 -17.543  1.00 13.14
ATOM   1827  CZ   ARG A 224     -5.903  42.357 -18.159  1.00 15.80
ATOM   1828  NH1  ARG A 224     -6.054  43.420 -17.400  1.00 15.28
ATOM   1829  NH2  ARG A 224     -5.885  42.413 -19.461  1.00 21.44
ATOM   1830  N    PRO A 225     -1.676  36.218 -18.065  1.00  8.38
ATOM   1831  CA   PRO A 225     -0.714  35.529 -18.958  1.00 11.44
ATOM   1832  C    PRO A 225     -0.329  36.393 -20.195  1.00 12.14
ATOM   1833  O    PRO A 225     -1.078  37.226 -20.689  1.00 15.87
ATOM   1834  CB   PRO A 225     -1.450  34.244 -19.378  1.00  3.95
ATOM   1835  CG   PRO A 225     -2.899  34.631 -19.222  1.00  7.06
ATOM   1836  CD   PRO A 225     -2.988  35.657 -18.109  1.00  2.00
```

FIG. 11-35

```
ATOM   1837  N    ALA A 226      0.878  36.191 -20.723  1.00 14.99
ATOM   1838  CA   ALA A 226      1.233  36.742 -22.062  1.00 11.88
ATOM   1839  C    ALA A 226      0.386  36.175 -23.195  1.00  8.67
ATOM   1840  O    ALA A 226      0.371  34.980 -23.454  1.00 13.47
ATOM   1841  CB   ALA A 226      2.659  36.341 -22.384  1.00  5.22
ATOM   1842  N    PRO A 227     -0.355  36.994 -23.918  1.00  8.53
ATOM   1843  CA   PRO A 227     -1.249  36.365 -24.874  1.00 11.08
ATOM   1844  C    PRO A 227     -0.651  35.504 -25.965  1.00 16.60
ATOM   1845  O    PRO A 227     -1.336  34.645 -26.465  1.00 24.85
ATOM   1846  CB   PRO A 227     -2.009  37.540 -25.408  1.00  9.35
ATOM   1847  CG   PRO A 227     -1.907  38.643 -24.365  1.00  6.28
ATOM   1848  CD   PRO A 227     -0.484  38.432 -23.890  1.00 11.22
ATOM   1849  N    GLY A 228      0.631  35.657 -26.332  1.00 15.38
ATOM   1850  CA   GLY A 228      1.008  34.597 -27.299  1.00 12.94
ATOM   1851  C    GLY A 228      1.312  33.242 -26.725  1.00 14.69
ATOM   1852  O    GLY A 228      0.892  32.142 -27.040  1.00 19.20
ATOM   1853  N    THR A 229      2.181  33.377 -25.754  1.00 18.04
ATOM   1854  CA   THR A 229      2.648  32.135 -25.163  1.00 18.18
ATOM   1855  C    THR A 229      1.698  31.377 -24.251  1.00 23.24
ATOM   1856  O    THR A 229      1.822  30.147 -24.183  1.00 26.05
ATOM   1857  CB   THR A 229      3.943  32.390 -24.407  1.00 16.97
ATOM   1858  OG1  THR A 229      3.851  33.635 -23.723  1.00 19.63
ATOM   1859  CG2  THR A 229      5.154  32.454 -25.323  1.00 11.61
ATOM   1860  N    GLY A 230      0.890  32.206 -23.497  1.00 22.85
ATOM   1861  CA   GLY A 230      0.229  31.878 -22.202  1.00 21.38
ATOM   1862  C    GLY A 230      1.047  31.994 -20.878  1.00 21.55
ATOM   1863  O    GLY A 230      0.604  31.703 -19.772  1.00 25.83
ATOM   1864  N    LEU A 231      2.312  32.420 -21.008  1.00 18.05
ATOM   1865  CA   LEU A 231      3.140  32.318 -19.811  1.00 14.42
ATOM   1866  C    LEU A 231      2.633  33.261 -18.822  1.00 14.33
ATOM   1867  O    LEU A 231      2.301  34.356 -19.231  1.00 15.47
ATOM   1868  CB   LEU A 231      4.571  32.721 -20.092  1.00  9.37
ATOM   1869  CG   LEU A 231      5.268  31.522 -20.696  1.00 13.61
ATOM   1870  CD1  LEU A 231      5.787  30.532 -19.707  1.00  5.28
ATOM   1871  CD2  LEU A 231      6.470  31.949 -21.517  1.00 21.48
ATOM   1872  N    VAL A 232      2.608  32.849 -17.572  1.00 15.65
ATOM   1873  CA   VAL A 232      2.487  33.883 -16.547  1.00 17.64
ATOM   1874  C    VAL A 232      3.711  34.153 -15.683  1.00 18.23
ATOM   1875  O    VAL A 232      4.444  33.276 -15.252  1.00 19.58
ATOM   1876  CB   VAL A 232      1.136  33.801 -15.770  1.00 21.54
ATOM   1877  CG1  VAL A 232      1.158  34.189 -14.278  1.00 17.60
ATOM   1878  CG2  VAL A 232      0.441  32.487 -16.054  1.00 20.48
ATOM   1879  N    ASP A 233      3.935  35.451 -15.465  1.00 17.15
ATOM   1880  CA   ASP A 233      5.093  35.772 -14.614  1.00 18.47
ATOM   1881  C    ASP A 233      4.689  35.727 -13.108  1.00 19.86
ATOM   1882  O    ASP A 233      3.849  36.471 -12.575  1.00 21.51
ATOM   1883  CB   ASP A 233      5.831  37.017 -15.226  1.00 10.70
ATOM   1884  CG   ASP A 233      6.737  37.810 -14.301  1.00 13.64
ATOM   1885  OD1  ASP A 233      6.827  39.017 -14.458  1.00 19.81
ATOM   1886  OD2  ASP A 233      7.329  37.267 -13.382  1.00 22.72
ATOM   1887  N    MET A 234      5.261  34.694 -12.479  1.00 18.59
ATOM   1888  CA   MET A 234      5.009  34.458 -11.057  1.00 20.55
ATOM   1889  C    MET A 234      5.880  35.216 -10.060  1.00 23.54
ATOM   1890  O    MET A 234      5.673  35.143  -8.859  1.00 23.29
```

FIG. 11-36

| ATOM | 1891 | CB  | MET A 234 |  4.943 | 32.962 | -10.758 | 1.00 | 16.41 |
| ATOM | 1892 | CG  | MET A 234 |  3.772 | 32.250 | -11.464 | 1.00 | 19.02 |
| ATOM | 1893 | SD  | MET A 234 |  2.145 | 32.631 | -10.749 | 1.00 | 11.18 |
| ATOM | 1894 | CE  | MET A 234 |  2.303 | 31.916 |  -9.117 | 1.00 |  6.73 |
| ATOM | 1895 | N   | SER A 235 |  6.812 | 36.039 | -10.590 | 1.00 | 26.65 |
| ATOM | 1896 | CA  | SER A 235 |  7.719 | 36.759 |  -9.660 | 1.00 | 26.94 |
| ATOM | 1897 | C   | SER A 235 |  7.054 | 37.672 |  -8.636 | 1.00 | 26.93 |
| ATOM | 1898 | O   | SER A 235 |  7.445 | 37.868 |  -7.491 | 1.00 | 27.13 |
| ATOM | 1899 | CB  | SER A 235 |  8.829 | 37.525 | -10.403 | 1.00 | 25.40 |
| ATOM | 1900 | OG  | SER A 235 |  8.364 | 38.773 | -10.894 | 1.00 | 25.75 |
| ATOM | 1901 | N   | ARG A 236 |  5.944 | 38.232 |  -9.114 | 1.00 | 27.95 |
| ATOM | 1902 | CA  | ARG A 236 |  5.169 | 39.074 |  -8.190 | 1.00 | 29.02 |
| ATOM | 1903 | C   | ARG A 236 |  4.380 | 38.327 |  -7.065 | 1.00 | 29.89 |
| ATOM | 1904 | O   | ARG A 236 |  3.833 | 38.976 |  -6.172 | 1.00 | 31.19 |
| ATOM | 1905 | CB  | ARG A 236 |  4.284 | 40.015 |  -9.035 | 1.00 | 27.99 |
| ATOM | 1906 | CG  | ARG A 236 |  4.764 | 41.462 |  -9.152 | 1.00 | 34.18 |
| ATOM | 1907 | CD  | ARG A 236 |  3.840 | 42.350 | -10.032 | 1.00 | 47.72 |
| ATOM | 1908 | NE  | ARG A 236 |  2.504 | 42.630 |  -9.446 | 1.00 | 59.37 |
| ATOM | 1909 | CZ  | ARG A 236 |  1.336 | 42.977 | -10.060 | 1.00 | 60.91 |
| ATOM | 1910 | NH1 | ARG A 236 |  0.312 | 43.293 |  -9.304 | 1.00 | 61.96 |
| ATOM | 1911 | NH2 | ARG A 236 |  1.182 | 43.026 | -11.370 | 1.00 | 62.69 |
| ATOM | 1912 | N   | ASP A 237 |  4.325 | 36.963 |  -7.139 | 1.00 | 27.03 |
| ATOM | 1913 | CA  | ASP A 237 |  3.781 | 36.159 |  -6.013 | 1.00 | 26.53 |
| ATOM | 1914 | C   | ASP A 237 |  4.591 | 36.048 |  -4.696 | 1.00 | 26.07 |
| ATOM | 1915 | O   | ASP A 237 |  5.580 | 35.367 |  -4.430 | 1.00 | 26.85 |
| ATOM | 1916 | CB  | ASP A 237 |  3.257 | 34.804 |  -6.532 | 1.00 | 27.42 |
| ATOM | 1917 | CG  | ASP A 237 |  2.625 | 33.798 |  -5.565 | 1.00 | 24.29 |
| ATOM | 1918 | OD1 | ASP A 237 |  2.813 | 32.620 |  -5.838 | 1.00 | 13.64 |
| ATOM | 1919 | OD2 | ASP A 237 |  1.927 | 34.138 |  -4.599 | 1.00 | 27.59 |
| ATOM | 1920 | N   | ARG A 238 |  4.052 | 36.843 |  -3.791 | 1.00 | 24.71 |
| ATOM | 1921 | CA  | ARG A 238 |  4.704 | 36.870 |  -2.512 | 1.00 | 25.09 |
| ATOM | 1922 | C   | ARG A 238 |  4.080 | 35.961 |  -1.445 | 1.00 | 25.67 |
| ATOM | 1923 | O   | ARG A 238 |  4.319 | 36.216 |  -0.264 | 1.00 | 25.12 |
| ATOM | 1924 | CB  | ARG A 238 |  4.664 | 38.315 |  -2.016 | 1.00 | 32.75 |
| ATOM | 1925 | CG  | ARG A 238 |  5.094 | 39.556 |  -2.853 | 1.00 | 40.15 |
| ATOM | 1926 | CD  | ARG A 238 |  4.733 | 40.911 |  -2.132 | 1.00 | 44.67 |
| ATOM | 1927 | NE  | ARG A 238 |  5.006 | 40.839 |  -0.665 | 1.00 | 46.60 |
| ATOM | 1928 | CZ  | ARG A 238 |  6.182 | 41.016 |  -0.017 | 1.00 | 42.09 |
| ATOM | 1929 | NH1 | ARG A 238 |  7.017 | 41.976 |  -0.323 | 1.00 | 45.87 |
| ATOM | 1930 | NH2 | ARG A 238 |  6.492 | 40.191 |   0.954 | 1.00 | 40.90 |
| ATOM | 1931 | N   | ASN A 239 |  3.224 | 34.965 |  -1.888 | 1.00 | 26.60 |
| ATOM | 1932 | CA  | ASN A 239 |  2.284 | 34.139 |  -1.063 | 1.00 | 22.52 |
| ATOM | 1933 | C   | ASN A 239 |  1.437 | 34.863 |  -0.031 | 1.00 | 22.52 |
| ATOM | 1934 | O   | ASN A 239 |  1.366 | 34.495 |   1.128 | 1.00 | 24.12 |
| ATOM | 1935 | CB  | ASN A 239 |  2.919 | 33.018 |  -0.260 | 1.00 | 20.91 |
| ATOM | 1936 | CG  | ASN A 239 |  3.887 | 32.286 |  -1.140 | 1.00 | 23.32 |
| ATOM | 1937 | OD1 | ASN A 239 |  3.534 | 31.482 |  -1.996 | 1.00 | 24.09 |
| ATOM | 1938 | ND2 | ASN A 239 |  5.155 | 32.582 |  -0.884 | 1.00 | 16.67 |
| ATOM | 1939 | N   | ILE A 240 |  0.809 | 35.926 |  -0.481 | 1.00 | 23.43 |
| ATOM | 1940 | CA  | ILE A 240 | -0.070 | 36.655 |   0.429 | 1.00 | 26.10 |
| ATOM | 1941 | C   | ILE A 240 | -1.535 | 36.363 |   0.197 | 1.00 | 25.69 |
| ATOM | 1942 | O   | ILE A 240 | -2.077 | 36.474 |  -0.897 | 1.00 | 25.45 |
| ATOM | 1943 | CB  | ILE A 240 |  0.252 | 38.162 |   0.282 | 1.00 | 29.11 |
| ATOM | 1944 | CG1 | ILE A 240 |  1.502 | 38.477 |   1.057 | 1.00 | 28.96 |

FIG. 11-37

```
ATOM   1945  CG2 ILE A 240     -0.777  39.179   0.772  1.00 34.47
ATOM   1946  CD1 ILE A 240      1.874  39.812   0.430  1.00 36.04
ATOM   1947  N   PRO A 241     -2.212  36.021   1.317  1.00 25.55
ATOM   1948  CA  PRO A 241     -3.645  35.753   1.186  1.00 22.78
ATOM   1949  C   PRO A 241     -4.420  36.931   0.732  1.00 17.53
ATOM   1950  O   PRO A 241     -4.003  38.064   0.909  1.00 14.10
ATOM   1951  CB  PRO A 241     -4.062  35.336   2.588  1.00 22.04
ATOM   1952  CG  PRO A 241     -3.018  35.936   3.516  1.00 25.18
ATOM   1953  CD  PRO A 241     -1.733  35.898   2.688  1.00 25.92
ATOM   1954  N   ARG A 242     -5.612  36.614   0.267  1.00 21.89
ATOM   1955  CA  ARG A 242     -6.751  37.570   0.320  1.00 25.81
ATOM   1956  C   ARG A 242     -7.137  38.330   1.645  1.00 31.68
ATOM   1957  O   ARG A 242     -7.435  37.816   2.733  1.00 31.98
ATOM   1958  CB  ARG A 242     -7.994  36.894  -0.300  1.00 14.35
ATOM   1959  CG  ARG A 242     -8.997  37.972  -0.659  1.00 11.01
ATOM   1960  CD  ARG A 242    -10.331  37.363  -1.045  1.00  8.89
ATOM   1961  NE  ARG A 242    -11.245  38.401  -1.448  1.00 10.31
ATOM   1962  CZ  ARG A 242    -12.355  38.057  -2.043  1.00 14.73
ATOM   1963  NH1 ARG A 242    -12.638  36.809  -2.235  1.00 20.41
ATOM   1964  NH2 ARG A 242    -13.180  38.963  -2.470  1.00 15.69
ATOM   1965  N   SER A 243     -7.137  39.669   1.485  1.00 35.63
ATOM   1966  CA  SER A 243     -7.755  40.473   2.562  1.00 34.56
ATOM   1967  C   SER A 243     -9.248  40.287   2.714  1.00 39.05
ATOM   1968  O   SER A 243     -9.973  40.230   1.727  1.00 39.20
ATOM   1969  CB  SER A 243     -7.520  41.959   2.341  1.00 29.93
ATOM   1970  OG  SER A 243     -6.170  42.317   2.714  1.00 36.73
ATOM   1971  N   PRO A 244     -9.696  40.219   3.998  1.00 47.16
ATOM   1972  CA  PRO A 244    -11.150  40.119   4.341  1.00 52.52
ATOM   1973  C   PRO A 244    -12.212  41.010   3.618  1.00 58.55
ATOM   1974  O   PRO A 244    -11.985  42.204   3.316  1.00 62.66
ATOM   1975  CB  PRO A 244    -11.138  40.351   5.857  1.00 51.12
ATOM   1976  CG  PRO A 244     -9.762  40.917   6.209  1.00 50.00
ATOM   1977  CD  PRO A 244     -8.861  40.211   5.207  1.00 48.00
ATOM   1978  N   THR A 245    -13.413  40.396   3.379  1.00 59.18
ATOM   1979  CA  THR A 245    -14.542  41.303   3.022  1.00 61.07
ATOM   1980  C   THR A 245    -15.409  41.765   4.227  1.00 62.30
ATOM   1981  O   THR A 245    -15.210  42.860   4.754  1.00 61.21
ATOM   1982  CB  THR A 245    -15.369  40.809   1.789  1.00 62.70
ATOM   1983  OG1 THR A 245    -14.487  40.113   0.867  1.00 59.13
ATOM   1984  CG2 THR A 245    -16.092  41.979   1.072  1.00 59.99
ATOM   1985  N   SER A 246    -16.289  40.871   4.723  1.00 65.13
ATOM   1986  CA  SER A 246    -16.793  40.949   6.125  1.00 64.23
ATOM   1987  C   SER A 246    -15.777  40.449   7.217  1.00 63.93
ATOM   1988  O   SER A 246    -14.687  40.004   6.887  1.00 59.17
ATOM   1989  CB  SER A 246    -18.146  40.177   6.184  1.00 62.14
ATOM   1990  OG  SER A 246    -17.943  38.880   6.783  1.00 61.39
ATOM   1991  N   PRO A 247    -16.122  40.486   8.549  1.00 67.42
ATOM   1992  CA  PRO A 247    -15.382  39.671   9.575  1.00 68.15
ATOM   1993  C   PRO A 247    -15.522  38.114   9.593  1.00 67.61
ATOM   1994  O   PRO A 247    -14.696  37.390  10.153  1.00 64.19
ATOM   1995  CB  PRO A 247    -15.875  40.242  10.905  1.00 67.32
ATOM   1996  CG  PRO A 247    -16.517  41.584  10.555  1.00 68.63
ATOM   1997  CD  PRO A 247    -17.125  41.340   9.183  1.00 67.90
ATOM   1998  N   GLY A 248    -16.633  37.645   8.945  1.00 68.48
```

FIG. 11-38

```
ATOM   1999  CA   GLY A 248     -16.868  36.201   8.703  1.00 65.79
ATOM   2000  C    GLY A 248     -15.827  35.474   7.851  1.00 64.41
ATOM   2001  O    GLY A 248     -15.515  34.308   8.088  1.00 65.17
ATOM   2002  N    GLU A 249     -15.305  36.270   6.865  1.00 62.60
ATOM   2003  CA   GLU A 249     -14.261  35.886   5.867  1.00 58.91
ATOM   2004  C    GLU A 249     -12.759  35.855   6.230  1.00 54.61
ATOM   2005  O    GLU A 249     -12.024  36.838   6.157  1.00 52.57
ATOM   2006  CB   GLU A 249     -14.422  36.680   4.562  1.00 59.84
ATOM   2007  CG   GLU A 249     -15.543  36.117   3.670  1.00 61.94
ATOM   2008  CD   GLU A 249     -16.577  37.187   3.341  1.00 64.70
ATOM   2009  OE1  GLU A 249     -16.859  38.007   4.227  1.00 65.11
ATOM   2010  OE2  GLU A 249     -17.087  37.188   2.211  1.00 65.05
ATOM   2011  N    GLY A 250     -12.346  34.619   6.586  1.00 51.32
ATOM   2012  CA   GLY A 250     -10.927  34.252   6.667  1.00 44.39
ATOM   2013  C    GLY A 250     -10.473  33.461   5.445  1.00 38.12
ATOM   2014  O    GLY A 250     -11.229  32.665   4.902  1.00 36.31
ATOM   2015  N    PHE A 251      -9.223  33.794   5.037  1.00 35.72
ATOM   2016  CA   PHE A 251      -8.610  33.383   3.735  1.00 30.65
ATOM   2017  C    PHE A 251      -7.243  32.700   3.828  1.00 30.34
ATOM   2018  O    PHE A 251      -6.322  33.194   4.494  1.00 27.97
ATOM   2019  CB   PHE A 251      -8.426  34.566   2.749  1.00 22.47
ATOM   2020  CG   PHE A 251      -9.775  35.018   2.238  1.00 22.58
ATOM   2021  CD1  PHE A 251     -10.236  36.305   2.587  1.00 20.43
ATOM   2022  CD2  PHE A 251     -10.591  34.117   1.498  1.00 17.22
ATOM   2023  CE1  PHE A 251     -11.556  36.647   2.267  1.00 16.98
ATOM   2024  CE2  PHE A 251     -11.901  34.458   1.157  1.00 10.80
ATOM   2025  CZ   PHE A 251     -12.374  35.709   1.586  1.00 17.82
ATOM   2026  N    VAL A 252      -7.145  31.549   3.119  1.00 29.62
ATOM   2027  CA   VAL A 252      -5.778  31.021   2.944  1.00 27.55
ATOM   2028  C    VAL A 252      -4.938  31.698   1.863  1.00 26.66
ATOM   2029  O    VAL A 252      -5.403  32.313   0.897  1.00 28.16
ATOM   2030  CB   VAL A 252      -5.761  29.505   2.771  1.00 26.65
ATOM   2031  CG1  VAL A 252      -6.872  29.061   1.845  1.00 27.01
ATOM   2032  CG2  VAL A 252      -5.960  28.784   4.097  1.00 27.70
ATOM   2033  N    ASN A 253      -3.624  31.589   2.098  1.00 25.65
ATOM   2034  CA   ASN A 253      -2.773  32.260   1.098  1.00 25.19
ATOM   2035  C    ASN A 253      -2.643  31.661  -0.324  1.00 25.85
ATOM   2036  O    ASN A 253      -2.483  32.385  -1.302  1.00 29.24
ATOM   2037  CB   ASN A 253      -1.427  32.639   1.708  1.00 25.19
ATOM   2038  CG   ASN A 253      -0.646  31.405   2.077  1.00 25.89
ATOM   2039  OD1  ASN A 253      -1.052  30.301   1.761  1.00 21.82
ATOM   2040  ND2  ASN A 253       0.455  31.615   2.796  1.00 19.12
ATOM   2041  N    PHE A 254      -2.739  30.315  -0.381  1.00 25.58
ATOM   2042  CA   PHE A 254      -2.758  29.540  -1.647  1.00 21.43
ATOM   2043  C    PHE A 254      -3.198  28.092  -1.511  1.00 18.53
ATOM   2044  O    PHE A 254      -3.270  27.592  -0.407  1.00 18.82
ATOM   2045  CB   PHE A 254      -1.390  29.519  -2.332  1.00 19.01
ATOM   2046  CG   PHE A 254      -0.279  29.053  -1.408  1.00 15.38
ATOM   2047  CD1  PHE A 254      -0.209  27.689  -0.978  1.00 17.98
ATOM   2048  CD2  PHE A 254       0.665  30.016  -0.987  1.00  9.90
ATOM   2049  CE1  PHE A 254       0.781  27.300  -0.049  1.00 15.57
ATOM   2050  CE2  PHE A 254       1.667  29.624  -0.082  1.00 15.50
ATOM   2051  CZ   PHE A 254       1.703  28.283   0.409  1.00 15.24
ATOM   2052  N    ASP A 255      -3.372  27.463  -2.668  1.00 16.41
```

FIG. 11-39

```
ATOM   2053  CA   ASP A 255      -3.481  25.996  -2.805  1.00 16.81
ATOM   2054  C    ASP A 255      -2.560  25.498  -3.921  1.00 19.18
ATOM   2055  O    ASP A 255      -2.148  26.224  -4.815  1.00 22.17
ATOM   2056  CB   ASP A 255      -4.915  25.596  -3.144  1.00 17.40
ATOM   2057  CG   ASP A 255      -5.321  24.154  -2.847  1.00 15.05
ATOM   2058  OD1  ASP A 255      -6.420  23.762  -3.239  1.00 18.93
ATOM   2059  OD2  ASP A 255      -4.574  23.430  -2.224  1.00 14.41
ATOM   2060  N    TYR A 256      -2.181  24.256  -3.791  1.00 19.89
ATOM   2061  CA   TYR A 256      -1.305  23.544  -4.722  1.00 18.85
ATOM   2062  C    TYR A 256      -1.881  22.143  -4.960  1.00 18.37
ATOM   2063  O    TYR A 256      -2.113  21.411  -4.007  1.00 11.63
ATOM   2064  CB   TYR A 256       0.099  23.248  -4.150  1.00 15.11
ATOM   2065  CG   TYR A 256       1.088  24.387  -4.161  1.00 13.13
ATOM   2066  CD1  TYR A 256       1.234  25.227  -3.019  1.00 13.67
ATOM   2067  CD2  TYR A 256       1.891  24.535  -5.307  1.00 12.96
ATOM   2068  CE1  TYR A 256       2.205  26.240  -3.048  1.00 14.01
ATOM   2069  CE2  TYR A 256       2.832  25.579  -5.357  1.00  9.87
ATOM   2070  CZ   TYR A 256       2.954  26.427  -4.249  1.00 14.06
ATOM   2071  OH   TYR A 256       3.805  27.508  -4.352  1.00 12.65
ATOM   2072  N    GLY A 257      -1.992  21.794  -6.262  1.00 20.82
ATOM   2073  CA   GLY A 257      -2.397  20.448  -6.709  1.00 14.79
ATOM   2074  C    GLY A 257      -1.469  19.756  -7.691  1.00 15.50
ATOM   2075  O    GLY A 257      -1.155  20.214  -8.784  1.00 15.30
ATOM   2076  N    TRP A 258      -1.039  18.581  -7.237  1.00 17.08
ATOM   2077  CA   TRP A 258      -0.213  17.655  -8.001  1.00 13.59
ATOM   2078  C    TRP A 258      -0.976  16.791  -9.001  1.00 15.39
ATOM   2079  O    TRP A 258      -1.880  16.027  -8.729  1.00 12.97
ATOM   2080  CB   TRP A 258       0.643  16.860  -7.010  1.00 10.44
ATOM   2081  CG   TRP A 258       1.634  15.949  -7.702  1.00 17.38
ATOM   2082  CD1  TRP A 258       1.444  14.583  -7.931  1.00 17.26
ATOM   2083  CD2  TRP A 258       2.958  16.235  -8.264  1.00 14.97
ATOM   2084  NE1  TRP A 258       2.490  14.010  -8.584  1.00 15.43
ATOM   2085  CE2  TRP A 258       3.452  15.003  -8.815  1.00 18.32
ATOM   2086  CE3  TRP A 258       3.779  17.397  -8.300  1.00  9.97
ATOM   2087  CZ2  TRP A 258       4.722  14.973  -9.435  1.00 15.19
ATOM   2088  CZ3  TRP A 258       5.053  17.351  -8.884  1.00  4.79
ATOM   2089  CH2  TRP A 258       5.495  16.153  -9.468  1.00 11.32
ATOM   2090  N    PHE A 259      -0.567  17.014 -10.252  1.00 17.62
ATOM   2091  CA   PHE A 259      -1.036  16.205 -11.376  1.00 12.44
ATOM   2092  C    PHE A 259      -0.024  15.173 -11.814  1.00 14.05
ATOM   2093  O    PHE A 259      -0.323  14.018 -12.090  1.00 17.06
ATOM   2094  CB   PHE A 259      -1.301  17.134 -12.550  1.00 12.94
ATOM   2095  CG   PHE A 259      -1.518  16.409 -13.865  1.00 14.61
ATOM   2096  CD1  PHE A 259      -0.520  16.439 -14.868  1.00 22.80
ATOM   2097  CD2  PHE A 259      -2.716  15.712 -14.104  1.00 16.33
ATOM   2098  CE1  PHE A 259      -0.716  15.788 -16.116  1.00 14.17
ATOM   2099  CE2  PHE A 259      -2.932  15.085 -15.350  1.00 14.85
ATOM   2100  CZ   PHE A 259      -1.933  15.142 -16.338  1.00 11.87
ATOM   2101  N    GLY A 260       1.209  15.675 -11.946  1.00 13.74
ATOM   2102  CA   GLY A 260       2.284  14.791 -12.409  1.00 16.04
ATOM   2103  C    GLY A 260       2.371  14.617 -13.925  1.00 13.79
ATOM   2104  O    GLY A 260       2.797  15.500 -14.650  1.00 14.87
ATOM   2105  N    ALA A 261       1.946  13.447 -14.369  1.00 12.59
ATOM   2106  CA   ALA A 261       2.131  13.199 -15.786  1.00 15.28
```

FIG. 11-40

| | | | | | | | | | |
|---|---|---|---|---|---|---|---|---|---|
| ATOM | 2107 | C | ALA | A | 261 | 1.228 | 12.147 | -16.397 | 1.00 19.81 |
| ATOM | 2108 | O | ALA | A | 261 | 1.599 | 11.350 | -17.249 | 1.00 26.00 |
| ATOM | 2109 | CB | ALA | A | 261 | 3.612 | 12.999 | -16.173 | 1.00 11.02 |
| ATOM | 2110 | N | GLN | A | 262 | -0.023 | 12.187 | -15.947 | 1.00 19.62 |
| ATOM | 2111 | CA | GLN | A | 262 | -1.002 | 11.201 | -16.465 | 1.00 19.17 |
| ATOM | 2112 | C | GLN | A | 262 | -1.308 | 11.159 | -17.965 | 1.00 25.44 |
| ATOM | 2113 | O | GLN | A | 262 | -1.291 | 12.137 | -18.717 | 1.00 26.73 |
| ATOM | 2114 | CB | GLN | A | 262 | -2.332 | 11.419 | -15.743 | 1.00 16.60 |
| ATOM | 2115 | CG | GLN | A | 262 | -2.246 | 11.063 | -14.236 | 1.00 18.60 |
| ATOM | 2116 | CD | GLN | A | 262 | -3.239 | 11.832 | -13.401 | 1.00 7.94 |
| ATOM | 2117 | OE1 | GLN | A | 262 | -4.424 | 11.688 | -13.635 | 1.00 12.01 |
| ATOM | 2118 | NE2 | GLN | A | 262 | -2.755 | 12.641 | -12.440 | 1.00 2.00 |
| ATOM | 2119 | N | THR | A | 263 | -1.687 | 9.957 | -18.422 | 1.00 30.55 |
| ATOM | 2120 | CA | THR | A | 263 | -1.876 | 9.852 | -19.891 | 1.00 26.86 |
| ATOM | 2121 | C | THR | A | 263 | -3.283 | 10.033 | -20.401 | 1.00 27.92 |
| ATOM | 2122 | O | THR | A | 263 | -3.576 | 10.385 | -21.533 | 1.00 28.52 |
| ATOM | 2123 | CB | THR | A | 263 | -1.349 | 8.534 | -20.401 | 1.00 27.50 |
| ATOM | 2124 | OG1 | THR | A | 263 | -2.174 | 7.431 | -20.005 | 1.00 33.19 |
| ATOM | 2125 | CG2 | THR | A | 263 | 0.099 | 8.388 | -19.966 | 1.00 26.21 |
| ATOM | 2126 | N | GLU | A | 264 | -4.163 | 9.878 | -19.396 | 1.00 30.90 |
| ATOM | 2127 | CA | GLU | A | 264 | -5.575 | 10.272 | -19.447 | 1.00 24.85 |
| ATOM | 2128 | C | GLU | A | 264 | -5.973 | 11.406 | -20.407 | 1.00 24.54 |
| ATOM | 2129 | O | GLU | A | 264 | -5.828 | 12.610 | -20.163 | 1.00 23.30 |
| ATOM | 2130 | CB | GLU | A | 264 | -6.016 | 10.482 | -17.978 | 1.00 18.52 |
| ATOM | 2131 | CG | GLU | A | 264 | -7.531 | 10.673 | -17.864 | 1.00 15.79 |
| ATOM | 2132 | CD | GLU | A | 264 | -8.327 | 9.482 | -18.403 | 1.00 16.47 |
| ATOM | 2133 | OE1 | GLU | A | 264 | -8.949 | 9.610 | -19.451 | 1.00 14.54 |
| ATOM | 2134 | OE2 | GLU | A | 264 | -8.362 | 8.425 | -17.760 | 1.00 23.45 |
| ATOM | 2135 | N | ALA | A | 265 | -6.500 | 10.985 | -21.545 | 1.00 23.50 |
| ATOM | 2136 | CA | ALA | A | 265 | -6.882 | 12.012 | -22.531 | 1.00 26.46 |
| ATOM | 2137 | C | ALA | A | 265 | -8.039 | 12.979 | -22.190 | 1.00 32.48 |
| ATOM | 2138 | O | ALA | A | 265 | -8.261 | 14.016 | -22.820 | 1.00 39.40 |
| ATOM | 2139 | CB | ALA | A | 265 | -7.219 | 11.324 | -23.849 | 1.00 18.93 |
| ATOM | 2140 | N | ASP | A | 266 | -8.793 | 12.599 | -21.164 | 1.00 33.93 |
| ATOM | 2141 | CA | ASP | A | 266 | -9.953 | 13.366 | -20.701 | 1.00 31.50 |
| ATOM | 2142 | C | ASP | A | 266 | -9.532 | 14.191 | -19.500 | 1.00 31.12 |
| ATOM | 2143 | O | ASP | A | 266 | -9.383 | 13.689 | -18.402 | 1.00 34.26 |
| ATOM | 2144 | CB | ASP | A | 266 | -11.013 | 12.332 | -20.333 | 1.00 31.07 |
| ATOM | 2145 | CG | ASP | A | 266 | -12.326 | 12.868 | -19.786 | 1.00 34.38 |
| ATOM | 2146 | OD1 | ASP | A | 266 | -13.279 | 12.114 | -19.805 | 1.00 38.63 |
| ATOM | 2147 | OD2 | ASP | A | 266 | -12.411 | 13.986 | -19.287 | 1.00 40.09 |
| ATOM | 2148 | N | ALA | A | 267 | -9.237 | 15.472 | -19.762 | 1.00 31.80 |
| ATOM | 2149 | CA | ALA | A | 267 | -8.708 | 16.330 | -18.680 | 1.00 30.06 |
| ATOM | 2150 | C | ALA | A | 267 | -9.546 | 16.320 | -17.414 | 1.00 31.41 |
| ATOM | 2151 | O | ALA | A | 267 | -9.017 | 16.006 | -16.352 | 1.00 32.15 |
| ATOM | 2152 | CB | ALA | A | 267 | -8.547 | 17.791 | -19.118 | 1.00 26.68 |
| ATOM | 2153 | N | ASP | A | 268 | -10.873 | 16.574 | -17.587 | 1.00 31.41 |
| ATOM | 2154 | CA | ASP | A | 268 | -11.868 | 16.296 | -16.522 | 1.00 28.22 |
| ATOM | 2155 | C | ASP | A | 268 | -11.758 | 15.138 | -15.483 | 1.00 25.83 |
| ATOM | 2156 | O | ASP | A | 268 | -12.109 | 15.329 | -14.318 | 1.00 31.90 |
| ATOM | 2157 | CB | ASP | A | 268 | -13.213 | 16.258 | -17.196 | 1.00 29.07 |
| ATOM | 2158 | CG | ASP | A | 268 | -13.807 | 17.646 | -17.195 | 1.00 30.50 |
| ATOM | 2159 | OD1 | ASP | A | 268 | -14.901 | 17.792 | -17.772 | 1.00 23.89 |
| ATOM | 2160 | OD2 | ASP | A | 268 | -13.191 | 18.516 | -16.557 | 1.00 27.40 |

FIG. 11-41

| ATOM | 2161 | N | LYS A 269 | -11.265 | 13.956 | -15.921 | 1.00 | 17.14 |
| --- | --- | --- | --- | --- | --- | --- | --- | --- |
| ATOM | 2162 | CA | LYS A 269 | -10.995 | 12.760 | -15.092 | 1.00 | 15.98 |
| ATOM | 2163 | C | LYS A 269 | -9.599 | 12.544 | -14.532 | 1.00 | 18.67 |
| ATOM | 2164 | O | LYS A 269 | -9.206 | 11.551 | -13.894 | 1.00 | 19.84 |
| ATOM | 2165 | CB | LYS A 269 | -11.084 | 11.466 | -15.840 | 1.00 | 13.71 |
| ATOM | 2166 | CG | LYS A 269 | -12.450 | 11.051 | -16.260 | 1.00 | 13.58 |
| ATOM | 2167 | CD | LYS A 269 | -12.228 | 9.698 | -16.936 | 1.00 | 15.30 |
| ATOM | 2168 | CE | LYS A 269 | -13.413 | 9.519 | -17.854 | 1.00 | 18.12 |
| ATOM | 2169 | NZ | LYS A 269 | -12.965 | 9.489 | -19.261 | 1.00 | 14.63 |
| ATOM | 2170 | N | THR A 270 | -8.807 | 13.529 | -14.864 | 1.00 | 18.57 |
| ATOM | 2171 | CA | THR A 270 | -7.445 | 13.505 | -14.318 | 1.00 | 16.68 |
| ATOM | 2172 | C | THR A 270 | -7.436 | 13.855 | -12.812 | 1.00 | 18.76 |
| ATOM | 2173 | O | THR A 270 | -8.292 | 14.606 | -12.319 | 1.00 | 17.34 |
| ATOM | 2174 | CB | THR A 270 | -6.814 | 14.469 | -15.323 | 1.00 | 14.24 |
| ATOM | 2175 | OG1 | THR A 270 | -5.896 | 13.835 | -16.199 | 1.00 | 23.98 |
| ATOM | 2176 | CG2 | THR A 270 | -6.432 | 15.836 | -14.943 | 1.00 | 5.95 |
| ATOM | 2177 | N | VAL A 271 | -6.500 | 13.243 | -12.069 | 1.00 | 19.22 |
| ATOM | 2178 | CA | VAL A 271 | -6.490 | 13.511 | -10.614 | 1.00 | 15.85 |
| ATOM | 2179 | C | VAL A 271 | -5.445 | 14.431 | -9.977 | 1.00 | 19.76 |
| ATOM | 2180 | O | VAL A 271 | -4.237 | 14.285 | -10.122 | 1.00 | 26.97 |
| ATOM | 2181 | CB | VAL A 271 | -6.736 | 12.242 | -9.777 | 1.00 | 11.90 |
| ATOM | 2182 | CG1 | VAL A 271 | -5.936 | 12.033 | -8.474 | 1.00 | 12.10 |
| ATOM | 2183 | CG2 | VAL A 271 | -6.708 | 11.030 | -10.662 | 1.00 | 17.30 |
| ATOM | 2184 | N | TRP A 272 | -5.987 | 15.382 | -9.197 | 1.00 | 18.25 |
| ATOM | 2185 | CA | TRP A 272 | -5.176 | 16.420 | -8.553 | 1.00 | 17.46 |
| ATOM | 2186 | C | TRP A 272 | -5.063 | 16.292 | -7.050 | 1.00 | 20.75 |
| ATOM | 2187 | O | TRP A 272 | -5.973 | 16.600 | -6.306 | 1.00 | 26.15 |
| ATOM | 2188 | CB | TRP A 272 | -5.694 | 17.810 | -8.894 | 1.00 | 12.46 |
| ATOM | 2189 | CG | TRP A 272 | -5.605 | 17.963 | -10.396 | 1.00 | 4.73 |
| ATOM | 2190 | CD1 | TRP A 272 | -6.337 | 17.301 | -11.401 | 1.00 | 10.33 |
| ATOM | 2191 | CD2 | TRP A 272 | -4.695 | 18.791 | -11.129 | 1.00 | 6.26 |
| ATOM | 2192 | NE1 | TRP A 272 | -5.937 | 17.651 | -12.655 | 1.00 | 9.92 |
| ATOM | 2193 | CE2 | TRP A 272 | -4.928 | 18.570 | -12.540 | 1.00 | 13.49 |
| ATOM | 2194 | CE3 | TRP A 272 | -3.709 | 19.722 | -10.724 | 1.00 | 7.10 |
| ATOM | 2195 | CZ2 | TRP A 272 | -4.190 | 19.292 | -13.501 | 1.00 | 12.35 |
| ATOM | 2196 | CZ3 | TRP A 272 | -2.960 | 20.428 | -11.685 | 1.00 | 2.10 |
| ATOM | 2197 | CH2 | TRP A 272 | -3.203 | 20.217 | -13.064 | 1.00 | 10.46 |
| ATOM | 2198 | N | THR A 273 | -3.918 | 15.778 | -6.632 | 1.00 | 17.42 |
| ATOM | 2199 | CA | THR A 273 | -3.692 | 15.553 | -5.213 | 1.00 | 15.79 |
| ATOM | 2200 | C | THR A 273 | -3.163 | 16.686 | -4.372 | 1.00 | 13.86 |
| ATOM | 2201 | O | THR A 273 | -2.177 | 17.318 | -4.679 | 1.00 | 11.64 |
| ATOM | 2202 | CB | THR A 273 | -2.770 | 14.370 | -5.045 | 1.00 | 13.24 |
| ATOM | 2203 | OG1 | THR A 273 | -3.239 | 13.328 | -5.870 | 1.00 | 20.22 |
| ATOM | 2204 | CG2 | THR A 273 | -2.640 | 13.867 | -3.619 | 1.00 | 13.12 |
| ATOM | 2205 | N | HIS A 274 | -3.843 | 16.885 | -3.249 | 1.00 | 18.28 |
| ATOM | 2206 | CA | HIS A 274 | -3.441 | 17.935 | -2.314 | 1.00 | 22.93 |
| ATOM | 2207 | C | HIS A 274 | -3.873 | 17.795 | -0.829 | 1.00 | 27.75 |
| ATOM | 2208 | O | HIS A 274 | -5.021 | 17.470 | -0.525 | 1.00 | 30.91 |
| ATOM | 2209 | CB | HIS A 274 | -3.812 | 19.316 | -2.915 | 1.00 | 23.67 |
| ATOM | 2210 | CG | HIS A 274 | -5.291 | 19.563 | -3.151 | 1.00 | 22.36 |
| ATOM | 2211 | ND1 | HIS A 274 | -5.908 | 20.708 | -2.777 | 1.00 | 17.45 |
| ATOM | 2212 | CD2 | HIS A 274 | -6.201 | 18.733 | -3.826 | 1.00 | 17.74 |
| ATOM | 2213 | CE1 | HIS A 274 | -7.197 | 20.611 | -3.217 | 1.00 | 20.56 |
| ATOM | 2214 | NE2 | HIS A 274 | -7.379 | 19.398 | -3.855 | 1.00 | 23.63 |

FIG. 11-42

```
ATOM   2215  N    GLY A 275      -2.929  18.037   0.123  1.00 27.24
ATOM   2216  CA   GLY A 275      -3.460  18.141   1.490  1.00 23.02
ATOM   2217  C    GLY A 275      -4.394  19.341   1.683  1.00 25.48
ATOM   2218  O    GLY A 275      -4.230  20.374   1.023  1.00 25.16
ATOM   2219  N    ASN A 276      -5.331  19.173   2.661  1.00 24.03
ATOM   2220  CA   ASN A 276      -6.163  20.314   3.170  1.00 17.75
ATOM   2221  C    ASN A 276      -5.485  21.458   3.883  1.00 14.37
ATOM   2222  O    ASN A 276      -5.856  22.616   3.754  1.00 14.12
ATOM   2223  CB   ASN A 276      -7.333  19.854   4.068  1.00 19.86
ATOM   2224  CG   ASN A 276      -6.847  18.977   5.216  1.00 18.36
ATOM   2225  OD1  ASN A 276      -5.658  18.801   5.383  1.00 25.27
ATOM   2226  ND2  ASN A 276      -7.752  18.354   5.968  1.00 19.44
ATOM   2227  N    HIS A 277      -4.468  21.096   4.677  1.00 15.18
ATOM   2228  CA   HIS A 277      -3.710  22.098   5.478  1.00 19.44
ATOM   2229  C    HIS A 277      -2.517  21.451   6.163  1.00 17.70
ATOM   2230  O    HIS A 277      -2.301  20.258   6.028  1.00 20.31
ATOM   2231  CB   HIS A 277      -4.529  22.815   6.622  1.00 22.49
ATOM   2232  CG   HIS A 277      -5.313  21.881   7.521  1.00 16.94
ATOM   2233  ND1  HIS A 277      -4.784  20.863   8.201  1.00 16.33
ATOM   2234  CD2  HIS A 277      -6.694  21.847   7.676  1.00 15.58
ATOM   2235  CE1  HIS A 277      -5.805  20.150   8.774  1.00 20.84
ATOM   2236  NE2  HIS A 277      -6.979  20.764   8.446  1.00 16.76
ATOM   2237  N    TYR A 278      -1.744  22.245   6.926  1.00 14.85
ATOM   2238  CA   TYR A 278      -0.623  21.597   7.567  1.00 13.33
ATOM   2239  C    TYR A 278      -1.087  20.557   8.552  1.00 14.52
ATOM   2240  O    TYR A 278      -2.250  20.557   8.878  1.00 19.78
ATOM   2241  CB   TYR A 278       0.329  22.667   8.133  1.00 15.16
ATOM   2242  CG   TYR A 278      -0.212  23.388   9.347  1.00 22.91
ATOM   2243  CD1  TYR A 278       0.190  22.997  10.638  1.00 23.52
ATOM   2244  CD2  TYR A 278      -1.107  24.449   9.156  1.00 23.06
ATOM   2245  CE1  TYR A 278      -0.244  23.746  11.741  1.00 20.07
ATOM   2246  CE2  TYR A 278      -1.503  25.202  10.265  1.00 22.97
ATOM   2247  CZ   TYR A 278      -1.026  24.879  11.529  1.00 17.29
ATOM   2248  OH   TYR A 278      -1.290  25.758  12.555  1.00 26.28
ATOM   2249  N    HIS A 279      -0.223  19.684   9.023  1.00 19.20
ATOM   2250  CA   HIS A 279      -0.614  18.717  10.068  1.00 21.16
ATOM   2251  C    HIS A 279      -0.657  19.257  11.533  1.00 25.90
ATOM   2252  O    HIS A 279       0.358  19.426  12.193  1.00 31.42
ATOM   2253  CB   HIS A 279       0.389  17.574   9.920  1.00 16.37
ATOM   2254  CG   HIS A 279      -0.094  16.261  10.458  1.00 13.38
ATOM   2255  ND1  HIS A 279       0.644  15.460  11.253  1.00 13.49
ATOM   2256  CD2  HIS A 279      -1.273  15.594  10.180  1.00 15.64
ATOM   2257  CE1  HIS A 279      -0.045  14.285  11.478  1.00 11.81
ATOM   2258  NE2  HIS A 279      -1.230  14.375  10.812  1.00 15.93
ATOM   2259  N    ALA A 280      -1.858  19.484  12.051  1.00 26.24
ATOM   2260  CA   ALA A 280      -1.920  19.803  13.486  1.00 26.82
ATOM   2261  C    ALA A 280      -2.744  18.807  14.341  1.00 26.12
ATOM   2262  O    ALA A 280      -3.807  19.114  14.855  1.00 30.50
ATOM   2263  CB   ALA A 280      -2.558  21.172  13.626  1.00 24.48
ATOM   2264  N    PRO A 281      -2.290  17.554  14.509  1.00 22.59
ATOM   2265  CA   PRO A 281      -3.240  16.621  15.067  1.00 25.00
ATOM   2266  C    PRO A 281      -3.546  16.934  16.529  1.00 31.32
ATOM   2267  O    PRO A 281      -4.571  16.602  17.120  1.00 34.77
ATOM   2268  CB   PRO A 281      -2.594  15.277  14.748  1.00 18.52
```

FIG. 11-43

| ATOM | 2269 | CG | PRO A 281 | -1.116 | 15.542 | 14.781 | 1.00 | 21.77 |
|---|---|---|---|---|---|---|---|---|
| ATOM | 2270 | CD | PRO A 281 | -1.011 | 16.945 | 14.218 | 1.00 | 22.96 |
| ATOM | 2271 | N | ASN A 282 | -2.611 | 17.697 | 17.091 | 1.00 | 33.10 |
| ATOM | 2272 | CA | ASN A 282 | -2.802 | 18.033 | 18.505 | 1.00 | 35.43 |
| ATOM | 2273 | C | ASN A 282 | -3.876 | 19.083 | 18.796 | 1.00 | 35.68 |
| ATOM | 2274 | O | ASN A 282 | -4.097 | 19.448 | 19.948 | 1.00 | 33.36 |
| ATOM | 2275 | CB | ASN A 282 | -1.463 | 18.483 | 19.088 | 1.00 | 38.17 |
| ATOM | 2276 | CG | ASN A 282 | -0.415 | 17.377 | 18.994 | 1.00 | 40.60 |
| ATOM | 2277 | OD1 | ASN A 282 | 0.652 | 17.529 | 18.416 | 1.00 | 44.47 |
| ATOM | 2278 | ND2 | ASN A 282 | -0.738 | 16.240 | 19.598 | 1.00 | 36.45 |
| ATOM | 2279 | N | GLY A 283 | -4.436 | 19.582 | 17.662 | 1.00 | 36.12 |
| ATOM | 2280 | CA | GLY A 283 | -4.894 | 20.967 | 17.540 | 1.00 | 30.77 |
| ATOM | 2281 | C | GLY A 283 | -6.130 | 21.109 | 16.694 | 1.00 | 30.63 |
| ATOM | 2282 | O | GLY A 283 | -6.748 | 20.162 | 16.232 | 1.00 | 32.93 |
| ATOM | 2283 | N | SER A 284 | -6.493 | 22.369 | 16.594 | 1.00 | 30.99 |
| ATOM | 2284 | CA | SER A 284 | -7.820 | 22.880 | 16.181 | 1.00 | 30.61 |
| ATOM | 2285 | C | SER A 284 | -8.136 | 22.628 | 14.737 | 1.00 | 31.81 |
| ATOM | 2286 | O | SER A 284 | -9.219 | 22.176 | 14.341 | 1.00 | 33.21 |
| ATOM | 2287 | CB | SER A 284 | -7.886 | 24.403 | 16.373 | 1.00 | 31.86 |
| ATOM | 2288 | OG | SER A 284 | -6.918 | 24.745 | 17.400 | 1.00 | 48.22 |
| ATOM | 2289 | N | LEU A 285 | -7.049 | 22.915 | 13.979 | 1.00 | 30.19 |
| ATOM | 2290 | CA | LEU A 285 | -7.007 | 22.652 | 12.546 | 1.00 | 24.66 |
| ATOM | 2291 | C | LEU A 285 | -7.253 | 21.203 | 12.222 | 1.00 | 22.00 |
| ATOM | 2292 | O | LEU A 285 | -8.037 | 20.785 | 11.376 | 1.00 | 26.33 |
| ATOM | 2293 | CB | LEU A 285 | -5.651 | 23.148 | 11.959 | 1.00 | 28.44 |
| ATOM | 2294 | CG | LEU A 285 | -5.659 | 24.562 | 11.314 | 1.00 | 31.46 |
| ATOM | 2295 | CD1 | LEU A 285 | -6.971 | 25.024 | 10.635 | 1.00 | 28.75 |
| ATOM | 2296 | CD2 | LEU A 285 | -4.574 | 24.628 | 10.259 | 1.00 | 30.22 |
| ATOM | 2297 | N | GLY A 286 | -6.542 | 20.426 | 13.017 | 1.00 | 22.19 |
| ATOM | 2298 | CA | GLY A 286 | -6.658 | 18.981 | 12.909 | 1.00 | 22.28 |
| ATOM | 2299 | C | GLY A 286 | -5.452 | 18.377 | 12.215 | 1.00 | 28.63 |
| ATOM | 2300 | O | GLY A 286 | -4.514 | 19.050 | 11.777 | 1.00 | 27.13 |
| ATOM | 2301 | N | ALA A 287 | -5.531 | 17.043 | 12.107 | 1.00 | 29.38 |
| ATOM | 2302 | CA | ALA A 287 | -4.662 | 16.406 | 11.119 | 1.00 | 29.01 |
| ATOM | 2303 | C | ALA A 287 | -4.871 | 16.795 | 9.651 | 1.00 | 30.19 |
| ATOM | 2304 | O | ALA A 287 | -5.975 | 16.929 | 9.113 | 1.00 | 32.35 |
| ATOM | 2305 | CB | ALA A 287 | -4.807 | 14.890 | 11.195 | 1.00 | 31.27 |
| ATOM | 2306 | N | MET A 288 | -3.711 | 16.904 | 9.002 | 1.00 | 24.02 |
| ATOM | 2307 | CA | MET A 288 | -3.771 | 16.886 | 7.556 | 1.00 | 18.39 |
| ATOM | 2308 | C | MET A 288 | -4.515 | 15.686 | 6.947 | 1.00 | 17.91 |
| ATOM | 2309 | O | MET A 288 | -4.296 | 14.517 | 7.213 | 1.00 | 17.40 |
| ATOM | 2310 | CB | MET A 288 | -2.350 | 17.089 | 7.063 | 1.00 | 15.28 |
| ATOM | 2311 | CG | MET A 288 | -2.155 | 17.001 | 5.553 | 1.00 | 20.43 |
| ATOM | 2312 | SD | MET A 288 | -0.437 | 17.234 | 5.148 | 1.00 | 19.53 |
| ATOM | 2313 | CE | MET A 288 | -0.480 | 16.813 | 3.406 | 1.00 | 17.77 |
| ATOM | 2314 | N | HIS A 289 | -5.449 | 16.028 | 6.088 | 1.00 | 17.54 |
| ATOM | 2315 | CA | HIS A 289 | -5.945 | 14.985 | 5.204 | 1.00 | 18.04 |
| ATOM | 2316 | C | HIS A 289 | -5.558 | 15.267 | 3.767 | 1.00 | 17.39 |
| ATOM | 2317 | O | HIS A 289 | -5.484 | 16.416 | 3.336 | 1.00 | 16.97 |
| ATOM | 2318 | CB | HIS A 289 | -7.474 | 14.802 | 5.294 | 1.00 | 20.34 |
| ATOM | 2319 | CG | HIS A 289 | -7.935 | 14.180 | 6.617 | 1.00 | 24.11 |
| ATOM | 2320 | ND1 | HIS A 289 | -8.929 | 13.267 | 6.694 | 1.00 | 21.96 |
| ATOM | 2321 | CD2 | HIS A 289 | -7.478 | 14.422 | 7.940 | 1.00 | 24.17 |
| ATOM | 2322 | CE1 | HIS A 289 | -9.098 | 12.934 | 8.021 | 1.00 | 20.60 |

FIG. 11-44

| ATOM | 2323 | NE2 | HIS | A | 289 | -8.209 | 13.649 | 8.789 | 1.00 | 22.28 |
|---|---|---|---|---|---|---|---|---|---|---|
| ATOM | 2324 | N | VAL | A | 290 | -5.323 | 14.164 | 3.025 | 1.00 | 17.14 |
| ATOM | 2325 | CA | VAL | A | 290 | -5.042 | 14.413 | 1.619 | 1.00 | 12.42 |
| ATOM | 2326 | C | VAL | A | 290 | -6.067 | 13.973 | 0.629 | 1.00 | 9.46 |
| ATOM | 2327 | O | VAL | A | 290 | -6.554 | 12.866 | 0.628 | 1.00 | 13.34 |
| ATOM | 2328 | CB | VAL | A | 290 | -3.529 | 14.248 | 1.172 | 1.00 | 13.02 |
| ATOM | 2329 | CG1 | VAL | A | 290 | -3.253 | 13.626 | -0.212 | 1.00 | 3.64 |
| ATOM | 2330 | CG2 | VAL | A | 290 | -2.618 | 13.723 | 2.290 | 1.00 | 13.06 |
| ATOM | 2331 | N | TYR | A | 291 | -6.379 | 14.921 | -0.241 | 1.00 | 10.78 |
| ATOM | 2332 | CA | TYR | A | 291 | -7.434 | 14.729 | -1.246 | 1.00 | 15.17 |
| ATOM | 2333 | C | TYR | A | 291 | -6.905 | 14.408 | -2.626 | 1.00 | 16.67 |
| ATOM | 2334 | O | TYR | A | 291 | -6.092 | 15.141 | -3.145 | 1.00 | 22.02 |
| ATOM | 2335 | CB | TYR | A | 291 | -8.261 | 16.036 | -1.354 | 1.00 | 17.57 |
| ATOM | 2336 | CG | TYR | A | 291 | -9.044 | 16.274 | -0.065 | 1.00 | 28.35 |
| ATOM | 2337 | CD1 | TYR | A | 291 | -8.356 | 16.437 | 1.156 | 1.00 | 24.48 |
| ATOM | 2338 | CD2 | TYR | A | 291 | -10.455 | 16.297 | -0.112 | 1.00 | 27.66 |
| ATOM | 2339 | CE1 | TYR | A | 291 | -9.066 | 16.592 | 2.333 | 1.00 | 19.99 |
| ATOM | 2340 | CE2 | TYR | A | 291 | -11.168 | 16.499 | 1.071 | 1.00 | 21.66 |
| ATOM | 2341 | CZ | TYR | A | 291 | -10.454 | 16.655 | 2.267 | 1.00 | 21.46 |
| ATOM | 2342 | OH | TYR | A | 291 | -11.137 | 16.905 | 3.447 | 1.00 | 34.29 |
| ATOM | 2343 | N | GLU | A | 292 | -7.420 | 13.350 | -3.239 | 1.00 | 17.56 |
| ATOM | 2344 | CA | GLU | A | 292 | -7.276 | 13.082 | -4.675 | 1.00 | 12.39 |
| ATOM | 2345 | C | GLU | A | 292 | -8.581 | 13.391 | -5.310 | 1.00 | 14.32 |
| ATOM | 2346 | O | GLU | A | 292 | -9.534 | 12.631 | -5.267 | 1.00 | 11.69 |
| ATOM | 2347 | CB | GLU | A | 292 | -6.941 | 11.620 | -4.931 | 1.00 | 13.39 |
| ATOM | 2348 | CG | GLU | A | 292 | -5.942 | 11.265 | -3.815 | 1.00 | 19.39 |
| ATOM | 2349 | CD | GLU | A | 292 | -5.713 | 9.784 | -3.776 | 1.00 | 27.73 |
| ATOM | 2350 | OE1 | GLU | A | 292 | -4.598 | 9.367 | -4.059 | 1.00 | 36.32 |
| ATOM | 2351 | OE2 | GLU | A | 292 | -6.621 | 9.021 | -3.474 | 1.00 | 28.54 |
| ATOM | 2352 | N | SER | A | 293 | -8.595 | 14.600 | -5.841 | 1.00 | 13.78 |
| ATOM | 2353 | CA | SER | A | 293 | -9.739 | 15.182 | -6.509 | 1.00 | 10.90 |
| ATOM | 2354 | C | SER | A | 293 | -9.685 | 15.194 | -8.020 | 1.00 | 13.05 |
| ATOM | 2355 | O | SER | A | 293 | -8.731 | 15.729 | -8.545 | 1.00 | 16.71 |
| ATOM | 2356 | CB | SER | A | 293 | -9.664 | 16.652 | -6.234 | 1.00 | 6.39 |
| ATOM | 2357 | OG | SER | A | 293 | -10.057 | 16.845 | -4.929 | 1.00 | 14.97 |
| ATOM | 2358 | N | LYS | A | 294 | -10.733 | 14.736 | -8.702 | 1.00 | 11.41 |
| ATOM | 2359 | CA | LYS | A | 294 | -10.856 | 15.026 | -10.131 | 1.00 | 11.81 |
| ATOM | 2360 | C | LYS | A | 294 | -10.550 | 16.444 | -10.662 | 1.00 | 12.14 |
| ATOM | 2361 | O | LYS | A | 294 | -10.750 | 17.402 | -9.938 | 1.00 | 17.45 |
| ATOM | 2362 | CB | LYS | A | 294 | -12.168 | 14.426 | -10.610 | 1.00 | 8.71 |
| ATOM | 2363 | CG | LYS | A | 294 | -11.869 | 12.917 | -10.589 | 1.00 | 17.13 |
| ATOM | 2364 | CD | LYS | A | 294 | -12.543 | 11.999 | -11.643 | 1.00 | 23.93 |
| ATOM | 2365 | CE | LYS | A | 294 | -13.754 | 11.181 | -11.233 | 1.00 | 30.42 |
| ATOM | 2366 | NZ | LYS | A | 294 | -14.732 | 12.095 | -10.641 | 1.00 | 44.41 |
| ATOM | 2367 | N | PHE | A | 295 | -10.055 | 16.593 | -11.916 | 1.00 | 10.14 |
| ATOM | 2368 | CA | PHE | A | 295 | -9.866 | 17.992 | -12.382 | 1.00 | 14.97 |
| ATOM | 2369 | C | PHE | A | 295 | -11.061 | 18.964 | -12.303 | 1.00 | 17.58 |
| ATOM | 2370 | O | PHE | A | 295 | -10.980 | 20.093 | -11.820 | 1.00 | 22.77 |
| ATOM | 2371 | CB | PHE | A | 295 | -9.353 | 18.041 | -13.819 | 1.00 | 11.74 |
| ATOM | 2372 | CG | PHE | A | 295 | -8.962 | 19.426 | -14.216 | 1.00 | 2.00 |
| ATOM | 2373 | CD1 | PHE | A | 295 | -9.676 | 20.058 | -15.224 | 1.00 | 7.82 |
| ATOM | 2374 | CD2 | PHE | A | 295 | -7.873 | 20.034 | -13.582 | 1.00 | 6.63 |
| ATOM | 2375 | CE1 | PHE | A | 295 | -9.328 | 21.374 | -15.560 | 1.00 | 10.15 |
| ATOM | 2376 | CE2 | PHE | A | 295 | -7.496 | 21.335 | -13.924 | 1.00 | 9.72 |

FIG. 11-45

| ATOM | 2377 | CZ   | PHE A 295 | -8.270  | 22.008 | -14.869 | 1.00 | 7.72  |
|------|------|------|-----------|---------|--------|---------|------|-------|
| ATOM | 2378 | N    | ARG A 296 | -12.221 | 18.465 | -12.737 | 1.00 | 20.83 |
| ATOM | 2379 | CA   | ARG A 296 | -13.431 | 19.305 | -12.528 | 1.00 | 23.01 |
| ATOM | 2380 | C    | ARG A 296 | -13.729 | 19.833 | -11.095 | 1.00 | 22.37 |
| ATOM | 2381 | O    | ARG A 296 | -14.315 | 20.883 | -10.858 | 1.00 | 21.58 |
| ATOM | 2382 | CB   | ARG A 296 | -14.657 | 18.604 | -13.124 | 1.00 | 26.70 |
| ATOM | 2383 | CG   | ARG A 296 | -14.805 | 17.106 | -12.849 | 1.00 | 28.42 |
| ATOM | 2384 | CD   | ARG A 296 | -16.261 | 16.805 | -13.151 | 1.00 | 33.54 |
| ATOM | 2385 | NE   | ARG A 296 | -16.369 | 15.396 | -13.428 | 1.00 | 39.72 |
| ATOM | 2386 | CZ   | ARG A 296 | -16.243 | 15.024 | -14.679 | 1.00 | 42.84 |
| ATOM | 2387 | NH1  | ARG A 296 | -16.179 | 15.924 | -15.640 | 1.00 | 47.03 |
| ATOM | 2388 | NH2  | ARG A 296 | -16.161 | 13.750 | -14.953 | 1.00 | 40.07 |
| ATOM | 2389 | N    | ASN A 297 | -13.185 | 19.055 | -10.141 | 1.00 | 19.61 |
| ATOM | 2390 | CA   | ASN A 297 | -13.114 | 19.489 | -8.763  | 1.00 | 17.45 |
| ATOM | 2391 | C    | ASN A 297 | -12.025 | 20.515 | -8.409  | 1.00 | 20.96 |
| ATOM | 2392 | O    | ASN A 297 | -12.331 | 21.592 | -7.917  | 1.00 | 26.59 |
| ATOM | 2393 | CB   | ASN A 297 | -12.895 | 18.297 | -7.868  | 1.00 | 16.52 |
| ATOM | 2394 | CG   | ASN A 297 | -14.076 | 17.395 | -7.783  | 1.00 | 17.84 |
| ATOM | 2395 | OD1  | ASN A 297 | -14.778 | 17.010 | -8.695  | 1.00 | 19.74 |
| ATOM | 2396 | ND2  | ASN A 297 | -14.214 | 16.981 | -6.551  | 1.00 | 25.01 |
| ATOM | 2397 | N    | TRP A 298 | -10.750 | 20.160 | -8.675  | 1.00 | 16.28 |
| ATOM | 2398 | CA   | TRP A 298 | -9.661  | 21.162 | -8.587  | 1.00 | 14.56 |
| ATOM | 2399 | C    | TRP A 298 | -9.960  | 22.602 | -9.126  | 1.00 | 13.90 |
| ATOM | 2400 | O    | TRP A 298 | -9.804  | 23.622 | -8.450  | 1.00 | 10.70 |
| ATOM | 2401 | CB   | TRP A 298 | -8.367  | 20.519 | -9.221  | 1.00 | 14.12 |
| ATOM | 2402 | CG   | TRP A 298 | -7.196  | 21.497 | -9.401  | 1.00 | 11.30 |
| ATOM | 2403 | CD1  | TRP A 298 | -6.853  | 22.225 | -10.589 | 1.00 | 6.34  |
| ATOM | 2404 | CD2  | TRP A 298 | -6.325  | 22.026 | -8.368  | 1.00 | 9.45  |
| ATOM | 2405 | NE1  | TRP A 298 | -5.879  | 23.150 | -10.333 | 1.00 | 6.64  |
| ATOM | 2406 | CE2  | TRP A 298 | -5.529  | 23.069 | -8.976  | 1.00 | 6.86  |
| ATOM | 2407 | CE3  | TRP A 298 | -6.183  | 21.751 | -6.982  | 1.00 | 10.09 |
| ATOM | 2408 | CZ2  | TRP A 298 | -4.642  | 23.821 | -8.160  | 1.00 | 8.12  |
| ATOM | 2409 | CZ3  | TRP A 298 | -5.275  | 22.511 | -6.210  | 1.00 | 10.47 |
| ATOM | 2410 | CH2  | TRP A 298 | -4.497  | 23.558 | -6.777  | 1.00 | 9.43  |
| ATOM | 2411 | N    | SER A 299 | -10.449 | 22.656 | -10.390 | 1.00 | 16.43 |
| ATOM | 2412 | CA   | SER A 299 | -10.651 | 24.025 | -10.964 | 1.00 | 20.80 |
| ATOM | 2413 | C    | SER A 299 | -11.858 | 24.900 | -10.573 | 1.00 | 24.58 |
| ATOM | 2414 | O    | SER A 299 | -11.984 | 26.060 | -10.953 | 1.00 | 25.75 |
| ATOM | 2415 | CB   | SER A 299 | -10.648 | 23.989 | -12.497 | 1.00 | 20.77 |
| ATOM | 2416 | OG   | SER A 299 | -11.512 | 22.966 | -13.003 | 1.00 | 13.34 |
| ATOM | 2417 | N    | GLU A 300 | -12.788 | 24.303 | -9.804  | 1.00 | 23.62 |
| ATOM | 2418 | CA   | GLU A 300 | -13.840 | 25.127 | -9.228  | 1.00 | 24.96 |
| ATOM | 2419 | C    | GLU A 300 | -13.435 | 26.274 | -8.268  | 1.00 | 26.28 |
| ATOM | 2420 | O    | GLU A 300 | -13.883 | 27.422 | -8.286  | 1.00 | 26.20 |
| ATOM | 2421 | CB   | GLU A 300 | -14.819 | 24.168 | -8.553  | 1.00 | 21.90 |
| ATOM | 2422 | CG   | GLU A 300 | -16.061 | 24.911 | -8.091  | 1.00 | 19.69 |
| ATOM | 2423 | CD   | GLU A 300 | -16.681 | 25.626 | -9.279  | 1.00 | 27.17 |
| ATOM | 2424 | OE1  | GLU A 300 | -17.037 | 24.987 | -10.274 | 1.00 | 30.81 |
| ATOM | 2425 | OE2  | GLU A 300 | -16.812 | 26.851 | -9.244  | 1.00 | 35.91 |
| ATOM | 2426 | N    | GLY A 301 | -12.552 | 25.862 | -7.364  | 1.00 | 29.00 |
| ATOM | 2427 | CA   | GLY A 301 | -13.101 | 25.820 | -6.004  | 1.00 | 31.59 |
| ATOM | 2428 | C    | GLY A 301 | -13.377 | 27.127 | -5.261  | 1.00 | 35.08 |
| ATOM | 2429 | O    | GLY A 301 | -14.508 | 27.482 | -4.906  | 1.00 | 36.37 |
| ATOM | 2430 | N    | TYR A 302 | -12.239 | 27.790 | -4.941  | 1.00 | 31.29 |

FIG. 11-46

```
ATOM   2431  CA   TYR A 302     -12.375  28.713  -3.803  1.00 28.48
ATOM   2432  C    TYR A 302     -12.543  30.209  -4.013  1.00 28.09
ATOM   2433  O    TYR A 302     -12.806  30.743  -5.078  1.00 32.38
ATOM   2434  CB   TYR A 302     -11.391  28.369  -2.667  1.00 26.88
ATOM   2435  CG   TYR A 302     -11.403  26.868  -2.392  1.00 24.72
ATOM   2436  CD1  TYR A 302     -10.339  26.110  -2.906  1.00 21.12
ATOM   2437  CD2  TYR A 302     -12.436  26.265  -1.642  1.00 28.63
ATOM   2438  CE1  TYR A 302     -10.311  24.726  -2.733  1.00 24.55
ATOM   2439  CE2  TYR A 302     -12.408  24.865  -1.445  1.00 30.15
ATOM   2440  CZ   TYR A 302     -11.371  24.115  -2.055  1.00 29.02
ATOM   2441  OH   TYR A 302     -11.389  22.737  -2.030  1.00 35.50
ATOM   2442  N    SER A 303     -12.451  30.929  -2.926  1.00 26.17
ATOM   2443  CA   SER A 303     -12.972  32.297  -3.029  1.00 25.38
ATOM   2444  C    SER A 303     -11.904  33.311  -2.710  1.00 20.32
ATOM   2445  O    SER A 303     -11.685  34.380  -3.263  1.00 14.44
ATOM   2446  CB   SER A 303     -14.129  32.387  -2.045  1.00 32.23
ATOM   2447  OG   SER A 303     -15.027  31.323  -2.370  1.00 39.47
ATOM   2448  N    ASP A 304     -11.154  32.731  -1.834  1.00 20.53
ATOM   2449  CA   ASP A 304      -9.749  32.850  -1.494  1.00 25.97
ATOM   2450  C    ASP A 304      -8.750  33.176  -2.601  1.00 24.52
ATOM   2451  O    ASP A 304      -7.734  33.813  -2.330  1.00 26.86
ATOM   2452  CB   ASP A 304      -9.273  31.523  -0.884  1.00 24.91
ATOM   2453  CG   ASP A 304     -10.203  30.964   0.163  1.00 26.81
ATOM   2454  OD1  ASP A 304      -9.751  30.866   1.310  1.00 26.27
ATOM   2455  OD2  ASP A 304     -11.339  30.618  -0.189  1.00 25.86
ATOM   2456  N    PHE A 305      -9.135  32.600  -3.793  1.00 20.43
ATOM   2457  CA   PHE A 305      -8.358  32.375  -5.034  1.00 13.66
ATOM   2458  C    PHE A 305      -8.971  32.996  -6.312  1.00 10.73
ATOM   2459  O    PHE A 305     -10.031  32.614  -6.814  1.00 12.48
ATOM   2460  CB   PHE A 305      -8.108  30.880  -5.279  1.00 10.86
ATOM   2461  CG   PHE A 305      -7.535  30.160  -4.081  1.00  6.29
ATOM   2462  CD1  PHE A 305      -8.031  28.884  -3.781  1.00  4.50
ATOM   2463  CD2  PHE A 305      -6.528  30.742  -3.265  1.00 12.39
ATOM   2464  CE1  PHE A 305      -7.520  28.196  -2.643  1.00  6.53
ATOM   2465  CE2  PHE A 305      -6.023  30.057  -2.124  1.00  7.78
ATOM   2466  CZ   PHE A 305      -6.530  28.778  -1.832  1.00  6.69
ATOM   2467  N    ASP A 306      -8.272  34.004  -6.822  1.00 10.88
ATOM   2468  CA   ASP A 306      -8.720  34.551  -8.119  1.00 13.47
ATOM   2469  C    ASP A 306      -7.807  34.315  -9.360  1.00 15.61
ATOM   2470  O    ASP A 306      -8.096  34.757 -10.476  1.00 18.55
ATOM   2471  CB   ASP A 306      -9.069  36.033  -7.985  1.00  7.37
ATOM   2472  CG   ASP A 306      -7.863  36.845  -7.629  1.00  8.24
ATOM   2473  OD1  ASP A 306      -6.783  36.288  -7.527  1.00 15.20
ATOM   2474  OD2  ASP A 306      -7.979  38.052  -7.516  1.00 13.08
ATOM   2475  N    ARG A 307      -6.709  33.581  -9.103  1.00 14.06
ATOM   2476  CA   ARG A 307      -5.812  33.211 -10.199  1.00 11.54
ATOM   2477  C    ARG A 307      -5.388  31.769 -10.086  1.00  8.14
ATOM   2478  O    ARG A 307      -5.225  31.275  -8.975  1.00 13.51
ATOM   2479  CB   ARG A 307      -4.552  34.074 -10.202  1.00 10.30
ATOM   2480  CG   ARG A 307      -4.546  35.582 -10.162  1.00  4.65
ATOM   2481  CD   ARG A 307      -4.810  36.304 -11.454  1.00  8.09
ATOM   2482  NE   ARG A 307      -6.229  36.545 -11.599  1.00 22.93
ATOM   2483  CZ   ARG A 307      -6.739  37.764 -11.577  1.00 26.35
ATOM   2484  NH1  ARG A 307      -5.915  38.786 -11.670  1.00 17.82
```

FIG. 11-47

```
ATOM   2485  NH2 ARG A 307      -8.060  37.915 -11.441  1.00 25.15
ATOM   2486  N   GLY A 308      -5.225  31.118 -11.251  1.00  9.71
ATOM   2487  CA  GLY A 308      -4.637  29.755 -11.274  1.00  9.41
ATOM   2488  C   GLY A 308      -3.428  29.574 -12.195  1.00  8.03
ATOM   2489  O   GLY A 308      -3.410  30.008 -13.335  1.00  6.98
ATOM   2490  N   ALA A 309      -2.386  28.978 -11.655  1.00  6.22
ATOM   2491  CA  ALA A 309      -1.194  28.770 -12.511  1.00 11.60
ATOM   2492  C   ALA A 309      -0.902  27.311 -12.855  1.00 10.63
ATOM   2493  O   ALA A 309      -1.005  26.475 -11.985  1.00 14.25
ATOM   2494  CB  ALA A 309       0.096  29.369 -11.913  1.00  6.69
ATOM   2495  N   TYR A 310      -0.564  27.013 -14.102  1.00  6.57
ATOM   2496  CA  TYR A 310      -0.243  25.627 -14.358  1.00 12.87
ATOM   2497  C   TYR A 310       1.249  25.443 -14.633  1.00 19.41
ATOM   2498  O   TYR A 310       1.789  25.938 -15.616  1.00 19.07
ATOM   2499  CB  TYR A 310      -1.141  25.059 -15.494  1.00 15.72
ATOM   2500  CG  TYR A 310      -2.559  24.870 -14.987  1.00 17.60
ATOM   2501  CD1 TYR A 310      -3.469  25.963 -14.961  1.00 14.47
ATOM   2502  CD2 TYR A 310      -2.908  23.607 -14.460  1.00 17.77
ATOM   2503  CE1 TYR A 310      -4.701  25.842 -14.328  1.00  4.76
ATOM   2504  CE2 TYR A 310      -4.143  23.494 -13.813  1.00 15.82
ATOM   2505  CZ  TYR A 310      -5.027  24.583 -13.805  1.00 10.58
ATOM   2506  OH  TYR A 310      -6.297  24.310 -13.358  1.00 25.71
ATOM   2507  N   VAL A 311       1.940  24.811 -13.674  1.00 21.31
ATOM   2508  CA  VAL A 311       3.395  24.920 -13.802  1.00 18.34
ATOM   2509  C   VAL A 311       4.099  23.676 -14.238  1.00 21.78
ATOM   2510  O   VAL A 311       3.663  22.574 -13.913  1.00 29.02
ATOM   2511  CB  VAL A 311       4.085  25.703 -12.642  1.00 18.76
ATOM   2512  CG1 VAL A 311       5.306  25.116 -11.997  1.00 17.85
ATOM   2513  CG2 VAL A 311       3.171  26.332 -11.633  1.00 15.08
ATOM   2514  N   ILE A 312       5.189  23.872 -15.027  1.00 19.02
ATOM   2515  CA  ILE A 312       6.017  22.696 -15.385  1.00 15.58
ATOM   2516  C   ILE A 312       7.359  22.654 -14.639  1.00 15.45
ATOM   2517  O   ILE A 312       8.006  23.666 -14.387  1.00 12.27
ATOM   2518  CB  ILE A 312       6.193  22.661 -16.922  1.00 17.55
ATOM   2519  CG1 ILE A 312       4.845  22.550 -17.665  1.00  5.96
ATOM   2520  CG2 ILE A 312       7.133  21.508 -17.360  1.00 18.63
ATOM   2521  CD1 ILE A 312       4.906  22.847 -19.145  1.00  2.96
ATOM   2522  N   THR A 313       7.775  21.445 -14.227  1.00 19.05
ATOM   2523  CA  THR A 313       9.153  21.180 -13.716  1.00 18.35
ATOM   2524  C   THR A 313       9.603  19.792 -14.203  1.00 14.55
ATOM   2525  O   THR A 313       8.921  19.175 -15.016  1.00 11.43
ATOM   2526  CB  THR A 313       9.323  21.427 -12.165  1.00 21.60
ATOM   2527  OG1 THR A 313      10.704  21.502 -11.646  1.00 23.73
ATOM   2528  CG2 THR A 313       8.503  20.417 -11.362  1.00 14.71
ATOM   2529  N   PHE A 314      10.765  19.326 -13.764  1.00 14.30
ATOM   2530  CA  PHE A 314      11.121  17.999 -14.285  1.00 14.69
ATOM   2531  C   PHE A 314      11.621  17.225 -13.115  1.00 19.10
ATOM   2532  O   PHE A 314      12.235  17.779 -12.203  1.00 18.65
ATOM   2533  CB  PHE A 314      12.286  17.948 -15.294  1.00 10.92
ATOM   2534  CG  PHE A 314      11.957  18.735 -16.522  1.00 15.00
ATOM   2535  CD1 PHE A 314      12.074  20.149 -16.510  1.00  9.68
ATOM   2536  CD2 PHE A 314      11.533  18.041 -17.694  1.00 17.95
ATOM   2537  CE1 PHE A 314      11.800  20.837 -17.728  1.00 10.31
ATOM   2538  CE2 PHE A 314      11.261  18.741 -18.898  1.00  4.39
```

FIG. 11-48

| | | | | | | | | | |
|---|---|---|---|---|---|---|---|---|---|
| ATOM | 2539 | CZ  | PHE | A | 314 | 11.445 | 20.142 | -18.916 | 1.00  2.00 |
| ATOM | 2540 | N   | ILE | A | 315 | 11.324 | 15.931 | -13.221 | 1.00 19.98 |
| ATOM | 2541 | CA  | ILE | A | 315 | 11.880 | 14.978 | -12.265 | 1.00 19.39 |
| ATOM | 2542 | C   | ILE | A | 315 | 12.623 | 13.865 | -13.036 | 1.00 21.07 |
| ATOM | 2543 | O   | ILE | A | 315 | 12.290 | 13.647 | -14.214 | 1.00 24.99 |
| ATOM | 2544 | CB  | ILE | A | 315 | 10.708 | 14.371 | -11.436 | 1.00 19.86 |
| ATOM | 2545 | CG1 | ILE | A | 315 |  9.665 | 13.600 | -12.287 | 1.00 15.50 |
| ATOM | 2546 | CG2 | ILE | A | 315 | 10.072 | 15.429 | -10.524 | 1.00 17.25 |
| ATOM | 2547 | CD1 | ILE | A | 315 |  9.048 | 12.392 | -11.569 | 1.00 15.41 |
| ATOM | 2548 | N   | PRO | A | 316 | 13.617 | 13.156 | -12.381 | 1.00 16.28 |
| ATOM | 2549 | CA  | PRO | A | 316 | 14.206 | 11.945 | -12.995 | 1.00 13.66 |
| ATOM | 2550 | C   | PRO | A | 316 | 13.225 | 10.902 | -13.536 | 1.00 19.68 |
| ATOM | 2551 | O   | PRO | A | 316 | 12.163 | 10.653 | -13.007 | 1.00 25.61 |
| ATOM | 2552 | CB  | PRO | A | 316 | 15.083 | 11.437 | -11.881 | 1.00 13.68 |
| ATOM | 2553 | CG  | PRO | A | 316 | 15.465 | 12.654 | -11.039 | 1.00  9.70 |
| ATOM | 2554 | CD  | PRO | A | 316 | 14.260 | 13.550 | -11.142 | 1.00 12.03 |
| ATOM | 2555 | N   | LYS | A | 317 | 13.568 | 10.243 | -14.620 | 1.00 23.33 |
| ATOM | 2556 | CA  | LYS | A | 317 | 12.565 |  9.290 | -15.167 | 1.00 27.17 |
| ATOM | 2557 | C   | LYS | A | 317 | 12.392 |  7.938 | -14.414 | 1.00 28.85 |
| ATOM | 2558 | O   | LYS | A | 317 | 11.502 |  7.136 | -14.678 | 1.00 28.34 |
| ATOM | 2559 | CB  | LYS | A | 317 | 12.976 |  9.111 | -16.637 | 1.00 30.76 |
| ATOM | 2560 | CG  | LYS | A | 317 | 12.074 |  8.618 | -17.768 | 1.00 30.62 |
| ATOM | 2561 | CD  | LYS | A | 317 | 12.799 |  9.071 | -19.061 | 1.00 41.96 |
| ATOM | 2562 | CE  | LYS | A | 317 | 12.098 |  9.023 | -20.455 | 1.00 49.97 |
| ATOM | 2563 | NZ  | LYS | A | 317 | 12.712 |  9.985 | -21.424 | 1.00 52.51 |
| ATOM | 2564 | N   | SER | A | 318 | 13.362 |  7.715 | -13.480 | 1.00 30.22 |
| ATOM | 2565 | CA  | SER | A | 318 | 13.490 |  6.519 | -12.578 | 1.00 31.55 |
| ATOM | 2566 | C   | SER | A | 318 | 12.591 |  6.432 | -11.304 | 1.00 30.78 |
| ATOM | 2567 | O   | SER | A | 318 | 12.306 |  5.381 | -10.715 | 1.00 32.61 |
| ATOM | 2568 | CB  | SER | A | 318 | 14.926 |  6.445 | -12.029 | 1.00 27.98 |
| ATOM | 2569 | OG  | SER | A | 318 | 15.294 |  7.732 | -11.479 | 1.00 28.20 |
| ATOM | 2570 | N   | TRP | A | 319 | 12.226 |  7.672 | -10.901 | 1.00 24.84 |
| ATOM | 2571 | CA  | TRP | A | 319 | 11.248 |  7.929 |  -9.863 | 1.00 22.28 |
| ATOM | 2572 | C   | TRP | A | 319 |  9.860 |  7.489 | -10.300 | 1.00 25.34 |
| ATOM | 2573 | O   | TRP | A | 319 |  9.620 |  7.503 | -11.508 | 1.00 25.50 |
| ATOM | 2574 | CB  | TRP | A | 319 | 11.124 |  9.406 |  -9.732 | 1.00 16.96 |
| ATOM | 2575 | CG  | TRP | A | 319 | 12.284 | 10.088 |  -9.114 | 1.00 13.31 |
| ATOM | 2576 | CD1 | TRP | A | 319 | 13.616 |  9.675 |  -9.035 | 1.00 13.22 |
| ATOM | 2577 | CD2 | TRP | A | 319 | 12.258 | 11.417 |  -8.554 | 1.00 15.06 |
| ATOM | 2578 | NE1 | TRP | A | 319 | 14.390 | 10.655 |  -8.486 | 1.00 12.44 |
| ATOM | 2579 | CE2 | TRP | A | 319 | 13.597 | 11.749 |  -8.168 | 1.00 17.50 |
| ATOM | 2580 | CE3 | TRP | A | 319 | 11.230 | 12.354 |  -8.378 | 1.00 14.98 |
| ATOM | 2581 | CZ2 | TRP | A | 319 | 13.868 | 13.022 |  -7.616 | 1.00 19.25 |
| ATOM | 2582 | CZ3 | TRP | A | 319 | 11.513 | 13.606 |  -7.819 | 1.00 13.34 |
| ATOM | 2583 | CH2 | TRP | A | 319 | 12.813 | 13.952 |  -7.446 | 1.00 15.98 |
| ATOM | 2584 | N   | ASN | A | 320 |  8.965 |  7.207 |  -9.290 | 1.00 26.91 |
| ATOM | 2585 | CA  | ASN | A | 320 |  7.541 |  6.877 |  -9.655 | 1.00 28.46 |
| ATOM | 2586 | C   | ASN | A | 320 |  6.425 |  7.862 |  -9.196 | 1.00 28.73 |
| ATOM | 2587 | O   | ASN | A | 320 |  5.229 |  7.598 |  -9.113 | 1.00 30.41 |
| ATOM | 2588 | CB  | ASN | A | 320 |  7.149 |  5.423 |  -9.289 | 1.00 25.04 |
| ATOM | 2589 | CG  | ASN | A | 320 |  6.177 |  4.782 | -10.298 | 1.00 26.50 |
| ATOM | 2590 | OD1 | ASN | A | 320 |  5.969 |  5.153 | -11.446 | 1.00 30.37 |
| ATOM | 2591 | ND2 | ASN | A | 320 |  5.512 |  3.765 |  -9.816 | 1.00 22.88 |
| ATOM | 2592 | N   | THR | A | 321 |  6.871 |  9.072 |  -8.880 | 1.00 26.48 |

FIG. 11-49

| ATOM | 2593 | CA  | THR | A | 321 | 5.853  | 9.989  | -8.392  | 1.00 | 21.38 |
| ---- | ---- | --- | --- | - | --- | ------ | ------ | ------- | ---- | ----- |
| ATOM | 2594 | C   | THR | A | 321 | 5.003  | 10.631 | -9.442  | 1.00 | 25.91 |
| ATOM | 2595 | O   | THR | A | 321 | 3.992  | 11.236 | -9.168  | 1.00 | 31.08 |
| ATOM | 2596 | CB  | THR | A | 321 | 6.459  | 11.072 | -7.604  | 1.00 | 18.26 |
| ATOM | 2597 | OG1 | THR | A | 321 | 7.157  | 11.963 | -8.468  | 1.00 | 17.29 |
| ATOM | 2598 | CG2 | THR | A | 321 | 7.356  | 10.481 | -6.522  | 1.00 | 15.10 |
| ATOM | 2599 | N   | ALA | A | 322 | 5.409  | 10.476 | -10.703 | 1.00 | 28.22 |
| ATOM | 2600 | CA  | ALA | A | 322 | 4.475  | 10.970 | -11.725 | 1.00 | 20.76 |
| ATOM | 2601 | C   | ALA | A | 322 | 4.028  | 9.979  | -12.805 | 1.00 | 18.85 |
| ATOM | 2602 | O   | ALA | A | 322 | 4.231  | 10.175 | -14.001 | 1.00 | 23.12 |
| ATOM | 2603 | CB  | ALA | A | 322 | 5.033  | 12.212 | -12.366 | 1.00 | 12.19 |
| ATOM | 2604 | N   | PRO | A | 323 | 3.385  | 8.880  | -12.342 | 1.00 | 17.31 |
| ATOM | 2605 | CA  | PRO | A | 323 | 3.077  | 7.743  | -13.236 | 1.00 | 19.28 |
| ATOM | 2606 | C   | PRO | A | 323 | 2.013  | 7.990  | -14.304 | 1.00 | 21.85 |
| ATOM | 2607 | O   | PRO | A | 323 | 1.272  | 8.960  | -14.291 | 1.00 | 28.50 |
| ATOM | 2608 | CB  | PRO | A | 323 | 2.620  | 6.687  | -12.221 | 1.00 | 18.23 |
| ATOM | 2609 | CG  | PRO | A | 323 | 2.008  | 7.465  | -11.040 | 1.00 | 12.18 |
| ATOM | 2610 | CD  | PRO | A | 323 | 2.963  | 8.632  | -10.948 | 1.00 | 14.97 |
| ATOM | 2611 | N   | ASP | A | 324 | 1.891  | 7.047  | -15.198 | 1.00 | 22.89 |
| ATOM | 2612 | CA  | ASP | A | 324 | 0.950  | 7.312  | -16.303 | 1.00 | 24.98 |
| ATOM | 2613 | C   | ASP | A | 324 | -0.533 | 7.341  | -15.972 | 1.00 | 24.67 |
| ATOM | 2614 | O   | ASP | A | 324 | -1.356 | 8.137  | -16.430 | 1.00 | 23.45 |
| ATOM | 2615 | CB  | ASP | A | 324 | 1.242  | 6.317  | -17.444 | 1.00 | 26.72 |
| ATOM | 2616 | CG  | ASP | A | 324 | 2.552  | 6.644  | -18.192 | 1.00 | 26.37 |
| ATOM | 2617 | OD1 | ASP | A | 324 | 2.907  | 5.840  | -19.043 | 1.00 | 27.36 |
| ATOM | 2618 | OD2 | ASP | A | 324 | 3.230  | 7.656  | -17.915 | 1.00 | 28.25 |
| ATOM | 2619 | N   | LYS | A | 325 | -0.862 | 6.413  | -15.079 | 1.00 | 28.53 |
| ATOM | 2620 | CA  | LYS | A | 325 | -2.114 | 6.674  | -14.369 | 1.00 | 35.41 |
| ATOM | 2621 | C   | LYS | A | 325 | -2.075 | 6.780  | -12.822 | 1.00 | 33.45 |
| ATOM | 2622 | O   | LYS | A | 325 | -1.438 | 6.033  | -12.072 | 1.00 | 37.22 |
| ATOM | 2623 | CB  | LYS | A | 325 | -3.341 | 5.885  | -14.923 | 1.00 | 43.09 |
| ATOM | 2624 | CG  | LYS | A | 325 | -4.582 | 6.792  | -15.272 | 1.00 | 53.66 |
| ATOM | 2625 | CD  | LYS | A | 325 | -5.956 | 6.290  | -14.694 | 1.00 | 53.41 |
| ATOM | 2626 | CE  | LYS | A | 325 | -7.318 | 6.772  | -15.313 | 1.00 | 54.86 |
| ATOM | 2627 | NZ  | LYS | A | 325 | -7.699 | 8.201  | -15.158 | 1.00 | 51.20 |
| ATOM | 2628 | N   | VAL | A | 326 | -2.819 | 7.811  | -12.398 | 1.00 | 25.94 |
| ATOM | 2629 | CA  | VAL | A | 326 | -3.213 | 7.788  | -11.019 | 1.00 | 19.50 |
| ATOM | 2630 | C   | VAL | A | 326 | -4.659 | 7.546  | -10.766 | 1.00 | 20.79 |
| ATOM | 2631 | O   | VAL | A | 326 | -5.552 | 8.089  | -11.405 | 1.00 | 20.50 |
| ATOM | 2632 | CB  | VAL | A | 326 | -2.624 | 8.917  | -10.182 | 1.00 | 18.64 |
| ATOM | 2633 | CG1 | VAL | A | 326 | -3.604 | 9.810  | -9.497  | 1.00 | 11.20 |
| ATOM | 2634 | CG2 | VAL | A | 326 | -1.514 | 9.629  | -10.917 | 1.00 | 21.59 |
| ATOM | 2635 | N   | LYS | A | 327 | -4.827 | 6.638  | -9.777  | 1.00 | 25.69 |
| ATOM | 2636 | CA  | LYS | A | 327 | -6.171 | 6.411  | -9.196  | 1.00 | 25.39 |
| ATOM | 2637 | C   | LYS | A | 327 | -6.504 | 7.083  | -7.876  | 1.00 | 18.93 |
| ATOM | 2638 | O   | LYS | A | 327 | -5.738 | 7.105  | -6.905  | 1.00 | 15.85 |
| ATOM | 2639 | CB  | LYS | A | 327 | -6.540 | 4.931  | -9.165  | 1.00 | 27.36 |
| ATOM | 2640 | CG  | LYS | A | 327 | -5.503 | 4.052  | -8.531  | 1.00 | 37.80 |
| ATOM | 2641 | CD  | LYS | A | 327 | -5.389 | 4.219  | -7.028  | 1.00 | 42.31 |
| ATOM | 2642 | CE  | LYS | A | 327 | -4.612 | 3.063  | -6.453  | 1.00 | 41.11 |
| ATOM | 2643 | NZ  | LYS | A | 327 | -3.283 | 3.349  | -5.957  | 1.00 | 35.32 |
| ATOM | 2644 | N   | GLN | A | 328 | -7.732 | 7.576  | -7.918  | 1.00 | 15.56 |
| ATOM | 2645 | CA  | GLN | A | 328 | -8.482 | 7.780  | -6.660  | 1.00 | 18.29 |
| ATOM | 2646 | C   | GLN | A | 328 | -8.690 | 6.635  | -5.668  | 1.00 | 17.67 |

FIG. 11-50

```
ATOM   2647  O    GLN A 328      -9.258    5.588   -5.913  1.00 17.82
ATOM   2648  CB   GLN A 328      -9.817    8.374   -6.991  1.00 17.11
ATOM   2649  CG   GLN A 328      -9.532    9.832   -7.211  1.00  9.09
ATOM   2650  CD   GLN A 328     -10.767   10.375   -7.731  1.00 10.75
ATOM   2651  OE1  GLN A 328     -11.543    9.853   -8.512  1.00 15.98
ATOM   2652  NE2  GLN A 328     -10.926   11.544   -7.258  1.00 14.27
ATOM   2653  N    GLY A 329      -8.178    6.884   -4.494  1.00 19.24
ATOM   2654  CA   GLY A 329      -8.552    5.824   -3.553  1.00 22.88
ATOM   2655  C    GLY A 329      -7.598    4.713   -3.161  1.00 27.31
ATOM   2656  O    GLY A 329      -6.420    4.612   -3.524  1.00 27.36
ATOM   2657  N    TRP A 330      -8.222    3.971   -2.272  1.00 28.42
ATOM   2658  CA   TRP A 330      -7.724    2.647   -1.987  1.00 30.34
ATOM   2659  C    TRP A 330      -8.801    1.505   -1.897  1.00 36.15
ATOM   2660  O    TRP A 330      -9.774    1.523   -1.132  1.00 37.22
ATOM   2661  CB   TRP A 330      -6.723    2.726   -0.873  1.00 26.82
ATOM   2662  CG   TRP A 330      -5.909    1.438   -0.921  1.00 31.32
ATOM   2663  CD1  TRP A 330      -6.197    0.282   -0.182  1.00 32.69
ATOM   2664  CD2  TRP A 330      -4.658    1.136   -1.586  1.00 32.07
ATOM   2665  NE1  TRP A 330      -5.256   -0.673   -0.293  1.00 28.82
ATOM   2666  CE2  TRP A 330      -4.267   -0.179   -1.134  1.00 30.54
ATOM   2667  CE3  TRP A 330      -3.818    1.863   -2.478  1.00 30.29
ATOM   2668  CZ2  TRP A 330      -3.017   -0.700   -1.543  1.00 34.49
ATOM   2669  CZ3  TRP A 330      -2.575    1.319   -2.889  1.00 28.13
ATOM   2670  CH2  TRP A 330      -2.169    0.058   -2.405  1.00 31.58
ATOM   2671  N    PRO A 331      -8.592    0.451   -2.701  1.00 38.37
ATOM   2672  CA   PRO A 331      -7.439    0.258   -3.621  1.00 40.60
ATOM   2673  C    PRO A 331      -6.980    1.254   -4.682  1.00 51.34
ATOM   2674  OCT1 PRO A 331      -7.491    2.377   -4.841  1.00 63.20
ATOM   2675  CB   PRO A 331      -7.709   -1.043   -4.293  1.00 35.58
ATOM   2676  CG   PRO A 331      -8.861   -1.679   -3.585  1.00 36.42
ATOM   2677  CD   PRO A 331      -9.425   -0.708   -2.582  1.00 34.08
ATOM   2678  OCT2 PRO A 331      -6.048    0.868   -5.378  1.00 55.17
END
```

POLYNUCLEOTIDE ENCODING A MUTANT TRANSGLUTAMINASE

CROSS-REFERENCE TO RELATED APPLICATIONS

The present application is divisional application of U.S. Ser. No. 10/365,434, filed on Feb. 13, 2003, which is a continuation PCT/JP01/07038, filed on Aug. 15, 2001, which claims priority to JP 2000-247664, filed on Aug. 17, 2000, and JP 2000-396695-61793, filed on Dec. 27, 2000.

BACKGROUND OF THE INVENTION

The present invention relates to a method for designing and preparing mutant transglutaminase on the basis of the three-dimensional structure of transglutaminase derived from *Streptoverticillium mobaraense* (hereinafter referred to as "MTG") determined by X-ray crystal structure analysis techniques, and the mutant MTGs thus prepared. MTG is widely used for processing foods or the like because it forms a gelatinus substance by forming crosslinking between proteins. The mutant MTG improved in the transglutaminase activity and heat stability contributes to reduce the required amount thereof, and also the mutant MTG having modified substrate specificity and optimum pH will allow the application of the enzyme to a new field.

Transglutaminase is an enzyme which catalyzes the acyl transfer reaction of γ-carboxamide group existing in a peptide chain of a protein. By reacting a protein with this enzyme, ε-(γ-Glu)-Lys crosslinking reaction and replacement reaction of Gln with Glu by deamidation may occur.

Transglutaminases from animals and those from microorganisms are so far known. The former is a $Ca^{2+}$-dependent enzyme and it is widely distributed in organs, skin and blood of animals. This includes, for example, guinea pig liver transglutaminase [K. Ikura et al., Biochemistry, Vol. 27, p. 2898 (1988)], human epidermal keratin cell transglutaminase [M. A. Phillips et al., Proc. Natl. Acad. Sci., USA, Vol. 87, p. 9333 (1990)] and human blood coagulation factor XIII [A. Ichinose et al., Biochemistry, Vol. 25, p. 6900 (1990)]. As for the latter, the $Ca^{2+}$-independent ones were found in *Streptoverticillium* bacteria such as *Streptoverticillium griseocarneum* IFO 12776, *Streptoverticillium cinnamoneum* sub sp. *cinnamoneum* IFO 12852 and *Streptoverticillium mobaraense* IFO 13819. Among these enzymes, the transglutaminase found in a culture supernatant of a variant of *Streptoverticillium mobaraense* is referred to as MTG (Microbial Transglutaminase). Also, a $Ca^{2+}$-independent transglutaminase was found in *Streptomyces lydicus* NRRL B-3446 (JP-Kokai No. 10-504721).

MTG is a monomeric protein composed of 331 amino acids and having a molecular weight of about 38,000 [Journal of Biological Chemistry, vol. 268, p. 11565 (1993)]. A method for producing active MTG by secretion expression using *E. coli* or yeast was reported (JP-Kokai No. Hei 5-199883). There has also been reported a method for producing the same wherein MTG is expressed as a protein inclusion body in *E. coli*, then the inclusion body is solubilized with a protein denaturing agent and it is then regenerate through removing the denaturing agent to obtain active MTG (JP-Kokai No. 6-30771).

Unlike transglutaminases from animals, the transglutaminases from microorganisms, such as MTG, are $Ca^{2+}$-independent. They are therefore utilized for the production of gelled foods such as jellies, as well as yogurts, cheeses or cosmetics in gel form, and also for the improvement of the quality of meats (JP-Kokai No. 64-27471). They are highly useful in the industry in that they are used as materials for heat stable microcapsules or as carriers for immobilized enzymes.

As for the conditions of the enzymatic reaction, for example, gelatinized foods cannot be gelled when the enzymatic reaction time is short, on the contrary, they become too hard to be the commercial products when the enzymatic reaction time is excessively long. Therefore, when MTG is used for producing gelatinized foods such as jellies; yogurts; cheeses; or cosmetics in gel form; or for improving the quality of meats, the concentration of the substrate and enzyme, reaction temperature and reaction time are controlled suitably for the intended product. However, as the foods and reagents produced by using MTG became various, it occurred that the intended products could not be produced in some cases by only controlling the concentration, temperature, time, etc. Thus, the modification of the enzymatic activity of MTG has become necesssary.

For modifying the enzymatic activity of MTG, it is required to produce a MTG mutant and to evaluate the activity, substrate specificity, etc. of the mutant to find out a good mutant. For producing mutants, it is necessary to manipulate wild type genes and, accordingly, it is prerequisite that a recombinant protein can be prepared. For MTG, a large-scale expression system using *E. coli* has been established (JP-Kokai No. 6-30771). However, MTG thus expressed in a large amount in *E. coli* is accumulated as insoluble protein inclusion bodies in the microbial cells. The denatured MTG in the protein inclusion body must be activated by refolding it after solubilizing it. Thus, it takes 2 to 3 weeks to prepare one mutant MTG. It has therefore been required to develop a method for reasonably modify MTG using some technique other than the techniques of randomly introducing the mutations through the entire molecule.

SUMMARY OF THE INVENTION

The object of the present invention is to provide a method for improving MTG.

Another object of the present invention is to provide a transglutaminase having an improved reactivity on substrates.

After intensive investigations made for the purpose of solving the above-described problems, the inventors have found that a transglutaminase improved in the reactivity on a substrate can be prepared on the basis of the three-dimensional structure. The present invention has been completed on the basis of this finding.

Namely, the summary of the present invention is as follows:

(1) A method for designing and preparing a mutant transglutaminase by extrapolating the binding site of MTG for a substrate on the basis of the three-dimensional structure obtained by X-ray crystal structure analysis and replacing, inserting or deleting amino acid residues positioned at the extrapolated substrate-binding site of the transglutaminase.

(2) A mutant MTG having modified substrate specificity, in which at least one of the following positions (residues positioned within 20 Å from active residue Cys 64 and exposed on the surface of the presumed binding site for acyl acceptor) in MTG amino acid sequences indicated as SEQ ID NO: 2 is modified: 1-5, 26, 28, 58-59, 62, 69, 74-75, 77, 79, 235-236, 238-244, 248-250, 252-254, 277-278, 282-287, 289, 291, 296,-297 and 300-304.

(3) A mutant transglutaminase having transglutaminase activity and modified substrate specificity, wherein when the alignment of the sequence of said mutant transglutaminase with the MTG amino acid sequence according to SEQ ID NO: 2 is carried out, at least one of the positions corresponding to the following positions (residues positioned within 20 Å from active residue Cys 64 and exposed on the surface of the presumed binding site for acyl acceptor) in the MTG amino acid sequence according to SEQ ID NO: 2 is modified: 1-5, 26, 28, 58-59, 62, 69, 74-75, 77, 79, 235-236, 238-244, 248-250, 252-254, 277-278, 282-287, 289, 291, 296,-297 and 300-304.

(4) A mutant transglutaminase having the transglutaminase activity and a modified substrate specificity, wherein when the alignment of the sequence of said mutant transglutaminase with the MTG amino acid sequence according to SEQ ID NO: 2 is carried out by treading method, at least one of the positions corresponding to the following positions (residues within 20 Å from active residue Cys 64 and exposed on the surface of the extrapolated binding site for acyl acceptor) in the MTG amino acid sequence according to SEQ ID NO: 2 is modified: 1-5, 26, 28, 58-59, 62, 69, 74-75, 77, 79, 235-236, 238-244, 248-250, 252-254, 277-278, 282-287, 289, 291, 296,-297 and 300-304.

(5) A mutant MTG or a mutant transglutaminase having changed substrate specificities through reducing the negative charge by modifying acidic amino acid residues located at the positions defined in any one of the above items (2) to (4) or amino acid residues adjacent to said acidic amino acid residues.

(6) A gene encoding the mutant MTG or the mutant transglutaminase defined in any one of the above items (2) to (5).

(7) A recombinant DNA containing the gene defined in above item (6).

(8) A microorganism harboring the recombinant DNA defined in above item (7).

(9) A method for producing a mutant MTG or a mutant transglutaminase, which comprises culturing the microorganisms defined in item (8) and collecting the mutant MTG or the mutant transglutaminase.

(10) A monoclinic MTG crystal belonging to $P2_1$ space group.

Namely, the present invention provides a method for rationally designing and preparing a mutant MTG on the basis of the three-dimensional structure of MTG, and the mutant MTG thus prepared.

BRIEF DESCRIPTION OF THE DRAWINGS

FIG. 3 shows the alignments of amino acid sequences of MTG and TG from *Streptoverticillium cinnamoneum*. The top sequence is from *Streptoverticillium mobaraense* (SEQ ID NO:2) and the bottom sequence is from *Streptoverticillium cinnamoneum* (SEQ ID NO:6).

FIG. 4 shows the alignments of amino acid sequences of MTG and TG from *Streptoverticillium lydicus*. The top sequence is from *Streptoverticillium mobaraense* (SEQ ID NO:2) and the bottom sequence is from *Streptoverticillium cinnamoneum* (SEQ ID NO:8).

FIG. 5 shows the primer sets used for the site-directed mutagenesis of S2Y•S2R•S2D mutants. The sequences appearing in this figure are represented in the Sequence Listing as follows: S2Y(s)=SEQ ID NO: 13, S2Y(as)=SEQ ID NO: 14, S2R(s)=SEQ ID NO: 15, S2R(as)=SEQ ID NO: 16, S2D(s)=SEQ ID NO: 17, S2D(as)=SEQ ID NO: 18, translated amino acid sequence for S2Y=SEQ ID NO: 30, translated amino acid sequence for S2R=SEQ ID NO: 31, and translated amino acid sequence for S2D=SEQ ID NO: 32.

FIG. 6 shows the primer sets used for site-directed mutagenesis of del 1-2 and del 1-3 mutants. The sequences appearing in this figure are represented in the Sequence Listing as follows: del 1-2(s)=SEQ ID NO: 19, del 1-2(as)=SEQ ID NO: 20, del 1-3(s)=SEQ ID NO: 21, del 1-3(as)=SEQ ID NO: 22, translated amino acid sequence for del 1-2=SEQ ID NO: 33, and translated amino acid sequence for del 1-3=SEQ ID NO: 34.

FIG. 11-1 to 11-50 show the atomic coordinates of MTG (SEQ ID NO: 2).

DESCRIPTION OF THE PREFERRED EMBODIMENTS

Figure 1:
FIG. 1 is a ribbon model showing the crystal structure of MTG.

The present invention will be concretely described thereinafter.

Transglutaminase is widely used for the production of foods such as gelatins, cheeses, yogurts, tofu, boiled fish pastes, hams, sausages and noodles and also for improving the quality of meats (JP-Kokai No. 64-27471). Transglutaminase is also used for various industrial purposes, for example, in the production of materials for heat stable microcapsules and the production of carriers for immobilized enzymes. Transglutaminase catalyzes the acyl transfer reaction of γ-carboxamide group of glutamine residue present in the peptide chain of a protein molecule. When ε-amino group of lysine residue in a protein molecule acts as an acyl acceptor, ε-(γ-Glu)-Lys bond is formed in the protein molecule and between the molecules.

The inventors found that transglutaminase does not react with all glutamine residues, namely, the possibility of the reaction, i.e. reactivity of transglutaminase varies depending on the kinds and positions of the residues surrounding the glutamine residues. Therefore, modification of the reactivity of transglutaminase on the glutamine residues under specified environment lead to the modification of the gelation rate and, as a result, the range of the use of transglutaminase may be further widened.

In the present invention, for modifying the substrate specificity of MTG, the three-dimensional structure thereof is determined by X-ray crystal structure analysis and the manner of binding to the substrate is predicted and the mutations suitable for the purpose are designed and introduced. The term "substrate specificity" herein used indicates the reactivity with each glutamine residue in the acyl acceptor.

The determination of the three-dimensional structure of a protein by X-ray crystal structure analysis will be carried out by the following procedure:

(1) The protein is crystallized. The crystallization is indispensable for determining the three-dimensional structure.

In addition, the crystallization is industrially useful for the purification of a protein in high purity and also for a method of stable storage of a protein in high density, which method is highly resistant against proteases.

(2) The crystals thus obtained are irradiated with X-ray to collect the diffraction data. In many cases, protein crystals are damaged by the X-ray irradiation which reduces the diffraction capacity thereof. In such cases, low temperature measurement technique has recently been spread wherein the crystals are rapidly cooled to about −173° C. and the diffraction data are collected in this state. Finally, the synchrotron radiation with high intensity is utilized for collecting the high-resolution data used in the determination of the structure.

(3) For the analysis of the crystal structure, the phase information is required in addition to the diffraction data. The MTG structure cannot be determined by molecular replacement method because the crystal structures of analogous proteins are yet unknown. Thus, the phase problem must be solved by heavy atom isomorphous replacement method. This method comprises introducing a metal atom having a large atomic number such as mercury or platinum into the crystal and obtaining the phase information taking advantage of the contribution of the large X-ray scattering capacity of the metal atom to the X-ray diffraction data. The phase thus determined can be improved by smoothing the electron density in the solvent region in the crystal. Since the electron density of water molecules in the solvent region is scarcely observed because of their have high fluctuation, the electron density very close to the true electron density can be obtained by approximating the electron density in this region to 0, which improves the phase. When plural molecules are contained in an asymmetric unit, the phase will be further remarkably improved by averaging the electron density of these molecules. A protein model is fit to the electron density map calculated using thus improved phase. This process is carried out using a program such as QUANTA (MSI Co., U.S.A.) by computer graphics. Then the structure is refined using a program such as X-PLOR (MSI Co., U.S.A.) to complete the structure analysis.

The inventors crystallized purified natural MTG from *Streptoverticillium mobaraense* and recombinant MTG (Met type) with additional Met originating from initiation codon at the N-terminal, but could not obtained a crystal suitable to be analyzed. However, because better crystals were obtained with natural MTG rather than with Met-type MTG, the inventors prepared Asp-type MTG (Example 1) after having considered that the recombinant MTG (Asp type MTG) starting with Asp1, like the natural one, obtained by removing Met at the N-terminal, might have the possibility of resulting in the crystals tolerable to the analysis. As a result, Asp-type MTG yielded a good crystal (Example 2), and the three-dimensional structure was successfully obtained (Example 3). The atomic coordinates in the MTG three-dimensional structure are shown in FIGS. 11 to 60.

The reaction mechanism of transglutaminase is considered to be as follows: An acyl donor containing Gln reacts with a transglutaminase to form a reaction intermediate. Then an acyl acceptor containing Lys attacks the intermediate to form ε-(γ-Glu)-Lys bond between the acyl donor and the acyl acceptor. For using a protein as the acyl donor, it is not sufficient that it contains Gln, but it is required that the region around Gln can be bound appropriately to the substrate-binding site of MTG. On the contrary, it is enough in most cases for the protein to contain a primary amine to serve as the acyl acceptor. Therefore, modifying the substrate specificity of MTG means modifying the structure of the binding sites for the acyl donor. If MTG can be modified so as to reduce the substrate specificity thereof or, in other words, so as to accept a larger amount of the acyl donor, the cases increases wherein the joining of proteins may be possible using a smaller amount of MTG, and therefore, the reduction of the amount used is expected. Further, if the joining of proteins in which the cross-linking is presently impossible become possible, the application of MTG in a new field will become possible. The three-dimensional structure of MTG is indispensable for extrapolating the binding manner between MTG and the acyl donor.

Figure 2:
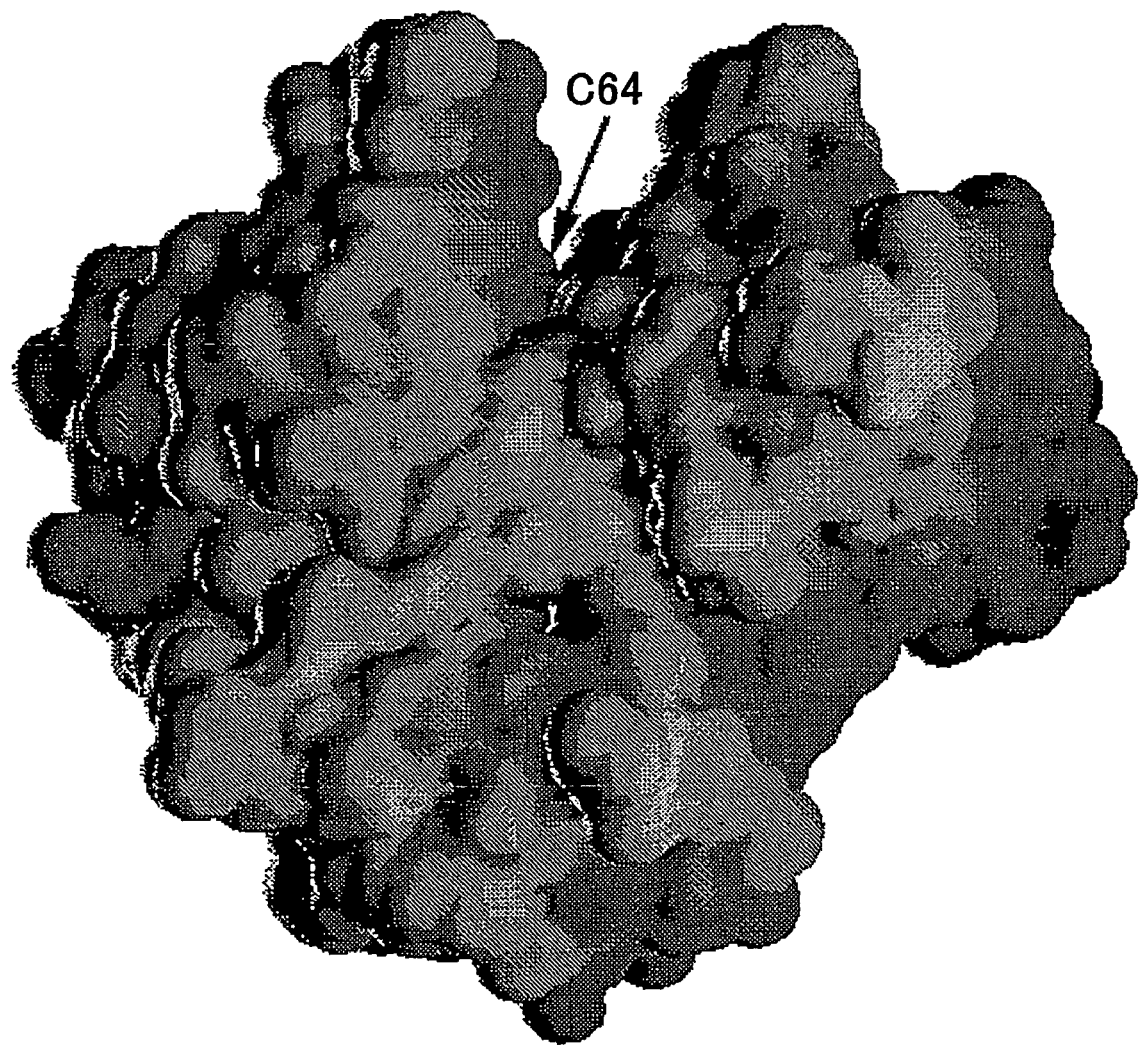
FIG. 2 shows the surface roughness of the crystal structure of MTG observed in the same direction as that in FIG. 1.

MTG molecule elucidated in the present invention is in the shape of discoid form having a size of 65×59×41 Å (see FIGS. 1 and 2). Namely, in FIG. 1, the crystal structure of MTG is shown by a ribbon model. α-helices and β-sheets are shown by spirals and arrows, respectively. An active residue, $Cys^{64}$, is shown by boll and stick model (upper central part).

FIG. 2 shows the surface concavoconvex of the crystal structure of MTG in the same direction as in FIG. 1. The regions having the electric charge are indicated in dark color and those free of the electric charge are indicated in light color. Observing the disk from upper side, it has a wedge-shaped cleft. In the inner part of the cleft, active residue $Cys^{64}$ is located. The fact that $Asp^{255}$ is positioned in the neighborhood of the active residue $Cys^{64}$ suggests that SH group of $Cys^{64}$, which may be dehydrogenated by $Asp^{255}$, causes the reaction. The side chain of $Cys^{64}$ faces the solution side and it can approach the acyl donor and acyl acceptor. In $Ca^{2+}$-dependent human blood coagulation factor XIII, the active residue Cys is not exposed to the solvent. Therefore, for binding with the acyl donor, human blood coagulation factor XIII must undergo a significant structure change for the active residue to bind to the acyl donor. On the other hand, MTG is considered to be able to bind to the acyl donor without changing its structure. Therefore, it is supposed that MTG can use more Gln residues as the substrates than human blood coagulation factor XIII uses. Further, MTG has a merit in that a mutant having further reduced substrate specificity can be easily designed, because it is not required to take the structural change associated with the binding to the acyl donor into consideration. Furthermore, the molecular weight of MTG is as low as 38,000, while that of human blood coagulation factor XIII is 166,000, which make the determination of the binding site of MTG for the acyl donor easy. By observing the structure of MTG, it would be understood that the substrate is very likely to bind in the wedge-shaped cleft leading from the solvent to $Cys^{64}$.

Many hydrophobic amino acid residues and aromatic amino acid residues are positioned in the cleft leading to active residue $Cys^{64}$, and thus the mutual action thereof with hydrophobic residues or aromatic residues in the acyl donor is considered to be one of the keys for the determination of the substrate specificity. The polar resides including Asp are also scattered on the cleft surface, which suggests that they play an important role in the recognition of the acyl donor. A mutant transglutaminase having a modified substrate specificity can be obtained by the replacement, insertion or deletion of amino acid residues located in the cleft which is supposed to be the acyl donor binding region, preferably by the replacement of the polar residues (Asp, Glu, Lys and Arg) or aromatic residues (Phe, Tyr and Trp) with other amino acids, the replacement thereof with polar residues or aromatic residues, the deletion of the polar residues or aromatic residues or insertion of polar residues or aromatic residues. It is to be noted, however, since it is supposed that the activity will be lost by modifying $Cys^{64}$ and $Asp^{255}$ which play an important role for the activity, these residues should be excluded in the production of the mutants.

As shown in Examples given below, acidic amino acids present adjacent to the reactive site in the substrate proteins. Glutamine residues reactive with MTG are positioned on the surface of the substrate protein in many cases and it is considered that acidic amino acids which may easily exposed to the solvent are likely to present around them. When acidic residues are present at the interaction site of the substrate protein of MTG, the negative charge in MTG and that in the substrate protein repel each other to reduce the enzymatic reaction velocity. The negative charge can be removed by modifying the acidic amino acid residues exposed on the surface of the cleft of MTG containing $Cys^{64}$ which is supposed to be bound by the acyl donor or, alternatively, the negative charge can be relaxed by converting amino acid residues sequentially or spatially adjacent to the acidic amino acids into basic amino acids to obtain the transglutaminase having a modified substrate specificity. Such acidic amino acids include the residues Nos. 1, 3, 4, 28, 58, 249, 300 and 304 of MTG described in SEQ ID NO: 2.

The amino acids adjacent to the acidic amino acids are the amino acid residues within 5 Å from carboxyl groups of the acidic amino acids such as aspartic acid and glutamic acid, and are preferably amino acid residues having the degree of exposition to the solvent of at least 10%. They include residues Nos. 2, 5, 59, 248-250, 252, 278, 283-285, 289, 291, 296-297 and 302-303 of MTG described in SEQ ID NO: 2.

The amino acid sequence of MTG is shown in SEQ ID NO: 2, and the nucleotide sequence of the gene encoding MTG is shown in SEQ ID NO: 1.

As shown in Example 5, it was confirmed that the reaction rate on a particular glutamine residue in a protein molecule could be elevated by the deletion of $Asp^1$ or $Asp^3$ or by the replacement of Ser2. Because the distance from active residue $Cys^{64}$ to $Asp^1$ at the N-terminal is 20 Å, it is suggested that there is a possibility that the substrate specificity can be modified by modifying the amino acid residues located within 20 Å from $Cys^{64}$. In addition, because it was confirmed that at least the loop regions (233-253 and 276-288) defined the substrate specificity, it was considered that the substrate specificity could be modified by modifying these regions. The possibility of changing the substrate specificity is further increased by modifying the residues exposed on the surface of the cleft having $Cys^{64}$ supposed to be bound by the acyl donor. To know whether the amino acid residues are exposed to the solvent or not, the solvent accessibility may be calculated using a program such as QUANTA. The solvent accessibility is the value resulting from dividing the exposure area to the solvent of a residue in the protein by the exposure area to the solvent of the amino acid in its free form, which is indicated as a percentage. The possibility of changing the substrate specificity of MTG may be high when the residues existing within 20 Å from $Cys^{64}$ and having a solvent accessibility of at least 10% are modified. Such residues correspond to residue Nos. 1-5, 26, 28, 58-59, 62, 69, 74-75, 77, 79, 235-236, 238-244, 248-250, 252-254, 277-278, 282-287, 289, 291, 296-297 and 300-304 of MTG described in SEQ ID NO: 2.

In designing and producing a mutant transglutaminase, the codon in the gene encoding the transglutaminase corresponding to the amino acid residues at the above-described substrate-binding site may be modified by site-directed mutagenesis and the obtained gene may be introduced into a suitable vector and transferred into a host, and then the transformant may be cultured. The intended mutant transglutaminase may be recovered from the transformed cultured microbial cells of and evaluated.

The site-directed mutagenesis methods for introducing intended mutation at the intended sites of DNA include, for example, a PCR method shown in Examples [Higuchi, R., 61, in PCR technology; Stockton Press edited by Erlich, H. A. (1989); Carter P., Meth. In Enzymol., Vol. 154, p. 3382 (1987)]; and a method wherein a phage is used [Kramer, W. and Frits, H. J., Methods in Enzymology, Vol. 54, p. 350 (1987), Kunkel, T. A. et al., Methods in Enzymology, Vol. 154, p. 367 (1987)]. The vectors for introducing the genes encoding mutant transglutaminase are not particularly limited so far as they can be replicated in hosts. When *Escherichia coli* is used as a host, plasmids capable of autonomously replicating in this bacterium can be used. For example, pUC19, pET or pGEMEX can be used.

Preferred hosts are, for example, strains of *Escherichia coli*, however, any bacterium can be used as the host so far as the replication origin of the constructed recombinant DNA and the mutant transglutaminase genes can function, the mutant DNA can be replicated and the expression of the mutant transglutaminase genes can be expressed in the bacterium. The representative preferred host is *Escherichia coli* BL21(DE3)pLysS when T7 promoter is used or *Escherichia coli* JM109 in other cases.

An ordinary method can be employed, without any particular limitation, for introducing the recombinant DNA obtained by ligating the vector with the DNA fragment containing the gene encoding the mutant transglutaminase into the host. When *Escherichia coli* is used as the host, there can be employed calcium chloride method [J. Mol. Biol., Vol. 53, p. 159 (1970)], Hanahan method [J. Mol. Biol., Vol. 166, p. 557 (1983)], SEM method [Gene, Vol. 96, p. 23 (1990)] and Method of Chung et al. [Proceedings of the National Academy of Sciences of the USA, Vol. 86, p. 2172 (1989)].

MTG may be expressed in the bacterial cell at a high level by culturing the transformant harboring the recombinant DNA containing the gene encoding the mutant transglutaminase in a suitable medium containing a carbon source, a nitrogen source, an inorganic ion and, if necessary, further containing an organic nutrient source. For extracting the mutant transglutaminase from the cultured cells, the cells are collected after culturing them, suspended in a buffer solution, and subjected to the lysozyme treatment, freezing-and-thawing treatment, ultrasonic disruption, etc., and then, they are disrupted and centrifuged to separate the suspension into the supernatant and the precipitant.

Since the mutant transglutaminase is produced in the form of a protein inclusion body and separated as the precipitant, it may be solubilized with a denaturing agent or the like and then the denaturing agent may be removed to isolate and purify the protein. The denaturing agents for solubilizing the produced protein inclusion body may be, for example, urea (for example, 8M) and guanidine hydrochloride (for example, 6 M). By reducing the concentration of the denaturing agent by dilution or the like, the protein having transglutaminase activity is regenerated. The solutions used for the dilution may include phosphate buffers and Tris buffers.

After regenerating the activity, the active protein can be isolated and purified by a suitable combination of known isolation method and purification method. Examples of these methods are salting out, dialysis, ultrafiltration, gel filtration, ion exchange chromatography, affinity chromatography and reversed-phase high-performance chromatography.

The term "substrate specificity" in the context of the present invention indicates the reactivity of each glutamine residue in the substrate protein molecule to a transglutaminase. The change in the substrate specificity of a transglutaminase means the change in the reactivity of at least one glutamine residue. When the mutant transglutaminase having the changed substrate specificity is reacted on a protein, the degree of crosslinking of the protein, namely, the degree of the gelation, is also changed compared with the results obtained by reacting the original transglutaminase.

Methods for comparing the substrate specificities of transglutaminases include, for example, the method wherein the gelation time of casein is determined, the method wherein the cross-linked polymer obtained after the transglutaminase reaction is analyzed by electrophoresis, and the method wherein the reaction product is fragmented and then analyzed. It is also possible that the substrate protein is reacted with $^{15}N$-labeled ammonium ion by using the transglutaminase and then the labeled glutamine residues are detected by NMR (JP-Application No. 2000-141152).

The analysis of substrate specificity by the latter method is the method of comparing the reactivity of individual glutamine residue in the protein, taking advantage of the fact that the carboxamide nitrogen in the glutamine residue, which functions as a substrate, is $^{15}N$-labeled by a transglutaminase. The substrate specificities of the transglutaminases can be compared with each other, taking advantage of that glutamine residue which acts as a substrate for transglutaminase is specifically $^{15}N$-labeled and that the labeling rate varies depending on the reactivity of the transglutaminase to the glutamine residue.

The unit activity of transglutaminase is determined and defined as follows: The reaction is carried out using benzyloxycarbonyl-L-glutaminylglycine and hydroxylamine as the substrates, the resulting hydroxamic acid is converted into an iron complex hereof in the presence of trichloroacetic acid and then the amount thereof is determined as an absorbance at 525 nm. Thus the calibration curve is prepared based on the amount of hydroxamic acid. The amount of the enzyme which produces 1 μmole of hydroxamate per one minute is defined to be the unit of transglutaminase activity, one unit. The details of this determination method were previously reported (for example, JP-Kokai No. 64-27471).

Besides the transglutaminase from *Streptoverticillium mobaraence* (MTG), it is also possible to modify an enzyme which has the transglutaminase activity and amino acid sequence homologous to MTG, or an enzyme which has the transglutaminase activity and which is supposed to have the three-dimensional structure similar to that of MTG, on the basis of the three-dimensional structure of MTG. The amino acid replacement effective for the modification of the substrate specificity or the like of MTG is also effective for analogous enzymes such as those from *Streptoverticillium cinnamoneum* and *Streptoverticillium lydicus* (JP-Kokai No. 10-504721). The amino acid sequence of the transglutaminase from *Streptoverticillium cinnamoneum* is shown in SEQ ID NO: 6, the nucleotide sequence of the gene encoding the amino acid sequence is shown in SEQ ID NO: 5, the amino acid sequence of the transglutaminase from *Streptomyces lydicus* is shown in SEQ ID NO: 8, and the nucleotide sequence of the gene encoding the amino acid sequence is shown in SEQ ID NO: 7. In this connection, the homology of the amino acid sequence between MTG and transglutaminase from *Streptoverticillium cinnamoneum* is 78% (FIG. 3), and that of the amino acid sequence between MTG and transglutaminase from *Streptomyces lydicus* is 79% (FIG. 4). Namely, FIG. 3 shows the alignment of amino acid sequences of MTG and transglutaminase from *Streptoverticillium cinnamoneum*. Conserved amino acid residues are shown by "*".

FIG. 4 shows the alignment of amino acid sequences of MTG and the transglutaminase from *Streptoverticillium lydicus*. Conserved amino acid residues are shown by "*".

The coordinate assignment of amino acid residues of two different proteins may be revealed from the alignment of the amino acid sequences (Sequence Alignment) when the homology between the amino acid sequences of them is above about 20%, and it may be revealed from the three-dimensional structures and the alignment of the amino acid sequences (Threading) when the homology is below about 20%. The former can be carried out using a program such as BLAST and the latter can be carried out using a program such as INSIGHT II. BLAST can be obtained by using ftp as the file adapted to the computer to be used among the files existing in "/blast/executable" of ncbi.nlm.nih.gov. The operating instructions are described in detail in http://genome.nhgri.nih.gov/blastall/blast install. INSIGHT II is commercially available (MSI Co.).

A mutant transglutaminase having modified substrate specificity is usable for the preparation of gelled foods such as jellies, as well as yogurts, cheeses and gelled cosmetics; for the improvement in the quality of meats; for the production of materials of thermally stable microcapsules and carriers for immobilized enzymes; and for the enzymatic labeling of proteins. When a protein is $^{15}N$-labeled, the structure analysis by NMR is made possible (JP-Application No. 2000-141151), and when it is labeled with a primary amine, the solubility and stability thereof can be improved (JP-Application No. 2000-141152). Proteins usable as the substrates for the transglutaminase may vary. Thy include those constituting muscle such as actin and myosin; human plasma components such as albumin, immunoglobulin and blood coagulation factors; enzymes such as protease and transferase; hormones such as growth hormone and erythropoietin; cell growth factors for proliferating or inhibiting cells; immune reaction modulators for cell differentiation, induction and stimulation; and biologically active proteins produced by cells, such as monokine, cytokine and lymphokine. The origins of those proteins are not particularly limited and the proteins may be derived from animals, vegetables and microorganisms. Further, the proteins may be those expressed in *Escherichia coli*, yeast and animal cells by introducing the genes of these proteins into them or those expressed by using a cell-free protein synthesis system.

The reaction of such a protein in the presence of the transglutaminase is carried out under conditions where the transglutaminase can function. For example, the substrate protein and the transglutaminase are kept at a pH in the range of about 5.0 to 9.0, preferably abut 6.0 to 8.0 and at a temperature in the range of about 4 to 55° C., preferably about 25 to 40° C. in an aqueous solvent. In this reaction, the concentration of the substrate protein is preferably in the range of 1 μM to 1 M, and the amount of the transglutaminase is desirably in the range of about 10 nM to 100 μM which corresponds to about 0.01 to 20 units per mmol of the protein. However, the reaction conditions are not limited to those described above.

The range of the industrial utilization of MTG can be further widened when the heat stability and optimum pH can be modified in addition to the modification of the substrate specificity. If the heat stability is improved, the gelation of protein at a higher temperature may become possible. In the production of tofu (bean curd) filled into a pack, which is commonly sold in supermarkets, MTG is added to soybean milk and then the obtained mixture is tightly closed in the pack and then heated. Therefore, the temperature easily elevates to a point at which MTG is denatured. If the heat stability of MTG can be improved, the amount of protein inactivated by denature can be reduced, whereby the cost is lowered. The thermal stability can be improved by, for example, the introduction of proline residue, the replacement of the residues forming the counterclockwise helix structure with glycine residues [Protein Engng, Vol. 6, pp. 85-91 (1993)], or filling of the cavities in the protein [Biochemistry, Vol. 32, pp. 6171 to 6178 (1993)]. Further, if the optimum pH can be shifted to the alkaline region, the gelation efficiency of a substance which reacts under an alkaline reaction condition can be elevated such as the case of udon which are prepared by joining gluten. The modification of optimum pH can be achieved by modifying pKa of the active residues [Protein Engineering, Vol. 11, pp. 383-388 (1998)].

EXAMPLES

The following Examples will further illustrate the present invention, which by no means limit the invention.

Example 1

Preparation of Recombinant Native Type (Asp Type) MTG

MTG expression plasmid pETMTGXa-01 which will be described below was constructed to produce recombinant MTG having the same N-terminal amino acid sequence as that of native type in *Escherichia coli*. pETMTGXa-01 is a plasmid capable of expressing a fused protein having the recognition sequence (IEGR) of factor Xa between the amino terminal region of T7 gene 10 protein and MTG. The procedures for constructing pETMTGXa-01 are described hereinafter. Firstly, primer pGEXMTGF01 (SEQ ID NO: 9 in the sequence listing) containing the sequence encoding BamHI cleavage site and Factor Xa recognition site at the upstream side of MTG gene and also primer pGEXMTGR01 containing Sac I cleavage site (SEQ ID NO: 10 in the sequence listing) were synthesized. PCR was carried out using these primers and MTG genes in MTG expression plasmid pUC-TRPMTG-02(+) (JP Kokai No. 11-75876) as a template, and the amplified fragment was cloned in pGEM-T Easy Vector (Promega). PCR were carried out by 25 cycles of "96° C. for 30 seconds, 50° C. for 15 seconds and 60° C. for 1 minute". The cloning of the amplified fragment was carried out according to the instructions of supplier. Clone in which the amplified fragments were inserted in an opposite direction to lacZ gene were selected. The nucleotide sequences of the plasmids in the clones were analyzed and the plasmid having the intended correct sequence was named "pGEMMTGXa". Then pET5a (Takara Shuzo Co., Ltd.) vector was cleaved by EcoRI, bunt-ended, and cleaved by BamHI. pGEMMTGXa was cleaved by SalI, blunt-ended, cleaved by BamHI, and the obtained fragment containing MTG gene was subcloned in the above-described enzymatically digested pET5a to construct pETMTGXa-01.

*Escherichia coli* BL21(DE3)pLysS (Promega) having pETMTGXa-01 introduced therein was inoculated in 50 ml of L medium (10 g/L of Tryptone, 5 g/L of yeast extract, 5 g/L of NaCl and 1 g/L of glucose; pH: 7.2) containing 200 µg/ml of ampicillin and pre-cultured at 37° C. for 6 hours. Then, 8 ml of the pre-culture was subcultured for 4 hours at 37° C. in M9 casamino acid medium (8 g/L of casamino acids, 5 g/L of ammonium chloride, 0.2 g/L of yeast extract, 2 mg/L of vitamin $B_1$ hydrochloride, 14.5 mg/L of calcium chloride dihydrate, 15.1 g/L of disodium hydrogen phosphate 12 hydrate, 3 g/L of potassium dihydrogen phosphate, 0.5 g/L of magnesium sulfate heptahydrate and 5 g/L of glucose; wherein magnesium sulfate heptahydrate and glucose were separately sterilized) containing 200 µg/ml of ampicillin. When $OD_{660}$ reached to about 2.0, 0.8 ml of 1M IPTG was added to the culture, and the culture was further continued at 37° C. for 14 hours.

The cells were collected from the broth by centrifugation and suspended in 200 ml of a mixture of 20 mM Tris-HCl, 30 mM of NaCl and 5 mM of EDTA, pH 7.5. 1 mg/ml of lysozyme was added to the obtained suspension. After leaving the resultant mixture at 4° C. for 1 hour, the cells were crushed by ultrasonication. Protein inclusion bodies containing denatured MTG were collected by centrifugation. The protein inclusion bodies were thoroughly suspended in a small amount of water. Reagents and water were added to the obtained suspension so that the suspension contains 8 M of urea, 20 mM of sodium phosphate, 1 mM of EDTA and 20 mM of DTT/30 ml to dissolve the protein inclusion bodies. After incubating at 37° C. for 2 hours, pH was lowered to 4 by adding dropwise 1 M of hydrochloric acid, and the precipitant was removed after centrifugation. The concentration of the solubilized MTG was determined, which was found to be about 20 mg/ml. 20 ml of the above solubilized MTG solution were slowly added dropwise to 1000 ml of 20 mM sodium acetate, pH 4.0, containing 2 mM DTT, and the mixture was left to stand for 2 hours. After 2 hours, 4 M of sodium hydroxide was added dropwise to the mixture to elevate pH to 6 to complete the refolding. The concentration of MTG was determined to be about 0.14 mg/ml. The refolding procedure was totally carried out in a cold room at 4° C.

The total solution thus obtained was concentrated to a volume of 200 ml by ultrafiltration (Hydrosart, 10 kDa Molecular cut off; Sartocon Slice Casette, Sartorius). and the solvent was replaced with 20 mM Tris-HCl (pH 7.5) by using Sephadex G25 (M) (Pharmacia Aktiebolag). 5 mg of bovine factor Xa (Hematologic Technology Inc.) was added to 250 ml of the obtained solution and then the mixture was left to stand overnight at 5° C. The concentration of MTG was determined to be about 0.36 mg/ml. The N-terminal amino acid sequence of MTG cleaved by factor Xa was analyzed with a protein sequencer (Shimadzu Corporation) to confirm that the sequence attached to the N-terminal had been completely cleaved by factor Xa and also that there was only the recombinant MTG having the mature type N-terminal amino acid sequence.

After the cleavage with factor Xa, pH of the solution was adjusted to 5.8 with 1 M hydrochloric acid and then the solution was diluted 5-fold with a buffer solution (20 mM sodium acetate, pH 5.8) used for equilibration of cation exchange chromatography. The obtained solution was applied to the cation column (CM Sepharose FF, 2.6 φ×10 cm; Amersham Pharmacia Biotech) sufficiently equilibrated with the buffer solution. After the re-equilibration with the same buffer solution, a protein fraction (46 ml) eluted according to the linear concentration gradient of 0-0.4 M NaCl was recovered using UV absorption at a wavelength of 280 nm as an index. The recovered fraction was diluted 10-fold with a buffer solution (20 mM sodium acetate, pH 5.5) used for the equilibration of the cation exchange chromatography. ⅓ of the diluted solution was applied to the cation column (6 ml of Resource S; Amersham Pharmacia Biotech) sufficiently equilibrated with the same buffer solution. After the re-equilibration with the same buffer solution, a protein fraction eluted according to the linear concentration gradient of 0-0.5 M NaCl was fractionated using UV absorption at a wavelength of 280 nm as an index. A fraction (2 ml) in which no impurities were detected by reversed-phase HPLC and which was free from low pI form of MTG was recovered from the front side of the peak top. The similar purification was carried out twice, and the side fraction of the recovered fraction was re-chromatographed to finally recover the fraction of 8 ml (40 mg). Again, the solvent was replaced with 20 mM phosphoric acid, pH 6.0 by using Sephadex G25(M). The recovered fraction was analyzed by isoelectric focusing to confirm that it was the recombinant MTG of a high purity substantially free from analogues having different pI. All of the chromatography procedures were carried out at room temperature.

Example 2

Crystallization

The crystallization was carried out using the hanging drop mode of vapor diffusion method. Recombinant Asp type MTG solution (concentration: 15 mg/ml) and 83 mM buffer (pH 5.0) of sodium cacodylate containing 25% polyethylene glycol 1000 and 25 mM calcium chloride were dropped in the same amounts (2 μl) on a siliconized cover glass and mixed together. The cover glass was placed on the buffer in such a manner that the drops of the mixed liquid were hanging over the well filled with 500 μl of the buffer, and they were left to stand at 20° C. Crystals were formed one week after. 10 days after, the crystals grew into plate-like crystals of a measurable size (about 0.5×0.3×0.1 mm). The MTG crystal was analyzed at a low temperature, because MTG crystal would be damaged by X-ray which leads to the gradual reduction of resolution when analyzed at ambient temperature. The crystal was transferred into 117 mM buffer (pH 5.0) of sodium cacodylate containing 35% of polyethylene glycol 1000 and 35 mM of calcium chloride and rapidly cooled by blowing nitrogen gas at −173° C.

X-ray diffraction data of 2.7 Å resolution were obtained with a X ray diffractometer, R-AXIS IIc (Rigaku Co., Ltd.) and the crystallographic parameters were determined. The space group was $P2_1$, lattice constants were as follows: a=78.4 Å, b=117.1 Å, c=85.7 Å and β=112.9°. Assuming that the asymmetric unit contains 4 molecules (molecular weight: 38,000), water content of the crystals was calculated at 50%.

Example 3

Determination of Three-Dimensional Structure

The crystals were immersed in a solution of heavy metal salts and the heavy atom derivatives were screened. The diffraction data of the heavy atom derivative crystals were obtained by using SMART 6000 (Bruker) and the synchrotron radiation facilities BL-6B of the National Laboratory for High Energy Physics. From difference Patterson map compared with the native data, it was shown that EMTS, $K_2OSCl_6$ and $K_2IrCl_6$ provided good heavy atom isomorphous-replacement crystals. Major heavy atom sites were determined from the differential Patterson maps of the respective heavy atom isomorphous replacement crystals, and then, other minor heavy atom sites were determined using the difference Fourier maps. The coordinates of these heavy atom sites were refined by the phase determination program "MLPHARE" and the phase was calculated. The phase was improved by solvent flattering and histogram matching using the program DM and then an electron density map was prepared. In the electron density map, 4 MTG molecules were refined in an asymmetric unit. The electron density corresponding to the 4 molecules was averaged using the program DM to remarkably improve the quality of the electron density. The electron density map prepared with 2.7 Å resolution was very good and all the amino acid residues from N terminal to C terminal could be fitted into the electron density.

The first model was constructed on computer graphics using QUANTA program, and the structure was refined using X-PLOR program. The final models (FIGS. 1 and 2) refined with X-ray diffraction data of a 2.4 Å resolution at the synchrotron radiation facilities BL-6B (National Laboratory for High Energy Physics, Tsukuba,) contained all of the 331 amino acid residues and 400 water molecules. The crystallographic reliability factor (R factor) determined by using the reflection at 10 to 2.4 Å resolution was 19.6%. In a Ramachandran plot prepared with the program PROCHECK, it was shown that 82% of residues other than glycine located in the most desirable region and 15% thereof located in the second most desirable region.

Example 4

Preparation of Site-Directed Mutant

Because N-terminal $Asp^1$ is positioned at the entrance of the cleft, it is supposed that it has some responsibility on the recognition of the substrate (FIGS. 1 and 2). The side chain of $Asp^1$ has no interaction with other residues constituting the enzyme and, therefore, it is considered that even when the residue is modified, there is no risk of distorting the three-dimensional structure of the protein. The effects of $Asp^1$ on the substrate specificity can be examined by preparing a mutant in which this residue has been removed (hereinafter referred to as "Ser type mutant" because it starts with $Ser^2$) and then comparing the substrate specificity thereof with that of the wild type. Because *Escherichia coli* obtained by transforming plasmid containing a gene encoding Ser-type mutant had been already constructed (JP-Kokai No. 11-075876), we designed to prepare the Ser-type mutant using this plasmid.

It was also supposed that the substrate specificity could be modified also by replacing $Ser^2$ located at the entrance of the channel with another amino acid. we designed to prepare three mutants, i.e. S2Y obtained by replacing $Ser^2$ with Tyr for the purpose of enhancing the hydrophobic mutual action and S2R and S2D obtained by replacing $Ser^2$ with Arg and Asp, respectively, for the purpose of enhancing the electrostatic interaction. These mutations were introduced into MTG having additional Met corresponding to the initiation codon at the N-terminal (Met type).

Additionally, insulin A chain (Sigma) wherein cysteine residue had been oxidized was bought as the substrate protein, and the glutamine residues which could be the substrates of MTG were examined. Insulin A chain is a protein (SEQ ID NO: 23) consisting of 21 amino acid residues, which has glutamine residues at the $5^{th}$ position and the $15^{th}$ position from the N-terminal. The reasons why insulin A chain was selected for examining the structural characteristics of the substrate protein are that it contains plural glutamine residues and the positions of the glutamine residues reacted with MTG can be easily determined because it has a low molecular weight.

200 μl of 1 M $^{15}NH_4Cl$ and 2 μl of 1 mM MTG were added to 1 mg of insulin A chain wherein the cysteine residues were oxidized and then they were stirred and subjected to mass spectrometry. The mass spectrometry was carried out during fragmenting individual amino acid residues to identify the $^{15}N$-labeled residue which was proved to be the $15^{th}$ glutamine residue from the N-terminal. As a result, it was found that in the two glutamine residues in insulin A chain, the $15^{th}$ glutamine residue was the substrate of MTG.

Glutamic acid is present at position 17 in insulin A chain. This glutamic acid residue is located adjacent to the 15$^{th}$ glutamine residue with the insertion of one residue. Since amino acid side chains on a polypeptide chain incline to face the same direction when they are located with the insertion of one residue, the glutamine residue at position 15 and the glutamic acid at position 17 are therefore considered to be not only close to each other in the sequence but also to be spatially close to each other. Because acidic amino acid is present near the 15$^{th}$ glutamine residue, it is not preferred that an amino acid having a negative electric charge is present at the substrate binding site of MTG. In most cases, the glutamine residues reactive with MTG are positioned on the surface of the substrate protein. It is considered that acidic amino acids which may easily exposed to the solvent may present surrounding the glutamine residue. This is also applicable to the substrate proteins other than insulin.

Accordingly, it is supposed that the substrate specificity can be improved when the negative charge is reduced by modifying the acidic amino acids or by converting the surrounding amino acids into basic amino acids to obtain a mutant transglutaminase having a modified substrate specificity. Ser-type MTG was the one in which the aspartic acid in SEQ ID No: 2 had been removed, and S2R mutant was the one in which basic amino acids were arranged near the acidic amino acids to reduce the negative charge, all of which meet the above criterion. They satisfy the above-described conditions. Additionally, del 1-2 was prepared by removing residue Nos. 1 and 2 and del 1-3 was prepared by removing residue Nos. 1 to 3 to remove the negative charge of Asp$^1$ and Asp$^3$, respectively.

Because the two loops (233-253 and 276-288) which locate to surround the active residue Cys$^{64}$ are positioned as if the substrate is sandwiched by them, they are likely to define the substrate specificity. However, the loops cannot be blindly removed because they also play an important role in the folding of MTG. Therefore, the sites satisfying the following conditions (1) and (2) were searched based on the three-dimensional structure of MTG: (1) the site hardly interact with the sites other than the loops and it does not affect the folding and (2) the distance between N-terminal and C-terminal of the deleted site (residue) is not longer than 7 Å and it can be replaced with 3 glycine residues. The 3 glycine residues are mentioned only considering that the turn structure can be formed with them, and they are not restrictively mentioned. For example, because residues Nos. 241 to 252 have substantially no interaction with other sites and since the distance between N-terminal of residue No. 241 and C-terminal of residue No. 252 is about 6 Å, residue Nos. 241-252 can be replaced by 3 glycine residues. It was attempted to produce Sg4 by replacing residue Nos. 241 to 252 with 3 glycine residues and Sg7 by replacing residue Nos. 278 to 287 with 3 glycine residues as the mutants satisfying such conditions in which the loops were removed to elucidate the contribution of the two loops surrounding Cys$^{64}$ active residue.

(1) Preparation of Ser-type MTG

*Escherichia coli* JM109 harboring plasmid pUCTRP-MTG-02(+) containing Ser-type MTG gene (JP-Kokai No. 11-075876) having Ser-type MTG gene was inoculated into 50 ml of L medium containing 200 μl/ml of ampicillin, and pre-cultured at 30° C. for 7 hours. 16 ml of the pre-culture was transferred into 800 ml of M9 medium, and the culture was further continued at 37° C. for 24 hours. The cells were collected from the broth by centrifugation and suspended in 12.5 ml of 20 mM Tris and 30 mM of NaCl. 1 mg/ml of lysozyme and 0.5 MEDTA were added to the obtained suspension, and they were left to stand at 4° C. for 1 hour. Then the cells were crushed by ultrasonication for 20 minutes. The protein inclusion bodies containing denatured MTG were collected by centrifugation. The protein inclusion bodies were thoroughly suspended in a small amount of water, and then, the reagents and water were added to the obtained suspension to a final concentration of 8 M urea·20 mM sodium phosphate·1 mM MEDTA·20 mM DTT/5 ml to dissolve the protein inclusion bodies.

After incubating at 37° C. for 2 hours, pH was lowered to 4 and the mixture was centrifuged to remove the precipitant. The solution of solubilized MTG was slowly dropped into 250 ml of 20 mM sodium acetate (pH 4.0) 2 mM DTT, and the mixture was left to stand for 2 hours. After 2 hours, pH was elevated to 5, and the insoluble matter was removed by centrifugation. pH was elevated to 6 to complete the refolding. The whole refolding procedure was carried out in a cold room at 4° C.

After replacing 250 ml of the solution with 20 mM sodium acetate (pH 5.8) with Sephadex G25(M) (Pharmacia), a protein fraction (55 ml) was recovered, which was eluted from an ion exchange resin (CM Sepharose FF) (Pharmacia) by the linear concentration gradient of 0 to 0.4 M of sodium chloride in 20 mM sodium acetate (pH 5.8). Again the solvent was replaced with 20 mM sodium phosphate (pH 6.0) with G25 (M).

When the subsequent amino acid of N-terminal Met is Ser, since N-terminal Met will be removed by methionine aminopeptidase of *Escherichia coli*, the codon corresponding to Ser may be positioned after the initiation codon to prepare the Ser-type mutant having Ser at the N-terminal.

(2) Preparation of Mutant by Replacing Ser 2

For producing three mutant MTGs (S2Y, S2R and S2D) by *Escherichia coli*, MTG expression plasmid pGEMMTG3 (encoding the amino acid sequence in SEQ ID No: 4 and containing the base sequence of SEQ ID No: 3) was constructed and used as a template for the site-specific mutagenesis using PCR. pGEMMTG3 is a plasmid highly expressing MTG by T7 promoter inducibly, and which was constructed by removing T7 gene 10 protein gene from plasmid pGEM15TG(Xa) expressing the fusion protein of amino-terminal side region of T7 gene 10 protein and MTG [Biosci. Biotech. Biochem. Vol. 61 (5), pp. 830-835 (1997)] and introducing a synthetic gene designed so that a high expression is possible in *Escherichia coli* as described in JP-Kokai No. 11-75876.

The procedures for constructing pGEMMTG3 are described below. Firstly, primer pGEMTGF01 (SEQ ID No: 11) which was designed so that 42 residues from T7 gene 10 protein were deleted and which had PstI cleavage site at its 5' terminal and primer pGEMTGR01 (SEQ ID No: 12) having EcoRI cleavage site in MTG gene were synthesized. PCR was carried out by using these primers and pGEM15TG(Xa) as a template, and the amplified fragments were cloned into pUC19 (Takara Shuzo Co., Ltd.). 25 cycles of PCR were carried out with the conditions of 96° C. for 30 sec, 50° C. for 15 sec and 60° C. for 1 minute. The nucleotide sequence of the insert-containing plasmid was analyzed and the plasmid having the intended correct sequence was named "pUCTGN". Because pGEM15TG(Xa) had two NdeI cleavage sites, NdeI/EcoRI fragment of pUCTGN was replaced by NdeI/EcoRI fragment of pGEM15TG(Xa) through multiple steps as described below. Namely, the small fragment obtained by cleaving pGEM15TG(Xa) with SmaI and EcoRI was subcloned into pBluescript (Toyobo Co., Ltd.) vector which had been cleaved by SmaI and EcoRI to obtain "pBS15TG(SE)".

Then the fragment containing TG gene obtained by cleaving pUCTGN with NdeI and EcoRI was ligated to the segment obtained by cleaving pBS15TG(SE) with NdeI and EcoRI, which did not contain TG gene, to obtain "pBSTG(SE)". Further, the large fragment obtained by cleaving pGEM15TG (Xa) with SmaI and EcoRI was ligated to the fragment containing TG gene obtained by cleaving pBSTG(SE) with NdeI and EcoRI to obtain "pGEMTG". Finally, the MTG gene segment (PvuII-HindIII cleavage fragment) of pGEMTG was replaced with MTG gene (PvuII-HindIII cleavage fragment) of pUCTRPMTG-02(+) (described in JP-Kokai No. 11-75876) to construct pGEMMTG3.

The mutation was introduced using quick exchange (registered trade mark) site-directed mutagenesis kit (Stratagene) with a primer (FIG. 5, SEQ ID NOS: 13-18) corresponding to each mutant enzyme according to the manufacturer's protocol. Namely, FIG. 5 shows the primer sets used in the site-directed mutagenesis for S2Y·S2R·S2D mutant. *Escherichia coli* JM109 (Takara Shuzo Co., Ltd.) was transformed by using the PCR product. The transformed cells were plated on L agar medium plates containing 100 µl/ml of ampicillin and incubated at 37° C. for 16 hours. Colonies thus formed were taken and cultured in L-medium containing 100 µl/ml of ampicillin by shaking overnight. The cells were recovered from the broth by centrifugation, and the plasmid was extracted by using Automatic DNA Isolation System PI-50 (KURABO) according to the manufacturer's protocol. The nucleotide sequence encoding each mutant MTG was confirmed by DNA sequencing. The plasmid was transformed into *Escherichia coli* BL21 (Promega).

*Escherichia coli* BL21(DE3) into which the mutant MTG gene had been introduced was inoculated into 50 ml of L medium (10 g/L of Tryptone, 5 g/L of yeast extract, 15 g/L of NaCl and 1 g/L of glucose, pH 7.2) containing 200 µg/ml of ampicillin, and pre-cultured at 37° C. for 6 hours. 8 ml of the pre-culture was transferred into M9 Casamino acid medium (8 g/L of casamino acid, 5 g/L of ammonium chloride, 0.2 g/L of yeast extract, 2 mg/L of vitamin $B_1$ hydrochloride, 14.5 mg/L of calcium chloride dihydrate, 15.1 g/L of disodium hydrogen phosphate 12 hydrate, 3 g/L of potassium dihydrogen phosphate, 0.5 g/L of magnesium sulfate heptahydrate and 5 g/L of glucose, pH 7.0) containing 200 µg/ml of ampicillin, and further cultured at 37° C. for 4 hours. When $OD_{660}$ reached to about 0.6, 0.8 ml of 1 M IPTG was added to the culture, and the culture was further continued for 14 hours at 37° C. The treatment of the cells after the culture, the solubilization of the protein inclusion body, the protein refolding and the purification of the protein were carried out as described in (1).

(3) Preparation of Mutants in which the Acidic Amino Acid Residues are Modified

MTG expression plasmid pGEMMTG3 was used as the template for the site-specific mutagenesis and synthetic DNA (SEQ ID NOS: 19-22 in FIG. 6) corresponding to each mutant enzyme was used as the primer. The construction of the mutant plasmid, the culture, the treatment of the cells, the solubilization of the protein inclusion body, the protein refolding and the purification of protein were carried out as described in Example 4 (2).

(4) Preparation of the Mutants, Sg4 and Sg7 in which the Loops were Removed

For Sg4 genes, the genes corresponding to residue Nos. 1-240 and 253-331 were excised, and for Sg7 gene, the genes corresponding to residue Nos. 1-277 and 288-331 was excised, and then the two fragments were ligated together, respectively. Methods for constructing the Sg4 expression plasmid and the Sg7 expression plasmid are described below. PCR was carried out by using the primer (SEQ ID NO: 24) having SmaI cleavage site at the 5'-terminal and the primers (SEQ ID NOS: 25 and 26) containing a fragment encoding 3 glycine residues at the 3'-terminal, and pGEMMTG3 as the template. Similarly, PCR was carried out by using the primers (SEQ ID NOS: 27 and 28) containing a fragment encoding 3 glycine residues at the 5'-terminal and the primer (SEQ ID NO: 29) having HindIII cleavage site at the 3'-terminal, and pGEMMTG3 as the template. PCR was then carried out by using the primer (SEQ ID NO: 24) having SmaI cleavage site at the 5'-terminal and the primer (SEQ ID NO: 29) having HindIII cleavage site at the 3'-terminal together with the two amplified DNA fragments as the templates to obtain amplified Sg4 gene and Sg7 gene. For Sg7 gene, the fragment was cleaved by SmaI and HindIII, and cloned in pGEMMTG3 between SmaI site and HindIII site. On the other hand, for Sg7, the fragment was cleaved by EcoRI and HindIII, and cloned in pGEMMTG3 between EcoRI site and HindIII site. Further, the nucleotide sequences of the inserts of the obtained plasmids were confirmed to complete the construction of the Sg4 expression plasmid and the Sg7 expression plasmid.

The methods of the culture, cell treatment, solubilization of the protein inclusion body, protein refolding and protein purification were carried out as described in Example 4 (2).

Example 5

Comparison of Substrate Specificity

For comparing the substrate specificity, ovalbumin was employed as the substrate protein. Ovalbumin has 12 glutamine residues, and the reactivity to each of them was traced by NMR. For utilizing the protein in the fields of foods, medicines, etc., for example, the crosslinking rate of the protein molecules should be increased. Therefore, for some of the mutants, the time required for gelling casein in the respective cases was also compared with each other.

Figure 7:
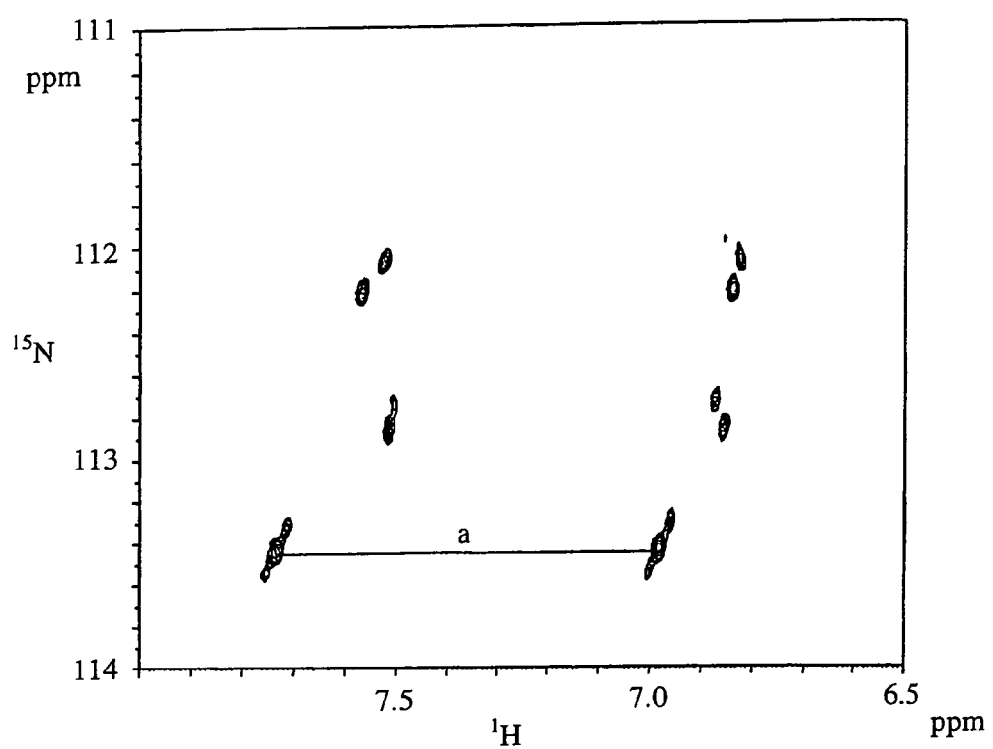
FIG. 7 shows 1H-15N HSQC spectrum of ovalbumin reacted with the wild type in the presence of $^{15}NH_4Cl$.
Figure 8:
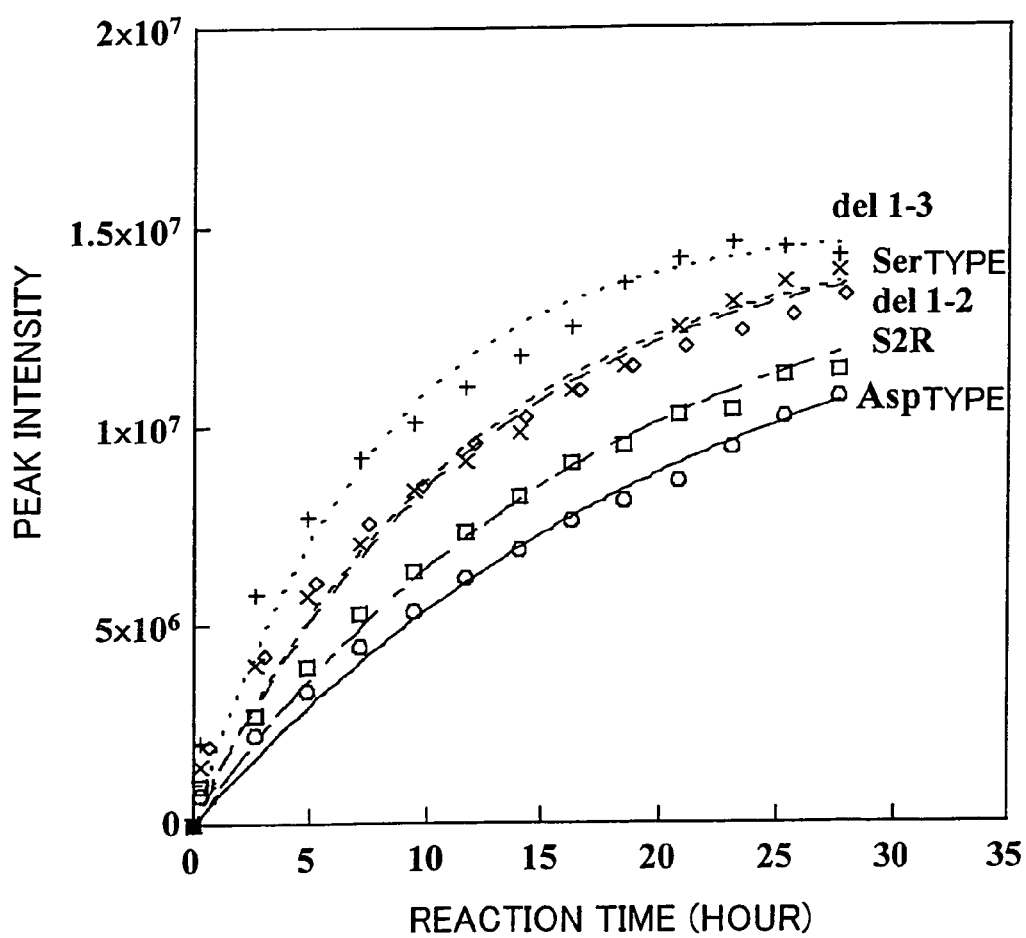
FIG. 8 shows the peak intensity of signal "a" in FIG. 7 in the glutamine residues of ovalbumin reacted with the wild type, Ser type, S2R, del 1-2 or del 1-3 in the presence of $^{15}NH_4Cl$, plotted vs. the reaction time.

(1) Analysis of Substrate Specificity using NMR (1-1) Comparison between Wild Type and Ser Type Ovalbumin, $^{15}NH_4Cl$ and transglutaminase were mixed together so that the final concentration is 100 mg/ml for ovalbumin, 200 mM for $^{15}NH_4Cl$ and 1 µM for transglutaminase. The first $^1H$-$^{15}N$ HSQC determination was carried out 20 minutes after, and then the $^1H$-$^{15}N$ HSQC determination was repeated 13 times at an interval of 2 hours and 15 minutes. An example of $^1H$-$^{15}N$ HSQC obtained after reacting the wild type for 3 hours is shown in FIG. 7. For both of the wild type and Ser type, the signal peak intensity (longitudinal axis) shown as "a" in FIG. 7 was plotted against the reaction time (hour; horizontal axis) (FIG. 8). As a result, it was found that the glutamine residue generating the signal indicated as "a" in FIG. 7 was more rapidly $^{15}N$-labeled when it was reacted with the Ser-type rather than when reacted with the wild type.

(1-2) Comparison of Wild Type with S2Y·S2R·S2D Mutant

Figure 9:
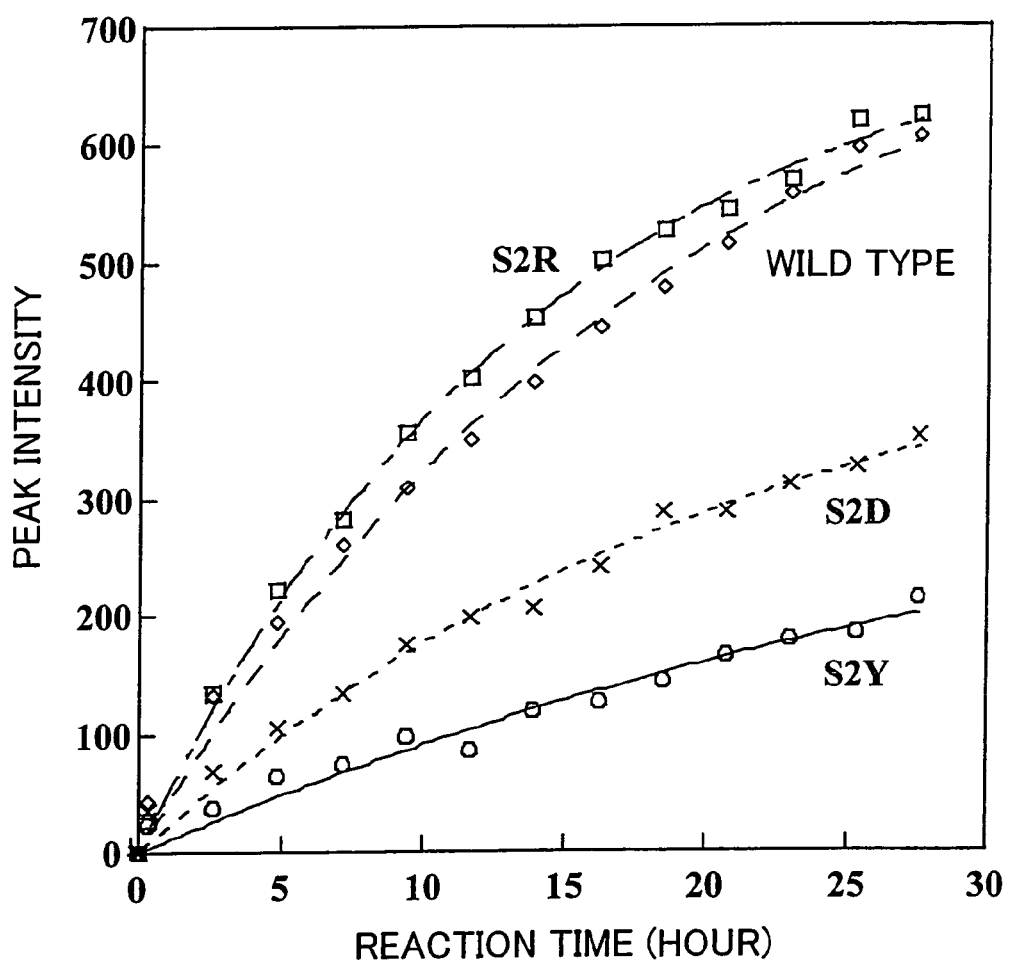
FIG. 9 shows the peak intensity of signal "a" in FIG. 7 in the glutamine residues of ovalbumin reacted with the wild type, S2Y, S2R or S2D mutant in the presence of $^{15}NH_4Cl$, plotted vs. the reaction time.

Ovalbumin, $^{15}NH_4Cl$ and transglutaminase were mixed together so that the final concentration is 100 mg/ml for ovalbumin, 200 mM for $^{15}NH_4Cl$ and 1 µM for transglutaminase. 20 minutes after, the first $^1H$-$^{15}N$ HSQC determination was carried out and then the $^1H$-$^{15}N$ HSQC determination was repeated 13 times at an interval of 2 hours and 15 minutes. The peak intensity (longitudinal axis) of the spectra obtained by reacting the wild type, S2Y or S2D on the glutamine residue giving the signal "a" in FIG. 7, was plotted, respectively (FIG. 9). As a result, it was found that as for the glutamine residue generating the signal "a" in FIG. 7, the order of the $^{15}$N-labeling rate was S2Y<S2D<wild type<S2R.

(1-3) Comparison with Mutants having Modified Acidic Amino Acid Residues

Ovalbumin, $^{15}$NH$_4$Cl and transglutaminase were mixed together so that the final concentration is 100 mg/ml for ovalbumin, 200 mM for $^{15}$NH$_4$Cl and 1 μM for transglutaminase. 20 minutes after, the first $^1$H-$^{15}$N HSQC determination was carried out and then the $^1$H-$^{15}$N HSQC determination was repeated 13 times at an interval of 2 hours and 15 minutes. The peak intensity (longitudinal axis) of the spectra obtained by reacting wild type, Ser type, S2R, del 1-2 or del 1-3 to the glutamine residue giving the signal "a" in FIG. 7 was plotted (FIG. 8) respectively in the same manner as that of Example 5. As a result, it was found that the reactivity of each of del 1-2 and del 1-3 was improved as compared with that of the wild type. Furthermore, it can be understood that the reactivity of del 1-3 was even much higher than that of Ser type or S2R.

Thus, the cross-linking of proteins can be carried out by using smaller amount of transglutaminase than the amount used in the prior art by generating a mutant transglutaminase having modified substrate specificity by reducing the negative charge through modifying acidic amino acid residues or converting amino acid residues adjacent to those acidic amino acid residues into basic ones, which leads the remarkable reduction of the costs.

(14) Comparison with Mutants in which the Loop Region is Removed

Figure 10:
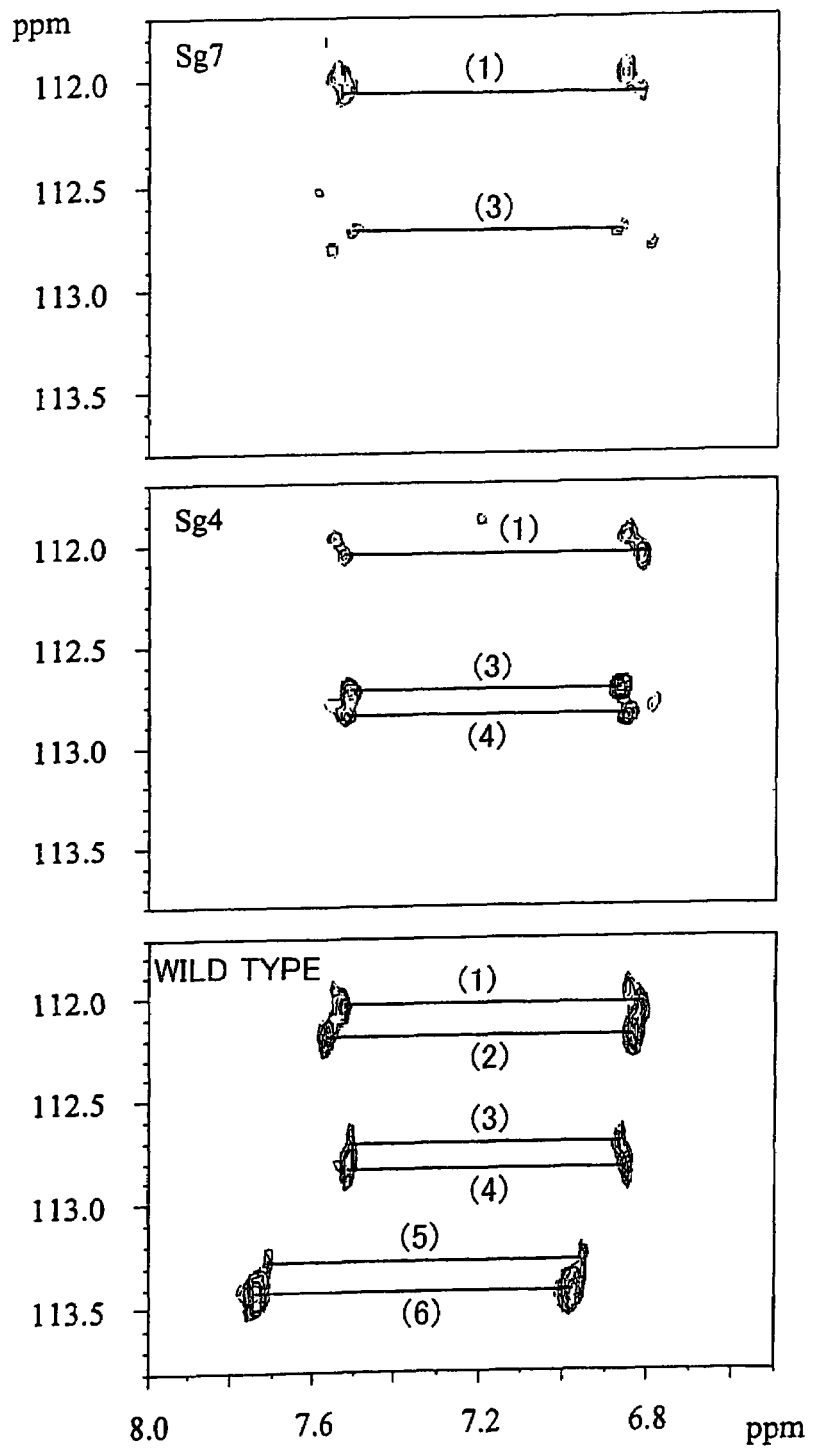
FIG. 10 shows $^{1}H$-$^{15}N$ HSQC spectrum of ovalbumin reacted with the wild type, Sg4 or Sg7 in the presence of $^{15}NH_4Cl$.

Ovalbumin, $^{15}$NH$_4$Cl and transglutaminase were mixed together so that the final concentration is 100 mg/ml for ovalbumin, 200 mM for $^{15}$NH$_4$Cl and 1 μM for transglutaminase. 6 hours after, the $^1$H-$^{15}$N HSQC determination was carried out to find that only 3 groups and 2 groups of the signals were found when Sg4 and Sg7 were used, respectively, while 6 groups of the signals were found when the wild type was used (FIG. 10). It was known from the transglutaminase-free experiments that among the signals observed in FIG. 10, unnumbered ones are not from the glutamine residues labeled by the transglutaminase reaction. As for the spectrum of ovalbumin labeled using Sg7, the figure extracted from a lower level is shown because the reactivity of Sg7 was reduced to lower the labeling efficiency. It is to be noted that, for this reason, unnumbered signals were slightly emphasized.

Only glutamine residues corresponding to (1), (3) and (4) were labeled using Sg4, while those corresponding to (1) to (6) were labeled with the wild type. Therefore, it was shown that when Sg4 was used, the number of glutamine residues which could serve as the substrates decreased, namely its substrate specificity was higher, compared with the case when the wild type was used. It was also shown that with Sg7, glutamine residues only corresponding to (1) and (3) can be the substrate, although the reactivity was reduced. It was considered that the binding area for the substrate was reduced by removing the loop, and that the kinds of the substrates with which the mutant could be reacted were reduced. As the results, it was suggested that the substrate specificity of MTG could be modified by preparing mutants thereof based on the three-dimensional structure. By using the transglutaminase having modified substrate specificity, the application of transglutaminase to subjects different from previously described may be possible, and the new development in industries is expected.

(2) Comparison of the Time of Gelatinization of Casein 57.6 μg of wild, Ser type, S2Y, S2R or S2D mutant was respectively added to 2.5 g of 8% (w/w) casein solution, and the time required for the gelatination of casein in each case was compared with each other. The reaction temperature was 40° C. The time required for the gelation was 90 minutes for wile type, 85 minutes for Ser type, 100 minutes for S2Y mutant, 85 minutes for S2R mutant and 95 minutes for S2D mutant. Thus, it was shown that the gelatinization proceeded in a short period for Ser type or S2R mutant, and the gelatination slowly proceeded for S2Y and S2D.

According to the present invention, the improvement of MTG on the basis of the three-dimensional structure is facilitated. In particular, transglutaminase having an improved reactivity on the substrate can be provided by the present invention. Further, new products and novel techniques can be provided with the transglutaminase having the improved reactivity on the substrate.

What is claimed is:

1. An isolated polynucleotide encoding a mutant MTG having transglutaminase activity wherein the mutant MTG has the amino acid sequence of SEQ ID NO: 2 with a mutation, where said mutation is introduced into the sequence by:
   a) replacing Ser2 with Arg, Tyr, or Asp;
   b) deleting amino acid residue Nos. 1-2 or 1-3 at the N-terminus;
   c) replacing amino acid residue Nos. 241-252 with three Gly residues; or
   d) replacing amino acid residue Nos. 278-287 with three Gly residues.

2. A recombinant DNA containing the polynucleotide according to claim 1.

3. A microorganism containing the recombinant DNA according to claim 2.

4. A method for producing a mutant MTG, which comprises culturing the microorganism according to claim 3 and collecting the mutant MTG.

* * * * *

SEQUENCE LISTING

<160> NUMBER OF SEQ ID NOS: 34

<210> SEQ ID NO 1
<211> LENGTH: 993
<212> TYPE: DNA
<213> ORGANISM: Streptoverticillium mobaraense
<220> FEATURE:
<221> NAME/KEY: CDS
<222> LOCATION: (1)..(993)

<400> SEQUENCE: 1

```
gac tcc gac gac agg gtc acc cct ccc gcc gag ccg ctc gac agg atg        48
Asp Ser Asp Asp Arg Val Thr Pro Pro Ala Glu Pro Leu Asp Arg Met
  1               5                  10                  15 ccc gac ccg tac cgt ccc tcg tac ggc agg gcc gag acg gtc gtc aac        96
Pro Asp Pro Tyr Arg Pro Ser Tyr Gly Arg Ala Glu Thr Val Val Asn
             20                  25                  30 aac tac ata cgc aag tgg cag cag gtc tac agc cac cgc gac ggc agg       144
Asn Tyr Ile Arg Lys Trp Gln Gln Val Tyr Ser His Arg Asp Gly Arg
```

```
                    35                  40                    45
aag cag cag atg acc gag gag cag cgg gag tgg ctg tcc tac ggc tgc    192
Lys Gln Gln Met Thr Glu Glu Gln Arg Glu Trp Leu Ser Tyr Gly Cys
     50                  55                  60 gtc ggt gtc acc tgg gtc aat tcg ggt cag tac ccg acg aac aga ctg    240
Val Gly Val Thr Trp Val Asn Ser Gly Gln Tyr Pro Thr Asn Arg Leu
 65                  70                  75                  80 gcc ttc gcg tcc ttc gac gag gac agg ttc aag aac gag ctg aag aac    288
Ala Phe Ala Ser Phe Asp Glu Asp Arg Phe Lys Asn Glu Leu Lys Asn
                 85                  90                  95 ggc agg ccc cgg tcc ggc gag acg cgg gcg gag ttc gag ggc cgc gtc    336
Gly Arg Pro Arg Ser Gly Glu Thr Arg Ala Glu Phe Glu Gly Arg Val
            100                 105                 110 gcg aag gag agc ttc gac gag gag aag ggc ttc cag cgg gcg cgt gag    384
Ala Lys Glu Ser Phe Asp Glu Glu Lys Gly Phe Gln Arg Ala Arg Glu
        115                 120                 125 gtg gcg tcc gtc atg aac agg gcc ctg gag aac gcc cac gac gag agc    432
Val Ala Ser Val Met Asn Arg Ala Leu Glu Asn Ala His Asp Glu Ser
    130                 135                 140 gct tac ctc gac aac ctc aag aag gaa ctg gcg aac ggc aac gac gcc    480
Ala Tyr Leu Asp Asn Leu Lys Lys Glu Leu Ala Asn Gly Asn Asp Ala
145                 150                 155                 160 ctg cgc aac gag gac gcc cgt tcc ccg ttc tac tcg gcg ctg cgg aac    528
Leu Arg Asn Glu Asp Ala Arg Ser Pro Phe Tyr Ser Ala Leu Arg Asn
                165                 170                 175 acg ccg tcc ttc aag gag cgg aac gga ggc aat cac gac ccg tcc agg    576
Thr Pro Ser Phe Lys Glu Arg Asn Gly Gly Asn His Asp Pro Ser Arg
            180                 185                 190 atg aag gcc gtc atc tac tcg aag cac ttc tgg agc ggc cag gac cgg    624
Met Lys Ala Val Ile Tyr Ser Lys His Phe Trp Ser Gly Gln Asp Arg
        195                 200                 205 tcg agt tcg gcc gac aag agg aag tac ggc gac ccg gac gcc ttc cgc    672
Ser Ser Ser Ala Asp Lys Arg Lys Tyr Gly Asp Pro Asp Ala Phe Arg
    210                 215                 220 ccc gcc ccg ggc acc ggc ctg gtc gac atg tcg agg gac agg aac att    720
Pro Ala Pro Gly Thr Gly Leu Val Asp Met Ser Arg Asp Arg Asn Ile
225                 230                 235                 240 ccg cgc agc ccc acc agc ccc ggt gag gga ttc gtc aat ttc gac tac    768
Pro Arg Ser Pro Thr Ser Pro Gly Glu Gly Phe Val Asn Phe Asp Tyr
                245                 250                 255 ggc tgg ttc ggc gcc cag acg gaa gcg gac gcc gac aag acc gtc tgg    816
Gly Trp Phe Gly Ala Gln Thr Glu Ala Asp Ala Asp Lys Thr Val Trp
            260                 265                 270 acc cac gga aat cac tat cac gcg ccc aat ggc agc ctg ggt gcc atg    864
Thr His Gly Asn His Tyr His Ala Pro Asn Gly Ser Leu Gly Ala Met
        275                 280                 285 cat gtc tac gag agc aag ttc cgc aac tgg tcc gag ggt tac tcg gac    912
His Val Tyr Glu Ser Lys Phe Arg Asn Trp Ser Glu Gly Tyr Ser Asp
    290                 295                 300 ttc gac cgc gga gcc tat gtg atc acc ttc atc ccc aag agc tgg aac    960
Phe Asp Arg Gly Ala Tyr Val Ile Thr Phe Ile Pro Lys Ser Trp Asn
305                 310                 315                 320 acc gcc ccc gac aag gta aag cag ggc tgg ccg                        993
Thr Ala Pro Asp Lys Val Lys Gln Gly Trp Pro
                325                 330

<210> SEQ ID NO 2
<211> LENGTH: 331
<212> TYPE: PRT
<213> ORGANISM: Streptoverticillium mobaraense
```

<400> SEQUENCE: 2

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65              70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205

Ser Ser Ser Ala Asp Lys Arg Lys Tyr Gly Asp Pro Asp Ala Phe Arg
    210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Glu Gly Tyr Ser Asp
    290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 3
<211> LENGTH: 996
<212> TYPE: DNA
<213> ORGANISM: Streptoverticillium mobaraense
<220> FEATURE:
<221> NAME/KEY: CDS
<222> LOCATION: (1)..(996)
<220> FEATURE:
<221> NAME/KEY: mat_peptide
<222> LOCATION: (4)..(996)

<400> SEQUENCE: 3

-continued

| | |
|---|---|
| atg gat tct gac gat cga gtc act cca cca gct gaa cca ctg gat cgt<br>Met Asp Ser Asp Asp Arg Val Thr Pro Pro Ala Glu Pro Leu Asp Arg<br>-1  1                    5                    10                 15 | 48 |
| atg cca gat cca tat cgt cca tct tat ggt cgt gct gaa act gtt gtt<br>Met Pro Asp Pro Tyr Arg Pro Ser Tyr Gly Arg Ala Glu Thr Val Val<br>                  20                   25                   30 | 96 |
| aat aat tat att cgt aaa tgg caa caa gtt tat tct cat cgt gat ggt<br>Asn Asn Tyr Ile Arg Lys Trp Gln Gln Val Tyr Ser His Arg Asp Gly<br>                 35                  40                  45 | 144 |
| cgt aaa caa caa atg act gaa gaa caa cgt gaa tgg ctg tct tat ggt<br>Arg Lys Gln Gln Met Thr Glu Glu Gln Arg Glu Trp Leu Ser Tyr Gly<br>        50                  55                  60 | 192 |
| tgc gtt ggt gtt act tgg gtt aac tct ggt cag tat ccg act aac cgt<br>Cys Val Gly Val Thr Trp Val Asn Ser Gly Gln Tyr Pro Thr Asn Arg<br>65                    70                   75 | 240 |
| ctg gca ttc gct tcc ttc gat gaa gat cgt ttc aag aac gaa ctg aag<br>Leu Ala Phe Ala Ser Phe Asp Glu Asp Arg Phe Lys Asn Glu Leu Lys<br>80                    85                   90                 95 | 288 |
| aac ggt cgt ccg cgt tct ggt gaa act cgt gct gaa ttc gaa ggt cgt<br>Asn Gly Arg Pro Arg Ser Gly Glu Thr Arg Ala Glu Phe Glu Gly Arg<br>                 100                105              110 | 336 |
| gtt gct aag gaa tcc ttc gat gaa gag aaa ggc ttc cag cgt gct cgt<br>Val Ala Lys Glu Ser Phe Asp Glu Glu Lys Gly Phe Gln Arg Ala Arg<br>            115                  120                125 | 384 |
| gaa gtt gct tct gtt atg aac cgt gct cta gag aac gct cat gat gaa<br>Glu Val Ala Ser Val Met Asn Arg Ala Leu Glu Asn Ala His Asp Glu<br>        130                  135                140 | 432 |
| tct gct tac ctg gat aac ctg aag aag gaa ctg gct aac ggt aac gat<br>Ser Ala Tyr Leu Asp Asn Leu Lys Lys Glu Leu Ala Asn Gly Asn Asp<br>145                     150                  155 | 480 |
| gct ctg cgt aac gaa gat gct cgt tct ccg ttc tac tct gct ctg cgt<br>Ala Leu Arg Asn Glu Asp Ala Arg Ser Pro Phe Tyr Ser Ala Leu Arg<br>160                     165                  170                175 | 528 |
| aac act ccg tcc ttc aaa gaa cgt aac ggt ggt aac cat gat ccg tct<br>Asn Thr Pro Ser Phe Lys Glu Arg Asn Gly Gly Asn His Asp Pro Ser<br>                 180                185              190 | 576 |
| cgt atg aaa gct gtt atc tac tct aaa cat ttc tgg tct ggt cag gat<br>Arg Met Lys Ala Val Ile Tyr Ser Lys His Phe Trp Ser Gly Gln Asp<br>            195                  200                205 | 624 |
| aga tct tct tct gct gat aaa cgt aaa tac ggt gat ccg gat gca ttc<br>Arg Ser Ser Ser Ala Asp Lys Arg Lys Tyr Gly Asp Pro Asp Ala Phe<br>        210                  215                220 | 672 |
| cgt ccg gct ccg ggt act ggt ctg gta gac atg tct cgt gat cgt aac<br>Arg Pro Ala Pro Gly Thr Gly Leu Val Asp Met Ser Arg Asp Arg Asn<br>225                     230                  235 | 720 |
| atc ccg cgt tct ccg act tct ccg ggt gaa ggc ttc gtt aac ttc gat<br>Ile Pro Arg Ser Pro Thr Ser Pro Gly Glu Gly Phe Val Asn Phe Asp<br>240                     245                  250                255 | 768 |
| tac ggt tgg ttc ggt gct cag act gaa gct gat gct gat aag act gta<br>Tyr Gly Trp Phe Gly Ala Gln Thr Glu Ala Asp Ala Asp Lys Thr Val<br>            260                  265                270 | 816 |
| tgg acc cat ggt aac cat tac cat gct ccg aac ggt tct ctg ggt gct<br>Trp Thr His Gly Asn His Tyr His Ala Pro Asn Gly Ser Leu Gly Ala<br>                 275                280              285 | 864 |
| atg cat gta tac gaa tct aaa ttc cgt aac tgg tct gaa ggt tac tct<br>Met His Val Tyr Glu Ser Lys Phe Arg Asn Trp Ser Glu Gly Tyr Ser<br>        290                  295                300 | 912 |
| gac ttc gat cgt ggt gct tac gtt atc acc ttc att ccg aaa tct tgg<br>Asp Phe Asp Arg Gly Ala Tyr Val Ile Thr Phe Ile Pro Lys Ser Trp | 960 |

```
                305                 310                 315
aac act gct ccg gac aaa gtt aaa cag ggt tgg ccg                              996
Asn Thr Ala Pro Asp Lys Val Lys Gln Gly Trp Pro
320                 325                 330
```

<210> SEQ ID NO 4
<211> LENGTH: 332
<212> TYPE: PRT
<213> ORGANISM: Streptoverticillium mobaraense

<400> SEQUENCE: 4

```
Met Asp Ser Asp Asp Arg Val Thr Pro Pro Ala Glu Pro Leu Asp Arg
 -1   1               5                  10                  15

Met Pro Asp Pro Tyr Arg Pro Ser Tyr Gly Arg Ala Glu Thr Val Val
                 20                  25                  30

Asn Asn Tyr Ile Arg Lys Trp Gln Gln Val Tyr Ser His Arg Asp Gly
                 35                  40                  45

Arg Lys Gln Gln Met Thr Glu Glu Gln Arg Glu Trp Leu Ser Tyr Gly
             50                  55                  60

Cys Val Gly Val Thr Trp Val Asn Ser Gly Gln Tyr Pro Thr Asn Arg
 65                  70                  75

Leu Ala Phe Ala Ser Phe Asp Glu Asp Arg Phe Lys Asn Glu Leu Lys
 80                  85                  90                  95

Asn Gly Arg Pro Arg Ser Gly Glu Thr Arg Ala Glu Phe Glu Gly Arg
                100                 105                 110

Val Ala Lys Glu Ser Phe Asp Glu Glu Lys Gly Phe Gln Arg Ala Arg
            115                 120                 125

Glu Val Ala Ser Val Met Asn Arg Ala Leu Glu Asn Ala His Asp Glu
            130                 135                 140

Ser Ala Tyr Leu Asp Asn Leu Lys Lys Glu Leu Ala Asn Gly Asn Asp
145                 150                 155

Ala Leu Arg Asn Glu Asp Ala Arg Ser Pro Phe Tyr Ser Ala Leu Arg
160                 165                 170                 175

Asn Thr Pro Ser Phe Lys Glu Arg Asn Gly Gly Asn His Asp Pro Ser
                180                 185                 190

Arg Met Lys Ala Val Ile Tyr Ser Lys His Phe Trp Ser Gly Gln Asp
            195                 200                 205

Arg Ser Ser Ser Ala Asp Lys Arg Lys Tyr Gly Asp Pro Asp Ala Phe
        210                 215                 220

Arg Pro Ala Pro Gly Thr Gly Leu Val Asp Met Ser Arg Asp Arg Asn
225                 230                 235

Ile Pro Arg Ser Pro Thr Ser Pro Gly Glu Gly Phe Val Asn Phe Asp
240                 245                 250                 255

Tyr Gly Trp Phe Gly Ala Gln Thr Glu Ala Asp Ala Asp Lys Thr Val
                260                 265                 270

Trp Thr His Gly Asn His Tyr His Ala Pro Asn Gly Ser Leu Gly Ala
            275                 280                 285

Met His Val Tyr Glu Ser Lys Phe Arg Asn Trp Ser Glu Gly Tyr Ser
            290                 295                 300

Asp Phe Asp Arg Gly Ala Tyr Val Ile Thr Phe Ile Pro Lys Ser Trp
305                 310                 315

Asn Thr Ala Pro Asp Lys Val Lys Gln Gly Trp Pro
320                 325                 330
```

<210> SEQ ID NO 5

<211> LENGTH: 990
<212> TYPE: DNA
<213> ORGANISM: Streptoverticillium cinnamoneum
<220> FEATURE:
<221> NAME/KEY: CDS
<222> LOCATION: (1)..(990)

<400> SEQUENCE: 5

| | | | | | | | | | | | | | | | | |
|---|---|---|---|---|---|---|---|---|---|---|---|---|---|---|---|---|
| tcc | cgg | gcc | ccc | tcc | gat | gac | cgg | gaa | act | cct | ccc | gcc | gag | ccg | ctc | 48 |
| Ser | Arg | Ala | Pro | Ser | Asp | Asp | Arg | Glu | Thr | Pro | Pro | Ala | Glu | Pro | Leu | |
| 1 | | | | 5 | | | | | 10 | | | | | 15 | | |
| gac | agg | atg | cct | gag | gcg | tac | cgg | gcc | tac | gga | ggc | agg | gcc | act | acg | 96 |
| Asp | Arg | Met | Pro | Glu | Ala | Tyr | Arg | Ala | Tyr | Gly | Gly | Arg | Ala | Thr | Thr | |
| | | | 20 | | | | | 25 | | | | | 30 | | | |
| gtc | gtc | aac | aac | tac | ata | cgc | aag | tgg | cag | cag | gtc | tac | agt | cac | cgc | 144 |
| Val | Val | Asn | Asn | Tyr | Ile | Arg | Lys | Trp | Gln | Gln | Val | Tyr | Ser | His | Arg | |
| | | | | 35 | | | | | 40 | | | | | 45 | | |
| gac | gga | aag | aaa | cag | caa | atg | acc | gaa | gag | cag | cga | gaa | aag | ctg | tcc | 192 |
| Asp | Gly | Lys | Lys | Gln | Gln | Met | Thr | Glu | Glu | Gln | Arg | Glu | Lys | Leu | Ser | |
| | | 50 | | | | | 55 | | | | | 60 | | | | |
| tac | ggt | tgc | gtt | ggc | gtc | acc | tgg | gtc | aac | tcg | ggc | ccc | tac | ccg | acg | 240 |
| Tyr | Gly | Cys | Val | Gly | Val | Thr | Trp | Val | Asn | Ser | Gly | Pro | Tyr | Pro | Thr | |
| 65 | | | | 70 | | | | | 75 | | | | | 80 | | |
| aac | aga | ttg | gcg | ttc | ggt | ccc | ttc | gac | gag | aac | aag | tac | aag | aac | gac | 288 |
| Asn | Arg | Leu | Ala | Phe | Gly | Pro | Phe | Asp | Glu | Asn | Lys | Tyr | Lys | Asn | Asp | |
| | | | | 85 | | | | | 90 | | | | | 95 | | |
| ctg | aag | aac | acc | agc | ccc | cga | ccc | gat | gaa | acg | cgg | gcg | gag | ttc | gag | 336 |
| Leu | Lys | Asn | Thr | Ser | Pro | Arg | Pro | Asp | Glu | Thr | Arg | Ala | Glu | Phe | Glu | |
| | | | 100 | | | | | 105 | | | | | 110 | | | |
| ggt | cgc | atc | aag | ggc | agt | ttc | gac | gag | ggg | aag | ggt | ttc | aag | cgg | gcg | 384 |
| Gly | Arg | Ile | Lys | Gly | Ser | Phe | Asp | Glu | Gly | Lys | Gly | Phe | Lys | Arg | Ala | |
| | | | 115 | | | | | 120 | | | | | 125 | | | |
| cgt | gat | gtg | gcg | tcc | gtc | atg | aac | aag | gcc | cgg | gaa | aat | gcc | cac | gac | 432 |
| Arg | Asp | Val | Ala | Ser | Val | Met | Asn | Lys | Ala | Arg | Glu | Asn | Ala | His | Asp | |
| | 130 | | | | | 135 | | | | | 140 | | | | | |
| gag | ggg | act | tac | atc | aac | aac | ctc | aag | acg | gag | ctc | acg | aac | aac | aat | 480 |
| Glu | Gly | Thr | Tyr | Ile | Asn | Asn | Leu | Lys | Thr | Glu | Leu | Thr | Asn | Asn | Asn | |
| 145 | | | | | 150 | | | | | 155 | | | | | 160 | |
| gcg | ctc | cgc | cgc | gag | gac | agc | cgc | tcg | aac | ttc | tac | tcg | gcg | ctg | agg | 528 |
| Ala | Leu | Arg | Arg | Glu | Asp | Ser | Arg | Ser | Asn | Phe | Tyr | Ser | Ala | Leu | Arg | |
| | | | | 165 | | | | | 170 | | | | | 175 | | |
| aac | aca | ccg | tcc | ttc | aag | gaa | agg | gac | ggc | ggc | aac | tac | gac | ccg | tcc | 576 |
| Asn | Thr | Pro | Ser | Phe | Lys | Glu | Arg | Asp | Gly | Gly | Asn | Tyr | Asp | Pro | Ser | |
| | | | 180 | | | | | 185 | | | | | 190 | | | |
| aag | atg | aag | gcg | gtg | atc | tac | tcg | aag | cac | ttc | tgg | agc | ggg | cag | gac | 624 |
| Lys | Met | Lys | Ala | Val | Ile | Tyr | Ser | Lys | His | Phe | Trp | Ser | Gly | Gln | Asp | |
| | | | 195 | | | | | 200 | | | | | 205 | | | |
| cag | cgg | ggc | tcc | tcc | gac | aag | agg | aag | tac | ggc | gac | ccg | gaa | gcc | ttc | 672 |
| Gln | Arg | Gly | Ser | Ser | Asp | Lys | Arg | Lys | Tyr | Gly | Asp | Pro | Glu | Ala | Phe | |
| | 210 | | | | | 215 | | | | | 220 | | | | | |
| cgc | ccc | gta | cca | ggt | acc | ggc | ctg | gtc | gac | atg | tcg | aag | gac | aga | agc | 720 |
| Arg | Pro | Val | Pro | Gly | Thr | Gly | Leu | Val | Asp | Met | Ser | Lys | Asp | Arg | Ser | |
| 225 | | | | | 230 | | | | | 235 | | | | | 240 | |
| att | ccg | cgc | agt | ccg | gcc | aag | ccc | ggc | gaa | ggt | tgg | gtc | aat | ttc | gac | 768 |
| Ile | Pro | Arg | Ser | Pro | Ala | Lys | Pro | Gly | Glu | Gly | Trp | Val | Asn | Phe | Asp | |
| | | | | 245 | | | | | 250 | | | | | 255 | | |
| tac | ggt | tgg | ttc | ggg | gct | caa | aca | gaa | gcg | gat | cgc | gac | aaa | acc | aca | 816 |
| Tyr | Gly | Trp | Phe | Gly | Ala | Gln | Thr | Glu | Ala | Asp | Arg | Asp | Lys | Thr | Thr | |
| | | | 260 | | | | | 265 | | | | | 270 | | | |
| tgg | acc | cac | ggc | gac | cac | tac | cac | gcg | ccc | aat | agc | gac | ctg | ggc | ccc | 864 |
| Trp | Thr | His | Gly | Asp | His | Tyr | His | Ala | Pro | Asn | Ser | Asp | Leu | Gly | Pro | |

```
              275                 280                 285
atg cac gta cac gag agc aag ttc cgg aag tgg tct gcc ggg tac gcg      912
Met His Val His Glu Ser Lys Phe Arg Lys Trp Ser Ala Gly Tyr Ala
    290                 295                 300 gac ttc ggc gcc tac gtg atc acg ttc ata ccc aag agc tgg aac acc      960
Asp Phe Gly Ala Tyr Val Ile Thr Phe Ile Pro Lys Ser Trp Asn Thr
305                 310                 315                 320 gcc ccc gcc aag gtg gag caa ggc tgg ccg                              990
Ala Pro Ala Lys Val Glu Gln Gly Trp Pro
                325                 330

<210> SEQ ID NO 6
<211> LENGTH: 330
<212> TYPE: PRT
<213> ORGANISM: Streptoverticillium cinnamoneum

<400> SEQUENCE: 6

Ser Arg Ala Pro Ser Asp Arg Glu Thr Pro Ala Glu Pro Leu
  1               5                  10                  15

Asp Arg Met Pro Glu Ala Tyr Arg Ala Tyr Gly Gly Arg Ala Thr Thr
             20                  25                  30

Val Val Asn Asn Tyr Ile Arg Lys Trp Gln Gln Val Tyr Ser His Arg
         35                  40                  45

Asp Gly Lys Lys Gln Gln Met Thr Glu Glu Gln Arg Glu Lys Leu Ser
     50                  55                  60

Tyr Gly Cys Val Gly Val Thr Trp Val Asn Ser Gly Pro Tyr Pro Thr
 65                  70                  75                  80

Asn Arg Leu Ala Phe Gly Pro Phe Asp Glu Asn Lys Tyr Lys Asn Asp
                 85                  90                  95

Leu Lys Asn Thr Ser Pro Arg Pro Asp Glu Thr Arg Ala Glu Phe Glu
            100                 105                 110

Gly Arg Ile Lys Gly Ser Phe Asp Glu Gly Lys Gly Phe Lys Arg Ala
        115                 120                 125

Arg Asp Val Ala Ser Val Met Asn Lys Ala Arg Glu Asn Ala His Asp
    130                 135                 140

Glu Gly Thr Tyr Ile Asn Asn Leu Lys Thr Glu Leu Thr Asn Asn Asn
145                 150                 155                 160

Ala Leu Arg Arg Glu Asp Ser Arg Ser Asn Phe Tyr Ser Ala Leu Arg
                165                 170                 175

Asn Thr Pro Ser Phe Lys Glu Arg Asp Gly Asn Tyr Asp Pro Ser
            180                 185                 190

Lys Met Lys Ala Val Ile Tyr Ser Lys His Phe Trp Ser Gly Gln Asp
        195                 200                 205

Gln Arg Gly Ser Ser Asp Lys Arg Lys Tyr Gly Asp Pro Glu Ala Phe
    210                 215                 220

Arg Pro Val Pro Gly Thr Gly Leu Val Asp Met Ser Lys Asp Arg Ser
225                 230                 235                 240

Ile Pro Arg Ser Pro Ala Lys Pro Gly Glu Gly Trp Val Asn Phe Asp
                245                 250                 255

Tyr Gly Trp Phe Gly Ala Gln Thr Glu Ala Asp Arg Asp Lys Thr Thr
            260                 265                 270

Trp Thr His Gly Asp His Tyr His Ala Pro Asn Ser Asp Leu Gly Pro
        275                 280                 285

Met His Val His Glu Ser Lys Phe Arg Lys Trp Ser Ala Gly Tyr Ala
    290                 295                 300
```

```
Asp Phe Gly Ala Tyr Val Ile Thr Phe Ile Pro Lys Ser Trp Asn Thr
305                 310                 315                 320

Ala Pro Ala Lys Val Glu Gln Gly Trp Pro
                325                 330

<210> SEQ ID NO 7
<211> LENGTH: 993
<212> TYPE: DNA
<213> ORGANISM: Streptomyces lydicus
<220> FEATURE:
<221> NAME/KEY: CDS
<222> LOCATION: (1)..(993)

<400> SEQUENCE: 7 gca gcc gac gaa agg gtc acc cct ccc gcc gag ccg ctc aac cgg atg      48
Ala Ala Asp Glu Arg Val Thr Pro Pro Ala Glu Pro Leu Asn Arg Met
 1               5                  10                  15 cct gac gcg tac cgg gcc tac gga ggt agg gcc act acg gtc gtc aac      96
Pro Asp Ala Tyr Arg Ala Tyr Gly Gly Arg Ala Thr Thr Val Val Asn
             20                  25                  30 aac tac ata cgc aag tgg cag cag gtc tac agt cac cgc gac ggc atc     144
Asn Tyr Ile Arg Lys Trp Gln Gln Val Tyr Ser His Arg Asp Gly Ile
         35                  40                  45 caa cag caa atg acc gaa gag cag cga gaa aag ctg tcc tac ggc tgc     192
Gln Gln Gln Met Thr Glu Glu Gln Arg Glu Lys Leu Ser Tyr Gly Cys
 50                  55                  60 gtc ggc atc acc tgg gtc aat tcg ggc ccc tac ccg acg aat aaa ttg     240
Val Gly Ile Thr Trp Val Asn Ser Gly Pro Tyr Pro Thr Asn Lys Leu
 65                  70                  75                  80 gcg ttc gcg ttc ttc gac gag aac aag tac aag agt gac ctg gaa aac     288
Ala Phe Ala Phe Phe Asp Glu Asn Lys Tyr Lys Ser Asp Leu Glu Asn
                 85                  90                  95 agc agg cca cgc ccc aat gag acg caa gcc gag ttt gag ggg cgc atc     336
Ser Arg Pro Arg Pro Asn Glu Thr Gln Ala Glu Phe Glu Gly Arg Ile
            100                 105                 110 gtc aag gac agt ttc gac gag ggg aag ggt ttc aag cgg gcg cgt gat     384
Val Lys Asp Ser Phe Asp Glu Gly Lys Gly Phe Lys Arg Ala Arg Asp
        115                 120                 125 gtg gcg tcc gtc atg aac aag gcc ctg gat agt gcg cac gac gag ggg     432
Val Ala Ser Val Met Asn Lys Ala Leu Asp Ser Ala His Asp Glu Gly
    130                 135                 140 act tac atc gac aac ctc aag acg gag ctc gcg aac aaa aat gac gct     480
Thr Tyr Ile Asp Asn Leu Lys Thr Glu Leu Ala Asn Lys Asn Asp Ala
145                 150                 155                 160 ctg cgc tac gag gac ggt cgc tcg aac ttt tac tcg gcg ctg agg aat     528
Leu Arg Tyr Glu Asp Gly Arg Ser Asn Phe Tyr Ser Ala Leu Arg Asn
                165                 170                 175 acg ccg tcc ttc aag gaa agg gat gga ggt aac tac gac cca tcc aag     576
Thr Pro Ser Phe Lys Glu Arg Asp Gly Gly Asn Tyr Asp Pro Ser Lys
            180                 185                 190 atg aag gcg gtg gtc tac tcg aaa cac ttc tgg agc ggg cag gac cag     624
Met Lys Ala Val Val Tyr Ser Lys His Phe Trp Ser Gly Gln Asp Gln
        195                 200                 205 cgg ggc tcc tct gac aag agg aag tac ggc gac ccg gat gcc ttc cgc     672
Arg Gly Ser Ser Asp Lys Arg Lys Tyr Gly Asp Pro Asp Ala Phe Arg
    210                 215                 220 ccc gac cag ggc aca ggc ctg gta gac atg tcg aag gac agg aat att     720
Pro Asp Gln Gly Thr Gly Leu Val Asp Met Ser Lys Asp Arg Asn Ile
225                 230                 235                 240 ccg cgc agt ccc gcc caa cct ggc gaa agt tgg gtc aat ttc gac tac     768
Pro Arg Ser Pro Ala Gln Pro Gly Glu Ser Trp Val Asn Phe Asp Tyr
```

```
                245                 250                 255
ggc tgg ttt ggg gct cag acg gaa tcg gac gcc gac aaa acc ata tgg    816
Gly Trp Phe Gly Ala Gln Thr Glu Ser Asp Ala Asp Lys Thr Ile Trp
            260                 265                 270 acc cac gcc aac cac tat cac gcg ccc aac ggc ggc ctg ggc ccc atg    864
Thr His Ala Asn His Tyr His Ala Pro Asn Gly Gly Leu Gly Pro Met
        275                 280                 285 aac gta tat gag agc aag ttc cgg aac tgg tct gcc ggg tac gcg gat    912
Asn Val Tyr Glu Ser Lys Phe Arg Asn Trp Ser Ala Gly Tyr Ala Asp
    290                 295                 300 ttc gac cgc gga acc tac gtc atc acg ttc ata ccc aag agc tgg aac    960
Phe Asp Arg Gly Thr Tyr Val Ile Thr Phe Ile Pro Lys Ser Trp Asn
305                 310                 315                 320 acc gcc ccc gcc gag gta aag cag ggc tgg tcg                        993
Thr Ala Pro Ala Glu Val Lys Gln Gly Trp Ser
                325                 330

<210> SEQ ID NO 8
<211> LENGTH: 331
<212> TYPE: PRT
<213> ORGANISM: Streptomyces lydicus

<400> SEQUENCE: 8

Ala Ala Asp Glu Arg Val Thr Pro Pro Ala Glu Pro Leu Asn Arg Met
1               5                   10                  15

Pro Asp Ala Tyr Arg Ala Tyr Gly Gly Arg Ala Thr Thr Val Val Asn
            20                  25                  30

Asn Tyr Ile Arg Lys Trp Gln Gln Val Tyr Ser His Arg Asp Gly Ile
        35                  40                  45

Gln Gln Gln Met Thr Glu Glu Gln Arg Glu Lys Leu Ser Tyr Gly Cys
    50                  55                  60

Val Gly Ile Thr Trp Val Asn Ser Gly Pro Tyr Pro Thr Asn Lys Leu
65                  70                  75                  80

Ala Phe Ala Phe Phe Asp Glu Asn Lys Tyr Lys Ser Asp Leu Glu Asn
                85                  90                  95

Ser Arg Pro Arg Pro Asn Glu Thr Gln Ala Glu Phe Glu Gly Arg Ile
            100                 105                 110

Val Lys Asp Ser Phe Asp Glu Gly Lys Gly Phe Lys Arg Ala Arg Asp
        115                 120                 125

Val Ala Ser Val Met Asn Lys Ala Leu Asp Ser Ala His Asp Glu Gly
    130                 135                 140

Thr Tyr Ile Asp Asn Leu Lys Thr Glu Leu Ala Asn Lys Asn Asp Ala
145                 150                 155                 160

Leu Arg Tyr Glu Asp Gly Arg Ser Asn Phe Tyr Ser Ala Leu Arg Asn
                165                 170                 175

Thr Pro Ser Phe Lys Glu Arg Asp Gly Gly Asn Tyr Asp Pro Ser Lys
            180                 185                 190

Met Lys Ala Val Val Tyr Ser Lys His Phe Trp Ser Gly Gln Asp Gln
        195                 200                 205

Arg Gly Ser Ser Asp Lys Arg Lys Tyr Gly Asp Pro Asp Ala Phe Arg
    210                 215                 220

Pro Asp Gln Gly Thr Gly Leu Val Asp Met Ser Lys Asp Arg Asn Ile
225                 230                 235                 240

Pro Arg Ser Pro Ala Gln Pro Gly Glu Ser Trp Val Asn Phe Asp Tyr
                245                 250                 255

Gly Trp Phe Gly Ala Gln Thr Glu Ser Asp Ala Asp Lys Thr Ile Trp
```

-continued

```
                   260                 265                 270
Thr His Ala Asn His Tyr His Ala Pro Asn Gly Gly Leu Gly Pro Met
        275                 280                 285

Asn Val Tyr Glu Ser Lys Phe Arg Asn Trp Ser Ala Gly Tyr Ala Asp
    290                 295                 300

Phe Asp Arg Gly Thr Tyr Val Ile Thr Phe Ile Pro Lys Ser Trp Asn
305                 310                 315                 320

Thr Ala Pro Ala Glu Val Lys Gln Gly Trp Ser
                325                 330

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence:PCR primer

<400> SEQUENCE: 9
cggatccatc gaaggtcgtg attctgacga tcgtgttact cc                           42

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 10
caatttgcga gctcattacg gccaaccctg                                         30

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence:PCR primer

<400> SEQUENCE: 11
cctgcagaag gagatataca tatggattct gacgatcgag tc                           42

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:PCR primer

<400> SEQUENCE: 12
catcgaaaga ttccttagc                                                     19

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 13
ggagatatac atatggatta cgacgatcgt gttactcc                                38

<210> SEQ ID NO 14
<211> LENGTH: 38
<212> TYPE: DNA
<213> ORGANISM: Artificial Sequence
```

<220> FEATURE:
<223> OTHER INFORMATION: Description of Artificial Sequence:PCR primer

<400> SEQUENCE: 14
ggagtaacac gatcgtcgta atccatatgt atatctcc                    38

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 15
ggagatatac atatggatcg tgacgatcgt gttactcc                    38

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 16
ggagtaacac gatcgtcacg atccatatgt atatctcc                    38

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 17
ggagatatac atatggatga cgacgatcgt gttactcc                    38

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 18
ggagtaacac gatcgtcgtc atccatatgt atatctcc                    38

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 19
ggagatatac atatggacga tcgtgttact ccaccagc                    38

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence:PCR primer

<400> SEQUENCE: 20
gctggtggag taacacgatc gtccatatgt atatctcc                    38

-continued

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence:PCR primer

<400> SEQUENCE: 21
gaaggagata tacatatgga tcgtgttact ccaccagctg                              40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:PCR primer

<400> SEQUENCE: 22
cagctggtgg agtaacacga tccatatgta tatctccttc                              40

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence:oxidized
      bovine insulin, chain A
<220> FEATURE:
<221> NAME/KEY: MOD_RES
<222> LOCATION: (6)
<223> OTHER INFORMATION: oxidized
<220> FEATURE:
<221> NAME/KEY: MOD_RES
<222> LOCATION: (7)
<223> OTHER INFORMATION: oxidized
<220> FEATURE:
<221> NAME/KEY: MOD_RES
<222> LOCATION: (11)
<223> OTHER INFORMATION: oxidized
<220> FEATURE:
<221> NAME/KEY: MOD_RES
<222> LOCATION: (20)
<223> OTHER INFORMATION: oxidized

<400> SEQUENCE: 23

Gly Ile Val Glu Gln Cys Cys Ala Ser Val Cys Ser Leu Tyr Gln Leu
 1               5                  10                  15

Glu Asn Tyr Cys Asn
            20

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence:PCR primer

<400> SEQUENCE: 24
gattcattaa tgcagcccgg gagatc                                             26

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence:PCR primer

<400> SEQUENCE: 25
ccgatatcga agttaccgcc accgatgtta cgatcacgag acatgtctac          50

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence:PCR primer

<400> SEQUENCE: 26
gattcgtata catgcatacc gccaccatgg ttaccatggg tccatacagt c          51

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence:PCR primer

<400> SEQUENCE: 27
ggtggcggta acttcgatta cggttggttc ggtgc          35

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence:PCR primer

<400> SEQUENCE: 28
ggtggcggta tgcatgtata cgaatctaaa ttccg          35

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 29
gaatactcaa gctttcatta cggcc          25

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:mutant

<400> SEQUENCE: 30

Met Asp Tyr Asp Asp Arg Val Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:mutant

<400> SEQUENCE: 31

Met Asp Arg Asp Asp Arg Val Thr
1               5

<210> SEQ ID NO 32
<211> LENGTH: 8

```
<212> TYPE: PRT
<213> ORGANISM: Artificial Sequence
<220> FEATURE:
<223> OTHER INFORMATION: Description of Artificial Sequence:mutant

<400> SEQUENCE: 32

Met Asp Asp Asp Asp Arg Val Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:mutant

<400> SEQUENCE: 33

Met Asp Asp Arg Val Thr Pro Pro
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:mutant

<400> SEQUENCE: 34

Met Asp Arg Val Thr Pro Pro Ala
1               5
```